(12) United States Patent
Slaugenhaupt et al.

(10) Patent No.: US 7,388,093 B2
(45) Date of Patent: Jun. 17, 2008

(54) GENE FOR IDENTIFYING INDIVIDUALS WITH FAMILIAL DYSAUTONOMIA

(75) Inventors: Susan Slaugenhaupt, Quincy, MA (US); James F. Gusella, Framingham, MA (US)

(73) Assignee: The General Hospital Corporation, Boston, MA (US)

( * ) Notice: Subject to any disclaimer, the term of this patent is extended or adjusted under 35 U.S.C. 154(b) by 70 days.

(21) Appl. No.: 10/041,856

(22) Filed: Jan. 7, 2002

(65) Prior Publication Data

US 2002/0169299 A1 Nov. 14, 2002

Related U.S. Application Data

(60) Provisional application No. 60/260,080, filed on Jan. 6, 2001.

(51) Int. Cl.
- C07H 21/02 (2006.01)
- C07H 21/04 (2006.01)
- C12Q 1/68 (2006.01)
- C12P 19/34 (2006.01)

(52) U.S. Cl. .................. 536/24.31; 435/6; 435/91.2; 536/23.1; 536/23.5; 536/24.33

(58) Field of Classification Search ................ 536/23.1, 536/23.5, 24.31, 24.33; 435/69.1, 320.1, 435/252.3
See application file for complete search history.

(56) References Cited

U.S. PATENT DOCUMENTS

| | | | | |
|---|---|---|---|---|
| 5,387,506 | A |  | 2/1995 | Blumenfeld et al. ........... 435/6 |
| 5,597,898 | A | * | 1/1997 | Ghosh .......................... 530/350 |
| 5,891,719 | A | * | 4/1999 | Cohen et al. ................. 435/325 |
| 5,968,740 | A | * | 10/1999 | Fodor et al. ..................... 435/6 |
| 5,998,133 | A |  | 12/1999 | Blumenfeld et al. |
| 6,262,250 | B1 |  | 7/2001 | Blumenfeld et al. |
| 2002/0168656 | A1 |  | 11/2002 | Rubin et al. ..................... 435/6 |
| 2003/0092019 | A1 |  | 5/2003 | Meyer et al. |

FOREIGN PATENT DOCUMENTS

| | | |
|---|---|---|
| EP | 1 225 232 A2 | 7/2002 |
| FR | 272295 | 1/1996 |
| WO | WO 93/24657 | 12/1993 |
| WO | WO 99/25730 | 5/1999 |
| WO | WO 01/68917 | 9/2001 |
| WO | WO 02/059381 | 8/2002 |

OTHER PUBLICATIONS

U.S. Appl. No. 60/262,284.*
Gill et al. NCBI Database, National Library of Medicine, NIH (Bethesda, MD, USA). GenBank Accession No. AF153419, Jan. 2, 2001.*
Boehringer Mannheim. Biochemicals for Molecular Biology. 1995. p 136.*
L. Cohen, et al., "IKAP is a scaffold protein of the I B kinase complex," Nature, 395:292-296, Sep. 17, 1998.
S. A. Slaugenhaupt, et al., "Tissue-Specific Express of a Splicing Mutation in the IKBKAP Gene Causes Familial Dysautonomia," Am. J. Hum. Genet., 68:598-605, 2001.
S. A. Slaugenhaupt, et al., Database EMBL 'Online! EBI; "Homo sapiens IkappaBkinase complex-associated protein (IKBKAP) mRNA," retrieved from HTTP://www.EBI.AC.UK, Database accession No. AF153419, Jan. 2, 2001 updated Feb. 28, 2001.
S. L. Anderson, et al., "Familial Dysautonomia is Caused by Mutations of the JKAP Gene," AM. J. Hum. Genet., 68: 753-758, Mar. 2001.
Takeoka S., et al., Amino-acid substitutions in the IKAP gene product significantly increase risk for bronchial asthma in children., J Hum Genet. 2001;46(2):57-63.
Krappmann D., et al.; The I kappa B kinase (IKK) complex is tripartite and contains IKK gamma but not IKAP as a regular component; J Biol Chem. Sep. 22, 2000:275(38):29779-87.
Dong, J., et al., Familial dysautonomia:detection of the IKAP IVS20(+6T—C) and R696P mutations and frequencies among Ashkenazi Jew, Am. J. Med. Genet. Jul. 1, 2002;110(3):253-7.
Cuajungco MP, Cloning characterization, and genomic structure of the mouse IKbkap gene, DNA Cell Biol. Sep. 2001;20(9):579-86.
Gusella, James F. "Mechanism of Familial Dysautonomia." CRISP abstract for grant application to the National Institute of Neurological Disorders and Stroke, Project Start Date: Apr. 15, 1997. Accompanying grant application included.

(Continued)

Primary Examiner—Carla J. Myers
(74) Attorney, Agent, or Firm—King & Spalding LLP; Kenneth H. Sonnenfeld; Margaret B. Brivanlou

(57) ABSTRACT

This invention relates to methods and compositions useful for detecting mutations which cause Familial Dysautonomia. Familial dysautonomia (FD; Riley-Day syndrome), an Ashkenazi Jewish disorder, is the best known and most frequent of a group of congenital sensory neuropathies and is characterized by widespread sensory and variable autonomic dysfunction. Previously, we mapped the FD gene, DYS, to a 0.5 cM region of chromosome 9q31 and showed that the ethnic bias is due to a founder effect, with >99.5% of disease alleles sharing a common ancestral haplotype. To investigate the molecular basis of FD, we sequenced the minimal candidate region and cloned and characterized its 5 genes. One of these, IKBKAP, harbors two mutations that can cause FD. The major haplotype mutation is located in the donor splice site of intron 20. This mutation can result in skipping of exon 20 in the mRNA from FD patients, although they continue to express varying levels of wild-type message in a tissue-specific manner. RNA isolated from patient lymphoblasts is primarily wild-type, whereas only the deleted message is seen in RNA isolated from brain. The mutation associated with the minor haplotype in four patients is a missense (R696P) mutation in exon 19 that is predicted to disrupt a potential phosphorylation site. Our findings indicate that almost all cases of FD are caused by an unusual splice defect that displays tissue-specific expression; and they also provide the basis for rapid carrier screening in the Ashkenazi Jewish population.

10 Claims, 62 Drawing Sheets

OTHER PUBLICATIONS

Liebert, et al., 1993, "Identification of Simple Sequence Report 9SSR) Polymorphisms on Human Chromosome 9," Second International Chromosome 9 Workshop, Cytogenetics and Cell Genetics, vol. 64, p. 116, 1993.

Slaugenhaupt et al., 1993, "Physical Mapping of the Familial Dysautonomia Gene Region of Human Chromosome 9, " Second International Chromosome 9 Workshop, Cytogenetics and Cell Genetics, vol. 64, p. 120, 1993.

GDB Home, Amplimer -Name D9S310 Accession I.D. No. GDB 548985 (Apr. 1995), Downloaded from <<http://www.gdb.org>> on Oct. 29, 2007.

GDB Home, Amplimer -Name D9S309, Accession I.D. No. GDB; 548966 (Apr. 1995), Downloaded from <<http://www.gdb.org>> on Oct. 29, 2007.

Mull et al., "Isolation and Characterization of a Novel Human Transcript in the Familial Dysautonomia Candidate Region on Human Chromosome 9q31," Am. J. Human Genetics, 65(4) A37, Oct. 1999.

Gill et al., "Genomic Structure and Localization of the IKBKAP Gene to the Familial Dysautonomia Candidate Region on 9q31," Am. J. Human Genetics, 65(4) A186, Oct. 1999.

Gill et al., "Survey of Ashkenzai Jewish SNPs in a 471 kb Region of Chromosome 9q31 as Compared to the Public SNP Database (dbSNP)," The American Journal of Human Genetics, vol. 69, No. 4, Oct. 2001.

Slaugenhaupt et al., "Characterization of the Spicing Mutation in IKBKAP that Causes Familial Dysautonomia," The American Journal of Human Genetics, A2763, vol. 69, No. 4, Oct. 2001.

Leyne et al., "Complete Genomic Sequence of the 471 kb Familial Dysautonomia Candidate Region on Chromosome 9q31," The American Journal of Human Genetics, vol. 65, No. 4, Oct. 1999.

Slaugenhaupt et al., "Saturation of the Genetic Map and Expansion of the Physical Map Surrounding the Familial Dysautonomia Gene on Human Chromosome 9," Annals of Human Genetics, vol. 61, part 3, p. 223, May 1997.

Blumenfeld et al., "Carrier Diagnosis of Familial Dysautonomia Using Linkage Disequilirbrium Analysis," The American Journal of Human Genetics, vol. 59, No. 4, Oct. 1996.

Slaugenhaupt et al., "Refinement of the Candidate Region and Isolation of Candidate Genes for Familial Dysautonomia on Human Chromosome 9q31," The American Journal of Human Genetics, vol. 59, No. 4, Oct. 1996.

Leyne et al., "Analysis and Complete Genomic Sequence of the Refined 178 kb Familial Dysautonomia Candidate Region Chromosome 9q31," The American Journal of Human Genetics, vol. 67, No. 4, Oct. 2000.

Blumenfeld et al., "Localization of th Gene for Familial Dysautonomia on Chromosome 9 and Definition of DNA Markers for Genetic Diagnosis," Nature Genetics, vol. 4, pp. 160-164, Jun. 1993.

Eng et al., "Prenatal Diagnosis of Familial Dysautonomia by Analysis of Linked CA-Repeat Polymorphisms on Chromosome 9q31-q33," American Journal of Medical Genetics, vol. 59, pp. 349-355, 1995.

Blumenfeld et al., "Precise Genetic Mapping and Haplotype Analysiss of Familial Dysautonomia Gene on Human Chromosome 9q31," American Journal of Medical Genetics, vol. 64, pp. 1110-1118, 1999.

Chadwick et al., "Cloning, Mapping, and Expression of a Novel Brain-Specific Transcript in the Familial Dysautonomia Candidate Region on Chromosome 9q31," Mammalian Genome, vol. 11, pp. 81-83, 2000.

Cuajunco et al., Society for Neuroscience Abstracts, 27(2), p. 2061, Nov. 10-15, 2001.

Leyne et al., Am. J. Med. Genetics, vol. 118A, pp. 305-308, 2003.

Demacio et al., Genome, vol. 44, pp. 990-994, 2001.

Hirschhorn et al., Genetics in Medicine, vol. 4, No. 2, pp. 45-61, Mar. 2002.

Ioannidis, Nature Genetics, vol. 29, pp. 306-309, Nov. 2001.

Oddoux et al., Prenatal Diagnosis, vol. 15, pp. 817-826, 1995.

Coli et al., "Genomic Organization and Chromosomal Localization of the mouse for IKBKAP Gene," Gene, 279:81-89, 2001.

English Abstract of FR 2722295.

Lathrop et al., 1988 "Mapped set of Genetic Markers for Human Chromosome 9," Genomics 3:361-366.

Proceedings of the 8th International Congress of Human Genetics, Washington, D.C., USA, Oct. 6-11, 1991. AM J Hum Genet 49 (4 Suppl.). 1991. 336. Coden: AJHGAG ISSN: 0002-9297 6-(C) File Biosis Blumenfeld A., et al., "Advances in Linkage Analysis in Familial Dysautonomia".

Blumenfeld A. et al. Linkage Analysis in Familial Dysautonomia, Bonne~Tamir, B. and A. Adam (Ed.) Genetic Diversity Among Jews; Disease and Markers of the DNA Level; Goodman's International Conference Israel, Jun. 1990, XXVIII +460P. Oxford University Press: New York, New York, USA, pp. 179-193.

Blumenfeld et al., 1993, "Exclusion of Familial Dysautonomia from More than 60 Percent of the Genome" J. Med Genet 30 (1):47-52, ISSN 0022-2593 2.

Kwaitkowski, et al., 1992, "Construction of a GT Polymorphism Map of Human 9q" Genomics 12:229-240.

Wilkie et al., 1992, "Linkage Map of Human chromosome 9 Microsatellite Polymorphisms" Genomics 12:607-609.

Trofatter et al., 1991, "Dinucleotide Repeat Polymorphism at the Debrisoquine 4-hydroxylase (CYP2D) Locus" Nucleic Acid Research 19(10):2802.

Browne et al., 1991, "Dinucleotide Repeat Polymorphism at the DXS538 Locus" Nucleic Acid Research 19(5):1161.

Tsilfidis et al., "An Ssti RFLP Detected by the Probe pKE2.1(D19S116) Localized to Human Chromosome 19q13.3" Nucleic Acid Research 19(5):1158.

Bowen et al., 1991, "Aatil Polymorphism in Von Wilebrand factor Gene at Codon 471" Nucleic Acid Research 19(11):3159.

Altherr et al., 1991, "A Highly Polymorphic VNTR Locus on the Long Arm of Chromosome 4" Nucleic Acid Research 19(5):1168.

Weissenbach et al., 1992, "A Second Generation Linkage Map of the Human Genome" Nature 359:794-801.

Povey, et al., 1994, "Report on the Third International Workshop on Chromosome 9" Ann. Am. Genet, 58:117-199.

Pericak-Vance, et al., 1995, "Report on the Fourth International Workshop on Chromosome 9," Ann. Hum. Genet. 59:347-365.

U.S. Appl. No. 11/073,203, filed Mar. 4, 2005, Susan Slaugenhaupt et al.

U.S. Appl. No. 10/806,573, filed Mar. 22, 2004, Anat Blumenfeld et al.

U.S. Appl. No. 10/221,836, filed Oct. 1, 2003, Anat Blumenfeld et al.

* cited by examiner

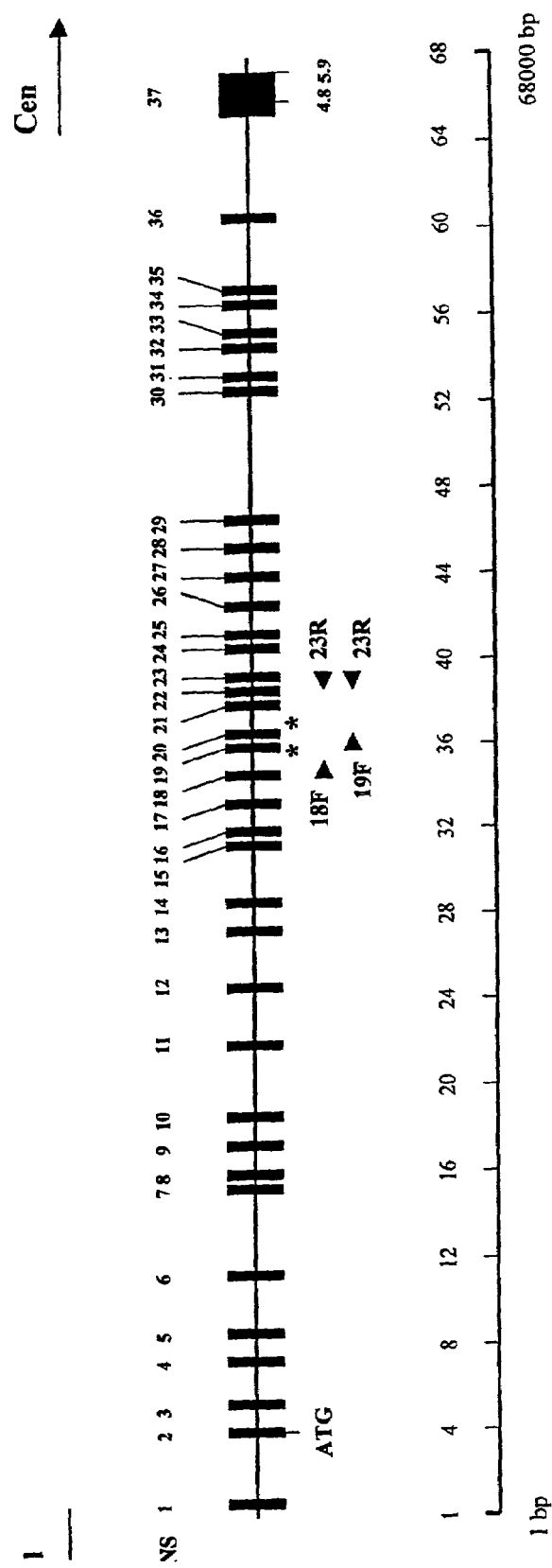

FIG. 6A

IKBKAPgenomic.seq Length: 66479

```
   1 CCAGTGCTGC GGCTGCCTAG TTGACGCACC CATTGAGTCG CTGGCTTCTT
  51 TGCAGCGCTT CAGCGTTTTC CCCTGGAGGG CGCCTCCATC CTTGGAGGCC
 101 TAGTGCCGTC GGAGAGAGAG CGGGAGCCGC GGACAGAGAC GCGTGCGCAA
 151 TTCGGAGCCG ACTCTGGGTG CGGACTGTGG GAGCTGACTC TGGGTAGCCG
 201 GCTGCGCGTG GCTGGGGAGG CGAGGCCGGA CGCACCTCTG TTTGGGGGTC
 251 CTCAGGTAAG CGATCCATCC AGGGTAGGGG CACGGGAGTG GACCTCTCCG
 301 CCGGCGGTGT CCGGGTGAAG GAGACCCGGA GCCTCCTCTG CCTGCTGCGG
 351 GCCGGGGACT GGAGTGCGGG CTGCACCACC TCTTTCCTAG AGCCTTAAAT
 401 TCTTTTTGCA GCCTTGCCAC CTGCTCCATC GGGGGCGCTG GGAGGCGCGA
 451 CAGCCCAGGG ATGCCTGCTG CCCCTCCAGC CGGACTTAAC CCAGCCTCTT
 501 GATTGCTTGC AGGGGGTTGA TAATAACGCT GAAAGCGAGA GTATTAATTC
 551 ACGATGGAAG GCGGCGGTTA ATAGAGGCTC GGGTGCTGTG GTGCGGGTCC
 601 TTTCTCGCGT GTGAGACTTT TTCGTGGAGG TGGTGTCCTC TGTGCTTCTC
 651 CATCTAACGT GGTGTTTTAC GTGGCTTTCT CTCCCGTTAA CGATGATCTC
 701 CGTGGAGACA GTGGCTGAGT AATCTTCAGA TCCCAGTACT TAGCAAGTGC
 751 TCAGTCGGTG TTGGATGTAG GCCACAAACC GGATCGTAAA GAATTCAACT
 801 GTATATTGAC AGCCACGGAA CTAATCAATG AATAGATCCG TATGAAGAGT
 851 AAGCAAAAAG GCAGCAAAGA CAGTTTTTCA GCTTGGGGAC ATAGAGTAGA
 901 AATGGTCTGT CCCCAAATAG TGGGAACTGT CATTTGGGGG AAGAATAGCA
 951 AGTTCTTTGC TTTCCAGGTC GCATTTGATG TGCATGTGAG ACATGCTTGT
1001 GATTCTATCA GGAGGTTGAA AATGTGGGTT TAGTGGTAAG TTTGGGCTAA
1051 TTCAGTCAGG GCTAGGCATT TAGGCCTAAT CAGCGTATTG GTGATCTACC
1101 TGGTATATGT AATCATGCAT GTGATGTCTA GCCAAGAGGT GGATAGTCGA
1151 AGGAGCAAGG GAAGAAAATG AAGCAGTTAT CAGGAAATTA AGAGAGAATC
1201 CACGATTGAC CTTTGGTGTG GAGGGATCTT TAGCACATTT AAGAACTGCG
```

FIG. 6B

```
1251 AAGAGTTTGA ATCAGTGGAG GCAGGAAGGT TGGAGGTTGC AGATGTCCAA
1301 GAAAGAGTAC TAATAGGCCT AGGTCCTGTG GCAATATGGA GGATATTCCT
1351 TTCCTAGCCT GGAAAGAAGT GGAGGGAAGT CTTCCTCCGA GAAGATAAGG
1401 GAATAAGGCT GATGGGTGTG AAATTTCAGA GAAACTAGTT TTGAGGCGTT
1451 TTTATGATGT TTAAAGATGA AAAACGAGCA GGCACGGTGG CTCAGGCCTG
1501 TAATCCCAGC ACTTTGGGAG GCAGAGGCGG GTGGATCACT TGAGGTTAGG
1551 AGTTCAAGAA CAGCCTGGGC AACATGGTGA AACCCTGTCT CTACTAAAAA
1601 TaCAAAAaTT AACTGGGCAT GGTGCCGgGC GCCTGTAATC CCAGCTACTC
1651 CGGAGGCTGA GGCAGGAGAA TCGCTTGAAC CCGGAAGGCA GATGTTGCGG
1701 TGAGCCGAGA TCGCGCCATT GCACCCCAGC CTGGGCAATA AGAGCGAAAC
1751 TCCGTCTCAA AAAACAAAAA AACCTGCATG ATATGTTAGA GGTTCAAGTA
1801 ATTTCTAGCA GTTCTTGAAT ATAATTGTCA CCAAAACTTA CTAAAATCAT
1851 TGTCTTCCTC ACTTCCATCA TATATAAACT TACCTTTCTC TTATCCCACA
1901 TTATATATTA TATAATTCCT ATGACACTTG ACATTATCTT CTGTGTACTA
1951 TTAGGATTGA TTCATCTTTA TTCTTTCTAT GTCATACATA TGTGGGGTGC
2001 CAAGATGAGA GAAGTCTCCT TGGATTAAAG TGACAATAAG ACCGGTGTGG
2051 TCCTTGTAAT TGCTACCCCT AACATAAGTT AGGGACTTAC AATCATAAGC
2101 CTTAAAGGGA TCTGAATATA AATAACTAGC ACAGTAACAT TTTTTTCCCC
2151 TACTTAGGTA ATGTTATGCA TTTAAGCAAG CCTGATTTTG CCAGACCAAA
2201 GTAGATGTCT TGTTAGCAC TCTTTTCTCA CGTTTTATAT TGTCCTGGGA
2251 AAAGCCTGGC CAGAAGAACA AAGTTACTGG AAGTAGTTAT GTCAGGTCAT
2301 CAGGGTCCTT GAAATGTTGG TCATCATTTT GAAGTAAATT GTTGTCATGT
2351 CCCAGTATTT TCTCTTCCCC TTTAGAACAG TAAATGCTTT TCTATCTTTG
2401 ATTTCAGTTT TTTTATGAAT GTATAAAACC AGTTTATAAA TGAATAGACC
2451 TGGTGAATAT TAAAGTCATT TCAGATTCTC TTCAACTGCC AGTATATAAA
2501 AATGGATTTT CAAATAGTGC TAATCAGTGG GATACCCTTT TGTTTTTCCT
2551 CATGATTTTA TAAAGATGTC CTAATATGCA AAAATAAAAT GTTTCCCCAT
2601 TCATTTGTTC TTTCAACTTT CCCAAAGGAA TAACTGATAT TACATCTTTT
```

FIG. 6C

2651 TTGAAGAAAA CATTCTAAAG TTGAGAATCT TGCCTCTCCT AAAAAGAACA
2701 TAAAATAGGT TTCAGAATTC CTAATTTGTA GACCATAACT GTATAGAGTG
2751 GGTCAGGTTG CTGCTATAAT CCATACATGG GTGTGTACTC AGAGAGGTAA
2801 GTTTTTTCTT TTCTTGGTTA TTCTGATTCT GACTACCACT TCTTCACCCC
2851 CTGAATCATT TCATTTAAAT AAATATGGTC ATTTATCACT ATTAAGCTAT
2901 TTATTTTTCT CTTAGAGATT AATGATTCAT CAAGGGATAG TTGTACTTGT
2951 CTCGTGGGAA TCACTTCATC ATGCGAAATC TGAAATTATT TCGGACCCTG
3001 GAGTTCAGGG ATATTCAAGG TCCAGGGAAT CCTCAGTGCT TCTCTCTCCG
3051 AACTGAACAG GGGACGGTGC TCATTGGTTC AGAACATGGC CTGATAGAAG
3101 TAGACCCTGT CTCAAGAGAA GTAAGTTACT GATGTAGAAT GCCAGCATGT
3151 GGGTATGACC CTTGATTTCT CTTCTTCCAA ATTTCTTTCC CCACATGGTC
3201 TTTCTTTATA TCTTATTGAA TTTATATCCT CCCAAATAAA CATCTTTTGC
3251 TTCATATATA TGCCATGTTA GACATAGCTT AAATCGTAAT CCTTCTTTAA
3301 CTCTGCTGCT ATTTTAACCT AAGTCAGTAG AACTCTGACC TTACTTTTTG
3351 AGTGTGTGCC GTACTTTTTA CCCTCTTTGT CATGCAAATT CTGTTTATAA
3401 GAGTGGTTTT TTTTTTTTTT TTTTTGAGAC GGAGTCTCGC TCTGTCACCC
3451 AGGCTGGAGT GCAGTGGTGT GATCGTGGCT CACTGCAAGC TCCGCCTCCC
3501 CGGGTTCACA CCATTCTCCT GCCTCAGCCT CCCGAGAAGC TGGGACTACA
3551 GGCGCCCGCC ACCGCGCCCG GCTAATTTTT TGTATTTTTA GTAGATGTGC
3601 GGTTTCACCG TGTTAGCCAG GATGGTCTTG ATCTCCTGAC CTCGTGATCC
3651 GCCTGCCTCA GCGCCCGGCC AAGAGTGGTT TTTAATTGGG AATGAACACG
3701 AAAGTTGCCC ATGGAGCTTT CTAAAAGTTT GAGCCCACAT CTCATGTCAA
3751 CTAAATCAGA ATCTTTAGTG TTGGCTCCTA ACTATATGTA CTTTAAAAAC
3801 CTCTGTGGGT TGGTTTTGAT ATGGTCCCTT GATTATGTTC TTCTACTAAT
3851 ACATTTTAGG CAGTTACATC CTTTAGTGCC TTTTCCCCAT ACTATAGAAA
3901 TCTTAGAAAA GCATAGCTAT TAGCATCATA TTTTAGTGGA CAATTTTAAA
3951 GAGACCAGGC TTATTGTTTT TGTTTTTGTG TTTGTTTGGC AAAAAGGTCA
4001 CATTACCTAT TTTTCTTGTT AGAGATGACA GAGTAGTGAT ATTTCTCAAA

FIG. 6D

```
4051 TGAAAGTTTG GATTTTCATC TAGAAAAAAT ATTTTTGAAA GCTTTTATGT
4101 AATAAAAGAA GCATTAAAAA GTATTTCTGG AAATGTTATC AATTATTCTT
4151 GAAAGTAGAC TGGGTTAATT TGCTTGTGTT TACTTTGGTG AAAGGTGAAA
4201 AATGAAGTTT CTTTGGTGGC AGAAGGCTTT CTCCCAGAGG ATGGAAGTGG
4251 CCGCATTGTT GGTGTTCAGG ACTTGCTGGA TCAGGAGTCT GTGTGTGTGG
4301 CCACAGCCTC TGGAGACGTC ATACTCTGCA GTCTCAGCAC ACAACAGGTA
4351 AGTGGAAGAC TCCAGTGAGG GGGGAGTCTC AAGCATCCTC AAATAGGTTA
4401 CTTGCTATTT GTGGAAGTTT TCAAATCAGT AGCCATAATA GTTACACTTT
4451 TGCTAATTAA TTTTTGCATT ATATATTTCT TTATTTAAAA AATTGTTAAC
4501 ATGGCTTTAT CTATATGTTA AGATTCTTCT AAAACTGAGT TTTGTCTGCT
4551 GCATCTATTA ATCAGAGTGA TCAGAATGTT CCAAATGAGA ATATATTTTT
4601 TTAAAAGTTA AAACTGGCTA TTCTTATGTG GTGTAGATCA CCTCTTATCA
4651 GACCCTCATC TTGAGTTGCA ACCTTTGTTT CTCAATTTAG GAAGTCTTTG
4701 TTTATCTGAC TTAGATTTTC TGTTATGAAT GTTGATTGGC TAAATTTAGA
4751 GTCCCTGAAG TCTAGGCACT AAAGTAAATA CATTGTCATT ACCTGCACAT
4801 GTGATGACTG CCAGTAGAGC TAGACTTCAA GCAATTGCTT CTTTCTCTAC
4851 TTTAGTGTAT AGTTGAGTTT CTGATTTCTA TCCTCACCTT CTTAACAGCA
4901 AGGGTTTCAA ATTACACTTG GCTGATTCTT TAAATCTTCT TCCATTACTT
4951 CATTAGTTGT GATCTCCTTA ACATTGATTA TGTCACAGAA GTTAGAGTAT
5001 TACTAATAGT AGGATAATGA TAGCAGCTTA CATTTATTAA CTATCATGTG
5051 CCTGGCACTT TTTAAAGTGC TTTTCATGCA AATTTATTTA ATCTTCACCA
5101 TGACCTTATG CAGTAGGTTG TTGTTTCCTA TTCTTCAGAA GAGGCAGTTA
5151 AGGCACAGAG TGCTTAAGTA ATTAGACCAG GGTCACACAG TAATCAAATG
5201 GGGTTTGACC CTAGCAGTCT AAATCTGGCA CCTCTGCTCT TAACCATTCC
5251 ATTTAGTACA ATCATAAACC TTTACTTGCA GTTCATGGTG GGAAATATCA
5301 AACTTGTCAT ATACAGCTTG TTTTTTTTTC GTATTTGAAA GATAGATGCT
5351 TTTACTTTCC AAACATTTTG TAGCATTGTT TCCTGGTTAC TGAGCTCTTC
5401 CAGTCTATTT ATCTTCATTT AATGGTGCTG ATTCTGCCCT TTAGTGGCTT
```

FIG. 6E

5451 CTCAATTGTC TGAAAGGTAG AGCCCACTAT TGTGCCTTAT AAGCCC CTTT
5501 CACTATCTGT TCCCCACATT CCTTTTTAGC CTCATCCCCC CATTGTTCCT
5551 GTGTGTACGT AAACCTTATG TTTTAGTTGC AGCTGATTTT TAACTGCTCT
5601 TTTTTCTGGC TTTGTGCCTC TACACTGTGT TTTCTTCCTG GTCTCTCTTT
5651 CCTGTCCTTA TTACCACTCT TTGAAACACG TCAGAAAAAC TTTTTCTGGA
5701 CTTTGGGCCA CTTGTCATTC CCTGTGCTGA GACGCATTTT GCTTCCAGA
5751 GATCTTGGTC ATTGCTGTTA TCCTCTGTAG GGTCTTCTTT TATCTCCCTC
5801 GTGAGACAGC TCTGGGAAGA AAAGATATT TATTTCTAAT CCCTGTGCCT
5851 AATAACAGGT CTATTCTCTT GATATCCATT ACTGAAGAAA TGTTTGTTGA
5901 GTAAGTTCTT GTTTTAATTT TTAAATATAA ATTTTTAATT TTTATGAGTA
5951 CATAGTAGGT ACATATATTT ATGGGCTACA TGAGATGTTC TGATACAGGC
6001 ATGCAGTGCA AAATAACCAC ATCATGGAGA ATAGGATATC CATCCCATCA
6051 AGCGTTTATC CTTTGTGTTA CAAACAATCC AATTACAGTC TTTTAGTTAT
6101 TTTAAAATGT GCAATTACTG TTGACTGTAG TTACCTTGTT GTGCTATCAA
6151 ATAGCAGGTC TTATTTATTC TATTTTTTTT TGTACCTATT AACCATCCCA
6201 ACTTCCCTCA GCCCCTCACT ACCCTTCCCA GCCTCTGGTA ACCATCCTTG
6251 TACTCTCTGT GTCCGTGAGT TCAATTGTTT TGATTTTTAG ATCGCACAAA
6301 TAAGTGAGAA CATGTGATGT TTGTCTTTTT GTGTCTGGTT TATTTCACTT
6351 AATGTAATCA TCTCCAGTTC CATCTATGTT GTTGCAGATG ACAGGATCTT
6401 ATTCTTTTTT TATGGCTGAA TAGTACTCCA TTGTGTATAG TACCACAATT
6451 TCTTTATCCA GTCATCCATT GATGGACACT TAGGTTGCTT CCAAATCTTA
6501 GCTATTGTGA ACAGAGCTGC AACAAACATG AGAGTGCAGA TATCTCTTCC
6551 ATATACTGAT GTCTTTTCGT TTTGTTTTTT TAATTGTTTT GATTGAAGTT
6601 GCAGTCAGTT TTTACTGAGA TGCTAGTGTT TGAATCTCTC TTTTCAATTT
6651 TCTCTGTCTC AGCTGGAGTG TGTTGGGAGT GTAGCCAGTG GTATCTCTGT
6701 TATGAGTTGG AGTCCTGACC AAGAGCTGGT GCTTCTTGCC ACAGGTAAGC
6751 TTGTTACTGG TGCCTCACTG GCTTTTTTAA AACATTATTC CAGATGTCTT
6801 ACAGGCTTCA TCAGCTTTAG GCTGCTTGAA TTTCAAAAAA TTTCTTTGAA

FIG. 6F

```
6851  CCAGTATAAT ACCAATTATG AACCAGTATA ATACCAATTA TGTATGTGTG
6901  TGTGTATATA TATATAAAAC GTAGAGTGAT TTTTTTTTGG TGACTGAAGT
6951  TTTGCCTCTT AGTCTATCAT TATAAAAAGT TGTTTCATGT AACTTTTTAA
7001  GTCTTTGGGA GTAAGAAACA AAGTCATAAA ACTTGGGGAG GCTGCTAAGT
7051  CCCCAGTTAG AGTTAAAAAT GTCAGCAATA TGTATTTTAA CTTATTCTAA
7101  GAGTTGCTGT ATGGACACAT TCTAAAAGCC CTTCTTGGGT TCTGTTGCTG
7151  TTTTTCCCCT TTAAGTCTCA TCATTCCAGA TGAGTTTAGT AAACCAGCTC
7201  CACTGATGAC ATTTATATTT AGAGGTATCT TGGGGACAAG GAGTGTTGAA
7251  GTTAGTGGAG GAGGGCTTTG TGGACTTTTA AGTTCAACTG TACACACATT
7301  AATAGCTGAG CATAAGCACC AGGTGACTTA TCTAGGGAAA GCTTTTTGGG
7351  GTTTTTTGTC ATTGTTGTTT TTTTAAGTCA AAGCATTTTG GATGAATTCT
7401  GTCTGCTCTG TTCAGACTAA CTCCAGCTCC TTAGCTTACA GTGCCATAGG
7451  TACTTAGGAA TGGCAAATTT GTTACATGAA AACAAAATCA TTTTTGTTTG
7501  TGTTTCTCTA AGGTCAACAG ACCCTGATTA TGATGACAAA AGATTTTGAG
7551  CCAATCCTGG AGCAGCAGAT CCATCAGGAT GATTTTGGTG AAAGTAAGTA
7601  TAGCTTTGTG CAATATTTTG TGACCTACGT TTCTTCCCAT TTTTGACCAT
7651  TTCCTTGTGC ACTAATAGCC ATGTCATTAG GCCAAAGAAC TGTGAAAGTT
7701  AAACCCCCAG CTATTAAATG TCTATTAGCC CAGTTCCTTC AGCCCATCCC
7751  AAATCTTAAA AGGCCTACTG ATGCCTCTCC AGGTCTGAGG GTTTAAGGTC
7801  ACTTAGATAG TTATTACCCA AACCCTAGGA AAGTCTTAGG CTGGGCTTTC
7851  AGTGAAAGGG ACTGTACAAG GTAGTATTTC TGGGATACAG TTTTAGGGAG
7901  AAGAAAAGAA GAAAGATGGA ATAGAAGGCT GGTTTTTGTT ACTACGATTA
7951  GATCCAATCT GCATTTCCAT GGGAACAATC AGATTATTTT CTTGCTAAAA
8001  TCTAGCCAAG GTCATCTGGG CATTAAGGCT GTGGGGGTAT TGAAGGGCAG
8051  TGCAGGAGAA GAGAGACGCT TATTAAGCAT AAGCTTTGGC CATCTTGAAG
8101  TCACAAAGTA GCTGGCCTGA TTGAAGAGGG ATGGGGAAGA AGATGTTCCA
8151  ACTTCTGTTA TGGTCTAACT TCCTGCCTTC TTGCTCCATC AACTCTGAGA
8201  AATCATTTAG ACAACTTCTA CCCATTTATT TACAAATAAT GTATTTGTTC
```

FIG. 6G

```
8251 AGAAATAATT TTGGAGGGCT GGGCACAGTG GCTCATGCCT GTAATCCCAG
8301 CACTTTTGGA GGATGAGGCA GGAGGATTGC TTGAGCCCAG GAGTTTGATA
8351 CTAGCCTAGG CAACGTAGGG AGACCCAGCA TCTACAAAGA ATTTAAAAAT
8401 TAGCTGGGCT TGGTGGTATC AGCACAGTAA TGACATGATG TGCAGGTACT
8451 GGGGTAGCAT AAGGGAAGGA AACGAGTAAC TAGAGAGGGA TGATTTATTT
8501 CCCCTAGGAG GCCAACTTGA GCTGAGTCTC AGCTGAATTG GTGTTGGGTA
8551 GGTGAGGGAT AAGGGTGGGG AGTAGTCAGC TGAATTGGTA TTGGGCAGGT
8601 GAGGGATAAG GGTTTGGAGT AGTCAGCTGA ATTGGTATTG GGTAGGTGAG
8651 GGATAAGGGT GGGGAACAGT CCAAGCAAGT GAATGTGTCC ATTTCAAGTG
8701 TCCATTTCAA GGAGGGTTA TTTCATAGAA ACATTGTGGG TTACTCAGGG
8751 AACTGTGAGT AATTCAGCAT TGCTGAAGTG GCAGAATGTG AGTGTAGAAT
8801 GAAATAAATG GAACAGATTT GATTGAGTTT GTAGTAGGGA ATATGGACAT
8851 TGAGTTATAG TTGATCAGCC ATTACAAGTT TTGATGATAA GAGGTTTAAA
8901 GAGATTTATT TAATAGAAAG ATGGCTCGTG ATGGCATATT TTTGTTGTTT
8951 TTGTGTGTGG AGAGGGAAGA GATGAGAGGC AGGGTGATCA GGTAGGAGGT
9001 TGCTACAGGA ATCCAGATGA AAGATAAGGA AGGTTTGTGT GGGGCTAGAA
9051 GCAGGAATCA TTCAGGAAAA AACTTGATTC ACAATGAGGA TGGGAGTACA
9101 TTTTTTAGAA TTAGCTGGGA AACTTTTTTA GAATATATGT GCATGATTCC
9151 CCTTCTGCCC TAGGCCAGTT TGAGAAATAC CAATTTAGAA AGTGAAATAA
9201 ATAGGCTTTG CGTATGTAAG GTGAATAAGA AAAAGTTGAG CAGGACTCCA
9251 GCCAGAACCT CAGGTGTTGG GAATAAAGAT GCCAGTAACA GGGAAGATGG
9301 AGAAGTGCTG GTCTGTAAGG GGTGGGTGGT GAGATCTGTT TTGGATTTGT
9351 TGAAGGACCA TATGTGATTG CCATGTGGAG TATGCAAATA TAAGGCTGAA
9401 GCTCAGGAGA GGCCAGAGCT ATGGACTGAG AGTAGTGGGT ATGTAGGAAA
9451 TTCTGACAGT TTTGGGAACA GATGGACTGT CTCAGGGAGC AGATGCTGTA
9501 CAGGAAGAGT CTAGAATCCA GGGTGGAACT CTGGGGCATC CAGCTTTGAG
9551 GACAGTCAGA GAGAGAGTAA CAGCACACAG TATACTTTGG GATGGGAAAG
9601 TGCTCTGGGC CTGGTGTTTC CCACTGACTT TTTCACACAA ATCCTAATGC
```

FIG. 6H

```
9651   AGTAAATCAA AGGAAATGTA GGCCAAGTTA AGATCTTAGG TCTCAGAAAT
9701   GTGTTTCTCA GTACAAAAAA AAAAAAATCA TTCTATGGAG TGATGAATAT
9751   TTTTCCTCTA TCCTGGGGTC AGTAGACTTG TTCTGAAAAG GCTAGGTCA
9801   TGAATATGTT CAGCTTTGCA GGCTGTATGA TCTGTGTTGC AGCTGCTCAA
9851   TTCTAATGTT GAGGTGTGAA AGTTATACAT GATACATAAG CACATCTATG
9901   TTCCAGTAAA CGTTTGTTTG TAAAAGCAGA TGTAGGCTGT AGTTTTGCAA
9951   ATCCCTGCTG TAACCCCATC ATTTCTTGTC TTCCATTGGA AAAGTTCTCT
10001  TTCTTCATTC CTTGGTCCTT AATCTTTCTG TGGAAACTTG CAGATAGAAG
10051  CCTGGGGGTT TGCACCAGGA TAGTCACTAC CATTTGTACG CAGCAGCAAT
10101  TGAGGTACTG TAGCACTTGG ATGTGAGCAG ACAGGAAATG GTCATATGGA
10151  CCCATAATTT ATAGGAATTG CAAACAGCCC TGCTTCATCA GAATCAGAAT
10201  CAATGGCAGG AGGAAAGTAT TGGGTCCTGG ATTAGGTGAT GTTTTCAGGA
10251  CCATCTTTAT TGTGCTTCTT GCAAATGGAT CCTACCTCCA GGAACAGAAG
10301  GGTTGTGTTG TTTCAGCAAC TCTGCCTAAT AGTTTATATA AGAGAAGTGT
10351  TACGATCTAG AAAGAACCCC AGTCAGCCTG GAAGGCAGAA GACCTGTGTT
10401  CTACTTTTTG GCTCCACCAT TAGGGAGGGT CTCAATCTCT AAGTCTATGT
10451  GAGGAGCTGT TTTGTGACCT GCAGCCCCTC TATCACCAGT GAGAGCTTGC
10501  AATCAGAATT TTATTCCCAG TTCTCATCTT GGGGTTTTAT GTTCCGGACA
10551  TATTTTGTAA ACTCTTTATG TTTCATTCTT CTTACTTATA AGGTGAGGGT
10601  GAGATCGCTG ACTTGTGTCA TCAAAGAAAC TTGGAATATG TAAGATGGCA
10651  GTAAAATGCT TTCCAAAATA AGGAAGGGCA TTTCAAATTC TTCAAAGTCA
10701  CTGCTGCATA TAATATGAAA TGGGTTTTGT TTGTTTGTTT TGAGATGGGG
10751  GTCTCGCTGT GTTACCCAGG CTAGAGAGTG CAGTAGTACA ATCAGGGCTC
10801  ACTGCAGCCT TGAACTCCTG GGTTCAAGTG ATCCTCCTAC TTTAGTCTCT
10851  TGAGTAGCTG GGACCACAGG TGTGTGCCAT CATGTCCAGC TTATTTTGTA
10901  TACTTTTTGT AGAGATGGGT GTCTCCCTAT GTTGCCCAGG CTGGTCTCGA
10951  ACTCCTGGAC TCAAGTGATC CTCCTGCCTC AGCCTCCCAA AGTGTTGGGA
11001  CTATAGGCAT GAGCCACCAT GCCCAGCCTG AAACATAGGT TTCTCAAATA
```

FIG. 6I

```
11051 TTGACTGCTG GTCAATTTAT TGAGAGGCGT TAGAGGACCT GAGTAATTGC
11101 CAATGACTAA CTTCATGAAG AATAGCAGTG AAACTGTTTT TGTTTCATTT
11151 CATGTGGCTT ATTAGTTGTC TTGCCAATTG TTCTGTAGGC AAGTTTATCA
11201 CTGTTGGATG GGGTAGGAAG GAGACACAGT TCCATGGATC AGAAGGCAGA
11251 CAAGCAGCTT TTCAGATGCA AATGGTAAGT TTGGTTTGAT GGATAAAAAG
11301 CCTTGACTGG AACAAATGTA AGTTTGCCAC CCACCAGGAA CTCTTTGGTG
11351 TCCACTTAGA TGCCAGTAAT GAACAGTTCT CTTCTGCTTT AGTAAAACTG
11401 CCTAGAACCT TCAGGAAATG AATCCCTCTA GAAAGATCCT TTTTTTCCTT
11451 GTTATTGCCA AGTTGCTTTG TGATTTATTT TCATAGTAGC AAATAATTAT
11501 AACCAATATT CATCACCCAG TTTAAAAAAT AAAACATCAC AGACAAAGGA
11551 AACCCCCTGT GTATCCCGTC CCGATGTCCC TCCCCTTCCT CTCCAGAGAG
11601 AGCTGCCATC CTTCATTCAC ATGCATGTTC TCATACTTTT CCCATATATG
11651 TGTATATTAG ATATTTTTCT TTTTCTGTTG GATGAAACTC TTTGTTTTCC
11701 TTACTTCTGG ATTGGAAAAT TCTGAAGACC ATATAATGAT GTCTTGATGA
11751 CTCAAGGCAG GACTTTTTAA TCTTCTAATG TAGGCGGGGC GGCCCCTGAA
11801 GGCAGAGGTG TGTGGACACA AGAAGAGTGC AGACTCTTGG GGCACCTGGG
11851 GAAGTAGTGT CCGTGTCACA TTAAATTCAT TTAAACTCTT ATATTTTATT
11901 TTAATTTATA CAATATGAAT ATTTTTTAAA ACTATGAATT GAAAAGTATT
11951 ACCCTTGAGT AAAATTAATG CCCCAAGAAG ATGTGCCATA TTTACCCTCT
12001 GGCACACTAC CAAGTACCCC CAGGGGCATT ACAGATCTCT GTTAGAAAAG
12051 TACAGATTAC ATTATCCTCA TAACATTTAG AAGCTATGAG ACCTTGGCAG
12101 GGAAGTTTCC TAATGTTTCT GAGCCTCAGT ATTCTCTGTA AAGTGGACAA
12151 CATAATGTCT CCTTACAAGG GTTGAGATGG GCAGGTAATA GCATATATAA
12201 AACAGCTATC ATAGCATCAG CACAGTGTAG GCACTCAAAT GGTAGTTGCT
12251 GCTTTTGTTT TAGTAGACAA ATAATTTTTG AAACTTTTTA AAGCGTAGTT
12301 TTTATTTCAA AACAACTTTA TTGTGAGTAA AATATGCATA GTGGGTCTAA
12351 TTTAACATTC TGAAAGCTAT TGACTTATTA GAACAGTAAA GGATTATTAG
12401 AGGGCAGAAA CATGGAGTAA GTACTCTGAG ACACAACCTT GCTTCTTTGG
```

FIG. 6J

```
12451 GGGTGATCCA CTACAACTGC CCAGCTTTGG ACAAGTGGTT TTCATGTTCC
12501 CCTGATTTTT AAGTGATTTT TTTTTTTTTT GGCAGGACTT AAAAGGTATC
12551 CTTGACTAAA CAGGAACTTG ACCAAGTAAA TAGTTGGTGC AATTTGAATA
12601 TTCTTTCTTG CTATAAGCAA CAAGTAAATT ATGGTACAGC TTTCTAAGAC
12651 CATATCTTTT CGATTTAAAA ATAGCACTTT ACTCATACAT GTTATGACAT
12701 GGGTAAACCT CATAAAGATT ATGCTAAGTG AAAGAAGCCA GTCATAAAAG
12751 ATCACATATA ATATGATCCC ATTTGTATGA AGTGCCCAGA AGGGCAAAT
12801 CCACAGAGGC AGAAAGTAGA GTAGTGGTTG GGTAGGGCTG TGGGGTGGGG
12851 TGGGGAAGGG GTGACTGCTA ATGGATATGG GGTTTCTTTT GGGGATGATG
12901 AAAATGCTCA AAATTTAGAT TATGGTGATG GCTATTCAAC TTTGTAAATA
12951 TACTTTAAAA ACATTGATTC TTACCACTGA GTTTAAACAA CCAAAAAAAA
13001 ATCCCAAGGT GCATTGAATT GTGTACTTCA AATGGGTGAA CCTTAATAAT
13051 ATGTAAATTA TATCCCAGTA AAGGTGTTAA AAAATAGTAC TTTAAAGGAA
13101 TCTATGGTAG TTTTGAAAAT AAGGCAGTTT TCCATACTTT GTTAAACTCT
13151 GGAGAAGATG ACACTTTACT ACTGGTACCT GCTAGAGTAA GACTTATCTA
13201 GTATTAACAA AATTAGGGTT TATTAATGGT ATAGGATGAT CCAGGTAATG
13251 GGGGAAAAAA ACCGAGCATC CTGTTATCTA ATGTACTATC CAGTAAACTA
13301 CTCTAGCTTT TTTTCATGAA CTTTTTCTAA AGGCTTTCTA GGGCCTCGTC
13351 TTGGTTTGAA AGTTCACAGC TACCCTTCAG AAAAGAAAAC AAAAATCCAT
13401 GGAGTAGGCA GATACAAGTA CTCATGTGAG CATAATTTAC TTTGATTTTT
13451 TAAGTTGTGT TATTCTAGCC CTCAGCCTGT TCCCTGCCTG GGCTCTCCTA
13501 GTGCCCAGTA ACACTGATTC AAGAGGTTGC ATTTAGCTGG GCACAGTGGC
13551 TGATGCCTGC AATCCCAGCA CTTTGGGAGG CCAAGTTGGG CAGATCACCT
13601 GAGGTCAGGA GTTCAAGACC AGCATGTCCA ACATGGTGAA ATCCTATCTC
13651 TACTAAAAAT ACAAAAATTA GCCAGGCATG GTGGCAGATG CCTGTAATCT
13701 CAGCTACTTG AGAAGCTAAG GTAGTAGAAT CACTTGTACC TGGGAGGCAG
13751 AGGTTGCGGT GAGCCAAGAT TGTGCCACTG CACTCCAGCC TGGGCCATAA
13801 AGCAAGACTC CGTCTCAAAA AAAAAAAAAA AAAATTGGG TGAGAGGGAG
```

FIG. 6K

```
13851 GAATTGAGGA GGATACCAAG GGTTGGGCCT GAACAAATGG AAGCATAATT
13901 ATATGTAGAA ATTTCTATGA GCTACTCTTC TAGAATAGAT GACTCAATAA
13951 TACCCTGCTT GCCATCTACG TTTTCTGTCC TTAATTATTT CCAGTTCTAT
14001 TTCATATAAT GCCTATTTCA GGCCTTAACC CTTCAGTAAA GGAGGTTTGG
14051 TTTCTATACC CTAGGACAGT TTCATTGAGA ATAAATTTTG TTAGGCTACC
14101 TATGTATTCC CTACTGTGCA GACTACAGTA CAGTACTAGC AGAATTCTTA
14151 GGCTGTTACT AGAATATGAT GATGAATGCC CGGGTGGTCA TCTGTCTCCC
14201 ACCCGGTAGA GTTGGCTTCA GGATTGAGAT ACACGTGGCC CTGGAGGAGA
14251 CGTTTCTTCC CGTCATGCTG CAGAATGAGA ACATTTCCAT GTTTTCGTCA
14301 TTGTCTGCTG CTGCCTTTAC CACCTCTGTG GCTCCTCCCT ATTCACCTTG
14351 TTCACATCTT AACTCATCTG TGCCCTGTTG TGAAGCTTAC ACAATATGTA
14401 AACAAAACTC TACCCTGTTG GACAAATGGA ACACTTGTTT CCTTGTTGTA
14451 GTTACCTGAT AGGTTCCTTA GCTCATTATA TTCAGGATCT AGATCTGTAG
14501 CTCTTTTCCT CTTTTGCTGT TCTCAGAGGC CACTTTTTTT TTTTTTAATG
14551 CCGAAAGGAG GATTTTGTTT GTTTTACATT TTTTTCTTCT TTTTGATGAT
14601 TTCTGCGTTC TAAGAACCAA CCCTTGGATG GTTTCTGATT CTAGAGGCAG
14651 GCTTTCAAAG TAGCTTAAAC CTCTTAAAAA ACATCTGTAT CTAGTGGTCT
14701 GAGGCTTGTT TGATTCTGGG ATACTTAAGG TCCCCAGTA ATATTGGTGT
14751 TTGTTCCCCT TTTTAGCATG AGTCTGCTTT GCCCTGGGAT GACCATAGAC
14801 CACAAGTTAC CTGGCGGGGG GATGGACAGT TTTTGCTGT GAGTGTTGTT
14851 TGCCCAGAAA CAGGTATGGA AATATATTGC AGTTAAACAA CAATAAAAAA
14901 TTTTTATCTT ATTAAAATTA AGGAAAATTT TCTTTCTTTT GCTTTGAGTA
14951 GGGTATTAAT TATACATATG AGGCAAGGAT GTGCTGCTTT AAATGTGAAA
15001 TGAGGTTAGA GTTAAGAATT AGAAGAGTCC TTTGAGGCCA TTTGGTCCAT
15051 CCTCCTACCT GGTGGACACA AATTTGTAAC AAAATTAATC TAATTGGCTA
15101 TGTAAAACCA TGGCAGTTTT TATTTGTAAG GAAGGTGTTT GAATAGTTCT
15151 GAATTGACAA CTTTTATCAT AATGTTTTAA GTGTGTATGT GTGTTTGACT
15201 CCACTCCCGC ACAGGGGCTC GGAAGGTCAG AGTGTGGAAC CGAGAGTTTG
```

FIG. 6L

15251 CTTTGCAGTC AACCAGTGAG CCTGTGGCAG GACTGGGACC AGCC CTGGCT

15301 TGGAAGTGAG TGGGAGAAGA AACCTTAGAG AAATTCTTGG AACCAGAGTA

15351 GAGGTGGTGG TACACATGGA TACAGATGAT ACAGATGTTT GTGTAACACA

15401 AAAGGATTTT TACGTTTCTT CATTTGGTTA TAAGGCTGTA TCTATCTTTG

15451 TTTCTTCTTT TTTTTTTTTC TTATTCCCTG AAGTCTGAAT TCAACTCGAA

15501 TAGTAGATTT TACGCTTCTT CACAGATTTC ATTGTTCCAA GGCCGCATAT

15551 ATTTTGCATT CCTAACTCTT AAAAGGCTGT GGTTTTAAGG CAGGGTATAT

15601 ATGAAGCCAT TGTACAGAGC AGAAAATGGT GTTTAGAAGG GAAGGCCCAG

15651 TTTGCAAGGC TCTGTGGGGC AAATGGTGCT TTTGTGGAAA TTAGGGAAAG

15701 AGCCTCCTTC CTTGGCACAA AATTCCTACA GCAGAGGATC TGCTTGCCAA

15751 GGAGCATGCA GGCTGGATTC AGACCCTGCT CTTTCCTTCC ATCTCCTCC

15801 TTGGCCCAGT ACCCTTGTGC AGGTTACAAT TTGCCTGTCA TATGTGGCTG

15851 CCTGATTTTA GATAGAAGAT GTATCTCCTC TGTTTCGGTG ATATCTGTTG

15901 TATGTAGACC TCTTGTTTCC CACCAGTATC TGAATGGTAT TATATGATAG

15951 AGCAGAAGAG AAATGTATTT GAATTAAAAC CCTAGAGACA AATATGAATA

16001 AGATGAGGCA ATTAAGATGT TTTCAACATT TGGTGAAGTC TTAAAAAAGA

16051 CCTACTGGAG CATAGAATAT TTGCTGAAGT TGTATAATGG AAGGAGAAAT

16101 AGATTTTGAT TTTTAGGACA TTATACCTGG AATGGTTTAG ATAACTTATT

16151 ATTTTTAAAG TCATCCAAAT GCAATGTAAA TATGTAAGGT TTTGTGGGCA

16201 AATGGAGCCT CTGTGTAAAA CAGGAAAAGG CACTCTTTCC TCTGGGCAAG

16251 TACAGTCCCA CAGTGGGATG AACCGCTCGC CGAGAGACAA GGGACACATG

16301 GGATTTAAAA CTTCCTTGGA TAAAGATATT CATTAATTCG TTCATTCATT

16351 CATTCATGTT TGCTGGAAAA AAAACTCTTC TGGATTTTAT CTATTCTTTA

16401 GTTAGGTGAG CTTTCGATAT TGTAACACTC TGAGTTTGCT TTAAGACCCT

16451 CAGGCAGTTT GATTGCATCT ACACAAGATA AACCCAACCA GCAGGATATT

16501 GTGTTTTTTG AGAAAAATGG ACTCCTTCAT GGACACTTTA CACTTCCCTT

16551 CCTTAAAGAT GAGGTTAAGG TAAGTGCCTG AGTTTGTTTC ACCCTCGAAT

16601 GTAGAGGACT TTCCATAGCT ATAGAGGGAA TTTTTTTTTT TTTTTTTTGA

FIG. 6M

```
16651 GATGGAGTTT CATTCTTGTT GCCCAGGTTG GAGTGCGATA GTGCAATCTC
16701 GGTTCACTGC AACCTCCGCC TCCTAGGTTC AAGTGATTCT CCTGCCTCAG
16751 CCTCCCGAGT AGCTGGGATT ACAGGCTTGC GCCACCACAG CCAGCTAATT
16801 TTGTATTTTT AGTAGAGACG GGGTTTCTCC GTGTTGGTCA GGCTGGTCTC
16851 AAACCCCTGA CCTCAGGTGA TCCACCCGCC TCTGCCTCCC AAAGTGCTGG
16901 GATTACAGGC GTGAGCCACC ACGCCTGGCC TATAGAGGGG ATTTATATTT
16951 GATATGGATA TATAAATAGT AGCTTTAGAG TAAATAGTAA TAAAAATGGT
17001 GGCTTCCTAG AACTGATTTT TATTTAATAA AATATTGTTT TTCCAGTGAT
17051 TTTGCAAATA ATAGCATTTG TCCCCCACCT TAGATAAAAC AGAAGTAGGA
17101 AATAAAAATG CTAGTTTTTA TTGTTTATTT TGACAAAAGC ATAATTTTTC
17151 CAGTAATGAA GATGTTTTTC ATTTATAACA TTTAAATCTT AAGTGGTTTG
17201 TATACCATTA AGATTCTTGC TGAAGTGAGA ACACATCAAA TGGTATCTCT
17251 GTGTAAAATT TTAAACATCC TAAGTTGAGA GACGAGTTTA ATGAACTCCC
17301 ATGTAACTAT TACTCACTTT CAGTAGATAC CAACATTTTG CAAAACTATT
17351 TTCATCGGTC CGCAACTCTT TGGCCTATAC ATATATATAC TTACATATAT
17401 TTTTATTTCC TGGAGTTTTA ATTCTAGAAA TCATATTTTC AATATTTATT
17451 TATAACAGTT AAGGACATTT TTCTTTACAT AACCATAATT CTATTATTAC
17501 ATCTTATCTC TGTGTTGTCT AACACCCAGT CCATATTCCA GTTCTCTGA
17551 TTGTCTAAAA ATGTCACCTT GTATTTGGTT AAGTTTCTTA AGTCTCTTTT
17601 AATCTTTAAG CATAATGTAT TTCTTTTTTT TAAGTCCTCT ACATAATAAT
17651 GACATATTTT ACAGATTTGT TTAATGCCTC TGTAGGTTAG TGATTTACAG
17701 CTAGGGATGA GCTCAGGTAG TGGGATTATT TGATTTGAGA GAGGAAATAC
17751 AGCTATTATA AAGATTTGGA AGTAAATCCA TAACTGAAAG CCAATGACAG
17801 ATCTTTTTTC CCTTCTAGGT AAATGACTTG CTCTGGAATG CAGATTCCTC
17851 TGTGCTTGCA GTCTGGCTGG AAGACCTTCA GAGAGAAGAA AGCTCCATTC
17901 CGAAAACCTG TGGTAAGACA GCTGTAGTAC CCCAGCCTTC TGCCCCATAA
17951 AACGTAGTTG AAAGTAGACA GGTATGGGAT TTCCTTCATC CCTTCTACTT
18001 AGTCCCTTAG TAGAATCAAA GATGCTGAAG TGGGTAGGTG GAAATGGGGG
```

FIG. 6N

```
18051 TGGTTAGGTT TTGATTGATT GTGGATTTCA GTCATGTATT GGTTGGGGTT
18101 CTCTAGAGAA ACAAATAATA CATATATATA ATTCGTCCCT CAGTATTCTC
18151 GGGGGATTAG TTCTAGGATT GCCCATGGAC GCCAAAATCC ACACATGGTC
18201 AAGTCCTGCA GTCAACCCTG CAGAACACTC AGATATGAAA AGTCAGCCTT
18251 TTGTATACTT GGGTTTTGCA TTCCTCAAGT ACCATATTTT TGATGTGCGT
18301 TTGGTTGCGG GTATAGAATC CACAATATGA AGGGCCGACT GTATTCATTG
18351 AAAAAAATAC GAATATAAAT GGACCTGTGT AGTTCAAGCC TGTGTTGTTC
18401 AAGGGTCAGC TGTACTTACA TAGAGAGACG GTGAGAGAGG GAATAGGGTG
18451 GGGCGGGAGG GAGAGAGAGT AATAGAGTGT GGATAGATTT ACTTTAAAAG
18501 ATTAGCTAAT GTAGGGGATG GCAAGTTTGA AATTTGTGGG GGCAGGTTGG
18551 CAGGCTGGAA ATTCAGGTAA GAATTGATGT TGCTGTCTTG AGTATGAAAT
18601 CTGTAGGGCA GGCTGGAAAC TTAGGGAGGA TTTCTGTTAC AGCCTTAAGG
18651 CAGAATTTCT TCTTTTCTGC GAAGCCTCAG TTTTTGCTTT TAAGGTCTTC
18701 AGCTGAATGA ATGGGACCTT CCCACATTAT GGGGAATAAT CTGCTTTCCT
18751 TATAGTCAGC CGATTATAAA TATTAATCAC ATCTACAGAA TACCTTCACA
18801 GCAACATCTG GAGTTTAGCA GATAGCTGGG TGCCATAGCC TAGCCAACTT
18851 GACACAATAA AATTAACTGT TGTAAGTCAT CACGTGCTTT CCCTAGTGCA
18901 TGGTATTACC ACAGAAAAAA CACTAACCAA AGGAATTCTG TGGACGTGAA
18951 AGAAGATTTA GATTAAGCGT AAAAGTAAGA ATATTTTTAT AGCTTTTAAA
19001 ATGTATAAGT GTGTGGTTTT AAGTATTAAA TAATACTTGA AAATGTTAGA
19051 AAATAAGATG AGAAAAAAAT CTCATAGTTC TACCACTTCG TAATAATCAC
19101 TATTCAAATT TTCTTGTCTT CTAGGTTTTT CATGTATATA TCTCAGTATA
19151 GCTATCATCT TGTTTTTGTT AAAAGTGTAG TAGGTATGGG CCAGGTGCGG
19201 TGGCTCATGC ACTTTGGGGG CCCAGCACTT TGGGAGGCCG AGGCGGGCGG
19251 ATCACGAGGT CAGGAGATCG AGACCGTCCT GGCTAACACG GTGTAACCCC
19301 ATCTCTACTA AAAATACAAA AAATTAGCTG GGCGTGGTGG CAGGCGCCTG
19351 TAGTCCCAGC TACTCAGGAG GCTGAGGCAG GAGAATGGTG TGAACCTGGA
19401 GGAGGCGGAG CTTGCAGTGA ATGGAGATCG TGCCACTGCA CTCCAGCCTT
```

FIG. 6O

```
19451 GGCGACAGAG TGAGACTGTC TCAAAACAAA ACAAAAAAAA GTGTAGGTGT
19501 GATACATCTG CATCATTTTA AATTGCTGTA TAATACTCGT TTATTCTCGT
19551 TCATTAAATC TCATGCTGTT AGACATTTAC AGTTTTGTCA TTTCTCATTA
19601 TTGTAAACAG CAATGCATGG TACATTTTTG TTCATAAATC TTTTTACTTG
19651 ATTATTTTCT AAGTAGCTTT CAAACTCTTT AATCAGTAGA ACCCCCCCCC
19701 TTTTTTTTTT TTTTTGGAGA CGGAGTCTCT CTCTTTCCCC CAGGCTGGAG
19751 TGCAGTGGCC CGATCTCGGT CACTGCAAGC TCTGCCTCCC GGGTTCACTC
19801 CATTTTCCTG CCTCAGCTTC CCGAGTAGCT GGGTCTACAG GCGCCCGCCA
19851 CCAAGCCTGG CTAATTTTTT GTATTTTTGG TAGAGGCAGG GTTTCACCGC
19901 GTTAGCCAGG ATGGTCTCGA TCTCCATCTC GTGATCTGCC CGTCTCGGCC
19951 TCCCAAAGTG CTGGGATTAC AGGCGTGAGC CACCGTGCCC GGCCTCAGTA
20001 GAACCCTTTT AACTGCAATG TTAAGAAACT CATTATTCAT TCAACACAAT
20051 AGTTCTTAAC CCTGGCCACA CCTTTAGAAA AAAAATGATA TTCAGGCTTC
20101 ATCTAAGAGT TCAGTTCAGT GTGTTGGAAT GGAGATTATA CGTAAGTATT
20151 TAATTAAAAA CCAAAAGCCC CCAAGTGATT TTAAACAGCC GCAGTTGAGA
20201 ACCACCGATT AACCAGTGTG TCAAGGGATG GCACTGTGAT ATGCTGAGCA
20251 TAAAAATATT GCACAGGATG AAACCCTGTC TCTACTAAAA ATGCAAAAAT
20301 TAGTCCGGCG TGGTGGTGCG CGCCTGTAGT CCTAGCTACT CGGGAGGCTG
20351 AGACAAGGGA ATCGCTTGAA CTGGGAGGCA GAGGTTGCCG TGAGCCGAGA
20401 TTGAGCCACT GCACTCCAGC ATGGGTGACA GAGTGAGACT CCATCTCAAA
20451 AACATGTATA TATATATATA CACACACACA CACATTGCAC AAGAACAGCC
20501 ACAACATCTG TGCTCACAGA ACATCAGCAT GTGGTCTAAC TTCAAAGTGT
20551 TGTAATAATG CGGTTTGAGA CTAGGTTATG TTTGCTGTGA TCACTAAGTT
20601 AAGCATTAGT GAGCAAGGAG ATTGAGAAAA TCCTTAATAT AAATAATATT
20651 TCTTAATATA ACTATAATTC CTAATATAAC TAAGGTCTTA ATTTATATGT
20701 CATCTGTTTA GTAAAGGTTG GTTTTGGCAT GATTAAGTCT TGCTTGCTTA
20751 ATAGATGTTG GAAGGATAAT TTCATGCTTA TCTTCTTTGG ACAGCTGAAT
20801 CAGGATTAAT ACCCAGATAG CCTTGAACAT AAGTGCTTGC AAAGCACCTG
```

FIG. 6P

```
20851 AAAGAAAATA AGCATCTTAA GCCCAATACA ACACAATGAT GCTAGTCTAG
20901 ATCTTGGATT AAGTGTTTTA ATACTTTTAC TCTAATTGCC AAGTTATCTT
20951 CTTCCTAAAT CTTCATGAGA AAACCCACTA AAAGAATGCT TTTTCCTGGT
21001 AGCCTTCCAT TGTGATCATA AAGTTTGGAA GTAAAGTTGA AAATAAACAT
21051 GTGGGCCAGG CACGGTGGCT CAGGCCTGTA ATCTCAGCAC TTTGGGAGGC
21101 CGAGGCAGGC GGATCACAAG GTCAGGAGAT CAAGACCATC CTGGCTAACA
21151 CGGTGAAACC ATGTTTCTAC TAAAAATACA AAAAAAAAA ATTAGCCGGG
21201 TGTGGTGGTG GGCGCCTGTA GTCCTAGCTA CTCGAGAGGC TGAGGCAGGA
21251 GAATGGCATG AACCCGGGAG ATGGAGCTTG CAGTGAGCCG AGATTGCGCC
21301 ACTGCACTCC AGCCTGGCCG GCAGAGCGAG ACTCTGTGTC AATAAAAAA
21351 AAAAAAAAAC GAAAATAAAC ATATGAATAA AAGTTAAAAA TAGAAAAAA
21401 ACAAGAAAAT AAACATATAT TTCTGACCTT ATTGATTCTT GATATTTTAT
21451 CTGCATGGAA AGCTATTTTT TGGCAGTTAT TATTGTTCTT ATTTTAGAGA
21501 CGAGGCTGAG CAGGAAGGGT CCTTTGAAAA AGAAAAGATT GCCCTTGAAC
21551 CCCTCTGGCA AGTGGGATGA AGTCTGCTTC CCAGCCTCTA ACGGCCTTCT
21601 TTTCATTTTC CCTTGCAGTT CAGCTCTGGA CTGTTGGAAA CTATCACTGG
21651 TATCTCAAGC AAAGTTTATC CTTCAGCACC TGTGGGAAGA GCAAGATTGT
21701 GTCTCTGATG TGGGACCCTG TGACCCCATA CCGGCTGCAT GTTCTCTGTC
21751 AGGGCTGGCA TTACCTCGCC TATGATTGGC ACTGGACGAC TGACCGGAGC
21801 GTGGGAGATA ATTCAAGTGA CTTGTCCAAT GTGGCTGTCA TTGATGGAAG
21851 TAAGCTCCTG GGAAGTGTGT CCATGAGCCT GCAAGGGGTC CTGAGCCTAG
21901 GGCCTGCAGA TGTGGTGGTT TGACTGGAAC AGTGGGGAAT CTTTATTTGT
21951 TTTGGCTGTT TGGGTTACTT GTTTTTTTAT TGAATGGGAT ATAAGGTGGG
22001 GTATGTTCTC TCCTGAGAAC CATTGTCCCC CCTCCCCCAC CAGTTTCCTG
22051 TTATACTGCA TCTGTGGCCT TCACACGTTT ACTTGCCTGG CCTTTGAAGA
22101 CACTGAAAAC TTTGACTCTA GGTAGAGAGG ATGACAACAG TACAGTCTTG
22151 TGGGATTGGG TGTGTTAGCT TTATCTGTTT GCCCTGACAC AGATTTATAA
22201 TTGACCCTTA TACCACCCCA CTTGTGTTGC TTTGTTTCCT GATACAAATG
```

FIG. 6Q

```
22251 CTTGCTGATA TATACCTCTC CAGTATGTTC AGTTCATGCA TAAACGTTTG
22301 CCTAATATGA AGATTAGGTT TATATTTTAT AATGAGGTAG AAGGTTTTTT
22351 TAGGGGGTGG GGTGGGAAGG GCAAGACTGA AGAGTGAAGT AGTCACCTTA
22401 ATGAATAGTT TCATTGCTGA TATGAAAGGG AGCACTGGCT TCTAAGATTG
22451 TAATGTGAGG TGGATATTAA TTCATATTCT GTGTAATATT CTACATAATA
22501 CTGATTTTAT AGTCATGTAT TCTATATAGA GAACTTAATC AGATCTGCGT
22551 TATTACCAAA TCCACACATA GGAAAGTGCT TTAAGGATTT TGAAAGTATT
22601 AATTCCCTTG GTTTAGTGTG GCTTGGTTGC AGGCCCAGGT TTAAAGCTAG
22651 AGGTCTGACC TCTTGGCCTT TTTGCCTTAG TCCCTGGCAC CTGAAACTCC
22701 AGGTACTGAG ATGGACTCCC CTAGGCCTAG AGGTGACAAT AGCCAATTAT
22751 GGACAGAACC CATGACATTT CCCCATCCCA CACTGTTTTT AGACTTGTTC
22801 CTGAGAAAAA CATTGAAAGT TATTTTTTTG TGAATTGCCA TTATTGTTTA
22851 GATATACTGT GATGTTCAGA TGGCTTATCT TACAAATTGA ATATCCCTAG
22901 GTCTAATCCT CTTCTTTCTT TTTCACTGCA GACAGGGTGT TGGTGACAGT
22951 CTTCCGGCAG ACTGTGGTTC CGCCTCCCAT GTGCACCTAC CAACTGCTGT
23001 TCCCACACCC TGTGAATCAA GTCACATTCT TAGCACACCC TCAAAAGAGT
23051 AATGACCTTG CTGTTCTAGA TGCCAGTAAC CAGATTTCTG TTTATAAATG
23101 TGGTATGTTA TAAAACTTTT GCCAAGATGT TCTGAATCAA GTCCCTTCTA
23151 CTCCTACATA AAAGCAAATT ATAGTTTGGT GTTGCCATAG GTCTAGTGTT
23201 TCTCAAAATT TTTAAGTCTG CAGTTGATAT CATTATCATT ATGATATTTA
23251 ATTGCCTTGG GTTTTTGTTT TTTTTTTTTT TAATCCTATA CTGGTTTGTA
23301 CGAGCCATTC CTTTTCCCTT ACTGACTTGA AGAGTCAGTT ATTTAAGAAT
23351 AACATTGGAC TCTGGAAATA ACATAGTATG TTATACATTG TTAACATGTT
23401 TTACTCTTTT CATAGCCTTT ACACATATTT TCAGTTGATC TCATCCCTCC
23451 TAGGAGCTGT GTCAGAGATG GGGTTTTCCT CTTTTGTAGA TGAGGGAACA
23501 CAGTGTCAGA GGTTTTGTAA TTTGTTTGAA CAAGAATGGA CAAGGACCTC
23551 AACACAGGTG TTCTAGCTCC TAATCCACTT GTCCTGCCAC AGCCCCATTG
23601 CTGTCAGTTC TTCATTACTT TCCTGATGTG CTGGAGAATC TGAAATTTGT
```

FIG. 6R

```
23651  TTTTACTTGT GAGTTCTGTG GTTATGTCAT AAATTCTGCT GGCATATGGC
23701  AGTGTTAGCC TTGTTTTCAA ATATCTTTTG AATTCTCAGA AAAAGCCTAG
23751  ATAGTTGCCA AGAGAGAATA ATCAAAATTA ATTAATTTAA ATGGGAAGTC
23801  CTTACTTTCA TATCAGCTTT TCTGTTAAGT CAGCAGCCCA CTGTGTACAT
23851  GGATCCTATC TGGATGTATC ACCAGTTTCT CTGATTATAG TTTCAGTGTG
23901  TAAAATGCTG TTACAGTCCT CCTTAAACTT TTCAAAATAG CTTTAAAAAA
23951  AAGTGCAAAT ATGTTCATTG TCAAGGCAAA AAGAATCAGA TGTAAGCTTT
24001  TGTGGGACTT AACTGTATGA TGCTAATGAG TTTATATGTC ACTTTATGAT
24051  GTATGGTATG TTTTGTTCTG CATTCACTTA AAAAATAGCT TTATATCATT
24101  CATCTATTTA AAGTGTACAA TTCAATGGTT TATATGTGTG TGTATGAATA
24151  TATATACATA TGTATATGTA TATATATGTA TATTCACAGA GTTGTACAGC
24201  CATCACCACG ATCAATTTTA GGACGTTTTT ATCTCCTCAG AATGAAACCC
24251  TGTACCACCC TGCATTCATT TTACTTGAGA GAAAACTCCC TGTGATGAGA
24301  TAGGACAGGT TGAGAGCTCC ACTTTTGAAA GATTGTTCGG CATCAATATG
24351  TGGGGTTGGC CATAGGTCAG GGGCACCTGG AGGCAGAGAT TCTAGTTAGG
24401  AGAAGCTGTT GTCAAGTGTC CAGGCAGGAG CTAGCAAGAG CTTGAGCCAG
24451  AGCAGTGTTC ATAGAAATGG AAAGAAGAGA AAGATCATAA CAAATCCATG
24501  AAGTAAAAAC CCTGAGAAGT TAAAGAACCC ACTGGGGAGA GTTTGGATAT
24551  AAGAGAATCT GGAAAAAGAG ATCTTGGACT GGAACAGGTC AGGGCTCCGT
24601  GCCCAAGTGG AAGGGAAATT AAGAACTTGG AGTCAAGTGG TAGACATTTG
24651  AGTGGTGTGG AGACAAGTTC GTTGCCAAAG TTTTCAAAGA TGGTGTTTGA
24701  TGCATCCTGA GTATCACTCC TTTTTCCCCC TCATTGCTTC TTGATTGTTT
24751  ATTATATGCC AGGCTTTTTT CTAGTACTTG GCTTGTTGTA CTAGAAAACT
24801  AGTTGTACTT TGTCTACAAC TTGTTGTTCT AGGTGTAGAC AAAAGATATC
24851  AATTAAATAT GATCTATCAG ATGGCAAGTG CTGTGGAGAA AAATTAAGCA
24901  AAATAAGGGG TAGGGAGAGC TTAAGGATAA GGGTTTACAG GGGGAAGGTG
24951  TCTTTCCTAT TTAGTGTGAT CCCAAAGGCC TCTCTGTGAA GGTGACATTG
25001  AAGCAGAGAC CTGGTGAGAA TCACAGTGGG AGCCACGCAG ACATCTGGGG
```

FIG. 6S

```
25051 TAAGAGCGTC CCAAGCATTC TATGCTTGAA GGCAAAGAAG AAAAAAGAAA
25101 GAGCGTTCCA AGCAGAGTAA AAAGCAACCA CCGAAGTGCC TGTTGTGTTT
25151 AGGAAATAGC CAGGAGGCCA GGGTGGCTGC AGCAGAGCAA AGGAGGGGAA
25201 GGTGGTGGGT GAGTTCAGAG TGGTGATGGG AATCTGCTCT TGTAGGGCCT
25251 TGCGGCTTTT ACTCCGAGTG AGATAGGAGC CACCAGAGGG CTTAGAACAG
25301 AGGAGTGCAG TGTTCTGGCT GAATTTTTTA AAGGCTTGCA TTGGCTGCTG
25351 TGCAGTGAAT AAACTGGATG AAGAATAGAA AGAAAATGTC TTTTAAGCAG
25401 GTGCTTAGGA CTTTGGAGAA TTTGAGGATA TTGAGAGGTG GTTGAAGACA
25451 GTGGAGGAAA TTGTCCACAG CACTGGGCTG AGAGGGTAGC CCCTTCACCT
25501 GGTCTTGCTG AGATGTGGCC TTTGTCAGGG AAGATTATGA CTGATGTGTT
25551 CTTAAGAGGA AAGCAGAGAT TTTAAGGAGG TTGAGATGTG ATTATTTTCT
25601 AGATTGCTGT TTGCCTTCTA GAACTCATTA ATTGCAGACA CCATCCCCTT
25651 AGTATTAGGT GAAATCTTAT AATTTACGAT GATAATATTT GCATTTTTGT
25701 TTTCCAGGTG ATTGTCCAAG TGCTGACCCT ACAGTGAAAC TGGGAGCTGT
25751 GGGTGGAAGT GGATTTAAAG TTTGCCTTAG AACTCCTCAT TTGGAAAAGA
25801 GATACAAGTA GGTTCTTAAT TATCTTGGGC TTCTGGGAAC AGAATCAGCC
25851 AGCATGCAGT CCTAAATTCA GCCATCTGAT AACAGTTCTA TGCCTGTTGC
25901 TGAGTGGAAC AAGAAATAAA GACAACACCC AGGCCCTGAC TTTCGGATCT
25951 GATTGGAGAA GCCAGTCATG TAGTTTGTCT GAATGCCATA TAATTTGATA
26001 GGTAGCAGGA GAGCATGAGT TGTAAGCCAG CCTAGGACCT ACTCCCAATA
26051 GCGCTTGGTT CTCCAGGAAA AATCATGTGG GAAAGATGGA GATGACAATG
26101 ATAAGGCGGA GCTGCATTCT CTTACATAAA TGGGGATGTA TGGGTTGTTA
26151 ACATGGATGA CCTAATGCAG CCTCTGTCTT TGCTCCATCC CAGAATCTAG
26201 AACTTCTGGG TGCTGTGCTT TGAGGCTCCT GGGATGGAAA TCAGAATGCA
26251 TTCTTCCATT GAAACAGTAT TGTAAACAAT TGGATGTTAT TGAATACCTC
26301 AGGTACACTA TAGGCATTTG CAAAATGACC TAGAAACCAA ATTATAATGC
26351 CACATCTGTG AGAGAACTTT TTTAAAAAGT ACCACTTATT GAGTACTTAC
26401 AGATTAAAAA AACAAAGTGT AGAGGTTAGG TAACTTACCC AAGGTCATGG
```

FIG. 6T

26451 ACCTGGTAAC TAGAGAATTT AGGGTTTGAT TCTATTCTGT TTGATAAGTC
26501 CATGTTCTTC ATTACTAAAC TACTCTGCCT CCAGGGAACA TTTATTGTTA
26551 GATTAATAGA AATAATTAAC TGAGTACAAC AAATAGCAGA ATTTAATAAA
26601 TAATGTTTCT TAAATATATG TGATATATTT AATAAATACA GCAGAAGTGT
26651 TCAACCTCTG TATGATTTTG AGGCTGCCTG TATAATGCTT AGTAGTTTTT
26701 AAAGAGCATT TACATGCATT ATTTCACTTC ATAGACTTGA AACCACTAGA
26751 GTAGAGATAG AGGACAAATT AGAAAGTATG AGGCAGTTTA GAATATAGTT
26801 TCATTTAAAA AAAATTGATG GGGATAATGC CAATTCGTCT GAGATTTCAC
26851 AGAAGACATG AGTACTCATC GTGATCTTGG GGAAGGGATA GGTTTGGGGT
26901 TGGCAAAGAA TTGGGAACAT TGGGTCTGGT GGGGAAGAAA GTGTCAGTGA
26951 AAACCAGAGG TGGGACTGAT CCTCCATGGG ATACTCTATG TGAATGCAAT
27001 GGAGAGCCTG AGTCCGGGGA GAGATGTTTG AGGAGGAAGA TCAGGCTAGT
27051 GACCAACTTC TTCAGTGGGA GCTGCGGATT TGCCACCTGA TCTAAAAGGC
27101 AGGAAGTAGC CATTGTCGGT TCCTACGTGA GGTGACAAGA ACAGTGCGCT
27151 GGTCAGGTGT ATAAATGCTA CCAAAGAATG CATTAGAGAC ATGGAGACCA
27201 TCTCTCAAGC TAGTCAGTCA GTTTAATGTG AGGTGCTTAG GAAAGGACCC
27251 ATTCTACTGC AAGTGACATA CCTGCCAGAG CCTGGTTTGA ATGCTGGTAA
27301 GTCATGGCAG TGGAAAAGCT CTGGGGTTCA TTAGTGTAGG GACTAGGGCT
27351 GGTAATTTTC TTGTGTAGTC AGTTTCCTCA AGTGTTCTCT TCAAATTTAA
27401 AGATTTCAGG GTATGAGAAA TTTAGGGAAA ATATAAAAAC GTATTCTTAA
27451 GCCAGACAAA GATTAATTTT AGATTTTGTA GTATTTGGTA GTATCTCAGG
27501 TTTTGTCCCT CCAAATAATT AGGAGTGGAC TGTATACAAG ATGCTTCAGT
27551 CTTCCTTCAT CCAGGAACGT CTCAGTGGTT TTTAAGTTTT ATTCATGTCT
27601 TGGATATTCT TCAATATTTA CAATAGAATC CAGTTTGAGA ATAATGAAGA
27651 TCAAGATGTA AACCCGCTGA AACTAGGCCT TCTCACTTGG ATTGAAGAAG
27701 ACGTCTTCCT GGCTGTAAGC CACAGTGAGT TCAGCCCCCG GTCTGTCATT
27751 CACCATTTGA CTGCAGCTTC TTCTGAGATG GATGAAGAGC ATGGACAGCT
27801 CAATGTCAGG TATTGCAGTT TTTCCCTGTA CTCCACATGT TAAGCAAATG

FIG. 6U

```
27851 GAGTTAGGTT TTTGTCTTTT ATGAGCATAC AACTTTTGAC TTCTATTGAT
27901 CAAGGTTGAG GAGCAGTAGC TTTCTTGTTA GACACACTTA ACAAGAAGGT
27951 TAAGTCTAGT TATGAGCCAT GTCAAAATAA CAGACCAAAA ATATATCAAA
28001 AAGTGGTGAA AAATAGGATA AATATTAGTA GATGAAGCAA CTTTTTAAAG
28051 ATATGTTAAA TATTTTAATT TAGCATCTAC CCACATTTTT CCAGCGTGAT
28101 TGTTATATGT TATAATTGAT TTTAATAACT GTCAAGCATA ATTAGAGTGG
28151 CTAATTCTCA TGGGCTAATG TGATGGGAAG AAATTTTGTA TAAATGCAGT
28201 CATGCGCATA TATGTGTGTG TGTGTGTGTG TGTGTGTGTG TATACATACC
28251 TTTTCTATGT TTAGATACAC AAATACTTGA CATGGTATTA CAATTGCCTG
28301 TAGTATTCTG TAAAGTAACA TGCTGTCCAG GTTTGTAGCC TGGTAGCAAT
28351 AGGCCATACC CCATAGGCTA GGGGTGTAGT AGGCTACACC ACCTAGGTTT
28401 GTGTAAGTAC TCTATGATGT TTGCACAATG ATGAAATCAC CTAACAACAC
28451 ATTTCTCAGA CGTATCCCCA TCGTTAAATG ATGCATAATT GCACATATAT
28501 GCTTTGTTTT GATGTGGTGA CTTCAAAATG CTTCTTCCAG CCTCCTCTTC
28551 TATATATCCT ATTTTGTACC TGACTACATT TACCATTAGA AAGTCTCTAT
28601 TCTTCTTTGC TGAAATTTCA CTGTTCTCTG GGCCTGAGTT TTGTTTTGAT
28651 TCCTGACTAT ATCTTCATTA TGTAACAGGT TTCAGTTAAT GAATGCTCTT
28701 CTGTGTAATG TAAGCCCTGT TGTATAGTTG ATAGCATTTT CTAGCCAGTT
28751 CCCAGAACTC CTTGTTTCCA GTGTCAATAC TTGGCACCTT TGTCCACTGA
28801 CACTAATCCC CAGATTAATT TGTAATTAAA GCCCTACTGG TGAGATTTCT
28851 GAGAAACGTT GTTGCAAAAT TAGGAACCTT TCCTTTATAT ATATACATTA
28901 CATAAATTTA TAGACATAAA ACATTTTAAT GCAGTCATTT GCTGCTACTC
28951 TTTGACTCAT AGTCTTTCGT GATATTTTGA AAAAGCCTTT TGTTAACATG
29001 TCTAAATGCA GAATATGTTC TAGAAATATG TAGCACTTAA AGTAAGCCAT
29051 TAGATTACCT TTTGAAAAGC GGAGCAATTT ACTAAGTTTC TACTTCTTCA
29101 GATTTGAAAT TCTTCATCAT TAGCTTGTAG AGGCAAAAGC TTGATGCAGT
29151 CATCTCATTT GCTGTAAAGG AAATGAGAAG TCATTTACAG TATATTTCTA
29201 CTGCTTTGAC TTTTATTTCT CAAAAAGACT GTTTTGTTCA TATAAAATAT
```

FIG. 6V

```
29251 TAATGCTTTT GAGGACTACA AAGTCCCTCG ATTTAGTTTA CATTTACTTT
29301 AGCTTATACT TTGTAAAAAA TACTCTTCTA AATGCTTTGT CTGTTTTAGC
29351 TTACTTATTT CTCATAATAC CTCTGTAAAG TATATGCCAT TTGCACCATC
29401 ATTTTACAGA TGAGACAACT AAGACATGGA GCAGTTAGGT AACTTGCCTG
29451 AGATCATGCA GGTGGAGCCA GGATCAAATC CCAGCGAGTC TAGCTCCAGA
29501 GTTTGTTCTC TTCTTGACAG ATAATTTATC CTCACAAAAT TTGAAGCATT
29551 TGTAGAGGAA TTCCCTATTG TTATAATGTT TAGTTTTTTT GTAGATTGGT
29601 TAAAAACTTT GAATTAAATG TTAGCATTAA CATCATTTGC TTTTATCACT
29651 ACTTCTTTGT CTCTTTTTTC TTTTTTTAAT CACTACCTCT TCCTCCTCTT
29701 TTGAGAAATT CTGCTTCCGT GGCTATGGTC CAAGCTACTT GAGAAGGTGA
29751 GGTGGGAGGA TCACTTGAGC CTAGGAGGTT GAGATTGCGG TGAGCTGTGA
29801 TTGTGTCAAC TGCATTTCAA CCTGGGCAAC AGAGCAAGAC ACTGTCCAAA
29851 AAAAAAAAAA AAAATAGTGA AATTTTACTT CGCTCCATTG ACTCAGGGAA
29901 AAAATGTAAT GGTGATAACA AATTCCCTTC ATCTCATTAG TGAAAATCCA
29951 CAATTTTCCA TCAATCGATA TGATAGTGAT AGAGATATTG AGTGTGCTCA
30001 TTTTCCTACA GACCAGCTGC TTTAACTATT TTAAGCAGAC AGAAATGATA
30051 TTGGTACCAT CCATGTCTAA TGAAGGCAAT ACTTTGTAAT AAGTTGCAGT
30101 AAGTTGTGGC CAGAAGAGGA ATGATGACTT CACAGTGTAA ACAACTACCT
30151 TATTGGGTTT GTGGAAAATG GTGTCATGTA GCAGATGTGG CTTTATCTGG
30201 GCTTTGGTTT GGAGTAGTTT TATCTATTCA TCTAACCGTC TGTCTCTAAG
30251 TGTATAAGTG TGTGTGTGTG TGTGTGTATA GTATTGGGTG TGTATATATG
30301 TATTTTGTCT ACATTGTATT GAAGTAGGTA GTGCAGCATC AAAAGGAAAT
30351 TGTTGATTTT CAAAATCAGT GAAATGTCAC TATTTTTGAG AAAAATGGTC
30401 TGTTTACACT CCCTTCTCCT TTTTTTTGTC AGTTCATCTG CAGCGGTGGA
30451 TGGGGTCATA ATCAGTCTAT GTTGCAATTC CAAGACCAAG TCAGTAGTAT
30501 TACAGCTGGC TGATGGCCAG ATATTTAAGT ACCTTGGGG TGAGTATCAA
30551 GGTGTTAGGA AAGCATGTTA TGACTTACAT AGATGCTTAG TTCTTAAGAA
30601 CATGTACTTG TATCTTGTCA GTTCAATATT GATTGTCAGG TCTTTTAACT
```

FIG. 6W

```
30651 ACCCTGGAAA ACCCTAAGCT TTAGAGTGGA ATTGGCAAGT GTATTCTACT
30701 CCTGTTTCCT CTTTTAATGA ACTAACGTAC TCTTAAAAAA GTGATTGATG
30751 ACTATCGCAG GGACAAAAAA CGAAACACCG CATGTTCTCA CTCATAGGTG
30801 GGAACTGAAC AGTGAGAACA CTTGGACACA GGAAGGAGAA CATCACACAC
30851 TTGGGCCTGT CGTGGGGTGG GGGAGGGTGG AGGGATAGCA TTAGGAGATA
30901 TACCTAATGT AAATGACAAG TTAATGGGTG CAGCACACCA ACATGGCACA
30951 TGTATACATA TGTAACAAAC CTGCACATTG TGCACATGTA CCCTAGAACT
31001 TAAAGTATAA TAAAAATATA TATATAAATA AATAATGCCA GCATTAGAGA
31051 AAAAAAGTGA TTGAAATTGC ATGTTAAGTG TTTTAGCAAA TGTTGATGTT
31101 GATGGTTTTT TGCAAAGAGC GCATCAGCTA TTTGTGAACT AGATCTGTGA
31151 ATCTTGCAGA GTCACCTTCT CTGGCTATTA AACCATGGAA GAACTCTGGT
31201 GGATTTCCTG TTCGGTTTCC TTATCCATGC ACCCAGACCG AATTGGCCAT
31251 GATTGGAGAA GAGGTAGGTG AACACGGAGC AGGAAATTTA CTTAAAGTAG
31301 TTACCCAGGG ACTGATGGCA TTAAGTAGAA AGAGCGTGGG CTTTGGAGGT
31351 GGACTTGGGT CTCCACTAAA TGCCTAGACA ATAGTGGGAA ATGATCTCAC
31401 TTTCATAAGC CACACCTTAT TCATCTATAA AATGGGAAAA TCAGTATCTG
31451 TCTATCAGGG TTCAGAAGAC TAAATGAGAT AATATATGTG ATTAGCAACC
31501 TTTTATCCCT AGTTGTACAA ATCATTCAAA GTTAATTTTA TTTAGTAGGG
31551 GAAACAGAAA TGTGATCTTG AGAATAGTTT TAGTAGATTT TTATTCAACA
31601 CATACTAGAA TGCCTATAAT TGTGGTGGAT GGTAGAATGC AGTGGCTGGA
31651 AAACAAAACC GCTTGACTAA TTCCTGCTCT TCTGGAACTT GTGATCTATT
31701 AATTTCAATG TAATGATTCC CTTTGTTGGG AGTGTGATGG AAATGGACAG
31751 AGTATACTGG TAGAGAATAC TGAGATGTTT GAGGGGTAAT TTGAGGATGG
31801 TGGCTATGAG AATGGGAGTC CTGCATCTGG TGGTCCAGGA AGGCCTCTCG
31851 GAGGCAGTGA TGTGTGTGCT GAGATGTGAA GAAAAGAAG GCTCTGTCTC
31901 CAGGCAGAAG GAACAACAAA CTCCTTGAGC TTAGCAAGAG CTCATCTTAT
31951 TCAAGGGACT GGATGGAAGT ATTGTGGCTG GAGCTCAGTG ACAGTCATAG
32001 GAGGGAATTT GGGTTCTTTA ATTGAACAAA GATTAGAAAC TTCTTGTGAT
```

FIG. 6X

```
32051 TTTTAATAAC AGAGTAATGT GTTCTGCTTC ATGGTTTGGA CAGTGATTCT
32101 GGCTGCCCAG AAGAGACTTG ATTGGAGAGT GACGAGACTG GAATATGGGA
32151 TCAACACCGG TTGAGTGGAG TTAGTGAGGG GAAAAAGGAG ATGGGTTTGA
32201 GATATGTGTA GGAGATGGAG ATGTCAGGGC TCACTGATGG ATTGGATGGC
32251 TTCACATTCC GTTTTGCACT GGACCAGCCA CGTCTTAGGT ATCTATCTTT
32301 AGTCCTGATT ACAGGAACTT AGGTGTGAAA TCATAGGGTG GTAGAACTAT
32351 GTGATAGAAA AGGTAGGTTT AACTGATTTG AGATAGAATT GCTTGTGATT
32401 TCAGTTTTAT TTCTTTGCAG GAATGTGTCC TTGGTCTGAC TGACAGGTGT
32451 CGCTTTTTCA TCAATGACAT TGAGGTATCA AGGCTTGGTT TGGTGTTGGA
32501 TCCTTTTCAC AGTGTTAGCT CCGAGTAATC TAGCTAGCTT TCACCCATGC
32551 CTCTCTGGCC TTCTCTTGCA GGTTGCGTCA AATATCACGT CATTTGCAGT
32601 ATATGATGAG TTTTTATTGT TGACAACCCA TTCCCATACC TGCCAGTGTT
32651 TTTGCCTGAG GGATGCTTCA TTTAAAAGTA AGTTTTCAAT GTATAAAACA
32701 GAAATGGTCC CTTCTCCAAT GTCTTTTGGA GTCTTGATGA CTTTTTGAAT
32751 TCTTCATTTA TTTTGGCTTT TTATCAAGGA GTCCTAGGCT GGAGAAAATC
32801 TTTAGAGTTA TTTTACTTAG ACCCTAATCT CAACATAATA TCTCAGTTAA
32851 ATCATTCTGC ACTTTAGTAA AGACATCCAA GGAAGGGAGT TCCTTCCTTA
32901 AGCAGCACAT TCTAAAGTTA AAAACTTTTC AGGAAATTTT ATTATGTAAC
32951 TGATCTAATA TTTTATTTGG AATTACTATG TAGATCCCCA ATGTTTTACC
33001 TTCTGTGTAG TCTTTTCCCA CTGTGCCCAC CCTCCACTGT ACATCTGCGC
33051 TCCATCTAGT GGTTTGTAGG ATATTGGCTG CATTTTGTCT TCTGTTCCAT
33101 GCCCTATCTA TCTCTGTGTG TGTGGCGTGT ATGTGTGTGT GGCGTGTATG
33151 TGTGTGTGGC GTGTATGTGT GTGTGGCGTG TATGTGTGTG TGGCGTGTAT
33201 GTGTGTGTGG CGTGTATGTG TGTGTGGCGT GTATGTGTGT GTGGCGTGTA
33251 TGTGTGTGTG TGTTCCTTAT TCTAAAAAGC CAACTTATTT TCTTTGCTTC
33301 CAACTTGGAA ATAGGGAATC TTTCTTTCAT TGATATGATT ATAGTACACT
33351 GATAATGCTA AGAAATAGAG AAGTTGCCCC AATTCTTAAC TGTGTTTCTC
33401 CACATCATTT GAGAAGCTGT GTATGTGAAT GTGCATGAGG GCTCTGTAAG
```

FIG. 6Y

```
33451 AGAGAGGGCA AGTTCCAGGG ATGAGCGTGT TCATCAGCAG GGCTGATAGT
33501 CTTGAGGTTC AGTGGGAGAG CTAAGGCACA TGGTTGTTAT TTGTTCTCTT
33551 CTATTTCACA TAATGTGTGC GGTTTCAATT GCAGTTAATG GAGAGTGGCT
33601 TGTTGTGATA ATTAAGGCTT ATTAGTTAAT GGTGTGTTTA GCATTACAGG
33651 CCGGCCTGAG CAGCAATCAT GTGTCCCATG GGGAAGTTCT GCG GAAAGTG
33701 GAGAGGGGTT CACGGATTGT CACTGTTGTG CCCCAGGACA CAAAGCTTGT
33751 ATTACAGGTA AGCTGGTTTT TCAGACAAGA TAGATAGTCT GATTGTCATT
33801 CAGCCAAGTA CCAAGCATAA TTCTTGCAGG TTGTATTTTA GGCTTTCTTA
33851 TTCTTTGTAT CGTTTATTGT AAACCTTTCC TTGATAGTTT TCTGTTAGCT
33901 TTATTCAAAG GAGTGTTGAT ACAGGCTGTG ACCATAAGGC TCAAAGCGAA
33951 ACTTTTCTTG AAAGTCAAGA TAAATATAGA GAACAACAAG ATTCTGCTAA
34001 AAGTGTGCTG ATTTTAGAGA GTTGTGGTAA TTCTCTGTGA AGAGTTAGGT
34051 AAAATGGTGT ATCCTGGCTA TTTAAATGTT TTCTACTTAA TTAAAAATGT
34101 TACTGCTTTA ATTTATTTAA GATGCCAAGG GGAAACTTAG AAGTTGTTCA
34151 TCATCGAGCC CTGGTTTTAG CTCAGATTCG GAAGTGGTTG GACAAGTAAG
34201 TGCCATTGTA CTGTTTGCGA CTAGTTAGCT TGTGATTTAT GTGT GAAGAC
34251 AATAAGTATT TTATTACAAT TTCGAGAACT TAAAATTATG AAAAGCCCTC
34301 ATTACCTATA TCATCAATCA GATTCTTAGA GGCTCTTTTT TTTTTTTTTA
34351 ACTTTTTTAC TTTAATGCAG TATTTTGTAG TGGAGATTCC TAGCAGAAAG
34401 AATCGTGACA CTCATCATAT AAAGGAGGGC TTCTCTTAAC CTGAGGGAAC
34451 ACATGTGGGT TTTAGGTGGC CTGTGAACCC AGGGAGATTG TACACACCAA
34501 ACCTTGTCTT TGTGTATTTA TTCAAGTAGA AAGCCCACAG CTTTCAATAG
34551 ATTTACAGCG GGGCCTATGA CCCAGAAAAG CCTGAGCTAC TCTTGTGAAG
34601 GAAATGACTG ATTTTCTGAA CCTATTTGGA GGAAACTTTG TATTGGAAAG
34651 ATCTATACTA ATGTTTTGTT TAAAAAGTAG ACCTGAATTC CATGATGATT
34701 TTCTTTGTTT TTTTTTTGAG ACAGAGTCTT GCTCTGTCAC CCAGGCTGGA
34751 GTACAGTGGC GCAATCTCGG CTTACTGCAA CCTCTGCCTT CTGGGTTCAA
34801 GCAATCCTCC CACTTCAGCC TCCCGCATAG CTAGGATTAC AG GTGTGCAC
```

FIG. 6Z

```
34851 CACGCCTGGC TAATTTTTTT TTTTGTATTT TCAGTAGAGA CAGGGTTTCA
34901 CCATGTTGGC CAGGCTGGTC TCAAACTCCT GACCTCAAGT GTTCTGCCCA
34951 CCTCGGCCTC CCAAAGTGCT AGGATTACAG GTGTGAACCA CCGTGCCCGG
35001 GCTTCTGTAA TGATTTTCTG TTGTATGTAT GTGAAGATGT AGTTCTCAGA
35051 CAGTCATGAT GACTAAATTA CACCTTTTAA GAAGGTAAAT GAATGTGGTA
35101 CCTGATTTTT TTATTCTGTA ATTTCAGAGT AGAAATCCAG TGATAGTAGC
35151 TTGGCATTGG GGCTGTAATC TGATTATAAC TGGTTTGTAT CATAATGAAA
35201 ATATGCTGGG CCCATGGAGC TCAGTTTTTG TGAATATCTT TTCTATTCTT
35251 TCTCTGTCTT CTCACAGACT TATGTTTAAA GAGGCATTTG AATGCATGAG
35301 AAAGCTGAGA ATCAATCTCA ATCTGATTTA TGATCATAAC CCTAAGGTAA
35351 CTTTCTAAGC TGTCATTTAC TCTAGCTTAC TTTGTACTTA AACTAATATG
35401 ATCTGAACGA AGATGTTTTG TCCTTTTTTT GGTAGGTGTT TCTTGGAAAT
35451 GTGGAAACCT TCATTAAACA GATAGATTCT GTGAATCATA TTAACTTGTT
35501 TTTTACAGAA TTGAAGTAAG TATTTTGAAT AATTCATGTG TATCTTTTCC
35551 ATAGTTTTCT CTCTTCTTGT TAAGGAAATC AAGCATAAAT AGCTAGAGAA
35601 GAAAAATTCC TTACTGTTCA TTTTTAAAAA TTGCTATAAC TCTTAGATGC
35651 CAGTTGGTTT TTTGCTCTTT TCCGTTCTTT TTAAAACAGC CTGTTTAAAA
35701 CTATGTCCTT AAAACATGTC ATTCAGAATT ATTATTTCAC TTGATTTTTA
35751 GGTATACATA TAAAACTACT TGTTTTTCCT AGGAGACTGA AATCAAATGG
35801 CATCTTTCTC TCTGATGATC TTTCCCCTCA ACTTTTTAAT GAAACACTTT
35851 CAAAATAGAG AAAAGTTGAG AGAATTGTCC AGTAAGCAAC CTATATATAC
35901 CCCACCTGGA TTCGCCAGTT TATATTTTTC TGTATACACA TTCTCATTCT
35951 CTATAATCTG TCCATCCATC ATTCATCTTG TTTGTAGACA AATTGCTAAG
36001 TGAGTTGTAG ACATCAGTCC ACTCTACCAC CTGTACTTCT CCTTGTATAT
36051 CATTAACTAG AGGGCATTCT TTGTGTATGG GTTGGTTTTG TTGTGTTTTT
36101 TCAGGTCATA TTTATCTACA GTGAAATGTC CAAATCTTAA GTGTGCCACT
36151 TAGTGAGTTT TGGCAAATGT ACACTTCATG TAACCTGAAC CTCTGTCAAG
36201 TTAGAGGGCA TTTACTCCTT TTCAGAAAGC TGCTTCAGAT TCCTTTCAAT
```

FIG. 6A1

```
36251 CAGTCCCTGT CCCATTCCCC AGGCAACTAC TCTTCTGAAT TTTTTACCAT
36301 AAATCAGTTT TGCCTGTTCA AGAACTTCAC CTAAATGGAA GCATACAGTA
36351 TTACTCTTCT GCATAAAGCT GTTTTCATTC AGCATATTGT CTTGAGATTC
36401 ATCTGTGTTT TTATATGTAT CACTAGTTCA TTCTTTTTTT ATTGGTCAGT
36451 AGTATGCCGT TGTGTAAATA CACCACTATT TGCTTATTCA TTCCCCTGTT
36501 GCTGGACATG TGGATTGTAC TACCCTGTTT GGGGCTAATG TGACTAAAAC
36551 ATCTACAAAC ATTTGTATAA GTCTTTTGTG GACATGTTTT ATTTCTCAAT
36601 ATTTTTATAA TTCAACTCTT TTCCAAAAGT CATTTTTATT TATCATCATC
36651 AGCATGCCAG GTGTATGTTA GTAATTTGAT CGCTGGGCTA CATGTTCTGT
36701 TGATGACCAT TCCATACACA CCTGTTCTTA GAGAAGAAGA TGTCACGAAG
36751 ACCATGTACC CTGCACCAGT TACCAGCAGT GTCTACCTGT CCAGGGATCC
36801 TGACGGGAAT AAAATAGACC TTGTCTGCGA TGCTATGAGA GCAGTCATGG
36851 AGAGCATAAA TCCTCATAAG TATGTATGCT GTCACCAGGT GGCATCCTTT
36901 GAAAAACCGA AGTGTGTAGT TGTCCTTGTC CAGCCTACTT ACCTTTCTCA
36951 TTCTGGTGTT CTTCACTTAT TACCTCAGAT ACTGCCTATC CATACTTACA
37001 TCTCATGTAA AGAAGACAAC CCCAGAACTG GAAATTGTAC TGCAAAAAGT
37051 ACACGAGCTT CAAGGTAGAG ATCCGCTCAC AGAGAAAGTG CTTAAGGTGG
37101 CCGTGACTGC TACTAGTCTT CTGCAGGTGA CAATCACCAT GTCATTGCCA
37151 CACCACAGAT TTAACATGTG ACTTTTTAGT TGCCATTTTA AGACCCTTGT
37201 CAGTTTTTTT CAGTGCTGCC CTCTAAAGCA TATATAAAAG TATCAGAAGT
37251 ATATATTCTT CTGATGTCCA GTTCTATTGA GAAAAATTTA TTGTCTTTTT
37301 GGTTATGTTG TTAGGTCTGT GGATTTTTTC CCCAAATGAT TGTGTTCTGT
37351 TTTGTTTTCT AAACACTGTT AGGAAATGCT CCCTCTGATC CTGATGCTGT
37401 GAGTGCTGAA GAGGCCTTGA AATATTTGCT GCATCTGGTA GATGTTAATG
37451 AATTATATGA TCATTCTCTT GGCACCTATG ACTTTGATTT GGTCCTCATG
37501 GTAGCTGAGA AGTCACAGAA GGTATGTGGA GTTCTTACTT TTATGCCATT
37551 TGGTTCTTGT TTATATAATG ATAGTGTGAA ACCCTGCTTC TGGTAGTGCA
37601 GTAGCTTTTC TGCTATCACT CTGTGAGTGC AGGGCTGGAG ACAGATCTGT
```

FIG. 6A2

```
37651 GAGTTTCTAG GGCCCACATT CCTAAGCCCC TGTGCTTATG AAAGTGTTTT
37701 GATTGTGAGG TTGAAGAAGT GAAGTAAAAT TGCATGGCTT TTTTTTGTTT
37751 CTTTTTTTTT GAGACGGAGT CTCACTCAGT CGCCCAGGCT GGAGTGCAGT
37801 GGTGCGATCT CGGCTTACTG CAAGTTCCAC CTCCCGTGTT CACGCCATTC
37851 TCCTGCCTCA GCCTCTCTAG TAGCTGGGAC TACAGGTGCC CATCACCACG
37901 CCCGGCTAAT TTTTTGTATT TTTAGTAGAG ACAGGGTTTC ACTGTGTTAG
37951 CCAGGATGGT CTCCATCTCC TGACCTCGTG ATCCGCCTAC CTCAGTCTCC
38001 CAAAGTGCTG GAATTACAGG TGTGGGCCAC CATGTGCGGC CTAAAATTAC
38051 ATGGTTATTT TTAAGATGAT GGGCATATGT GTGAGCTAAT TTCTTCTCTT
38101 ATAAAGGAAA TGTAACAAGT GGTTCATGTT CCACTCCGGT TCTTTCTCAC
38151 ATGGCTCTTT TTTCTAGTGG AGGGTGGGCA CATGGAGCAC AGAAGGCTCA
38201 TGGCCTCCTT TCCTATGTTG GTACATTTGC TATGATCAAA AACTTTGAAC
38251 ACCACTGGTA TGCATATTTT TTATTTATTT TTTTGCAGCC TCAGTCTCTT
38301 CCCCATGACC TCTCCAAAAA TGAAAATCGG ATCCTTCATC TCTCTGCTTA
38351 AAATACTTCA TGAGCTCCCA TTGTTCCGAG GATATAATTC AGAAGCCATA
38401 ATACTGCTTA AAAACCCTTC CTTGACCTGG CCTCTGTGTA TCTTTCCATT
38451 CTCACTTCTT GGTATTGTCT TTTTTTCCTC TGCCCATGGA GGAAAGACAA
38501 TGCTTTTGTC CCCCTTCCCT TGCCCCTCAC CACCACATGC CTTGGTGGGC
38551 AGCATTACTT CTGCCATCCA TGGGCTTTGA CTGCTTCCAC CCTCACCATT
38601 CCCCTGGCTA ATTCTCACTA ATCTAGGTTA AAGGATGCCA AGGTGGCCTC
38651 TTCCCAGTAA GCCATTCATG CTTCCCTCCA GGGACTGGGT GAGGTGACCC
38701 TCCTATATGC TTCTGTTGCA CACAGTGCCT ACCCCTGCAG ACTACAGTGT
38751 GTCTTTATCT AGAGTGCGGT ATTTATTTAT TTATTTTTGA GACAAGGTCG
38801 GGCTCTATCA CCCGGGCTGG AGTGCAGTGG CACCATCTTG GCTCACTGCA
38851 ACCTACGCCT CCTAGGCTCA AGCAATCTCA CCTCAGCTTA CAGGCGTGCA
38901 CCACCATGCC TGGCTAAGTT TTGAATTTTT TTTGTTGAGA CGGGGTTTCG
38951 CCATGTTGCC CAGGCTGGTC TCAAACTTGT GAGCTGAAGC AATCCATCTG
39001 CCTCGGCCTC CCAGAGTGCT GGGAATGAGC ACTTAATTAT TTGTTGTCTT
```

FIG. 6A3

```
39051 GGGTTTTCTT CCTATGTTGT TCTTACATGT ATTTATCCTG TCAGCCCAGG
39101 GAAATTGCAT TAAAAACAGG AAACACCTCT CCATTAGGAA GAAAAACAAT
39151 TTGCTTACAG GGCATGGCAT AGAGCTGGAG ATGATAGTGC CAATAAATAC
39201 TAGGTTGGCA GGGTCTCAGA GTTTTGTGTC CAACTCAGTA TAATTTTATG
39251 TTTGTTTTAA TGTGATCATT TCAGGAGAGC ATGGAATGTC ATGAAAACAG
39301 CACCAAGAGC AATGTCTTAG ACTTTTAGGA GAAACTTAGA TGCATTTGTT
39351 GAATATCTTC TAGACTGAAA CCTTATTTCC CTTATTAGCC TATGAAATAA
39401 ATGATACTGT GAGACTTAGT TAAGGAAGTT ACTATTATTC CAAGTGTAAC
39451 TTATTAATAT CCGTATGTGA AAGCATTTTT GCCAAAGCTT GTTTGATGTT
39501 CAGCTGACCC TTGCACAACG TGAGTTTCAA CTGTGCGAGT TTGAACTGTG
39551 TGGGTTTATC TAAATGTGGA TCTCTCTCAA ACACAGTTGG CCCTTTGTGT
39601 CCACGGCTTC TGCATCCACA ATCAGTGTGG ATCAAAAGTA CAATATTTGC
39651 AGGATTTGAA ACTTGCAGAT ACAGAGGGCC AACATTTTGT GTATCCAGGC
39701 TCCATGGGGT CAAATGTAGG ACTGGGGTAT GCTTGGATTT TGGTATCCTT
39751 GGGGTGTCCT GGAACCAATT CCCCATAGAT ACTGGGGGAC AACTGTAGTT
39801 TGATTTTATA TATTATATAA TATGCAGTTA ATATATAATA CACATTTAAA
39851 AATTATGTAG CTTTGGGTTT ATTGCTATAT GTAAATGCTA GTTTCTATTC
39901 CTATATATGA ATATCACAAG TAATAAAGTT CTCATTAATC ATTTTTTTAG
39951 GATCCCAAAG AATATCTTCC ATTTCTTAAT ACACTTAAGA AAATGGAAAC
40001 TAATTATCAG CGGTTTACTA TAGACAAATA CTTGAAACGA TATGAAAAAG
40051 CCATTGGCCA CCTCAGCAAA TGTGGTAAGT GTGGGGATTA GTATGTTTAT
40101 CTCTACTTCA GATCTTCTTT GGAACTAGGC AAGGTATAAA TTAAACTGTT
40151 AGTTTAGACA GTGACTGATT TCACTTCCCA CTCCTGAAAA CTCTAACAAT
40201 TATGTATGCT CACGTTATTT TGTCCTGTGT TCTGAAAAGC TGAAGGTAAT
40251 CACTTTTAAT GAACTGGAGG AGCTCCCTAG GTAAGAACGT CAAGTAGATC
40301 CTTTTTTGGT TAAGAATGAG CACCTGTGAA GTTAACTTCA GTGTCTCAGA
40351 ATCAAAATTG GTTGACAGTT CTTCCTTCTC ATGCTGTTTG CAGACATGTC
40401 AGGGAAACTC TGCTTGTCTG GAGAGAGTGA TGAGGCCACC TCCCCGTGCC
```

FIG. 6A4

```
40451 CTGCAAGACG CAGTTTTAAT TGACAGTGAT GGGGTGCCAG TTGTTCTTCC
40501 CATGCTGGAA CAGTTGTGAT TCTTTACTGA GGACTGATGG GGGAAAGGAA
40551 GAATCACCTG GGGTGCATGT TAAGCCTTCA GCTGCTGGCA TCCTTGGAGA
40601 ATCTGATTCA GGTGGTCTGG GATAGGACTG AGGCGTGCAT GTGTCTAATA
40651 AGCTTCCCAG GTGATGTCTT TTCAAGGAGG CTGAGAAAAC ACTGGGCTGG
40701 AAAGCTGGGA CTCTTAAGTA GGATGCTGAT CCCAATCAGT GCTGCTCTTG
40751 CCTCAGAATC TGCAGTGGTG CTCATTAAAA ATTCAAATTC CAGGATCCCA
40801 TTCTTCAGAT TCTCTGATTA TTTAGGTCTT AAAAAGTTCC TCATTTATTT
40851 TGTTTGGTGA CCATTGGTAT AAATGAAGTC CATTATGCTT CCCATGTCTT
40901 AAGCCTGTCT TTGTGTGAAT CTTTTTCCTG CAGGACCTGA GTACTTCCCA
40951 GAATGCTTAA ACTTGATAAA AGATAAAAAC TTGTATAACG AAGCTCTGAA
41001 GTTATATTCA CCAAGCTCAC AACAGTACCA GGTATGTGGT ATGTGAAAAT
41051 GAGGCTCTCC TGGTTTTGCT TTTTGCTTTA GTAGGAAAGG AGTGAGGATC
41101 CTAAGTTCAT AACACCATCC TTGGCTTCAA AATTTATCTT AAAACTAATT
41151 AGCCTCAATT TGAACTTCTT ATCTGGGAGA ATGGTCCTGA CCTGTTCTCT
41201 GATTCCTCAT CTGGAATACC ACAGCACCTT CCTCGTGGGG TTCCCTGCTT
41251 CTTTCCCACC CCTCCTCTAG CCCAACCTTA CTGCTGTAAG TCTGATTATC
41301 CTAACAAGTA CAGATCTTTC CCATATATTT CAGCATAAAG GGAAATTTTT
41351 GTTTGCTTGA AAAAGCATCC CTTTAGCTTT TTTTATATAC CACACACTTT
41401 GCTTCTAAGT TAAATGTGTT ATATGATCCT CTTAACAGCC TCATAGGGTG
41451 CTGTACACAA TTTGTAGATG AGGAAGCAAC TTGCCTGAGG ATCCAGAGCT
41501 ACAAAGTGCT GGACCTGGGA TACAGAGCCC AGGCTGCCTG ACCACCCTGC
41551 CCATGCCATT AACCACCACT CTACCATGCC ACCAGCATCA CCATTTTCAG
41601 TTTGTCCTCA GACAATATAC ACATCTTTCT TTGATCAAGC CCCTGCCAGC
41651 TTCTTTAGCA CCAGCTTCTG CCACTGTCCA CATTCCCAGT TACTTGTAGG
41701 TAGTTCTACA GATGTCACAT CGTGTGATTC CTCTGTCATT TCTCTACCCA
41751 CCAGCCTTCC TTTAGCCCCA TTTGTCCATC AGAACCCTTG GGTTACTCCT
41801 GAATGCCATT CCTGGACCAG GCGCCAAACA CTGAGCCCCC AGAGCAGCCT
```

FIG. 6A5

```
41851  GCCCTCGCCT TGGTGATTGC ATTTGTCAAA CTGCTGATTA GCTGGTTTGT
41901  CACCTCCACC AGGCTGTGGG CTCCTTAAGG GCAGGGACTC CATGTTGTAT
41951  TCCTCTCTGA ATCTCTGGCT AACATCCAGC CTGGAGAATC GAGGATTTGG
42001  CCAGTGGATA CCTCTTTGCC CTTGTTTTCT GTTCTCTTCC ACACTCTCTC
42051  TGCTCTAGTC ACACTGGCCG TCCTGTTACT CCTCAGACCT GCTATACACA
42101  TTCCTGCTGC ATGGCCATGG TGCCTTCTGT GCCCTCTGCC TGGTGCCCCC
42151  TATCTCATCA CGTGGTTTAT TCTCCTGACA GCCATTAGAG CTCACACTCC
42201  CTGAGAGCTG CAAGGAGACT GTCCTCTGTC CCTTTACTCA CGTTTGCCAT
42251  TATGCTATAG ACTATATTTT GTCCCTAAGT CCATCCTCTG TTACTATAAG
42301  AGCAGCAACT TGGTGGTGGT TCTTATATGG TTTTTCATTT GTTTGGTTTT
42351  ATTTTTTGCC TTGCTGTAGT ATCCATACTG CCCAGAATGG TGCATATGTA
42401  GTTAAGAGTA ATTATTTGTT GAGTGAATAA ATGGCACATC CTCAGTAAGG
42451  TTTTGAATGA AAAAATGACT GTACTAACTG ATCAACTGTA AGATTTTCCC
42501  AGGTAATTCT TTCAAGGGAG TTCCAAGTAT AGGAACTAAG GCAGCTACAC
42551  TGGAGCTTTA GAGAAATGAT TGTCATATTT CCTCCTCAGT CCTAAATCTC
42601  CTCTTGTCAC AGGATATCAG CATTGCTTAT GGGGAGCACC TGATGCAGGA
42651  GCACATGTAT GAGCCAGCGG GGCTCATGTT TGCCCGTTGC GGTGCCCACG
42701  AGAAAGCTCT CTCAGCCTTT CTGACATGTG GCAACTGGAA GCAAGCCCTC
42751  TGTGTGGCAG CCCAGCTTAA CTTTACCAAA GACCAGCTGG TGGGCCTCGG
42801  CAGAACTCTG GCAGGTAAGT ACAATCATTT ATATGTTTAC ATCTACAAAG
42851  GTTTTAAAAA ATTTATTTCT TTTGTTTGGT AATTTTGCAA ATAAATTTAG
42901  GGCAGAATAC TCTGAGACAG TCTTGTTCTC ACTGATAAAA ATTAATTTAG
42951  AATGCTTTAA AGGATAAGCT ACTACAGCAA GAGTCCCAGA ATGCAGTGGC
43001  CCAATATGGA AAGAAGTTTA TTTCTCTCTC CCATAGGGAT TTATAGGCCC
43051  TTCCGTTGTG TGGCTCTGCA ACCTTTTAGG CAGATGGTTG TAGCTGGGTT
43101  ATCTCCACAG CTGTGGGGAA GGAAGGAGAG TGGGGAGAAG TTAGAATCAT
43151  GGTAAAACAT TTACCTTTAA GTTGGAAATG ACCTGGATGG AAGTTAAACT
43201  ATCACCTTCT ATTCCATCTC GGCCACGCCA TGTAGCTGGA TGGGCTGTGC
```

FIG. 6A6

```
43251 CCTGTAAGAA GGTAAAGATG AATTTTTGGA TGGGTCCATT CTGTTATAGA
43301 CAGTAGGTTG TTGGAATAGC CAGGAATGAG GTGGGGAAAA TAAAAGGCCA
43351 AATGTCGAAG CATTCTGAAA GCAAAGGCAG TTTAGCTGCG TCAGGGACAA
43401 GGGTTGCCCG AACCAGAGGC GAGGCTGGTA CCAGGGGCTC TAGTACCAGA
43451 GTGGAGGAAA GGGTAAGGAC ACCTATGAAA AGAGATGAGC AGAAGCTCTG
43501 GTCATCTCAG CAGTGCTTGA AGTAAAGCAA TGACTGGTAT ATTTTTTTCC
43551 CTAACTTGTA AATATTGTTG AGATCTCAAA GAAAAAAATA AAAAGCAGTC
43601 CTAAAAAAAT TCCAAACTCT ATCCTGTTAA ATTTTGTTAA ATTTATGTAC
43651 CAGTCCTTCT TTGTCATTTG CAGTATTCTT TTTTTCTTGG GATTATACCA
43701 GTGTATGGGA TTATCACTTT TCTTTTTCTG GTTATTAGCC TTTCCCAAAT
43751 CCCTCCGTTT CCATGCTGGC CTCTTTTTAC AAATGTCGAG AATTCCTTAT
43801 TTCAGGCCTT TTAGTTATTC GTTCGGTCTC CATTGTTCCT TTCTGCTTTA
43851 GAAATTTATG ATATTGGTTG TTTATACCTT CTATCTCTGT TCTTGGATCT
43901 CTTCTATTCT TTACAGCTCT TAGCTTGCTA TTTCCCATGT CTTATGAGGG
43951 AGTATTTCTA GTTTTTCTCA GATGTTTAGC AAAAGTAGGT GGGGAGGGCA
44001 GTGGTCAAAG ATGTTTGAGA AATGTTACAC ACTGGAGTCA CTCTGTGTGT
44051 ACATTTAACG TAGGCAGTTT ACACAAGAGA GCAAAGAAA GGTAACTATT
44101 TAAATAGTGG AGGTGATTTT ACCTACTTTT TTTAGTGATA TATGCACTGG
44151 AGTGAGCATG CAATGAGAGA CCGGAATCTA CCAGCTCCTT CGAAAGCCTT
44201 GGGTTCTCTG TGCCTCTCAT TGTGGTTTAT CTCAATTGGG CTGAGAGTGA
44251 TTCTAGGATC TAAAGACACT GCATGACTCA AACATAAGTC AGCTACCTCC
44301 ATCTAGTGCT CAACCAAAGA AATAGTGGTC TCTTACTGTT AAGGGACGAA
44351 GTGGTTTAGT GAGAGATACC AGGTCATTTT CCCATATACA TGCTTTGGAA
44401 GCATCTTTCA AGGCTAATTT TGGCTGTATA TGATTTTCAA TTCCTGTGCT
44451 AAATTTAGAT TCTAGCTGCC ATTTAAGATA GGACTCTGTG GTGTATATAC
44501 CTATTCCCTC ACAGAAATTC AGAAAGTACA TAGTTTCATA CATAATAAAG
44551 ACATATTAAA GAAGCACTTG AGCTAAAGTA TCTGTTTAAC TTTGTAGTCA
44601 ACTGCTGCTT ATTGTCTCTA CAGGAAAGCT GGTTGAGCAG AGGAAGCACA
```

FIG. 6A7

```
44651  TTGATGCGGC CATGGTTTTG GAAGAGTGTG CCCAGGTAAA CTCAATTCCT
44701  CCCTTCTAAA CCCCCCAGTC AGCAAGAAAG GTCTTCTCAA TTGTATCTTA
44751  GTGATCATGA AAGTTAAAGG AACTGTGCAT AATTGTTAAG TCCAGAGATA
44801  GTGTTTGCCC CAGAGGTCTT ATCTTGCTGG CTTGACTTGG AAATCTAAAT
44851  TTAGTACATC TCTAAGTTTG GTGAGGTAGA ATATGAAGGT GCTCTACTTT
44901  AACATACCAC TGGTTTGACC TTGGTAGAAA GTACTTAATT ACATCTCAAG
44951  GTAGCTGTGC TTTTTAAAAT TGAGTTTGCC AAAGTAGAAA CAATGAGAAA
45001  GGACCATTAT AAAACAGGAT CATTGAAGGC TACATACTCT TGGCTTTTAC
45051  TCTCATTCTC CCTATTGGAA ATGTCTCTTT TACCTCAGGG ACCTGGAGGT
45101  ACAGCAGATT ATAAGGATAA GTACCCATAT GAGCATTTGG TAGTATTATA
45151  GGATTTATTA TGAAAATAAT AAAACTGCAG TAACACTGGC CACAGACTAA
45201  CAGTACACAG GTGCACAGTT GACACCAGGG ATTATTGCCT TGTAGAGTTT
45251  TGACCTTTGA TGAGAGAGTG TTTTTTACAG TTGTTACTGA TAGCACATTT
45301  ATGTAACTTA ATTGTGCTTT AAAAATATTT AATTGTCTCT TGTGTAATAA
45351  CAGTAAGTGA AAGACGATAA CTAAAATTTT ATATAATTAG ATCCTGGAGA
45401  GAATATTTGT TGGGTGATTG AATTGAAAAT ACCAGTGAAT GAAACATACC
45451  TAAAAGGGTA GATAGGTTGG GTTGGAAAGA TATACCACAT CGAGGGTTAA
45501  TTAAATGGAT AAGATGTCAT TATCTTTTTT TCTTTGTAAA GGAAGATTAA
45551  TGCATAAAAT TATTTTGTGT AATTTACATA CAATAAAATT ATGTGTTGTA
45601  CAGTTGTATA ATTTACATAT AATAAAGCTA ATTCACCAAT TTTAGATGAA
45651  GAATTCAGTA CATTTGGACA TATGTTTGTA GCTGTGTAAC CACCATTGCA
45701  CTCATGATCT AGAACATTTC TAACACCCCC AAAAGTTCCC TACTTCCCCT
45751  TTTGCAGTCA GCCTTCTCCC TCCACTGCCA GCCTTTGGCA AACTGATCAG
45801  TCAGTAAAGT TTCACATTAT CTAGAATTTC ATATAAACAG AACCATATGG
45851  TATGTAGTCT TTTTAATCTG GCTCCTTTCA CTCACATAGT GCATTGGAGA
45901  TGCATCCATG TTGTAGTTTA TTCCTTTGTA TTGCTGAATA GTATCCCATT
45951  ATATGTATAT GTCAGAATTT GTTGATTTAC CAGTTGATGT ACATTTGGAT
46001  TGTTTTCAGT TTGGGGTTAT TATGAATAAC GCAGCCATGA ACATTCTAGT
```

FIG. 6A8

```
46051 GCAGGTCTTT ATGGGGACAG GAGTAGGAAT GCCACATCCC GTGGTAAGTG
46101 GATGTTTAAC TTTTTAGGAA GCTGCAGAAC TAATCTGCAG TGGCCGTATC
46151 ATTTTGCATT CCCCTCAGTG ATATGTGAGA GTGCTTCAGT GACTCCTATA
46201 CTCACCAACA CTGGGTGTAT TACTGTGACA CTAGATGTAT TATCTATTGC
46251 TACGTAACAA CTTACCTTAA AAGCTGGCAG CTTAAAACAA CAGACCCTAT
46301 TATCCCACTT TTTCAATGGG CCAAGAATCT TGGCTGGGCT TAGCTGGGGC
46351 CTCTGGCTCA GGGTCCTTTA CAAGGCTGCA ATTAAGGTAT TGGCCAGGGC
46401 TAGAGTCATC TCAAGGCTTG ACTAGTTTTT AATTTCATTT TCTAATGTTT
46451 TATTACTAGT ATATAGAAAT ATAGCTGAAG TGTTTTGCAG GGAGGCTGTA
46501 TAATTGACCT TGTATCCTGC AACCTTGCTA AACTCATTTA TTAGTTCTAG
46551 AAGCTCTTGG GTGTATTCTC TAGGATTTTC TACATCAACA AACATGGTTT
46601 CTATAAATAT AGTTTTATGT CTTTCTTACA ATCAATACTT TTTTCTATCT
46651 GTATTGCATT TTCTAGGGCT TCCAGTGTGG TGTTGAATAG AAGTGTTAAG
46701 AGTGAACATC CTTGCCTTTT TCCTGATATT GGAGAAAATT CACTTGTCTT
46751 TTAGCATTAA GTGTCATGTT TGCTTTTTTA AAATTTTATT CTATATTATT
46801 TTATTTTTGA GACAGAGTCT TGCTCTGTCA CCCAGGCTGG AGTGCAGTGG
46851 TGTGATCTCA GCTCACTACA ACCTTGACCT CCTAGGCTCA AGCGATCCTC
46901 CCACCTCAGC CTCCTGAGTA GCTGGGACTG CAGGAACATG CCACCATGCC
46951 TGGCTAATTT TTGTATTTTT TGTAGGGATG GGGTTTTGCC ATGTTGCCCA
47001 GGCTGGTCTT GAACTGTTGG ATTCAAGCAA TTCGCCTGTC TCAGCCTCCC
47051 AAAGTGCTGG GATTACAGGC ATGAGCCTCC GTGCCTGGCC TGATATTTGC
47101 TTTTTTTTTT TTTTTTAATG CTCTCTATTG CAGAGTTGGC AAACTACAAC
47151 CTGTGACAAA TCCAGCATGC CACCTGTTTT TGTAAATAAA GCTTTATTGG
47201 AGCATAGCCA TGCTCATTAG TTTACATCTT GTGTATGGCT GCTTTAACAC
47251 TACAGCAGCA GAGTTAGAGT TGTGACACAG ATAGTTTGGC CCATAAGGCC
47301 TATATTTACT GTCTAATCTT TTACAGGAAA AATTTGCCAA TTCCTGCCCT
47351 CTTGGTTTGA GGAAATTCCC TTCTGTTCCT TGTTCTGAGA GTTTGTATCA
47401 TGAATGGGTG TTAAATTTTG TCAAATGCAT TTTCAACTAT GAAGGGTTTT
```

FIG. 6A9

```
47451 GTTTTTAGAC GAGTGATATG GGGGACTAGG TGATTGATTT TCTACTGTTA
47501 AACCAACCTT GCATCTCTGG GTTCAACCCC ACTTGGTATT ATAGATTTAT
47551 TACCCTTTTT CTCTTGTGGC AGATTAGATC TACTAAAATT TTCTTGAGGA
47601 TTTTTGTGTT TGTGTTCATG AGGGATATTG TAGTTTTTTC GTGTCTTTGC
47651 CATGTTTTGG GTATCAGGAT AATGCTGCTG TCATTGAGGG GTGACAAAAA
47701 TGAGGGGTGG TGTCCTTTAC ACTTCTGTTT TCTGGAGGAT TTCATGTAGA
47751 ATTGGTATGA GAGTCTAGCT TATGGTTAAA AACCTATGTG TGATGTTTCA
47801 GACCTGACCA TAAACAATTA CAGACTTTAC CTAGGAGGCC ACATGGGGAA
47851 AAGCTGCCCT CCCTACACCA GACTTGGCGT ACTGCCAATG CATTACAGTT
47901 TCTAAAGGGA GTTGCAGTCA AGGACTCAGG GCCCCTGTT AGTCATGCTC
47951 TTGTAACAGT ATTTGCATTG AGAGTCCTGG CACTTTCATT CTTAGGTCTC
48001 TCTATCTGAG GACATGGGCC AAGGTCTTCT TCAGGCACCT CTGCCAAGGC
48051 CTGTTTATGC AAGAAGGAGT GGAAAAACCT TGACATTTTT TTCCACTGTG
48101 ACTCACTACC CAGTACTTTT CCACCCTTAG CCCCCTTCCT TTGCACCCAT
48151 ACCCCCAAGA TCCATCAAAC TGCTAAAGCC TTTTTTTCCA AGCTCCTTCA
48201 ACAGTGAACC AACCCTCATG TCTGTGTGGA TCCAGCTGAC TCTTGACTAG
48251 TGAGTTGTTC CTTGGGAAAA AATGGAACAG AGAGAGTTGG TGCTTTCCCT
48301 GGTTTTAGCC TCTTGCTTAT ACCAATGCAA TGCCTGAAGG CTTAATTCAT
48351 TTTTGACTTG TTGCTTTGAT CAGCTACTCC AACACCTGAC AGCTCAGCTC
48401 TTTCTCCCAG CTCTTGGGAG ATATTTTTTT CTTTAAATGT TTAGTAGAAT
48451 ATACCAGTAA GGCCATCTCG GCCAGGAGTT TTCTTTAATG AAAGTTTTTC
48501 ACTATTAGTT CAGTTACTTT AGTAGACATT AACCTATTCA AGTTTATCTG
48551 TGTCTTCTGG AATGAGCATT GGTAGTTTAT GTCTTTCAAG TAATTTGTTC
48601 ATTTCATCTA AATTGTCAGA TTTATTGGTA TGAAGTGTTT ATAGTATTCT
48651 CTTATTTTAC TGTCCGTAGG GTCTATGGTG ATGTCCTGTC TTTCATTGTA
48701 GATATTGATG TGTCTTCTTT TTTCTGATTA TTCTGGCCAG AGGTTTATCA
48751 ATTTTATTGA TCTTATTAAA GAATGAACTG TTTCATTGTT TTCTCTATG
48801 ATTTTTCTGT ATTCTATATC ATTCTTTTTT TATTATTTTA TTATTTTATT
```

FIG. 6A10

```
48851 TGCTCTTTAT TTTTCTAGTT TCTTAAGGTG ATGGCTTACT TTTATTTTTT
48901 TCTTATTTTT TTCTTTTGTT GTTGTTGTTT TTTTAAAGAA ACAGGGTCCC
48951 ACTCTTGCTC AGGCTGGAGT GCAGTGGCAC GATCATGGTT CACTGCAGTC
49001 TCAAACTCCT ACATTCAAGC TGTCCTCCCC CCTCAGCCTC CAGAGTAGTT
49051 GGGATTACAG GTGCATGCCA CCATGCCTGG CTAATTTTTA ATTTTTTTTG
49101 TAGAGATGGG GTGTTACTAG TTGCCCACGC TGGTCTGAAA CTCCTGGCCT
49151 CAAGTGATCC CTCCACCTCT GCCTCCCAAA GTGCTGGGAT TCCATGTGTA
49201 AGCCACTGTG CCTGGCCAAG GTGATGGCTT AAAGCTATTG ATTTGAGATG
49251 ATTCCTTACT TTATAGTTTA AGCATATAAT GCCATAATTT TCCTCAAGCA
49301 CCGTTTTAGT TACGTTATAC AAATTTTGAA ATGTTTTGTT TTCATTTCCT
49351 AATTTCCCTT GTGATTTCTT TATTGAACCT TGGCTTATTT AGAAGTATGT
49401 TTAACTTGCA GATATTGGAG ATTTGCCAGC CATCTTTTTG TTATTAATTT
49451 CTACTTTAAT TTTGTTGTGA TTAGAGAACA TACATTTTAT TAATTTAAAT
49501 TTATAATTTA TTTTAATTTA TAATATGGTC TGTTTTACAG AATGTTGTGT
49551 GTGTATTTGA AAATAATATG AAAGCTACTA TTATTGGATG GAGTGTTCTA
49601 TAAATGTCAG TTAGATTAGG TTGATCATGC TGTTCTAGCT TTTTATATCC
49651 TTATTGATTT CCTCACTACT TGCTCTATCA ATGACTGGGA AAGTGTTGAA
49701 GTCTCCCAGT ATTTGTCTAT TTCTCCTTTG ATTCTACCAG TGTTTGCTTA
49751 ATGTATTTTG AAGCTCTGTT ATAGGTGCAT ACATGTTTAT GAGTATGTTA
49801 TAGATGTATT CATTTTGATA TCCTTCTTTC TCTGTTACTA TTCCTAATTC
49851 TGAATTTGAC TTTAATGTTA TTAATATAAT TCTTCCAGCC TTCTCTTGGT
49901 TAGTCTTTTC ATTGCATATC TTTTTCTATC CTTTTACTTT TAATCTAGCT
49951 GAATGTAGTC TTTATTTTGA AAGTGCGTTC CTTGTTGATA GCATTATTGG
50001 TTCTTTTTTT TTTTTAAATC TAATTTGACA ATCTCTGTCT TTTAATTGGA
50051 GGGTTTAGAC ATTTGCATTG AATGTGATTA CCAATATAGT TAGATTTAAA
50101 CCTACAGTCT TGCTGTTTGC TTTTTGTTTG TTTCATTGAT CCTTTGTTTC
50151 TTGTTTTTTT CTTTTTTTGC TTTCCTTTGG ATTTAGTATT TTTCATAATT
50201 CCATTTTACC TCCACTGTTG GCTTATTAGC TATACTTCTT CATTTCAGTA
```

FIG. 6A11

```
50251 TTTTAGTGGT TGCTGTAGGA TTTATAATAA ATATCATTAA CTGACCATAT
50301 CTTCAGATAA TCGTATACTA CTTCATATAT AGTGTAAAAA CCTTACAAGA
50351 GTATTCACTC CATAATACTT TGTTATTGCT TTTGCTTTAA GTGATCAATG
50401 ATTGTTTAAG GAAATTTTTT AATGACCTTT CATGTTTATT CTTTTTTTTT
50451 TTTTTCCAAA AGATTCAGTA TTTTCCGAGT TTTCAAAAAC TGCTGGCCAC
50501 TCAAAGTGGA TCAACAAAAA TTTAAGAGCT AAAACTGTAA AACTCTTGAA
50551 GGCTGGGCAC AGAGGTTCAT GCCTGTGATT CCAGCACTTT GAGAAGCTGA
50601 GGTGGGACAA TCACTTGAGC CCAGGGGTTT GAGACCAGCC TGGGTAACAT
50651 AGAAAGACCT TGTTTCTACA AAAAATAAAA ACACAATTAG CCAGGCATGG
50701 CGGTGTGCAC CTGTAGTCCC AACTTCTTGG GAGGCCAAGG TGGCAGGATT
50751 TCCTGAGCCT GTAAGTTTGA GACTGCAGTG AGCTGAGTTC ACGCCACTGC
50801 ACTTCAGCCT GGACAACAGA ACAAGACCCT GTCTCAAAAC CAGAACGAAA
50851 CTATAAAACT CTTAGAAGAA AACAGGGCTA AATCTTCATG ACTTTGGATT
50901 TGGCAATGGA TGGTTAGAAT TAATACCAAA AACACAATCA ATAAATTGAT
50951 AAATTGGATT TAATAAAAAT TAAGAACTTT TGTGTATCAA GGACATTGTC
51001 AAGAATGTGA AAAGACAGCA TATAGAATGG AAGAAGATAT TTGCAAATCC
51051 TATATCTGAT AAAGGTTTAA TATCCAGAAT ATGTAAGGAA CTCCTGCAGC
51101 TCAACAACAG AAAGCCAGTT AAATCAATTT TGAAATGAGC AAACGCCTGT
51151 AAACCCAGCT GCTTGGCAGA TTGAGACAGG AGGATTGCTT GAGGCTAGGA
51201 GTTCAAGACC AACCTGGACA ACATAGTGAG ACCCTGTCTA AAACATTTT
51251 TTTAATTAGC TGGGTGTGGT GGCATATTCC TGTAGTCCCA GCTACATGGG
51301 AGACCGAGGC AGGAGGATCA CTTGGGGCCA GGCAGTCAAG GCTGCCGTGA
51351 GCTGTGATTA TGCCACTGCA TCCCAGCCTG GCGACAGAG TGAGACCCTG
51401 TCTGAGAAAA AAAAAAAAA AAGAACAAAA AAAATTTAG AAGATTGCTA
51451 TTCTAGTCTA CTATTTTTTC AAAGGGTGGT CTTGTTAACA ATTCTGGAGC
51501 CCACCTAAAC CTGCTAAATC AAACTTGGTA GTAAAGCTGG GGAGATGGGC
51551 ATGTCTAACA GACGTTTCTG GTGGTTTTGA TGTCCAGGCG TGCAGAGAGA
51601 TGATGCTTAC CTTGTGTTTT GTCATTATTT TCAGGATTTA CACCCCTTCC
```

FIG. 6A12

```
51651 TTGTCTTTTG TATCAATATT TATGGAGTCA TGAACTCTAG GATAGGCATG
51701 ATGTTGAGAA CTAGGAGTTC TCCCCTGGCC AGGGAGATAG AGGCAGGTCT
51751 GTGGTTAGTT TTGTAGTTGG CTGTGATGAC ATCTGACATG CTCTCTTCAC
51801 TTGTTGTCTT CTTCCTGTTC CCTTGTCAGG ATTATGAAGA AGCTGTGCTC
51851 TTGCTGTTAG AAGGAGCTGC CTGGGAAGAA GCTTTGAGGC TGGTAAGAAT
51901 CTTGTAAATC CTCTGGATGT TGGGTGCTAA GCAGAGAGAG CAAGCAAGGG
51951 ATTCCAGGTC AGTTGGAATC TCTTGTCTTC TGAGGTTCAT GAAATAAGTA
52001 GAAATAGGTC AGGTTCCTGG CTTAAGGAAA AGCGGTGTTA CTAAAATCAT
52051 TTTTATCATT CTTGATAATA ATTTGAAATA TTACTGTCTT TTACTGAAAT
52101 GAATTGAATT TCCTTGGCTG CCTTGTAGGA GGCCTGTTTT TCAGGAAAAT
52151 ATTCTGATTA CCTCTGAAAG TAATCCATGT CTTTCTAAGT ATCTTAACTC
52201 TCCAGTGACT AGAAGTTTTC CTTCCTAAAA TATCGTGTTT TTCCTTCTAG
52251 GTATGCAAAT ATAACAGACT GGATATTATA GAAACCAACG TAAAGCCTTC
52301 CATTTTAGAA GGTGAGGGTT CCATTTTAGA TAGAATTCCT CATTTGGAAG
52351 AAGGTGAGGA GAGAGAGATG AGAGAGTCTC CTCCTATTTA CTGTGTTTTC
52401 TTAATAATAT GTCATGTAGA CTCAATCAAA ATTACCACCT GGATATAATA
52451 TTTAATTCTC ACTAGAATTT TTAAATATGC TGAACTATTA AATGGTAACA
52501 AAATATTTAA ATGTTAGAAA CCTGTGATCA AATATGATTA AGAATCTTTG
52551 TATTTGGAAA TAGTAAACTT GAATATGAAC TATATTAGAT AATAATATAA
52601 CACTGATAAA TTTCTGGCAT TTAATAATCA TGTTGTGGTT ATATAAGATA
52651 ATATCCTATT ATTCTCAAGA GATAAATGCT GAAATATTTA GGAATGAAGG
52701 ATCATATCTC TGCCTTACTC TTAAAAGGTT CCACAAAAGT ATTAATGAAT
52751 GTGTGTATGC ATGCAGAGAA ACAGGAAGCA AAAAAATGTC AAAATGTTAG
52801 TAATTGGTAA ATCAAAGTGA AGGGTATATG TGTGTTCATT GAACTCTTAC
52851 AACTTTTATG TAGGTTTCAA CGTTTCAAAG TATTTTTTAA AAGTTACCTT
52901 TTCAAATGAA GTTTGTGGTT CTTAGAGAAC ATATGAATAT TACCAGTTCT
52951 AGAATACTCA GATGGTCACT GTGACCTCTT AAAAGCAAAG TGGAGAAGGA
53001 CATCAGTTTG ACTTATAGAA ACCTTAGGGA GTGGTTGATT TTAAGTTCTG
```

FIG. 6A13

```
53051 CATTTTTATG CACATCTACC CTGTAAGTAA CGTCTGGCCT TTCTGACATT
53101 TACATGTATG CACATTCTTA CCTTGTCTGC ACCCCCTTCC TCCATCCTAA
53151 TTAAAACGTT GCTGGGGTAC TTTTTATGTC ATTCACTTTA GGTACCTCTA
53201 ACTGGGTACT GAAAACATCA TTCCTCATCT ATAATAATCT AACCAGCTCT
53251 TACTTAGATT TTCACCACTA ATGAGAACCT TCTTAGATA AATGCCGATA
53301 ATTCATCTAC ATAGGCCCAA AACCTATTAA TAAAATGCAT CCTTGGATAG
53351 TAGTATTTTG CTTTTTTAAA ATGTATTCTA CTAGTGTTAT TTTTCTCTTG
53401 TGTATTTTTC CATTGGACAA TATTTATTAG ATACATTTTT TCCACATCCA
53451 TGGGCATTTT GATGGATGTT TAGCCAGAAA CATTTAGGTA ATTTTCTTCT
53501 TATTTTTGTT AACTGAGCTC CCCTCCCCTA CCCCCCCTTT TTTTGTTTGT
53551 TTGTTTTGTT TGTTTGTTTG TTTTGCCAAT CCTCCCTTGC TTTAGGTATC
53601 AAGTCTTCGT TCAGGTGATT TTACAAGTTC AGTGGTAGCG CATATTCTGG
53651 GATAATGTTG ATGAACTCTA AGATCTGGAA TCTCAGTCTC TAATTTGTTA
53701 ATGCTTATTA AGGAAAAAGA GCTCGCTTGG AAAACCTAGT AACCTCTTTC
53751 TTTTTGCTGA ATTTTAACCC TCCTTCACTG CTCCCCGCCT TTAGTTTTTT
53801 CTCTTTGCTT AAACCTCATG CTCAAACTAT TTTCCATTCT GCATCTCCAG
53851 CCCAGAAAAA TTATATGGCA TTTCTGGACT CTCAGACAGC CACATTCAGT
53901 CGCCACAAGA AACGTTTATT GGTAGTTCGA GAGCTCAAGG AGCAAGCCCA
53951 GCAGGCAGGT CTGGGTGAGT ATCTGCGTGA AGGCCATCGA CGTGCGGGGG
54001 CAGTGGGGTT GGGTAACGCC ACACATTGTC TAGATTGCTT GGTGATCCGC
54051 CTGCAATCTG ATTACTGTGC CATGGGCAAG TGTGAGGCTT CTGTGGAGCC
54101 CCTTCAGGGC CCTCTGTGTC TGTGTTTGTG TGTTGGTGAA GGCAGGACC
54151 AAGCATGAAT GGGGAGAGCT CTGCCAGACA TTCCCACCTA CCCCCATTCA
54201 CCCAGAGCAG CTGACCACTT CCGTGTCTAA CAAAATGAGT TTCCTCATTT
54251 CCAGAAAAAA GTTCAGGAAA CTACTGATTT ACATTAGTAA TTACTGTATT
54301 TAATATTATC TCATTCATTT TGAGATCAAC TTTGCAATCA TTTTCATCCA
54351 TCCTTTGATA TGCACCAGTT GACTCTAGTT AGTTCATTTA CCGCCCTGAA
54401 AGTAAACCCA CACATTAGCA GGCAGTGTTT TCATCGGCTT CTGGTTCTTC
```

FIG. 6A14

54451 TTTTCTAGAT GATGAGGTAC CCCACGGGCA AGAGTCAGAC CTCTTCTCTG
54501 AAACTAGCAG TGTCGTGAGT GGCAGTGAGA TGAGTGGCAA ATACTCCCAT
54551 AGTAACTCCA GGATATCAGC GTACGTATCA CATTGATTCA GCACATTGAC
54601 TATATCCTGG GCATATAGGG AAAGTGGAAG CAAATAGATT GGTTTTCTAC
54651 TGGGACGGTG TAGTGGGAGT GGGGAGAATA TTCTTCAGCG CTGTGTGGAA
54701 GTTGTTCAGA CACTTTCCCA GCATATCTGA GACATTAAAC TTGGCATTGG
54751 AAGGTTTTCT TCCTCAGCTT TGTGGCTTGT GTGTTTTCCC ATTCCCCACG
54801 AGGCAGTTCC TCCCCTGAAT GCTCAGTTTA TATTAACATC TGATTTTATT
54851 TTTTGAACAA ATGTTGTGAC TAAATTATAG GCACTGAAAA AATGAAAAGA
54901 TAAGCTTCTT CAATTCAAAA TCAGGATTGG AAGAGACCAT AAATGTAAAA
54951 TAAGTCATAA CACTTTTACC AAATATAGTA ATTTGTCAGA AATATTTATT
55001 CAGCACTCAT ATGGTAGGTG CAGTAGATGT TACCAAAAAC TTATAAGGAG
55051 ATATGAGTTA TAAGAGTTTA TAGTCTTGCT TGGGATGTGT AAAGCAATGC
55101 AAGATTATAT ATTCAAACTG AATTTTGCTT TAGGAATTTA AAATGGAGAT
55151 CTGTGAAGTT GTGTGGGGTC ATCAGCAACT GCAAGAAAGT AGCCAGGCAA
55201 GGTAGCACAT GCCTGTAGTC CTAGCTACTC AGGAGGCTTA AAAATATCTG
55251 TGTAATTTCT AACAGGAGAT CATCCAAGAA TCGCCGAAAA GCGGAGCGGA
55301 AGAAGCACAG CCTCAAAGAA GGCAGTCCGC TGGAGGACCT GGCCCTCCTG
55351 GAGGCACTGA GTGAAGTGGT GCAGAACACT GAAAACCTGA AAGGTATATT
55401 CTCAGTCCTG ATGATGATTC CTGACCACAA ACAATAGTGA ATAGGCAGTA
55451 CAGACAGGCA GAGTTCAGTA GGTGATTAAG CTACCATTTT CCCAATTTGA
55501 GGAAAGATGA GAACTTTTAG CAGGAAGGGT CATGTCTGCA CACATTCCTG
55551 AAGCAGCCCT TCTTAGCTGG TAACTGAGAA GCCTTCCTCC ATTTGGCATC
55601 CCCCTAACTG AACTGGGAGA GATGCTTAAG CCAGGATAAA GAATTGTGGG
55651 ACACTGCTTT CTGCGTAGGC CCCCCAGCGT GCTTGATTTT CTTTTTGTAG
55701 TACATGTGTT TAATTATTCC AGCATTTGGG AAGAAAAAAG ATAATGTGGG
55751 AGAAAGGACC TGCAGTGGGA TCATAGAAAT TTTTGGCTTT GGATAGAAGC
55801 TATGTATGAT TCTGTCAATG GAGCTGGGAA TATAACTTAC CACTCTTTCA

FIG. 6A15

```
55851  AATTTCTTCT CTCTAGATGA AGTATACCAT ATTTTAAAGG TACTCTTTCT
55901  CTTTGAGTTT GATGAACAAG GAAGGGAATT ACAGAAGGCC TTTGAAGATA
55951  CGCTGCAGTT GATGGAAAGG TCACTTCCAG AAATTTGGAC TCTTACTTAC
56001  CAGCAGAATT CAGCTACCCC GGTAAGTTTT CTCAGAGACG GTGTGCATTT
56051  TTTTCATCAT TTTCATGGGT TATTGTATTC ACACAATCTC CAAGTCAAAA
56101  AGTTTTCCTG TTCTTAAAAC ATAAGATGCC ATAGTTAAAT TATCTTAGCA
56151  TTTATGTGTA AGCTGTCAGT AAGATTTGAT ATTTGCCTGT AGAGTGACTA
56201  GTATACCTTG GCATAGGTTA AATGGACTGT CATTTTCCTT TCTGGATGAA
56251  GTAGCTGTCA TGGAGAAAAT GGGAAAGTCA CATGATTGCT CCTGGCCTTC
56301  AATGAGGTTG GAGTGGGGAG AGATGGGGGA AGATGGGGTC AGAGACGGCC
56351  TCTCACTTTC CTTTCAGAAC TCAGGGATGG GATCAGGCTT TAAAGGGACC
56401  CCAGGCAATT GCTTTTCCTT TTGTTTTATG AAAAATTTGA CTTGTCACTT
56451  CTATGTTGTT ATGATGGACT TTGCGGGTTG TGTTTAAGGC TGAATCAGCT
56501  TTGTATCGCA GAATTCTAGT ATATTGTCAT CTGTTTATTA TTTATACCTC
56551  TGTTCACTCT CTTATACTTC AAGTCTATTG TTAAGAGTTT TTATTTGGAT
56601  TCAAAAAGGC TGGTGTATCA GTCAAGATCT AGAAAGGAAA ACAAAAGCCT
56651  ATCTATTATT TTATCACAGA ATTTAATATA TGGATTTGTT AAATAAGTAT
56701  TAGAGGACTA AACAAGGCAA AAGGGAAATA CAGAGGAAGG ACATTGAGAT
56751  AGTAACTGTA GGAAGCAGCT TTACCCTCTA GCTGAGGGAA CAGGAGGAGT
56801  TGTTGGGAAT TATTAGAATT TAGAAGCCTG GAAGTGGGGC CCTGTAGAGC
56851  TGGCTCTTGA ACCTCTGAGA GGAGGGTGCC AGCCAGCTAA TCCTGGCATT
56901  TCTGAGGGAG CTGGTTCCAA GCGTACAGAA GTAAATGGAA ACTGGAAGGA
56951  ACAGCTGCTG CTGGGGGAAA AGCCAGCCGG TCGGGCCAGG TGTGGTGGTG
57001  GCTCACGCCT GTAATCCCAG CACTTTGGGA GGCCAAGGCA GGCGGATCAC
57051  CTGAAGTCAG GAGTTCGTGA CTAATGTGGC CAACATGGAG AAGCCCCGTC
57101  TCTACTAAAA ATACAAAATT ACCCGGGCAT GGTGGCGCAT GCCTGTAATC
57151  CCAGCTACTC AGGAGGCTGA GGCAAGAGAA TCGCTTGAAC CTGGGAGACA
57201  GAGGTTGTGA TGAGCCAAGA TCGTGCCATT GTACTCCAAC CTGGGCAGCA
```

FIG. 6A16

57251 AGAGCGAATC TCCGTTTAAA AAAAAAAAAA AAAAAGCCAG CCAATCACGG

57301 AAGAAATCTA GAAATCTTTT GTTCATCCTC CAGCTTTGTA CTCCCCCTCT

57351 GGTGTTCACT GTAGGCAGGA CATGATGGGA AGCCAGCAGC AAGGAAGAAT

57401 ATCTTTCAGG TGCCCAGCCC CAGCACCACA AGCAGTGGAT AGAAGGGTGG

57451 GTTGGAGCTG AGAGATTACA AATCAGCTCA GTGTTTAGAA ACACATACGC

57501 TTATCATGTC TTGATTTCCT CATTTAGAAA TGGGCATAAG ACTTCTCTGT

57551 GTGCTTCAAT AGAATGCTTT GAAGGTTAAA TAAGAGGGTG TGTGTAAAAG

57601 CACTTTACAA ACCGTTGAAA TAAAAGCAAC TAGGAATCAG GGCCCCAGAA

57651 CTTCTTGAAT TTATTATAAT AGGTATTTCT TAGAAGAAAT GTGATCATCA

57701 TCTTCAAAAC TGTAGTACTT TTGAAGATAA TTGTTTTTGT TTTTTGAGAC

57751 AGGGTCTCAC TCTGTTGCTC AGGCTGGAGT GCAGTGATCA CCGCTCACTG

57801 CAGCATCCAC CGCCCCGGGC TCAGGTGATC CTCCCACCTC AGCCTCTTGA

57851 GTAGCTGGGA CTACAGGCGC ATGCCACAAC ACCTGGTTAA TTTTCAAATT

57901 TTCTGTAGAG ACAGGGTGTC ACCAAGTTGT CCCCGCTGGT CTTGAACAAC

57951 TCCTGGGCTC AAGTGGTCTG CCCACCTCAC CTCTCCAAAG TGCTGGGACT

58001 ATAGGCATCA GCCACCATGC CCGGCTTGAA GATAATAATT TATAATACCA

58051 CTCCCATGAG TGATCTTCTC TTCTGATCAC ATATTCACAT TAAGGTCTAT

58101 TTTATTTTAT TTTTTTCTTG CTCTGTCACC CAGGCTAGAG TGCAGTGACA

58151 GTATGATCAA TCATGGCTTG GTGCAGCCTC GAATGCCTGG GCTAAAGCAG

58201 TCCTCCCACC GCAGTCTCCT GAGTAATTGG GACCACAGGT GCACACCACC

58251 ATGCCCAGCT AATTTTAAAA TTTTTTCCTA GACATGGGGA GAGGGAGTCT

58301 TGCTGTGTTG CCCAAGCTGG TCTTGAACTC CTGGCCTCAA GTGATCCTCC

58351 TGCCTTGGCC TCCCAAAGTG CTGAGATTAC AGGTGTAAGC CACCATGCCT

58401 CCCACATTAA GTTCTAAGAC ATCAATTTTA TGATTGTGGT TTTGATTGGT

58451 GAAGTATGGT TGTGGTATGT GCAGGATACC GTGAGTGACT TCTCATGGCA

58501 TTGCTCTTGA GAGTGTGCCA CCAAGGGTCT GCACTAACCA GGGGTGTGCC

58551 CAGAGGCTCG CTGCAGGCTT GAAATTCCTG CGGAGTCTTG TGTTTTACCT

58601 GGAGCACATG TGCACAGTTT CCATTCTGCT CCATAGTATG CACATGTTTG

FIG. 6A17

```
58651  TATTTATTTC AACCTAAAAA TGTTTGTTTC CCATAACTCT TTGCGTATAA
58701  TTGATACTCT ACGTATTTGT AGCCTCTTTT ACTCTTTTCC CTTTCCTCAG
58751  GGAGTGGTTT GCTCATTTAG AAAAGGCCAA GATATATCAC TGTAGAGTTT
58801  CGTTTCTTTT CTTTTCCTCC ACCCCCCATC TTTACCTTGT TCTGGGAGAA
58851  AGGAGAATTA GAAGTCTGAG TTGCAGCTGG AGAAACTGGC AAATTAAAAT
58901  CACATTGGGA AAGAGAATTA CTGTGTTTCA CACCATACCA GTAGAAATGA
58951  CAGGCTGTTT TCTGCTGGTA GGGATTTGGC CTTTGGTATT GGCAGTCTTG
59001  AGAAGTATTA GATAATCTTT GCTGATACAG TCTATTTTCT CCTCAGGTTC
59051  TAGGTCCCAA TTCTACTGCA AATAGTATCA TGGCATCTTA TCAGCAACAG
59101  AAGACTTCGG TTCCTGTTCT TGGTTAGTAT TTTTTCTCAT TTAATATTAC
59151  AATACTAAGC AGAAGGACTA TCTTTCTGTA AGTATTGAGA AGATCAGCAG
59201  TATAAGGAGA GATTGGATAC AATTTTTCAC TACAAAAAAT TGACTACAAT
59251  TCTTCCTCAA TTCTAAGACC GCATCTTTAG TATGATCAGT TTCATGCTTC
59301  TAGCGGTGGG GGACCTGGTG CAGGAAAATC CAGCATGACC ATTGTATGTG
59351  TAATTTTTAA AAATATTTAT GTGGCATATG CTTGTTCATA AAGGCACACC
59401  ACAGTTCCAG TTTCAGTCTA AACTGTCTAC ATTTACATAT ACATCAAAAG
59451  ATTCTTCTGA AGCATCATTA CTGGCTATTG GCAGTTATGC TTTGCATCTT
59501  GGGGGCATTT TCATAAACCT TGCTTATGAG TGGGACCTTT TTATTATGTT
59551  TAGGATTGAC AATATAATTT GAAGGCAAAT CCAAAGAATA TTAGCATTTT
59601  ATACATATTT CCTGTTTAGT TATGCATGAA GTGTTTTATT TGTTGAGGGG
59651  AGATGATTCT CAATTAGATT ACTTATTTCC CTAAAAATTA AAAACCCTAA
59701  GCGCTTTCTT TTGAAAGTTG GTTAGAAACA TTTGATGAGT CAGCTTGGGA
59751  CTTTCAGTAT TTGCCCTTAC TTATAGTTGG ATCAATGAAG CATCTTAGCT
59801  TTGAAAAGTG AATGATAGTT TCTAAAATAA TTGGCAGTTT TAACTGCTAT
59851  TATTTGCATT TCTAGCATGT GACAAGCAAC TTTCTGAAAT TTTTTTTCAC
59901  CGAAGTGCTA CACTGTAATA GCATTTTGAT GACATTTGAA GTAGCCTGTG
59951  GGGATTCAAA TTAAGTTTGA CTTTAACAGC TTATGTTGCT ACCAGGAAGA
60001  ACAGCTACCT TCCATCCCAG CTAAACTCAT ACATCCAGAC TGTAACTACT
```

FIG. 6A18

```
60051 GTATTCCTAG CTCCTCTTCT GTCTAGAGAA TGGCAAGGTT CTTTTGGTAT
60101 GCAGTTTCGA CATATCCACT TATTCCTTTT TTTTTCTTAA GTTTTTTCAT
60151 TTAGAAAAAA AAACAGATGG GGTCTTAATA TGTTGCCCAG GCTGGTCTCA
60201 GCCTCCTGGT CTCAAGTGAT CCTCCTGCCT CGGCCTCCCA AAGTGCTGGG
60251 ATTACAGGCG TCTGCCCCTG TGCCCAGCCC ACTTATTTCC CAGATGCTAG
60301 GAACTTACAT TAGACCTGAG GCCATTTGGT CATTGTTTAT TTTGTGCTGT
60351 AGTCCAATCC AGTTGTGATT TCTGCCTCCT GTGTTCCTCG TTGCTGGCCT
60401 GATGCTGACC TTCAGGTTAG GTCAGTCCCA TCATTCCCCA GGGTATTCTA
60451 GATGGCTTTC CCACTTCAAA GAGCACTTTC TTGTTTTCCA GCTGAGCCTT
60501 AAAGACACTC TGTAATATTT GAGAGCCCCT CATTATCTGA GTGTTTATTA
60551 TCATTACCCT TGTGGTTTCA AGGATGTATA GGAAAAGGTA AGTTCCTATA
60601 ATTCAAAAAT TGCCACTGAT GAACTAATCA CAAAATTAGT GCCACTCAAA
60651 TATTACTCAG CTGCCCCTCC CCAGCTAACA ATAGTTAAGT ATATTGGCAC
60701 ATCCCCACAA GTGAAATCAA TGACTTGATG GGTCATTTCT GATTGTTTCC
60751 TGCTTTGATG CAATACAATA TCATGCAGAT CAATTGCAAG TCTTGCAAAA
60801 ATTTAGTATT ACATAAAATA GATTAAAATG ATATTGGAAA AGTACTTGAA
60851 TCACAGCTGG GTTGGACTTG TTGCAATTGA TGACAAAATA AGTGCTTCAA
60901 ATGATTTTGA CTATCAAAGG ATTGAGAGAG GTCCTTAGAA AAATTGAAAA
60951 GCCCTCAAGT TATTTTTATA AAAATGGCCT TTTTTGTGTG CTGTGAAATC
61001 CACATATGGA AATGTGAAAT ATGTCATGTC CTGCTGTCAT ATAATTTGTC
61051 AGAATAATTA CTTTCTTGCC CAAAAGTCTG TACTTTGTGT TTATTTCAAG
61101 TTAAGTCTAG AATCAAATAT AGTTGTAGTT ATGCCTAATT TTAAAAAATG
61151 AGATAGAGCA CATTATTTTT GTAACTAGTT TTTTTTTTTT TTTTTCAGAC
61201 AGAGTCTTGC TCTGTGGCCC AGGCGGGAGT GCAGTGGCGC AATCTCGGCT
61251 CACTGCAAGC TCCGCCTCCC GGGTTCACGC CATTCTCCTG CCTCACCCTC
61301 CTGAGTAGCT GGGACTACAG GCGCCCGCCA TCACGCCCGG CTAATTTTTT
61351 TGTATTTTTA GTAGAGACGG GGTTTCACCG TGTTAGCCAG GATGGTCTCG
61401 ATCTCCTGAC CTCGTGATCC ACCCGCCTCG GCCTCCCAAA GTGCTGGGAT
```

FIG. 6A19

```
61451  TACAAGCGTG AGCCACCGCG CCCGGCCTGT AAATAGTTTT TTTAAGATAA
61501  AGTCTTATTC CAACTTTAAT TGGAATTTAT GAAATACCTT GTTGATAGTG
61551  AATTTATTTA AGTAGCCTTT TTTCAGTATT GATATTCTTA TATCTTTATG
61601  GCACCATTTA GTGGAGAGAA ATGTAAACAA ACATAAAGAT GTAGTATTAA
61651  ATCATAACTG CATAAAATTA ACTGTAGTAT GTACTGCACT ACTGTAATAA
61701  TTTTGTAGCT ACCTCCTGTT GCTATTGTGG TGAGTGAGCT CAAGTGTTAC
61751  CAATATCTGC TTAAAATGCC ATGTGCCGCT AACCATCTCC ACATGAGCAG
61801  CACATGAGAG TCTCCATTAA TTGCATATGG CAGCGAAAAG TGATCTCTTG
61851  CATTGTCGTG TATTTTTTAT CACGTTTAAT GTAATATCGT AAACCTTAAA
61901  TAACACCATG AGACCTATAG GAAGTACCAC AAGTGTTGCT CCCAGGAAGC
61951  AGAGAAAAGT CATAACATTA CAAGAAAAAG TTGACTTGCT CGATATGTAC
62001  TATAGATTGA GGTCTGCAGC TGTAGTTGCC CACCACTTCA AGATAAATGA
62051  ACCCAGTGCA AGGACTATTA TAAAAGAAAA GGAAATTTAT GAAGCTGTCA
62101  CTGCAGTTAT GCCAGCAGGC ATGAAAACCT TGTACTTTTT GCAAAATACC
62151  TTTTTATGTT GTATTGAAGA TGCAGCTTTT ATGTGGGTGC AGGATTGCTA
62201  TGAGAAAGGC ATACCTATAC AACTATTATG ATTTGAGAAA AAGCACAGTC
62251  ATTGTATGAG AACTTAAAGC AAAAAGATGA AGGATCAAAG CTGGAGAATT
62301  TAATGCCAGC AAAGGATGGT TTGATAATTT TAGAAAGAGG TTTGGCTTTG
62351  TAAATGTCTG GATAATAGGA AAAGCAGCTC CTGCCATCCA GGAGGCAGCA
62401  GCAAAGGCAG TCAGGTTTAT GATCAGGACT GCCCTTATCT GTAAAGCTGC
62451  TAACCCCCGA GCCTGGAAGG GAAAAGATTA ACACCAGCTG CCAGGCTTTT
62501  GGTTGTACCA TACAACAAGA AGGCTTGGAC AAGGAGAACA CTTTTTCTGG
62551  ATTGGTTCCA TTGTCGATTT GTCCCTGAAG TTAAGTAGTA TCTTGCCAGT
62601  AAGGGGACTG CCTTTTAAAG TTCTTTTGAT ACTGGAGAAT GCCCGAGGCC
62651  ACCCCAAACT CCATGAGTTC AACACCGAAG ACATTGAAGT GATCTACTTG
62701  CCCCCAAACA CACATCTCTA ATTCAGCCTC TAGATCAGGG TGTCATAAGG
62751  ACCTTTAAGG CTCGTTACAA ACAGTACTCT ATAGAAAGGA TTGTCAAATG
62801  TATGGAAAAG AACCTTGACA GAACATGAAA GTCTGAAAGA ATTACACCAT
```

FIG. 6A20

62851 CAATGATGCC ATCATTGTTA TAGAAAAAGC TGTGAAAGCC ATCAAGCCCA
62901 GGACAATAAA TTCCTGCTAG AGAAAACTGT GTCCAGATGT GCATGACTTC
62951 ACAGGCTTTA CGACAGCCAA TCAAGGAAAT CATGAAAAAG ATTGTGGATC
63001 TGGCACAAAA AAAAAAAAAA AAAAAAAAAA TGGTGCATGA AGGATTTCAA
63051 GATAGGAATC TTGGAGAAAT TCAAGAGGTG ATAGACATCA CACCGGAGGA
63101 ATTAACAGAA GATGACTTGA TGGAGATGAG TACTTCCAAA CCAGCGCCAG
63151 ACAATGAGGA AGATTACATA AAAGAAGCAG TGCCAGAAAA TAAATTGACA
63201 TTTGTTCCAA AGGTTCCAAT TATTCAAGAC TGCCTTTGGC TTCTTTTACA
63251 ACATGGATGA TTCTATGTTA TGGGCACTGA AACTAAAAGA AACTGTGGAA
63301 GGATTGGTAC CTTAGAGAAA TGAAAAAGCA AAAACATCAG AAATTATGGT
63351 GTATTTCTGT AAAGTTAGTG ACACTGAGTG TGCCCACCTC TCTTGCCTCC
63401 TCTTTAACCT CCCCTACCTG TTTCATCTCT ACCACCCCTG AGACAGCAAG
63451 ACCAACCCCT CCACTTCCTC CTCTACTTCA GCCTACTCAA CGTGGAGATG
63501 ACAAAGATGA AGACCTTTAT GATGATCCAC TTCCATTTAA TGAATAGTAA
63551 ATATTGTTTT CTTTATGATT TTCTTAATAT TTTCTTTTCT CTAGCTTACT
63601 TTATTGTAGG AATGTAGTAT ATAATACATA TAACATACAA AACATTTGTT
63651 AACTGACTTT TTATGCTGCC AATACACTGC CGAACAACAG TAAGCTATTG
63701 GTACTTGAGT TTTGGAGATT CAGAAGTTAA ACATGGGGCC AGGTGTGGTG
63751 GCTCACACCT GTAATCCCAG CACTTTGGGA GGCTGAGGTG GGTGGAACGA
63801 GACCAGGAGT TTTGAGAGTA GCCTGGGCAG CATGGTGAAA CCTTGTCTCT
63851 ACAGAAATTA GCCAGGTATG GTGGTGTACA CTTGTAGTCC CAGCTACTTG
63901 GGAGGCTGAG GCAGGAGAAT CGCTTGAACC CAGGGGGTCG AGGCTGCAGT
63951 GAGTCATGAT CGTGCCACTG CACTCCAACC TGGGCAACAA AATGAGACCC
64001 TGTCTCAAAA AAAGAAAAAA AAAAGGTATA TGCAGATTTT TGACTGTGCA
64051 GGGGGGTCCG CACCCATAAC CCTACATTCA AGGATCAACT GTAATTTTTC
64101 ATGCCTGCAT GGCTCATATG TACAGATTTA CTGCTGGAAG TTTATCATAA
64151 ATAATGCTGA AAAAGAAAAT CCTTATATAT ACATATTTTC TCCTATCTCT
64201 GCTTGCAGTA TATGATTCCT GGTTAGAAAA GAAACTTAAC AAATCTAAGT

FIG. 6A21

64251 GAAAGAGTGC CTGGGAGTTT TAGGTTACAA TGACAGAATC TTTTCCTAAC
64301 CCTCTCTCTC CATTCACTTT TTTTAAAGCA GGGGCATCTT TATTGATCAA
64351 CATGTTTGTC GAAgtTTCAT CATAAAGTAG TTCCTGTCCA TTAACTTCAC
64401 TTACTGAATA TGTGCTATCA CATTTTGCTA TTCCTTAAAA ATTGAGCTAG
64451 ACTTTACATA TAGTGAAATG CAGAGATTTC AGGTGTACAA TTTGATGAGT
64501 TTTAATAAAT GTATACAGCC ATGTGACTGC TGCCACCACC CCTCCCACCA
64551 GTTTGAAATA CAGAACATTC TTCCACTTTG AATCACTGGG TGAGCATGCC
64601 TGAGGTTGAA ATGCAGTCCC TCCTCTCAGG GCGGGGCCTC CAGGTTGTGT
64651 TTGCTCTGAC CTGGAGGTTG CAGGGGTAGC AGACACATGA ACTCTGGCTC
64701 TGATGGTCTT ATTGCTGCAA ACTCCACCTG CCTAGTTTGT TTAGTTTAGA
64751 GTTACTGCCT CAGCGCCCTC CAACAAGAGT ATGTCTGTCA CAATTTCCCT
64801 TCCTTTCTTG CTTTTAGATG CTGAGCTTTT TATACCACCA AAGATCAACA
64851 GAAGAACCCA GTGGAAGCTG AGCCTGCTAG ACTGAGTGAC TGCAGTTAGG
64901 AGGGATCCGA CAGAGAAGAC CATTTCCACT CATTCCTGTT GTCCTACCAC
64951 CCCTTGCTCT TTGAGGGCTG GCTATTGAGA ACTGGAAAGA GTAAAATGAT
65001 AACTTACCTT AGCATTGCCA AGAACTTCAG CAGACAACAA GCAATTCTAT
65051 TTATTTTATG TTGTGTATAC ATCTTGATCA TTAGCAAGAC ATTAAGCTTT
65101 AACCATTATG GCACCATTTT GTGAGAATGA TTGTTCTTTC ACTTGGGCTG
65151 TTTGAGAGCA TAATTATGGT AATCATGAGA TTAATGTTTC ATGATTTCTA
65201 CCTCCAAAGT GTGAAGACAA GTAAAACAAT GTTTCTAAAT TGTCTTATTT
65251 TGTTGGCGGA GAAGATTACA ATGGCTATTA GTGCTACATT TGGTCAAATG
65301 TAATCACTTA AATAGCTTCT TGTCACCTTA AACTAAAGCA GAATAAAAAG
65351 TATCCTTTGA AATTATAAGC CCTCCTTTGC TGACAGCTAT TATTTTGTAA
65401 CATCTTACCA GGTCATGTGC TTTCAGTTAT AACTGGGCTG AGCCTCCTAT
65451 AATTACAATG TCTATAGGGA CTGTTTTACT GCCTGTGTAT TTCTGCTAG
65501 AGAGTTAGCA ATGTTAGAGC TAGAACAGAT TAGAATTTCT AAACAGTATC
65551 ATGCACAGTT GGTGTGAGTG ATCAGTGTGC ATTGTATGGC ATGCATGGTT
65601 GTGAATTATT CTCTGTTCTC CAAATACTGT TTCTTTAACT CAGATATTTT

FIG. 6A22

```
65651  TGTTAGTGTC TAGGCCACTT CATTTATTTT TCGTCATGGT ACTTTACTGA
65701  CTTCTCTTTA TTCAATTCTC CACGCCCTCA CCAAAAAAAA CTGTCTCAAA
65751  ATGAGAATAT TTTATTTTCA TGGTGAGTCT AGAAAACGCC CACTTCATTC
65801  TGATTAAAAA TTCTTCCATG TTTTAAATAT CAGAACCAGA CCTTTCTTAC
65851  TGTGTATCTT AGCCCATTTG TGTCTCTATA ACAACAACCA GCTTTCAAAG
65901  GAACTAATAG AGTGAAAACT CACTCATTAC CACGAGGATG GCACAAGCGA
65951  TTCACGTAGG ATCTGCCCCT GTGACCAAAA CACCTCCCAT TGGGCCCCAC
66001  TTCCAACACT GGTGATCACA TTTCAACATG AGGTTTAGGG AAACAAATGC
66051  CTAAACTACA GCACTGTACA TAAACTAACA GGAAATGCTG CTTTTGATCC
66101  TCAAAGAAGT GATATAGCCA AAATTGTAAT TTAAGAAGCC TTTCCCAGTA
66151  TAGCAAGATG TTAACTATAG AATCAATCTA GGAGTATTCA CTGTAAAATT
66201  CAACTTTTCT GTATGTTTGA ACATTTTCAC AATCTCATAG GAGTTTTTAA
66251  AAAGAAGAGA AAGAAGATAT ACTTTGCTTT GGAGAAATCT ACTTTTTGAC
66301  TTACATGGGT TTGCTGTAAT TAAGTGCCCA ATATTGAAAG GCTGCAAGTA
66351  CTTTGTAATC ACTCTTTGGC ATGGGTAAAT AAGCATGGTA ACTTATATTG
66401  AAATATAGTG CTCTTGCTTT GGATAACTGT AAAGGGACCC ATGCTGATAG
66451  ACTGGAAATA GAAGTAAATG TGTTTATTG
```

FIGURE 7

```
   1 ccagtgctgg ggctgcctag ttgacgcacc cattgagtcg ctggcttctt tgcagcgctt
  61 cagcgttttc ccctggaggg cgcctccatc cttggaggcc tagtgccgtc ggagagagag
 121 cgggagccgc ggacagagac gcgtgcgcaa ttcgagsccg actctgggtg cggactgtgg
 181 gagctgactc tgggtagccg gctgcgcgtg gctggggagg cgaggccgga cgcacctctg
 241 tttggggtc ctcagagatt aatgattcat caagggatag ttgtactgtt ctcgtgggaa
 301 tcacttcatc atgcgaaatc tgaaattatt tcggaccctg gagttcaggg atattcaagg
 361 tccagggaat cctcagtgct tctctctccg aactgaacag gggacggtgc tcattggttc
 421 agaacatggc ctgatagaag tagaccctgt ctcaagagaa gtgaaaaatg aagtttcttt
 481 ggtggcagaa ggctttctcc cagaggatgg aagtggccgc attgttggtg ttcaggactt
 541 gctggatcag gagtctgtgt gtgtggccac agcctctgga gacgtcatac tctgcagtct
 601 cagcacacaa cagctggagt gtgttgggag tgtagccagt ggtatctctg ttatgagttg
 661 gagtcctgac caagagctgg tgcttcttgc cacaggtcaa cagaccctga ttatgatgac
 721 aaaagatttt gagccaatcc tggagcagca gatccatcag gatgatttg gtgaaagcaa
 781 gtttatcact gttggatgcg gtaggaagga gacacagttc catggatcag aaggcagaca
 841 agcagctttt cagatgcaaa tgcatgagtc tgctttgccc tggatgacc atagaccaca
 901 agttacctgg cgggggggatg gacagttttt tgctgtgagt gttgtttgcc cacaaacagg
 961 ggctcggaag gtcagagtgt ggaaccgaga gtttgctttg cagtcaacca gtgagcctgt
1021 ggcaggactg ggaccagccc tggcttggaa accctcaggc agtttgattg catctacaca
1081 agataaaccc aaccagcagg atattgtgtt ttttgagaaa atggactcc ttcatggaca
1141 ctttacactt cccttcctta aagatgaggt taaggtaaat gacttgctct ggaatgcaga
1201 ttcctctgtg cttgcagtct ggctggaaga ccttcagaga gaagaaagct ccattccgaa
1261 aacctgtgtt cagctctgga ctgttgaaa ctatcactgg tatctcaagc aaagtttatc
1321 cttcagcacc tgtgggaaga gcaagattgt gtctctgatg tgggaccctg tgaccccata
1381 ccggctgcat gttctctgtc agggctggca ttacctcgcc tatgattggc actggacgac
1441 tgaccggagc gtgggagata attcaagtga cttgtccaat gtggctgtca ttgatggaaa
1501 cagggtgttg gtgacagtct tccggcagac tgtggttccg cctcccatgt gcacctacca
1561 actgctgttc ccacaccctg tgaatcaagt cacattctta gcacacctc aaaagagtaa
1621 tgaccttgct gttctagatg ccagtaacca gatttctgtt tataaatgtg gtgattgtcc
1681 aagtgctgac cctacagtga aactgggagc tgtgggtgga agtggattta agtttgcct
1741 tagaactcct catttggaaa agagatacaa aatccagttt gagaataatg aagatcaaga
1801 tgtaaacccg ctgaaactag gccttctcac ttggattgaa gaagacgtct tcctggctgt
1861 aagccacagt gagttcagcc cccggtctgt cattcaccat ttgactgcag cttcttctga
1921 gatggatgaa gagcatggac agctcaatgt cagttcatct gcagcggtgg atggggtcat
1981 aatcagtcta tgttgcaatt ccaagaccaa gtcagtagta ttacagctgg ctgatggcca
2041 gatatttaag tacctttggg agtcaccttc tctggctatt aaaccatgga gaactctgg
2101 tggatttcct gttcggtttc cttatccatg cacccagacc gaattggcca tgattggaga
2161 agaggaatgt gtccttggtc tgactgacag gtgtcgcttt ttcatcaatg acattgaggt
2221 tgcgtcaaat atcacgtcat ttgcagtata tgatgagttt ttattgttga caacccattc
2281 ccatacctgc cagtgttttt gcctgaggga tgcttcattt aaaacattac aggccggcct
2341 gagcagcaat catgtgtccc atggggaagt tctgcggaaa gtggagaggg gttcacggat
2401 tgtcactgtt gtgccccagg acacaaagct tgtattacag atgccaaggg gaaacttaga
2461 agttgttcat catcgagccc tggttttagc tcagattcgg aagtggttgg acaaacttat
2521 gtttaaagag gcatttgaat gcatgagaaa gctgagaatc aatctcaatc tgatttatga
2581 tcataaccct aaggtgtttc ttggaaatgt ggaaaccttc attaaacaga tagattctgt
2641 gaatcatatt aacttgtttt ttacagaatt gaaagaagaa gatgtcacga agaccatgta
2701 ccctgcacca gttaccagca gtgtctacct gtccagggat cctgacggga ataaaataga
2761 ccttgtctgc gatgctatga gagcagtcat ggagagcata aatcctcata aatactgcct
2821 atccatactt acatctcatg taaagaagac aaccccagaa ctggaaattg tactgcaaaa
2881 agtacgcgag cttcaaggaa atgctccctc tgatcctgat gctgtgagtg ctgaagaggc
2941 cttgaaatat ttgctgcatc tggtagatgt taatgaatta tatgatcatt ctcttggcac
3001 ctatgacttt gatttggtcc tcatggtagc tgagaagtca cagaaggatc caaagaata
3061 tcttccatttt cttaatacac ttaagaaaat ggaaactaat tatcagcggt ttactataga
3121 caaatacttg aaacgatatg aaaaagccat tggccacctc agcaaatgtg gacctgagta
```

Figure 7
Continued

```
3181 cttcccagaa tgcttaaact tgataaaaga taaaaacttg tataacgaag ctctgaagtt
3241 atattcacca agctcacaac agtaccagga tatcagcatt gcttatgggg agcacctgat
3301 gcaggagcac atgtatgagc cagcggggct catgtttgcc cgttgcggtg cccacgagaa
3361 agctctctca gcctttctca catgtggcaa ctggaagcaa gccctctgtg tggcagccca
3421 gcttaacttt accaaagacc agctggtggg cctcggcaga actctggcag gaaagctggt
3481 tgagcagagg aagcacattg atgcggccat ggttttggaa gagagtgccc aggattatga
3541 agaagctgtg ctcttgctgt tagaaggagc tgcctgggaa gaagctttga ggctggtata
3601 caaatataac agactggata ttatagaaac caacgtaaag ccttccattt tagaagccca
3661 gaaaaattat atggcatttc tggactctca gacagccaca ttcagtcgcc acaagaaacg
3721 tttattggta gttcgagagc tcaaggagca agcccagcag gcaggtctgg atgatgaggt
3781 accccacggg caagagtcag acctcttctc tgaaactagc agtgtcgtga gtggcagtga
3841 gatgagtggc aaatactccc atagtaactc caggatatca gcgagatcat ccaagaatcg
3901 ccgaaaagcg gagcggaaga agcacagcct caaagaaggc agtccgctgg aggacctggc
3961 cctcctggag gcactgagtg aagtggtgca gaacactgaa aacctgaaag atgaagtata
4021 ccatatttta aaggtactct ttctctttga gtttgatgaa caaggaaggg aattacagaa
4081 ggcctttgaa gatacgctgc agttgatgga aaggtcactt ccagaaattt ggactcttac
4141 ttaccagcag aattcagcta ccccggttct aggtcccaat tctactgcaa atagtatcat
4201 ggcatcttat cagcaacaga agacttcggt tcctgttctt gatgctgagc tttttatacc
4261 accaaagatc aacagaagaa cccagtggaa gctgagcctg ctagactgag tgactgcagt
4321 taggagggat ccgacagaga agaccatttc cactcattcc tgttgtccta ccaccccttg
4381 ctctttgagg gctggctatt gagaactgga aagagtaaaa tgataactta ccttagcatt
4441 gccaagaact tcagcagaca acaagcaatt ctatttattt tatgttgtgt atacatcttg
4501 atcattagca agacattaag ctttaaccat tatggcacca ttttgtgaga atgattgttc
4561 tttcacttgg gctgtttgag agcataatta tggtaatcat gagattaatg tttcatgatt
4621 tctacctcca aagtgtgaag acaagtaaaa caatgtttct aaattgtctt attttgttgg
4681 cggagaagat tacaatggct attagtgcta catttggtca aatgtaatca cttaaatagc
4741 ttcttgtcac cttaaactaa agcagaataa aaagtatcct ttgaaattat aagccctcct
4801 ttgctgacag ctattatttt gtaacatctt accaggtcat gtgctttcag ttataactgg
4861 gctgagcctc ctataattac aatgtctata gggactgttt tactgcctgt gtattttctg
4921 ctagagagtt agcaatgtta gagctagaac agattagaat ttctaaacag tatcatgcac
4981 agttggtgtg agtgatcagt gtgcattgta tggcatgcat ggttgtgaat tattctctgt
5041 tctccaaata ctgtttcttt aactcagata ttttttgttag tgtctaggcc acttcattta
5101 tttttcgtca tggtacttta ctgacttctc tttattcaat tctccacgcc ctcaccaaaa
5161 aaaactgtct caaaatgaga atattttttat tcttcatggt gagtctagaa aacgccccac
5221 ttcattctga ttaaaaaatt cttccatgtt tttaaatatc agaaccagac ctttcttact
5281 gtgtatctta gcccatttgt gtctctataa caacaaccag ctttcaaagg aactaataga
5341 gtgaaaactc actcattacc acgaggatgg cacaagcgat tcacgtagga tctgcccctg
5401 tgaccaaaac acctcccatt gggcccact tccaacactg gtgatcacat ttcaacatga
5461 ggtttaggga aacaaatgcc taaactacag cactgtacat aaactaacag gaaatgctgc
5521 ttttgatcct caaagaagtg atatagccaa aattgtaatt taagaagcct ttgtcagtat
5581 agcaagatgt taactataga atcaatctag gagtattcac tgtaaaattc aacttttctg
5641 tatgtttgaa catttcaca atctcatagg agtttttaaa aagaagagaa agaagatata
5701 ctttgctttg gagaaatcta cttttttgact tacatgggtt tgctgtaatt aagtgcccaa
5761 tattgaaagg ctgcaagtac tttgtaatca ctctttggca tgggtaaata agcatggtaa
5821 cttatattga aatatagtgc tcttgctttg gataactgta aagggaccca tgctgataga
5881 ctggaaatag aagtaaatgt gtttattgaa aaaaaaaaa aaaa
```

FIGURE 8

```
   1  mrnlklfrtl  efrdiqgpgn  pqcfslrteq  gtvligsehg  lievdpvsre  vknevslvae
  61  gflpedgsgr  ivgvqdlldq  esvcvatasg  dvilcslstq  qlecvgsvas  gisvmswspd
 121  qelvllatgq  qtlimmtkdf  epileqqihq  ddfgeskfit  vgwgrketqf  hgsegrqaaf
 181  qmqmhesalp  wddhrpqvtw  rgdgqffavs  vvcpetgark  vrvwnrefal  qstsepvagl
 241  gpalawkpsg  sliastqdkp  nqqdivffek  ngllhghftl  pflkdevkvn  dllwnadssv
 301  lavrledlqr  ekssipktcv  qlwtvgnyhw  ylkqslsfst  cgkskivslm  wdpvtpyrlh
 361  vlcqgwhyla  ydwhwttdrs  vgdnssdlsn  vavidgnrvl  vtvfrqtvvp  ppmctyqllf
 421  phpvnqvtfl  ahpqksndla  vldasnqisv  ykcgdcpsad  ptvklgavgg  sgfkvclrtp
 481  hlekrykiqf  ennedqdvnp  lklglltwie  edvflavshs  efsprsvihh  ltaassemde
 541  ehgqlnvsss  aavdgviisl  ccnsktksvv  lqladgqifk  ylwespslai  kpwknsggfp
 601  vrfpypctqt  elamigeeec  vlgltdrcrf  findievasn  itsfavydef  llltthshtc
 661  qcfclrdasf  ktlqaglssn  hvshgevlrk  vergsrivtv  vpqdtklvlq  mprgnlevvh
 721  hralvlaqir  kwldklmfke  afecmrklri  nlnpiydhnp  kvflgnvetf  ikqidsvnhi
 781  nlfftelkee  dvtktmypap  vtssvylsrd  pdgnkidlvc  damravmesi  nphkyclsil
 841  tshvkkttpe  leivlqkvhe  lqgnapsdpd  avsaeealky  llhlvdvnel  ydhslgtydf
 901  dlvlmvaeks  qkdpkeylpf  lntlkkmetn  yqrftidkyl  kryekaighl  skcgpeyfpe
 961  clnlikdknl  ynealklysp  ssqqyqdisi  aygehlmqeh  myepaglmfa  rcgahekals
1021  afltcgnwkq  alcvaaqlnf  tkdqlvglgr  tlagklveqr  khidaamvle  esaqdyeeav
1081  llllegaawe  ealrlvykyn  rldiietnvk  psileaqkny  mafldsqtat  fsrhkkrllv
1141  vrelkeqaqq  aglddevphg  qesdlfsets  svvsgsemsg  kyshsnsris  arssknrrka
1201  erkkhslkeg  spledlalle  alsevvqnte  nlkdevyhil  kvlflfefde  qgrelqkafe
1261  dtlqlmersl  peiwtltyqq  nsatpvlgpn  stansimasy  qqqktsvpvl  daelfippki
1321  nrrtqwklsl  ld
```

FIG. 1. Comparison of the amino acid sequence of Ikap across several species. Alignment of the amino acid sequence of Ikap (M_musculus) with that of Homo sapiens (H_sapiens), Drosophila melanogaster (D_melanogaster), Saccharomyces cerevisiae (S_cerevisiae), Arabidopsis thaliana (A_thaliana), and Caenorhabditis elegans (C_elegans). Black boxes indicate identical AA, while conserved AA residues are shown in gray. Asterisk (*) at AA position 696 for mouse and human proteins indicates the location of the heterozygous R696P mutation found in only 4 FD patients. Sequence alignments were made using Pileup and Boxshade commands from GCG Wisconsin Package V.9.0 (Madison, WI).

```
M_musculus      1062 HSEAATVLEGYAQDYEEAVLLLLEGSAWEEALRLVYKYDRVDIIETSEKPSILEAQKNYM
H_sapiens       1062 HEAAMVLEESAQDYEEAVLLLLEGSAWEEALRLVYKNRLDIIETNVKPSILEAQKNYM
D_melanogaster   949 HEAYERKEBCQDRKRQFDYLLEGHLYSRAEYEAGLED..DDYSEKEAPELAYGVELE
S_cerevisiae    1096 YYEAADEQLEYLDNVKEAVALYCKRYRYDIASLYAIKAKEDEEBEVVDPGLGEGFGIEA
A_thaliana      1061 PAEAAKEALEYCSDISGEESLLENEREEEEALRYAELHTADDRES.VVKSSALECASGLE
C_elegans       1008 PKELAKAEKLAESSSTEIVHELCEEFELDASREVEVGK.....EEAEKKEAESREDEEL M_musculus      1122 DELDSETATFEREKNRLQVVRALEEQAPQVHEDHEVEHGPESDLF.SETSSIES.GSEMS
H_sapiens       1122 AFLDSCTATFSREKKRLLVVRELKEQAQQAGEDEEVPHGQESDLF.SETSSEES.GSEMS
D_melanogaster  1007 SSLQAELQLELEDYKQRLLDERRNQAKEGKEEEDTDV.NLKEVDLL.SDETASEES..SEYS
S_cerevisiae    1156 ELEADCKGQINSQLERLREERAKKEENPYAEYGEBTEQEDDVSEAPSETSEQESFFERYE
A_thaliana      1120 SEFKESIEKVGKEYLTRYEAVREREELLLAAKLKSEERSVVDLDDDTASEEASSNESGMSAYE
C_elegans       1063 MDEERRKTEEENYKKRLAVVRENKLKRVEQEAAGEV.....DDLRDDISVESISSR..

M_musculus      1180 .GEYSHSNSR.ISARSSKNRR..KAERKKHSLKEGSPLEGLALLEAL....SEVVQ.SVE
H_sapiens       1180 .GKYSHSNSR.ISARSSKNRR..KAERKKHSLKEGSPLEDLALLEAL....SEVVQ.ETE
D_melanogaster  1063 .GTSREEGK...EFRSSKNRR..KEERKLFSLKPGNPEEDEALEDALENEVEKEAQ.EQE
S_cerevisiae    1216 .GETGGEEKEGASERETAKNKR..EEERKEARGKKGEIEEE....BYEVQSVGREEE.RLN
A_thaliana      1180 LGTRRGSAESVSSENAESRAEDLERQRKSGKEEAGSAGEEMAEVDHE......KGER.MEE
C_elegans       1115 ......SGSSKESMASEVRRRK.QIEKKKSSLKEGGEYEDSALENVESENYRWEENIGSE M_musculus      1231 KLKDEVEAILKVLFLFEFEEQAKELQRAFESTLQLMERAVPEIWTPAGQQSS..ETPVLG
H_sapiens       1231 NLKDEVYHILKVLFLFEFDEQGEELQKAFEDTLQLMERSEPEIWTLEYQQNS..ETPVLG
D_melanogaster  1116 PVRDTCKAELQEANAAEADPLAAALQREEKTLLQAEDAAEDEIWTPELRGNGLEADEHTG
S_cerevisiae    1268 QTKPDAVREEEGECRRNMREQAEEEQKNEVEVEDDEEKANVKEEYSIEEKDRERVNEN..G
A_thaliana      1234 GGEREEKSEEICEVTLGEMESAQKLQQEAEN.FQVSQVAAVEE.AHDTVSSESEDEEVYC
C_elegans       1168 FCFPWNFNEEL~~~~~~~~~~~~~~~~~~~~~~~~~~~~~~~~~~~~~~

M_musculus      1289 PSSTANSIEASYQQKTCVPAELDAGVEEEPPKEDPRSQWKLSLLE
H_sapiens       1289 PNSTANSIEASYQQKTSVPEELDAEEFIPPKINRREQWKLSLLD
D_melanogaster  1176 PN..VDYEELQKEEQRYELESPLKR..EKPQLE..MMDEQHESLQ
S_cerevisiae    1326 EVYYIPEEPVPEIHDFPKSHEYDF~~~~~~~~~~~~~~~
A_thaliana      1292 FERYEQKTRSEARDSDEFSWEEK..EVFISE~~~~~~~~~
C_elegans       1178 ~~~~~~~~~~~~~~~~~~~~~~~~~~~~~~~~~~~~~~~~
```

Figure 9
Continued

TABLE 2. COMPARISON OF THE NOVEL MOUSE *Ikbkap* GENE WITH MULTIPLE SPECIES HOMOLOGS

| Species | Gene name | No. of amino acids | Molecular weight (kDa) | % aa identity with M.m. | GenBank Accession No. |
|---|---|---|---|---|---|
| *Mus musculus* (M.m.) | *Ikbkap* | 1332 | 149.11 | — | AF367244 |
| *Homo sapiens* | *IKBKAP* | 1332 | 149.11 | 80 | AF153419 |
| *Drosophila melanogaster* | *CG10535* | 1213 | 138.21 | 32 | AAF54670 |
| *Saccharomyces cerevisiae* | *Elp1/Iki3p* | 1349 | 152.99 | 29 | AAB67278 |
| *Arabidopsis thaliana* | Unknown | 1308 | 146.63 | 27 | BAB08695 |
| *Caenorhabditis elegans* | Unknown | 1177 | 134.80 | 24 | AAF60430 |

Figure 10

TABLE 1. MOUSE *Ikbkap* EXON AND INTRON BOUNDARIES

| Exon | Acceptor site | Donor site | Size (bp) | cDNA position |
|---|---|---|---|---|
| 1 |  | AGgtgagcattcgcccg | 129 | 1..129[a] |
| 2 | ttttttttccctcagAA | AAgtaggtcactgatgc | 163 | 130..292[b] |
| 3 | tatgctttgtgaaagGT | AGgtaggtgtaaggcct | 153 | 293..445 |
| 4 | ttttctctgatgcagCT | AGgtaagctttgcactg* | 82 | 446..527 |
| 5 | acatgaactcctaagCT | AGgtaagcgtttcttgg | 81 | 528..608 |
| 6 | cttgaaaaactgtagGC | TGgtaaggcgggatgat | 86 | 609..694 |
| 7 | ggtgtctctcttcagCC | TGgtgtctctcttcagc* | 97 | 695..791 |
| 8 | ctacctcctttgcagAG | AAgtgagtgagcataaa* | 91 | 792..882 |
| 9 | aggttctgctttcagAC | AGgtaggggtcagagtt | 124 | 883..1006 |
| 10 | ttttgtccctaccagGT | TGgtatgacagcttgtg | 94 | 1007..1100 |
| 11 | tccctccacacacagTC | AAgtaagttgctgcgaa | 231 | 1101..1331 |
| 12 | cttttcattgtgtagAC | TGgtaagtggaagcagg | 165 | 1332..1496 |
| 13 | tttttgttttctagGT | TCgtaagttcctaaata | 100 | 1497..1596 |
| 14 | ctaatatttgaacagGA | AGgtatcatggttcatc | 189 | 1597..1785 |
| 15 | tttttttgctttagTT | GGgtgaggatcagagtt | 107 | 1786..1892 |
| 16 | ttaatcttacaacagAG | AGgtgaatagacacggc | 104 | 1893..1996 |
| 17 | ttcatttctttgcagGA | AGgtatgtaggcttggt | 54 | 1997..2050 |
| 18 | tcttgcctgttgcagGT | AAgtaagctctcctata | 106 | 2051..2156 |
| 19 | cactggtattttagTG | AGgtaagctgactcttc* | 116 | 2157..2272 |
| 20 | gggttttatttgagAT | AAgtaagtatttattct* | 74 | 2273..2346 |
| 21 | ttcctgtcctcacagAC | AGgtacacttgcgtct | 79 | 2347..2425 |
| 22 | tactttctttgatagGT | AGgtaagtattttgata* | 80 | 2426..2505 |
| 23 | tactgtggttcttagGG | AAgtggggtctgtgtgt | 138 | 2506..2643 |
| 24 | cacttactacctcagGT | AGgtagagacctgcgcg* | 86 | 2644..2729 |
| 25 | cttaaactccaacagGA | AGgtatgtggagttgag* | 149 | 2730..2878 |
| 26 | aactttttttcctaggGA | TGgtaagggttttttt | 124 | 2879..3002 |
| 27 | ttttttttttttcagGA | AGgtatgtggtgggtta* | 98 | 3003..3100 |
| 28 | cgtctcttgtcacagGC | AGgtaagcagggccatt | 202 | 3101..3302 |
| 29 | ttgctgtcttttcagGA | AGgtgagctcctccccg | 62 | 3303..3364 |
| 30 | ctcttcccttgtcagGA | TGgtaaggaagctctga | 63 | 3365..3427 |
| 31 | tttcttccctcttagGT | AGgtgaggattacattt* | 61 | 3428..3488 |
| 32 | attatgcatcctcagCC | GGgtgagtgcctccaaa* | 114 | 3489..3602 |
| 33 | gttcatcttctctagAT | GCgtacgtacgagacct* | 112 | 3603..3714 |
| 34 | tgtaatttctgacagGA | AGgtatggcttcagtgc | 128 | 3715..3842 |
| 35 | ccatttcttctctagAT | CGgtaagcttcctcaga | 155 | 3843..3997 |
| 36 | ctgttttctgcttagGT | CGgtgtactgctcgttc | 76 | 3998..4073 |
| 37 | cattcttgcttccagAT |  | 709 | 4074..4799[c] |

Figure 11

GENE FOR IDENTIFYING INDIVIDUALS WITH FAMILIAL DYSAUTONOMIA

This application claims priority to provisional application Ser. No. 60/260,080 filed Jan. 6, 2001, the entirety of which is incorporated herein by reference.

This invention was made with government support under Grant Number NS36326 awarded by The National Institutes of Health. The U.S. government has certain rights in the invention.

FIELD OF THE INVENTION

This invention relates generally to the gene, and mutations thereto, that are responsible for the disease familial dysautonomia (FD). More particularly, the invention relates to the identification, isolation and cloning of the DNA sequence corresponding to the normal and mutant FD genes, as well as characterization of their transcripts and gene products. This invention also relates to genetic screening methods and kits for identifying FD mutant and wild-type alleles, and further relates to FD diagnosis, prenatal screening and diagnosis, and therapies of FD, including gene therapeutics and protein/antibody based therapeutics.

BACKGROUND OF THE INVENTION

Familial Dysautonomia (FD, Riley-Day Syndrome, Hereditary Sensory and Autonomic Neuropathy Type III) [OMIM 223900] is an autosomal recessive disorder present in 1 in 3,600 live births in the Ashkenazi Jewish population. This debilitating disorder is due to the poor development, survival, and progressive degeneration of the sensory and autonomic nervous system (Axelrod et al., 1974). FD was first described in 1949 based on five children who presented with defective lacrimation, excessive sweating, skin blotching, and hypertension (Riley et al., 1949). The following cardinal criteria have evolved for diagnosis of FD: absence of fungiform papillae on the tongue, absence of flare after injection of intradermal histamine, decreased or absent deep tendon reflexes, absence of overflow emotional tears, and Ashkenazi Jewish descent (Axelrod and Pearson, 1984, Axelrod 1984).

The loss of neuronal function in FD has many repercussions, with patients displaying gastrointestinal dysfunction, abnormal respiratory responses to hypoxic and hypercarbic states, scoliosis, gastroesophageal reflux, vomiting crises, lack of overflow tears, inappropriate sweating, and postural hypotension (Riley et al. 1949; Axelrod et al. 1974, Axelrod 1996). Despite recent advances in the management of FD, the disorder is inevitably fatal with only 50% of patients reaching 30 years of age. The clinical features of FD are due to a genetic defect that causes a striking, progressive depletion of unmyelinated sensory and autonomic neurons (Pearson and Pytel 1978a; Pearson and Pytel 1978b; Pearson et al. 1978; Axelrod 1995). This neuronal deficiency begins during development, as extensive pathology is evident even in the youngest subjects. Fetal development and postnatal maintenance of dorsal root ganglion (DRG) neurons is abnormal, significantly decreasing their numbers and resulting in DRG of grossly reduced size. Slow progressive degeneration is evidenced by continued neuronal depletion with increasing age. In the autonomic nervous system, superior cervical sympathetic ganglia are also reduced in size due to a severe decrease in the neuronal population.

Previously, the FD gene, DYS, was mapped to an 11-cM region of chromosome 9q31 (Blumenfeld et al. 1993) which was then narrowed by haplotype analysis to <0.5 cM or 471 kb (Blumenfeld et al. 1999). There is a single major haplotype that accounts for >99.5% of all FD chromosomes in the Ashkenazi Jewish (AJ) population. The recent identification of several single nucleotide polymorphisms (SNPs) in the candidate interval has allowed for further reduction of the candidate region to 177 kb by revealing a common core haplotype shared by the major and one previously described minor haplotype (Blumenfeld et al. 1999).

SUMMARY OF THE INVENTION

This invention relates to mutations in the IKBK4P gene which the inventors of this invention discovered and found to be associated with Familial Dysautonomia. The mutation associated with the major haplotype of FD is a base pair mutation, wherein the thymine nucleotide located at bp 6 of intron 20 in the IKBKAP gene is replaced with a cytosine nucleotide (T C) (hereinafter "FD1 mutation"). The mutation associated with the minor haplotype is a base pair mutation wherein the guanine nucleotide at bp 2397 (bp 73 of exon 19) is replaced with a cysteine nucleotide (G C) (hereinafter "FD2 mutation" This base pair mutation causes an arginine to proline missense mutation (R696P) in the amino acid sequence of the IKBKAP gene that is predicted to disrupt a potential phosphorylation site In accordance with one aspect of the present invention, there is provided an isolated nucleic acid comprising a nucleic acid sequence selected from the group consisting of:

nucleic acid sequences corresponding to the genomic sequence of the FD gene including introns and exons as shown in FIG. 6;

nucleic acid sequences corresponding to the nucleic acid sequence of the FD gene as shown in FIG. 6, wherein the thymine nucleotide at position 34,201 is replaced by a cytosine nucleotide;

nucleic acid sequences corresponding to the nucleic acid sequence of the FD gene as shown in FIG. 6, wherein the guanine nucleotide at position 33,714 is replaced by a cytosine nucleotide;

nucleic acid sequences corresponding to the nucleic acid sequence of the FD gene as shown in FIG. 6, wherein the thymine nucleotide at position 34,201 is replaced by a cytosine nucleotide and the guanine nucleotide at position 33,714 is replaced by a cyto sine nucleotide;

nucleic acid sequences corresponding to the cDNA sequence including the coding seqeunce of the FD gene as shown in FIG. 7;

nucleic acid sequences corresponding to the cDNA sequence shown in FIG. 7, wherein the arginine at position 696 is replaced by a proline;

In accordance with another aspect of the present invention, there is provided a nucleic acid probe, comprising a nucleotide sequence corresponding to a portion of a nucleic acid as set forth in any one of the foregoing nucleic acid sequences In accordance with another aspect of the present invention, there is provided a cloning vector comprising a coding sequence of a nucleic acid as set forth above and a replicon operative in a host cell for the vector.

In accordance with another aspect of the present invention, there is provided an expression vector comprising a coding sequence of a nucleic acid set forth above operably linked with a promoter sequence capable of directing expression of the coding sequence in host cells for the vector.

In accordance with another aspect of the present invention, there is provided host cells transformed with a vector as set forth above.

In accordance with another aspect of the present invention, there is provided a method of producing a mutant FD polypeptide comprising: transforming host cells with a vector capable of expressing a polypeptide from a nucleic acid sequence as set forth above; culturing the cells under conditions suitable for production of the polypeptide; and recovering the polypeptide.

In accordance with another aspect of the present invention, there is provided a peptide product selected from the group consisting of: a polypeptide having an amino acid sequence corresponding to the amino acid sequence shown in FIG. 8; a polypeptide containing a mutation in the amino acid sequence shown in FIG. 8, wherein the arginine at position 696 is replaced with a proline; a peptide comprising at least 6 amino acid residues corresponding to the amino acid sequence shown in FIG. 8, and a peptide comprising at least 6 amino acid residues corresponding to a mutated form of the amino acid sequence shown in FIG. 8. In one embodiment, the peptide is labeled. In another embodiment, the peptide is a fusion protein.

In accordance with another aspect of the present invention, there is provided a use of a peptide as set forth above as an immunogen for the production of antibodies. In one embodiment, there is provided an antibody produced in such application. In one embodiment, the antibody is labeled. In another embodiment, the antibody is bound to a solid support. In accordance with another aspect of the present invention, there is provided a method to determine the presence or absence of the familial dysautonomia (FD) gene mutation in an individual, comprising: isolating genomic DNA, cDNA, or RNA from a potential FD disease carrier or patient; and assessing the DNA for the presence or absence of an FD-associated allele, wherein said FD-associated allele is the FD1 and/or FD2 mutation wherein, the absence of either FD-associated allele indicates the absence of the FD gene mutation in the genome of the individual and the presence of the allele indicates that the individual is either affected with FD or a heterozygote carrier.

In one embodiment, the assessing step is performed by a process which comprises subjecting the DNA to amplification using oligonucleotide primers flanking the FD1 mutation and the FD2 mutation. In another embodiment, the assessing step further comprises an allele-specific oligonucleotide hybridization assay.

In another embodiment, DNA is amplified using the following oligonucleotide primers: 5'-GCCAGTGTTTTTGC-CTGAG-3'; (SEQ ID NO: 82); 5'-CGGATTGTCACTGT-TGTGC-3'; (SEQ ID NO: 83); 5'-GACTGCTCTCATAGCATCGC-3' (SEQ ID NO: 84). In another embodiment, the assessing step further comprises an allele-specific oligonucleotide hybridization assay. In another embodiment, the allele-specific oligonucleotide hybridization assay is accomplished using the following oligonucleotides: 5'-AAGTAAG(T/C)GCCATTG-3' (SEQ ID NO: 85) and 5'-GGTTCAC(G/C)GATTGTC (SEQ ID NO: 86). In yet another embodiment, neuronal tissue from an individual is screened for the presence of truncated IKBKAP mRNA or peptides, wherein the presence of said truncated mRNA or peptides indicates that said individual possesses the FD1 and/or FD2 mutation in the IKBKAP gene.

In accordance with another aspect of the present invention, there is provided an animal model for familial dysautonomia (FD), comprising a mammal possessing a mutant or knockout or knock-in FD gene. In another emodiment, there is provided a method of producing a transgenic animal expressing a mutant IKAP mRNA comprising:

(a) introducing into an embryonal cell of an animal a promoter operably linked to the nucleotide sequence containing a mutation associated with FD;

(b) transplanting the transgenic embryonal target cell formed thereby into a recipient female parent; and (c) identifying at least one offspring containing said nucleotide sequence in said offspring's genome.

In accordance with another aspect of the present invention, there is provided a method for screening potential therapeutic agents for activity, in connection with FD, comprising: providing a screening tool selected from the group consisting of a cell line, and a mammal containing or expressing a defective FD gene or gene product; contacting the screening tool with the potential therapeutic agent; and assaying the screening tool for an activity.

In accordance with another aspect of the present invention, there is provided a method for treating familial dysautonomia (FD) by gene therapy using recombinant DNA technology to deliver the normal form of the FD gene into patient cells or vectors which will supply the patient with gene product in vivo.

In another embodiment, there is provided a method for treating familial dysautonomia (FD), comprising: providing an antibody directed against an FD protein sequence or peptide product; and delivering the antibody to affected tissues or cells in a patient having FD.

In accordance with another aspect of the present invention, there is provided kits for carrying out the methods of the invention. These kits include nucleic acids, polypeptides and antibodies of the present invention. In another embodiment the kit for detecting FD mutations will also contain genetic tests for diagnosing additional genetic diseases, such as Canavan's disease, Tay-Sachs disease, Goucher disease, Cystic Fibrosis, Fanconi anemia, and Bloom syndrome.

It will be appreciated by a skilled worker in the art that the identification of the genetic defect in a genetic disease, coupled with the provision of the DNA sequences of both normal and disease-causing alleles, provides the full scope of diagnostic and therapeutic aspects of such an invention as can be envisaged using current technology.

BRIEF DESCRIPTION OF THE DRAWINGS

FIG. 1. Genomic structure of IKBKAP. The figure illustrates the orientation and placement of the 37 exons within a 68 kb genomic region of chromosome 9q31. The primers used for analysis of the splice defect are indicated as 18F (exon 18), 19F (exon 19) and 23R (exon 23). Asterick indicates the locations of the two mutations identified; the mutation associated with the major AJ haplotype is located at bp 6 of intron 20, whereas the mutation association with the minor AJ haplotype is located at bp 73 of exon 19. The 4.8 and 5.9 designations at exon 37 indicate the lengths of the two IKBKAP messages that differ only in the length of their 3' UTRs.

FIG. 2A shows the antisense sequence of the T-C mutation (shown by arrows adjacent to the G and A lanes) at bp 6 of intron 20 that is associated with the major FD haplotype. Lanes 1 and 2 are FD patients homozygous for the major haplotype (homozygous GG), lane 3 is an FD patient heterozygous for the major haplotype and minor haplotype 2 (heterozygous GA), lane 4 is an FD patient heterozygous for the major haplotype and minor haplotype 3 (heterozygous GA), and lanes 5 and 6 are non-FD controls (homozygous AA). FIG. 2b shows heterozygosity for the G-C mutation (shown by arrows adjacent to the G and C lanes) at bp 73 of exon 19. Lane 1 is an FD homozygous for the major haplotype (homozygous GG), lanes 2-4 are three patients heterozygous for the major haplotype and minor haplotype 2 (heterozygous GC), lane 5 is a patient heterozygous for the major haplotype and minor haplotype 3 (homozygous GG), and lane 6 is a non-FD control (homozygous GG). FIG. 2c shows the sequence of the cDNA generated from the RT-PCR of a patient heterozygous for the major and minor 2 haplotypes. The arrow points to the heterozygous G-C mutation in exon 19. The boundary of exons 19 and 20 is also indicated, illustrating that this patient expresses wild-type message that includes exon 20, despite the presence of the major mutation on one allele.

FIG. 3A is a human multiple tissue northern blot that was hybridized with IKBKAP exon 2 and shows the presence of two messages of 4.8 and 5.9 kb (northern blots hybridized with other IKBKAP probes yielded similar patterns). FIG. 3b is a northern blot generated using mRNA isolated from lymphoblast cell lines: lanes 1, 2, and 5 FD patients homozygous for the major haplotype; lane 3 individual carrying two definitively non-FD chromososomes, lane 4 FD patient heterozygous for the major haplotype and minor haplotype 2; lane 6 control brain RNA (Clontech). The level of expression of IKBKAP MRNA relative to β-actin MRNA is quite variable in lymphoblasts. We observed no consistent increase or decrease in mRNA levels between FD patients homozygous for the major haplotype, those heterozyous for the major haplotype and minor haplotype 2, and non-FD individuals.

FIG. 4A was generated using primers 18F (exon 18) and 23R (exon 23). Lanes 1 and 2 are FD patients homozygous for the major haplotype, lane 3 is an FD patient heterozygous for the major haplotype and minor haplotype 2, lanes 4 and 5 are non-FD controls, lane 6 is a water control. FIG. 4b is a western blot generated using cytoplasmic protein isolated from patient lymphoblast cell lines and detected with a carboxyl-terminal antibody. Lanes 2, 4, 6, and 8 are patients homozygous for the major haplotype, lanes 3, 5, 7, and 9 are non-FD controls, lane 1 is a patient heterozygous for the major and minor haplotype 3, and lane 10 is a patient heterozygous for the major and minor haplotype 2 and lane 10 is a Hela cell line sample.

FIGS. 6A-6A22. The genomic sequence for IKBKAP.

FIG. 7—The cDNA sequence for IKBKAP (SEQ ID NO: 2)

FIG. 8—the amino acid sequence of the IKBKAP gene (SEQ ID NO: 3)

Figure 9:
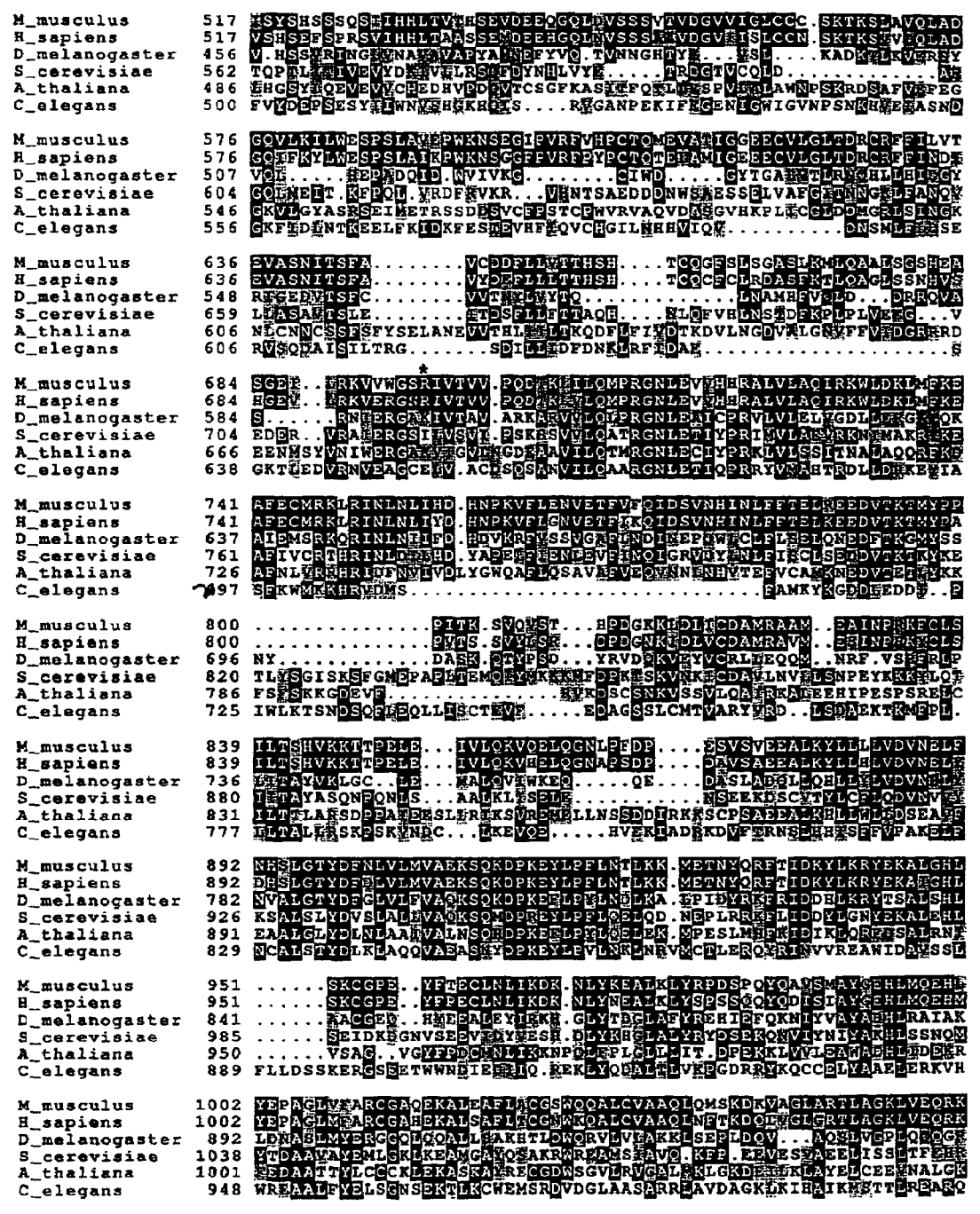

FIG. 9—Comparison of the amino acid sequence of Ikap across several species (SEQ ID NOS: 4-9), respectively, in order of appearance). Alignment of the amino acid sequence of Ikap (M_musculus) with that of Homo sapiens (H_sapiens), Drosophila melanogaster (D_melanogaster), Saccharomyces cerevisiae (S_celvisiae), Arabidopsis thaliana (A_thaliana), and Caenorhabditis elegans (C_elegans).

FIG. 10—Comparison of the Novel Mouse Ikbkap Gene with Multiple Species Homologs FIG. 11—Mouse Ikbkap Exon and Intron Boundaries (acceptor site sequences have been assigned SEQ ID NOS 10-45, respectively, in order of appearance. Donor site sequences have been assigned SEQ ID NOS 46-81, respectively, in order of appearance).

DETAILED DESCRIPTION OF THE INVENTION

Figure 2C:
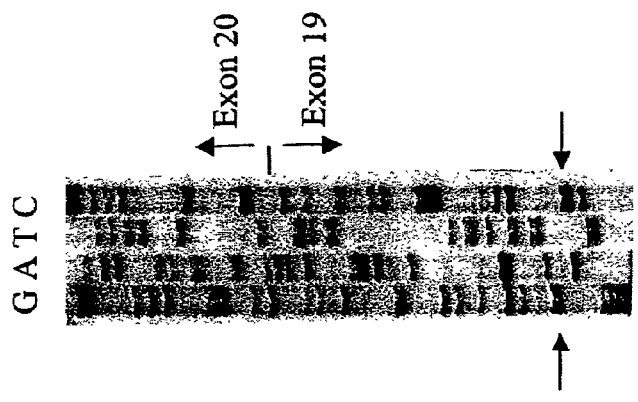
FIGS. 2A-2C. Demonstration of mutations in IKBKAP.

This invention relates to mutations in the IKBKAP gene, which the inventors of the instant application discovered are associated with Familial Dysautonomia. More specifically, the mutation associated with the major haplotype of FD is a T-C change located at bp 6 of intron 20 in the IKBKAP gene as shown in FIG. 1. This mutation can result in skipping of exon 20 in the mRNA from FD patients, although they continue to express varying levels of wild-type message in a tissue specific manner. The mutation associated with the minor haplotype is a single G-C change at bp 2397 (bp 73 of exon 19) that causes an arginine to proline missense mutation (R696P) that is predicted to disrupt a potential phosphorylation site.

These findings have direct implications for understanding the clinical manifestations of FD, for preventing it and potentially for treating it. The IKAP protein produced from IKBKAP gene was originally isolated as part of a large interleukin-1-inducible IKK complex and described as a regulator of kinases involved in pro-inflammatory cytokine signaling (Cohen et al. 1998). However, a recent report questioned this conclusion, by reporting that cellular IKK complexes do not contain IKAP based on various protein-protein interaction and functional assays. Rather, IKAP appears to be a member of a novel complex containing additional unidentified proteins of 100, 70, 45, and 39 kDa (Krappmann et al. 2000).

IKAP is homologous to the Elp1 protein of S. cerevisiae, which is encoded by the IKI3 locus and is required for sensitivity to pGKL killer toxin. The human and yeast proteins exhibit 29% identity and 46% similarity over their entire lengths. Yeast Elp1 protein is part of the RNA polymerase II-associated elongator complex, which also contains Elp2, a WD-40 repeat protein, and Elp3, a histone acetyltransferase (Otero et al. 1999). The human ELP3 gene encodes a 60 kDa histone acetyltransferase that shows more than 75% identity with yeast Elp3 protein, but no 60 kDa protein has been found in the human IKAP-containing protein complex. Consequently, it is considered unlikely that IKAP is a member of a functionally conserved mammalian elongator complex (Krappmann et al. 2000). Instead, it has been reported that the protein may play a role in general gene activation mechanisms, as overexpression of IKAP interferes with the activity of both NF-κB-dependent and independent reporter genes (Krappmann et al. 2000). Therefore, the FD phenotype may be caused by aberrant expression of genes crucial to the development of the sensory and autonomic nervous systems, secondary to the loss of a functional IKAP protein in specific tissues.

FD is unique among Ashkenazi Jewish disorders in that one mutation accounts for >99.5% of the disease chromosomes. As in other autosomal recessive diseases with no phenotype in heterozygous carriers, one might have expected to find several different types of mutations producing complete inactivation of the DYS gene in the AJ population. The fact that the major FD mutation does not produce complete inactivation, but rather allows variable tissue-specific expression of IKAP, may explain this lack of mutational diversity. Mutations causing complete inactivation of IKAP in all tissues might cause a more severe or even lethal phenotype. Indeed, CG10535, the apparent *Drosophila melanogaster* homologue of IKBKAP, maps coincident with a larval recessive lethal mutation (l(3)04629) supporting the essential nature of the protein (FlyBase). Thus, the array of mutations that can produce the FD phenotype may be limited if they must also allow expression of functional or partially functional IKAP in some tissues to permit survival. With the identification of IKBKAP as DYS, it will now be possible to test this inactivation hypothesis in a mammalian model system.

Despite the overwhelming predominance of a single mutation in FD patients, the disease phenotype is remarkably variable both within and between families. The nature of the major FD mutation makes it tempting to consider that this phenotypic variability might relate to the frequency of exon 20 skipping in specific tissues and at specific developmental stages, which may be governed by variations in many factors involved in RNA splicing. Even a small amount of normal IKAP protein expressed in critical tissues might permit sufficient neuronal survival to alleviate the most severe phenotypes. This possibility is supported by the relatively mild phenotype associated with the presence of the R696P mutation, which is predicted to permit expression of an altered full-length IKAP protein that may retain some functional capacity. To date, this minor FD mutation has only been seen in four patients heterozygous for the major mutation. Consequently, it is uncertain whether homozygotes for the R696P mutation would display any phenotypic abnormality characteristic of FD. The single patient with minor haplotype 3 and mixed ancestry, whose mutation has yet to be found, is also a compound heterozygote with the major haplotype. The existence of minor haplotype 3 indicates that IKBKAP mutations will be found outside the AJ population, but like the R696P mutation, it is difficult to predict the severity of phenotype that would result from homozygosity.

Since FD affects the development and maintenance of the sensory and autonomic nervous systems, the identification of IKBKAP as the DYS gene allows for further investigation of the role of IKAP and associated proteins in the sensory and autonomic nervous systems. Of more immediate practical importance, however, the discovery of the single base mutation that characterizes >99.5% of FD chromosomes will permit efficient, inexpensive carrier testing in the AJ population, to guide reproductive choices and reduce the incidence of FD. The nature of the major mutation also offers some hope for new approaches to treatment of FD. Despite the presence of this mutation, lymphoblastoid cells from patients are capable of producing full-length wild-type mRNA and normal IKAP protein, while in neuronal tissue exon 20 is skipped, presumably leading to a truncated product. Investigation of the mechanism that permits lymphoblasts to be relatively insensitive to the potential effect of the mutation on splicing may suggest strategies to prevent skipping of exon 20 in other cell types. An effective treatment to prevent the progressive neuronal loss of FD may be one aimed at facilitating the production of wild-type mRNA from the mutant gene rather than exogenous administration of the missing IKAP protein via gene therapy.

FD Screening

With knowledge of the primary mutation and secondary mutation of the FD gene as disclosed herein, screening for presymptomatic homozygotes, including prenatal diagnosis, and screening for heterozygous carriers can be readily carried out.

1. Nucleic Acid Based Screening

Individuals carrying mutations in the FD gene may be detected at either the DNA or RNA level using a variety of techniques that are well known in the art. The genomic DNA used for the diagnosis may be obtained from an individual's cells, such as those present in peripheral blood, urine, saliva, bucca, surgical specimen, and autopsy specimens. The DNA may be used directly or may be amplified enzymatically in vitro through use of PCR (Saiki et al. Science 239:487-491 (1988)) or other in vitro amplification methods such as the ligase chain reaction (LCR) (Wu and Wallace Genomics 4:560-569 (1989)), strand displacement amplification (SDA) (Walker et al. PNAS USA 89:392-396 (1992)), self-sustained sequence replication (3SR) (Fahy et al. PCR Methods Appl. 125-33 (1992)), prior to mutation analysis. in situ hybridization may also be used to detect the FD gene.

The methodology for preparing nucleic acids in a form that is suitable for mutation detection is well known in the art. For example, suitable probes for detecting a given mutation include the nucleotide sequence at the mutation site and encompass a sufficient number of nucleotides to provide a means of differentiating a normal from a mutant allele. Any probe or combination of probes capable of detecting any one of the FD mutations herein described are suitable for use in this invention. Examples of suitable probes include those complementary to either the coding or noncoding strand of the DNA. Similarly, suitable PCR primers are complementary to sequences flanking the mutation site. Production of these primers and probes can be carried out in accordance with any one of the many routine methods, e.g., as disclosed in Sambrook et al . . . sup. 45, and those disclosed in WO 93/06244 for assays for Goucher disease.

Probes for use with this invention should be long enough to specifically identify or amplify the relevant FD mutations with sufficient accuracy to be useful in evaluating the risk of an individual to be a carrier or having the FD disorder. In general, suitable probes and primers will comprise, preferably at a minimum, an oligomer of at least 16 nucleotides in length. Since calculations for mammalian genomes indicate that for an oligonucleotide 16 nucleotides in length, there is only one chance in ten that a typical cDNA library will fortuitously contain a sequence that exactly matches the sequence of the nucleotide. Therefore, suitable probes and primers are preferably 18 nucleotides long, which is the next larger oligonucleotide fully encoding an amino acid sequence (i.e., 6 amino acids in length).

By use of nucleotide and polypeptide sequences provided by this invention, safe, effective and accurate testing procedures are also made available to identify carriers of mutant alleles of IKBKAP, as well as pre- and postnatal diagnosis of fetuses and live born patients carrying either one or two mutant alleles. This affords potential parents the opportunity to make reproductive decisions prior to pregnancy, as well as afterwards, e.g., if chorionic villi sampling or amniocentesis is performed early in pregnancy. Thus, prospective parents who know that they are both carriers may wish to determine if their fetus will have the disease, and may wish to terminate such a pregnancy, or to provide the physician with the opportunity to begin treatment as soon as possible, including prenatally. In the case where such screening has not been performed, and therefore the carrier status of the patient is not known, and where FD disease is part of the differential diagnosis, the present invention also provides a method for making the diagnosis genetically.

Many versions of conventional genetic screening tests are known in the art. Several are disclosed in detail in WO 91/02796 for cystic fibrosis, in U.S. Pat. No. 5,217,865 for Tay-Sachs disease, in U.S. Pat. No. 5,227,292 for neurofibromatosis and in WO 93/06244 for Goucher disease. Thus, in accordance with the state of the art regarding assays for such genetic disorders, several types of assays are conventionally prepared using the nucleotides, polypeptides and antibodies of the present invention. For example: the detection of mutations in specific DNA sequences, such as the FD gene, can be accomplished by a variety of methods including, but not limited to, restriction-fragment-length-polymorphism detection based on allele-specific restriction-endonuclease cleavage (Kan and Dozy Lancet ii:910-912 (1978)), hybridization with allele-specific oligonucleotide probes (Wallace et al. Nucl Acids Res 6:3543-3557 (1978)), including immobilized oligonucleotides (Saiki et al. PNAS USA 86:6230-6234 (1989)) or oligonucleotide arrays (Maskos and Southern Nucl Acids Res 21:2269-2270 (1993)), allele-specific PCR (Newton et al. Nucl Acids Res 17:2503-25 16 (1989)), mismatch-repair detection (MRD) (Faham and Cox Genome Res 5:474-482 (1995)), binding of MutS protein (Wagner et al. Nucl Acids Res 23:3944-3948 (1995), denaturing-gradient gel electrophoresis (DGGE) (Fisher and Lerman et al. PNAS USA 80:1579-1583 (1983)), single-strand-conformation-polymorphism detection (Orita et al. Genomics 5:874-879 (1983)), RNAase cleavage at mismatched base-pairs (Myers et al. Science 230:1242 (1985)), chemical (Cotton et al. PNAS USA 8:4397-4401 (1988)) or enzymatic (Youil et al. PNAS USA 92:87-91 (1995)) cleavage of heteroduplex DNA, methods based on allele specific primer extension (Syvanen et al. Genomics 8:684-692 (1990)), genetic bit analysis (GBA) (Nikiforov et al. Nuci Acids Res 22:4167-4175 (1994)), the oligonucleotide-ligation assay (OLA) (Landegren et al. Science 241:1077 (1988)), the allele-specific ligation chain reaction (LCR) (Barrany PNAS USA 88:189-193 (1991)), gap-LCR (Abravaya et al. Nucl Acids Res 23:675-682 (1995)), and radioactive and/or fluorescent DNA sequencing using standard procedures well known in the art.

As will be appreciated, the mutation analysis may also be performed on samples of RNA by reverse transcription into cDNA therefrom. Furthermore, mutations may also be detected at the protein level using, for example, antibodies specific for the mutant and normal FD protein, respectively. It may also be possible to base an FD mutation assay on altered cellular or subcellular localization of the mutant form of the FD protein.

2. Antibodies

Antibodies can also be used for the screening of the presence of the FD gene, the mutant FD gene, and the protein products therefrom. In addition, antibodies are useful in a variety of other contexts in accordance with this invention. As will be appreciated, antibodies can be raised against various epitopes of the FD protein. Such antibodies can be utilized for the diagnosis of FD and, in certain applications, targeting of affected tissues.

For example, antibodies can be used to detect truncated FD protein in neuronal cells, the detection of which indicates that an individual possesses a mutation in the IKBKAP gene.

Thus, in accordance with another aspect of the present invention a kit is provided that is suitable for use in screening and assaying for the presence of the FD gene by an immunoassay through use of an antibody which specifically binds to a gene product of the FD gene in combination with a reagent for detecting the binding of the antibody to the gene product.

Antibodies raised in accordance with the invention can also be utilized to provide extensive information on the characteristics of the protein and of the disease process and other valuable information which includes but is not limited to:

1. Antibodies can be used for the immunostaining of cells and tissues to determine the precise localization of the FD protein. Immunofluorescence and immuno-electron microscopy techniques which are well known in the art can be used for this purpose. Defects in the FD gene or in other genes which cause an altered localization of the FD protein are expected to be localizable by this method.

2. Antibodies to distinct isoforms of the FD protein (i.e., wild-type or mutant-specific antibodies) can be raised and used to detect the presence or absence of the wild-type or mutant gene products by immunoblotting (Western blotting) or other immunostaining methods. Such antibodies can also be utilized for therapeutic applications where, for example, binding to a mutant form of the FD protein reduces the consequences of the mutation.

3. Antibodies can also be used as tools for affinity purification of FD protein. Methods such as immunoprecipitation or column chromatography using immobilized antibodies are well known in the art and are further described in Section (II)(B)(3), entitled "Protein Purification" herein.

4. Immunoprecipitation with specific antibodies is useful in characterizing the biochemical properties of the FD protein. Modifications of the FD protein (i.e., phosphorylation, glycosylation, ubiquitization, and the like) can be detected through use of this method. Immunoprecipitation and Western blotting are also useful for the identification of associating molecules that may be involved in the mammalian elongation complex.

5. Antibodies can also be utilized in connection with the isolation and characterization of tissues and cells which express FD protein. For example, FD protein expressing cells can be isolated from peripheral blood, bone marrow, liver, and other tissues, or from cultured cells by fluorescence activated cell sorting (FACS) Harlow et al., eds., Antibodies: A Laboratory Manual, pp. 394-395, Cold Spring Harbor Press, N.Y. (1988). Cells can be mixed with antibodies (primary antibodies) with or without conjugated dyes. If nonconjugated antibodies are used, a second dye-conjugated antibody (secondary antibody) which binds to the primary antibody can be added. This process allows the specific staining of cells or tissues which express the FD protein.

Antibodies against the FD protein are prepared by several methods which include, but are not limited to:

1. The potentially immunogenic domains of the protein are predicted from hydropathy and surface probability profiles. Then oligopeptides which span the predicted immunogenic sites are chemically synthesized. These oligopeptides can also be designed to contain the specific mutant amino acids to allow the detection of and discrimination between the mutant versus wild-type gene products. Rabbits or other animals are immunized with the synthesized oligopeptides coupled to a carrier such as KLH to produce anti-FD protein polyclonal antibodies. Alternatively, monoclonal antibodies can be produced against the synthesized oligopeptides using conventional techniques that are well known in the art Harlow et al., eds., Antibodies: A Laboratory Manual, pp. 151-154, Cold Spring Harbor Press, N.Y. (1988). Both in vivo and in vitro immunization techniques can be used. For therapeutic applications, "humanized" monoclonal antibodies having human constant and variable regions are often preferred so as to minimize the immune response of a patient against the antibody. Such antibodies can be generated by immunizing transgenic animals which contain human immunoglobulin genes. See Jakobovits et al. Ann NY Acad Sci 764:525-535 (1995).

2. Antibodies can also be raised against expressed FD protein products from cells. Such expression products can include the full length expression product or parts or fragments thereof. Expression can be accomplished using conventional expression systems, such as bacterial, baculovirus, yeast, mammalian, and other overexpression systems using conventional recombinant DNA techniques. The proteins can be expressed as fusion proteins with a histidine tag, glutathione-S-transferase, or other moieties, or as nonfused proteins. Expressed proteins can be purified using conventional protein purification methods or affinity purification methods that are well known in the art. Purified proteins are used as immunogens to generate polyclonal or monoclonal antibodies using methods similar to those described above for the generation of antipeptide antibodies.

In each of the techniques described above, once hybridoma cell lines are prepared, monoclonal antibodies can be made through conventional techniques of, for example, priming mice with pristane and interperitoneally injecting such mice with the hybrid cells to enable harvesting of the monoclonal antibodies from ascites fluid.

In connection with synthetic and semi-synthetic antibodies, such terms are intended to cover antibody fragments, isotype switched antibodies, humanized antibodies (mouse-human, human-mouse, and the like), hybrids, antibodies having plural specificities, fully synthetic antibody-like molecules, and the like.

3. Expression Systems

Expression systems for the FD gene product allow for the study of the function of the FD gene product, in either normal or wild-type form and/or mutated form. Such analyses are useful in providing insight into the disease causing process that is derived from mutations in the gene.

"Expression systems" refer to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

In general terms, the production of a recombinant form of FD gene product typically involves the following:

First a DNA encoding the mature (used here to include all normal and mutant forms of the proteins) protein, the preprotein, or a fusion of the FD protein to an additional sequence cleavable under controlled conditions such as treatment with peptidase to give an active protein, is obtained. If the sequence is uninterrupted by introns it is suitable for expression in any host. If there are introns, expression is obtainable in mammalian or other eukaryotic systems capable of processing them. This sequence should be in excisable and recoverable form. The excised or recovered coding sequence is then placed in operable linkage with suitable control sequences in an expression vector. The construct is used to transform a suitable host, and the transformed host is cultured under selective conditions to effect the production of the recombinant FD protein. Optionally the FD protein is isolated from the medium or from the cells and purified as described in Section entitled "Protein Purification".

Each of the foregoing steps can be done in a variety of ways. For example, the desired coding sequences can be obtained by preparing suitable cDNA from cellular mRNA and manipulating the cDNA to obtain the complete sequence. Alternatively, genomic fragments may be obtained and used directly in appropriate hosts. The construction of expression vectors operable in a variety of hosts are made using appropriate replicons and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene. Generally, prokaryotic, yeast, insect, or mammalian cells are presently useful as hosts. Prokaryotic hosts are in general the most efficient and convenient for the production of recombinant proteins. However, eukaryotic cells, and, in particular, yeast and mammalian cells, are often preferable because of their processing capacity and post-translational processing of human proteins.

Prokaryotes most frequently are represented by various strains of *E. coli*. However, other microbial strains may also be used, such as *Bacillus subtilis* and various species of Pseudomonas or other bacterial strains. In such prokaryotic systems, plasmid or bacteriophage vectors which contain origins of replication and control sequences compatible with the host are used. A wide variety of vectors for many prokaryotes are known (Maniatis et al. Molecular Cloning: A Laboratory Manual pp. 1.3-1.11, 2.3-2.125, 3.2-3.48, 2-4.64 (Cold Spring Harbor Laboratory, Cold Spring Harbor, N.Y. (1982)); Sambrook et al. Molecular Cloning: A Laboratory Manual pp. 1-54 (Cold Spring Harbor Laboratory, Cold Spring Harbor, N.Y. (1989)); Meth. Enzymology 68: 357-375 (1979); 101: 307-325 (1983); 152: 673-864 (1987) (Academic Press, Orlando, Fla. Pouwells et al. Cloning Vectors: A Laboratory Manual (Elsevier, Amsterdam (1987))). Commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems, the tryptophan (trp) promoter system and the lambda derived PL promoter and N-gene ribosome binding, site, which has become useful as a portable control cassette (U.S. Pat. No. 4,711,845). However, any available promoter system compatible with prokaryotes can be used (Sambrook et al. supra. (1989); Meth. Enzymology supra. (1979, 1983, 1987); John et al. Gene 61: 207-215 (1987).

In addition to bacteria, eukaryotic microbes, such as yeast, may also be used as hosts. Laboratory strain *Saccharomyces cerevisiae* or Baker's yeast, is most often used although other strains are commonly available.

Vectors employing the 2 micron origin of replication and other plasmid vectors suitable for yeast expression are known (Sambrook et al. supra. (1989); Meth. Enzymology supra. (1979, 1983, 1987); John et al. supra. (1987). Control sequences for yeast vectors include promoters for the synthesis of glycolytic enzymes. Additional promoters known in the art include the promoters for 3-phosphoglycerate kinase, and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization. See Sambrook et al. supra. (1989); Meth. Enzymology supra. John et al. supra. (1987). It is also believed that terminator sequences at the 3' end of the coding sequences are desirable. Such terminators are found in the 3' untranslated region following the coding sequences in yeast-derived genes. Many of the useful vectors contain control sequences derived from the enolase gene containing plasmid peno46 or the LEU2 gene obtained from Yep13, however, any vector containing a yeast compatible promoter, origin of replication, and other control sequences is suitable (Sambrook et al. supra. (1989); Meth. Enzymology supra. (1979, 1983, 1987); John et al. supra.

It is also, of course, possible to express genes encoding polypeptides in eukaryotic host cell cultures derived from multicellular organisms (Kruse and Patterson Tissue Culture pp. 475-500 (Academic Press, Orlando (1973)); Meth. Enzymology 68: 357-375 (1979); Freshney Culture of Animal Cells; A Manual of Basic Techniques pp. 329-334 (2d ed., Alan R. Liss, N.Y. (1987))). Useful host cell lines include murine myelomas N51, VERO and HeT cells, SF9 or other insect cell lines, and Chinese hamster ovary (CHO) cells. Expression vectors for such cells ordinarily include promoters and control sequences compatible with mammalian cells such as, for example, the commonly used early and later promoters from Simian Virus 40 (SV 40), or other viral promoters such as those from polyoma, adenovirus 2, bovine papilloma virus, or avian sarcoma viruses, herpes virus family (such as cytomegalovirus, herpes simplex virus, or Epstein-Barr virus), or immunoglobulin promoters and heat shock promoters (Sambrook et al. supra. pp. 16.3-16.74 (1989); Meth. Enzymology 152: 684-704 (1987); John et al. supra. In addition, regulated promoters, such as metallothionine (i.e., MT-1 and MT-2), glucocorticoid, or antibiotic gene "switches" can be used.

General aspects of mammalian cell host system transformations have been described by Axel (U.S. Pat. No. 4,399,216). Plant cells are also now available as hosts, and control sequences compatible with plant cells such as the nopaline synthase promoter and polyadenylation signal sequences are available (Pouwells et al. supra. (1987); Meth Enzymology 118: 627-639(Academic Press, Orlando (1986); Gelvin et al. J. Bact. 172: 1600-1608.

Depending on the host cell used, transformation is done using standard techniques appropriate to such cells (Sambrook et al. supra. pp. 16.30-16.5 (1989); Meth. Enzymology supra 68:357-375 (1979); 101: 307-325 (1983); 152: 673-864 (1987). U.S. Pat. No. 4,399,216; Meth Enzymology supra 118: 627-639 (1986); Gelvin et al. J. Bact. 172: 1600-1608 (1990). Such techniques include, without limitation, calcium treatment employing calcium chloride for prokaryotes or other cells which contain substantial cell wall barriers; infection with Agrobacterium tumefaciens for certain plant cells; calcium phosphate precipitation, DEAE, lipid transfection systems (such as LIPOFECTIN.™ and LIPOFECTAMINE.™), and electroporation methods for mammalian cells without cell walls, and, microprojectile bombardment for many cells including, plant cells. In addition, DNA may be delivered by viral delivery systems such as retroviruses or the herpes family, adenoviruses, baculoviruses, or semliki forest virus, as appropriate for the species of cell line chosen.

C. Therapeutics

Identification of the FD gene and its gene product also has therapeutic implications. Indeed, one of the major aims of this invention is the development of therapies to circumvent or overcome the defect leading to FD disease. Envisioned are pharmacological, protein replacement, antibody therapy, and gene therapy approaches. In addition the development of animal models useful for developing therapies and for understanding the molecular mechanisms of FD disease are envisioned.

1. Pharmacological

In the pharmacological approach, drugs which circumvent or overcome the defective FD gene function are sought. In this approach, modulation of FD gene function can be accomplished by agents or drugs which are designed to interact with different aspects of the FD protein structure or function.

Efficacy of a drug or agent, can be identified in a screening program in which modulation is monitored in vitro cell systems. Indeed, the present invention provides for host cell systems which express various mutant FD proteis (especially the T-C and G-C mutations noted in this application) and are suited for use as primary screening systems.

In vivo testing of FD disease-modifying compounds is also required as a confirmation of activity observed in the in vitro assays. Animal models of FD disease are envisioned and discussed in the section entitled "Animal Models", below, in the present application.

Drugs can be designed to modulate FD gene and FD protein activity from knowledge of the structure and function correlations of FD protein and from knowledge of the specific defect in various FD mutant proteins. For this, rational drug design by use of X-ray crystallography, computer-aided molecular modeling (CAMM), quantitative or qualitative structure-activity relationship (QSAR), and similar technologies can further focus drug discovery efforts. Rational design allows prediction of protein or synthetic structures which can interact with and modify the FD protein activity. Such structures may be synthesized chemically or expressed in biological systems. This approach has been reviewed in Capsey et al., Genetically Engineered Human Therapeutic Drugs, Stockton Press, New York (1988). Further, combinatorial libraries can be designed, synthesized and used in screening programs.

The present invention also envisions that the treatment of FD disease can take the form of modulation of another protein or step in the pathway in which the FD gene or its protein product participates in order to correct the physiological abnormality.

In order to administer therapeutic agents based on, or derived from, the present invention, it will be appreciated that suitable carriers, excipients, and other agents may be incorporated into the formulations to provide improved transfer, delivery, tolerance, and the like.

A multitude of appropriate formulations can be found in the formulary known to all pharmaceutical chemists: Remington's Pharmaceutical Sciences, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

Any of the foregoing formulations may be appropriate in treatments and therapies in accordance with the present invention, provided that the active agent in the formulation is not inactivated by the formulation and the formulation is physiologically compatible.

2. Protein Replacement Therapy

The present invention also relates to the use of polypeptide or protein replacement therapy for those individuals determined to have a defective FD gene. Treatment of FD disease could be performed by replacing the defective FD protein with normal protein or its functional equivalent in therapeutic amounts.

FD polypeptide can be prepared for therapy by any of several conventional procedures. First, FD protein can be produced by cloning the FD cDNA into an appropriate expression vector, expressing the FD gene product from this vector in an in vitro expression system (cell-free or cell-based) and isolating the FD protein from the medium or cells of the expression system. General expression vectors and systems are well known in the art. In addition, the invention envisions the potential need to express a stable form of the FD protein in order to obtain high yields and obtain a form readily amenable to intravenous administration. Stable high yield expression of proteins have been achieved through systems utilizing lipid-linked forms of proteins as described in Wettstein et al. J Exp Med 17:4219-228 (1991) and Lin et al. Science 249:677-679(1990).

FD protein can be prepared synthetically. Alternatively, the FD protein can be prepared from total protein samples by affinity chromatography. Sources would include tissues expressing normal FD protein, in vitro systems (outlined above), or synthetic materials. The affinity matrix would consist of antibodies (polyclonal or monoclonal) coupled to an inert matrix. In addition, various ligands which specifically interact with the FD protein could be immobilized on an inert matrix. General methods for preparation and use of affinity matrices are well known in the art.

Protein replacement therapy requires that FD protein be administered in an appropriate formulation. The FD protein can be formulated in conventional ways standard to the art for the administration of protein substances. Delivery may require packaging in lipid-containing vesicles (such as LIPOFECTIN.™ or other cationic or anionic lipid or certain surfactant proteins) that facilitate incorporation into the cell membrane. The FD protein formulations can be delivered to affected tissues by different methods depending on the affected tissue.

3. Gene Therapy

Gene therapy utilizing recombinant DNA technology to deliver the normal form, of the FD gene into patient cells or vectors which will supply the patient with gene product in vivo is also contemplated within the scope of the present invention. In gene therapy of FD disease, a normal version of the FD gene is delivered to affected tissue(s) in a form and amount such that the correct gene is expressed and will prepare sufficient quantities of FD protein to reverse the effects of the mutated FD gene. Current approaches to gene therapy include viral vectors, cell-based delivery systems and delivery agents. Further, ex vivo gene therapy could also be useful. In ex vivo gene therapy, cells (either autologous or otherwise) are transfected with the normal FD gene or a portion thereof and implanted or otherwise delivered into the patient. Such cells thereafter express the normal FD gene product in vivo and would be expected to assist a patient with FD disease in avoiding iron overload normally associated with FD disease. Ex vivo gene therapy is described in U.S. Pat. No. 5,399,346 to Anderson et al., the disclosure of which is hereby incorporated by reference in its entirety. Approaches to gene therapy are discussed below:

a. Viral Vectors

Retroviruses are often considered the preferred vector for somatic gene therapy. They provide high efficiency infection, stable integration and stable expression (Friedman, T. Progress Toward Human Gene Therapy. Science 244:1275 (1989)). The full length FD gene cDNA can be cloned into a retroviral vector driven by its endogenous promoter or from the retroviral LTR. Delivery of the virus could be accomplished by direct implantation of virus directly into the affected tissue.

Other delivery systems which can be utilized include adenovirus, adenoassociated virus (AAV), vaccinia virus, bovine papilloma virus or members of the herpes virus group such as Epstein-Barr virus. Viruses can be, and preferably are, replication deficient.

b. Non-viral Gene Transfer

Other methods of inserting the FD gene into the appropriate tissues may also be productive. Many of these agents, however, are of lower efficiency than viral vectors and would potentially require infection in vitro, selection of transfectants, and reimplantation. This would include calcium phosphate, DEAE dextran, electroporation, and protoplast fusion. A particularly attractive idea is the use of liposomes (i.e., LIPOFECTIN.™), which might be possible to carry out in vivo. Synthetic cationic lipids and DNA conjugates also appear to show some promise and may increase the efficiency and ease of carrying out this approach.

4. Animal Models

The generation of a mouse or other animal model of FD disease is important for both an understanding the biology of the disease but also for testing of potential therapies.

The present invention envisions the creation of an animal model of FD disease by introduction of the FD disease causing mutations in a number of species including mice, rats, pigs, and primates.

Techniques for specifically inactivating or mutating genes by homologous recombination in embryonic stem cells (ES cells) have been described (Capecci Science 244:1288 (1989)). Animals with the inactivated homologous FD gene can then be used to introduce the mutant or normal human FD gene or for introduction of the homologous gene to that species and containing the T-C, G-C or other FD disease-causing mutations. Methods for these transgenic procedures are well known to those versed in the art and have been described by Murphy and Carter, Curr. Opin. Cell Biol. 4:273-279(1992)

ILLUSTRATIVE EXAMPLES

The following examples are provided to illustrate certain aspects of the present invention and not intended as limiting the subject matter thereof.

Example 1

Identification of the IKBKAP gene and the mutations associated with FD were obtained as follows:

Patient Samples

Blood samples were collected from two major sources, the Dysautonomia Diagnostic and Treatment Center at New York University Medical Center and the Israeli Center for Familial Dysautonomia at Hadassah University Hospital, with approval from the institutional review boards at these institutions, Massachusetts General Hospital and Harvard Medical School. Either F. A. or C. M. diagnosed all patients using established criteria. Epstein Barr virus transformed lymphoblast lines using standard conditions. Fibroblast cell lines were obtained from the Coriell Cell Repositories, Camden, N.J. RNA isolated from post-mortem FD brain was obtained from the Dysautonomia Diagnostic and Treatment Center at NYU. Genomic DNA, total RNA, and mRNA were prepared using commercial kits (Invitrogen and Molecular Research Center, Inc.). Cytoplasmic protein was extracted from lymphoblasts as previously described (Krappmann et al. 2000).

Identification of IKBKAP and Mutation Analysis

Exon trapping experiments of cosmids from a physical map of the candidate region yielded 5 exons that were used to screen a human frontal cortex cDNA library. Several cDNA clones were isolated and assembled into a novel transcript encoding a 1332 AA protein that was later identified as IKBKAP (Cohen et al. 1998). The complete 5.9 kb cDNA sequence of IKBKAP has been submitted to GenBank under accession number AF153419. In order to screen for mutations in FD patients, total lymphoblast RNA was reverse transcribed and overlapping sections of IKBKAP were amplified by PCR and sequenced. Evaluation of the splicing defect was performed using the following primers: 18F: GCCAGT-GTTTTTGCCTGAG (SEQ ID NO: 82); 19F: CGGATTGT-CACTGTTGTGC (SEQ ID NO: 83); 23R: GACTGCTCT-CATAGCATCGC (SEQ ID NO: 84) (FIG. 1).

DNA Sequencing

Sequencing was performed using the AmpliCycle sequencing kit (Applied Biosystems) or on an ABI 377 automated DNA sequencer using the BigDye terminator cycle sequencing kit (Applied Biosystems). The control sequence of the candidate region was obtained by constructing subclone libraries from BACs and sequencing using vector specific primers. The FD sequence was generated by sequencing cosmids from a patient homozygous for the major FD haplotype using sequence specific primers.

Expression Studies

Several human multiple tissue northern blots (Clontech) were hybridized using the following radioactively labeled probes: IKBKAP exon 2, IKBKAP exons 18/19/20, IKBKAP exon 23, and a 400 bp fragment of the IKBKAP 3'UTR immediately following the stop codon. Poly (A)$^+$RNA was isolated from patient and control lymphoblast lines, northern blotted, and hybridized using a probe representing the full coding sequence of IKBKAP. Cytoplasmic protein extracted from lymphoblast cell lines was western blotted and detected using ECL (Amersham) with an antibody raised against a peptide comprising the extreme carboxyl terminus (AA 1313-1332) of human IKAP, the protein encoded by IKBKAP (Krappmann et al. 2000).

To identify DYS, exon trapping and cDNA selection were used to clone and characterize all of the genes in the 471 kb candidate region: EPB41L8 (unpublished data) or EHM2 (Shimizu et al. 2000), C9ORF4 (Chadwick et al. 1999a), C9ORF5 (Chadwick et al. 2000), CTNNAL1 (Zhang et al.1998), a novel gene with homology to the glycine cleavage system H proteins (CG-8) (unpublished data), IKBKAP (Cohen et al. 1998), and ACTL7A and ACTL7B (Chadwick et al. 1999b). As FD is a recessive disorder, the a priori expectation for the mutation was inactivation of one of these genes. Consequently, each of these were screened for mutations by RT-PCR of patient lymphoblast RNA and direct sequencing of all coding regions. Although many SNPs were identified, there was no evidence for a homozygous inactivating mutation. Thus, it was concluded that the mutation would be found in non-coding sequence and the control genomic sequence of the entire 471 kb candidate region was generated using BACs from a physical map. Direct sequence prediction using GEN-SCAN and comprehensive searches of the public databases did not reveal any additional genes in the candidate region beyond those found by cloning methods. However, SNPs identified during sequence analysis enabled us to refine the haplotype analysis and narrow the candidate interval to 177 kb shared by the major haplotype and the previously described minor haplotype 1 (Blumenfeld et al. 1999). This reduced interval contains 5 genes, CTNNAL1, CG-8, IKBKAP, ACTL7A and ACTL7B, all previously screened by RT-PCR without yielding a coding sequence mutation. A cosmid library was constructed from a patient homozygous for the major haplotype, assembled the minimal coverage contig for the now reduced candidate interval, and generated the sequence of the mutant chromosome.

Comparison of the FD and control sequences revealed 152 differences (excluding simple sequence repeat markers), which include 26 variations in the length of $dT_n$ tracts, 1 VNTR, and 125 base pair changes. Each of the 125 base pair changes was tested in a panel of 50 individuals known to carry two non-FD chromosomes by segregation in FD families. Of the 125 changes tested, only 1 was unique to patients carrying the major FD haplotype. This T-C change is located at bp 6 of intron 20 in the IKBKAP gene depicted in FIG. 1, and is demonstrated in FIG. 2A. IKAP was originally identified as an IκB kinase (IKK) complex-associated protein that can bind both NF-κB inducing kinase (MK) and IKKs through separate domains and assemble them into an active kinase complex (Cohen et al. 1998). Recent work, however, has shown that IKAP is not associated with IKKs and plays no specific role in cytokine-induced NF-κB signaling (Krappmann et al. 2000). Rather, IKAP was shown to be part of a novel multi-protein complex hypothesized to play a role in general transcriptional regulation.

Figure 3A:
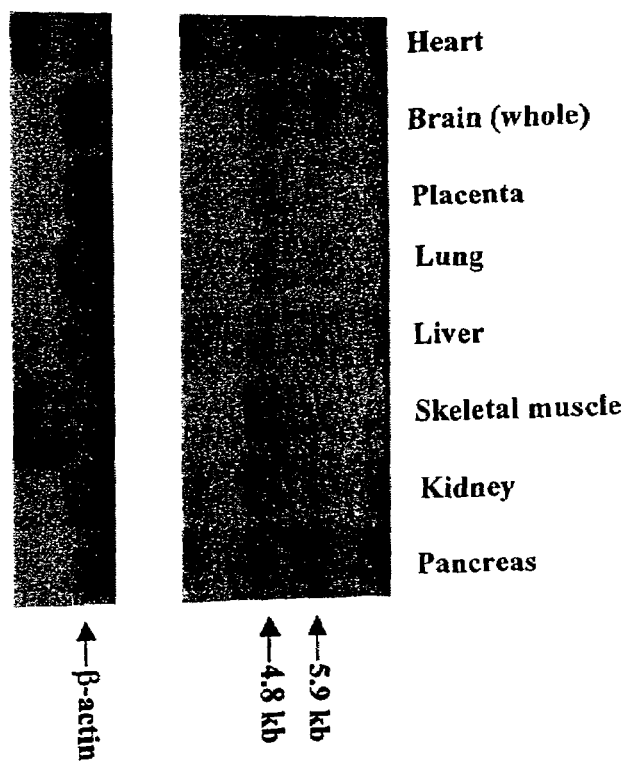
FIGS. 3A-3B. Northern blot analysis of IKBKAP.
Figure 3B:
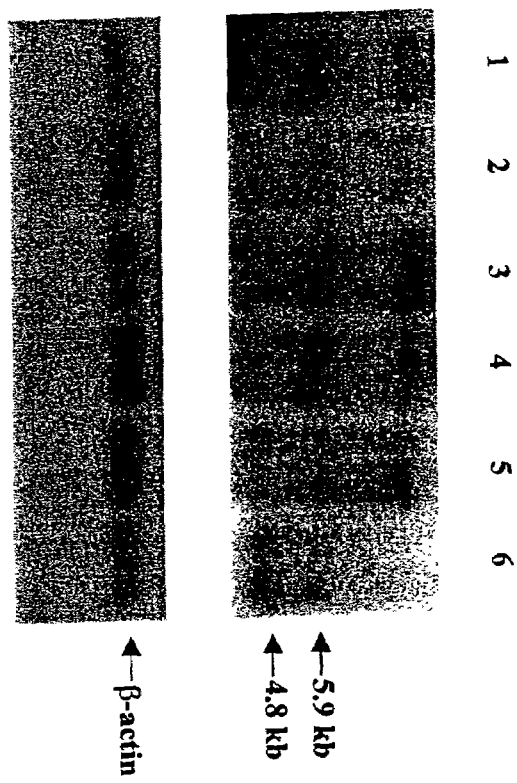

The IKBKAP gene contains 37 exons and encodes a 1332 amino acid protein. The full-length 5.9 kb cDNA (GenBank accession number AF153419) covers 68 kb of genomic sequence, with the start methionine encoded in exon 2. IKBKAP was previously assigned to chromosome 9q34 (GenBank accession number AF044195), but it clearly maps within the FD candidate region of 9q31. Northern analysis of IKBKAP revealed two mRNAs of 4.8 and 5.9 kb (FIGS. 3*a* and *b*). The wild-type 4.8 kb mRNA has been reported previously (Cohen et al. 1998), while the second 5.9 kb message differs only in the length of the 3' UTR and is predicted to encode an identical 150 kDa protein. As seen in FIG. 3*b*, the putative FD mutation does not eliminate expression of the IKBKAP mRNA in patient lymphoblasts.

Figure 4B:
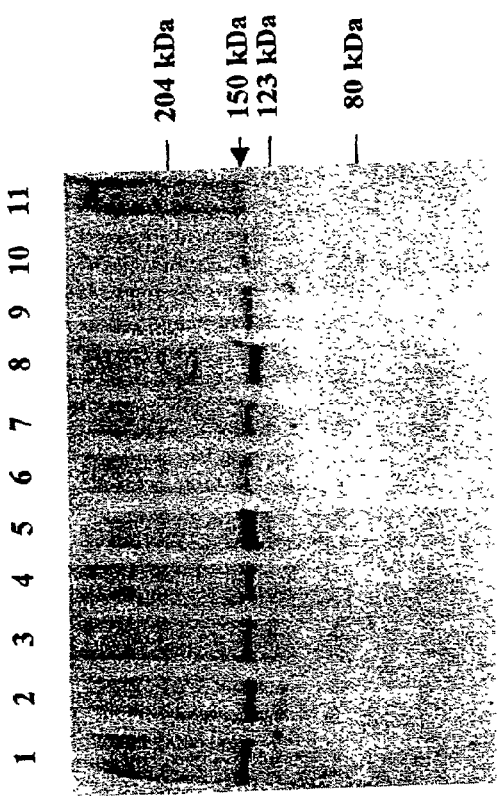
FIGS. 4A-4B: RT-PCR analysis of the exon 20 region of IKBKAP showing expression of the wild-type message and protein in patients.

A base pair change at position 6 of the splice donor site might be expected to result in skipping of exon 20 (74 bp), causing a frameshift and therefore producing a truncated protein. However, initial inspection of our RT-PCR experiments in patient lymphoblast RNA using primers located in exons 18 and 23 (FIG. 1) showed a normal length 500 bp fragment that contained exon 20 (FIG. 4A), indicating that patient lymphoblasts express normal IKBKAP message. The Western blot shown in FIG. 4B demonstrates that full-length IKAP protein is expressed in these patient lymphoblasts. However, as the antibody used was directed against the carboxyl-terminus of IKAP it would not be expected to detect any truncated protein should it be present. The presence of apparently normal IKAP in patient cells is at odds with the expectation of an inactivating mutation in this recessive disease.

In the absence of any evidence for a functional consequence of the intron 20 sequence change, the only alteration unique to FD chromosomes, additional genetic evidence was sought to support the view that it represents the FD mutation. The 658 FD chromosomes that carry the major haplotype all show the T-C change. In toto, 887 chromosomes have been tested that are definitively non-FD due to their failure to cause the disorder when present in individuals heterozygous for the major FD haplotype. None of these non-FD chromosomes exhibits the T-C mutation, strongly indicating that it is not a rare polymorphism. The frequency of the mutation in random AJ chromosomes was 14/1012 (gene frequency 1/72; carrier frequency 1/36), close to the expected carrier frequency of 1/32 (Maayan et al. 1987).

Figure 4A:
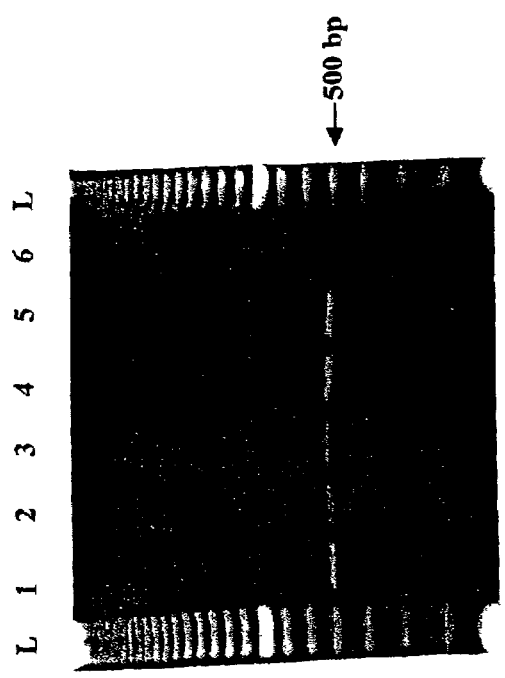
Figure 5:
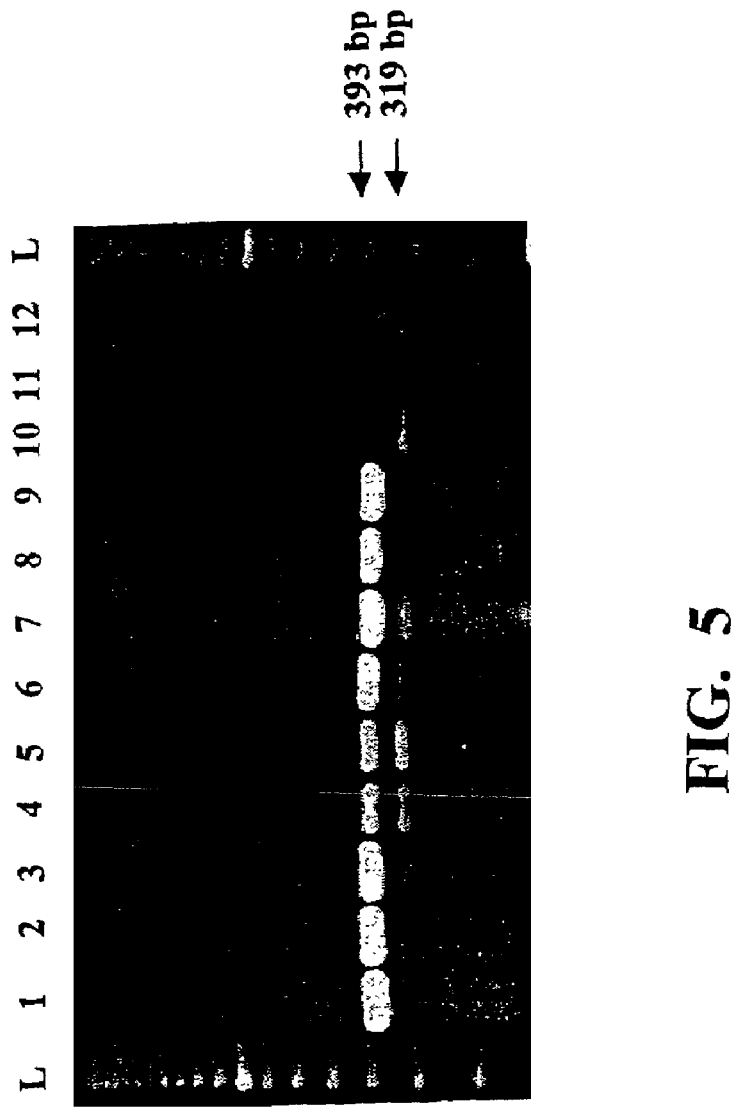
FIG. 5. RT-PCR analysis of the exon 20 region of IKBKAP showing variable expression of the mutant message in FD patients. The analysis was done using primers 19F (exon 19) and 23F (exon 23). Lanes 1 and 2, control fibroblasts; lanes 3, 4, and 5, FD fibroblasts homozygous for the major mutation; lanes 6 and 7 FD lymphoblasts homozygous for the major mutation, lanes 8 and 9 non-FD lymphoblasts, lane 10 FD patient brain stem, lane 11 FD patient temporal lobe (showing a faint 319 bp band and no 393 bp band), lane 12 water control. RT-PCR of control brain RNA (Clontech) showed only the 393 bp band (data not shown).
Figure 12:
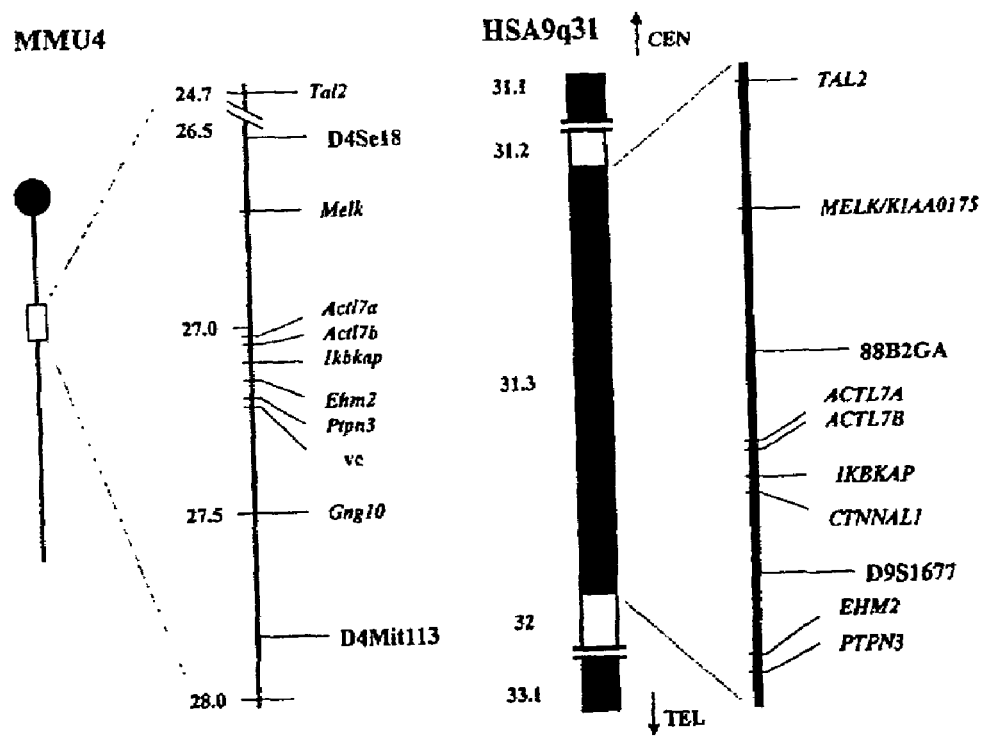
FIG. 12—Comparison of the synthetic regions of mouse chromosome 4 (MMU4) and human chromosome 9 (HSA9q31). This diagram on the left shows the location of Ikbkap in relation to mapped and genetic markers (boldface). Distances are given in centimorgans. The positions of the homologous genes that map to human chromosome 9q31 are shown on the right.

In view of the strong genetic evidence that this mutation must be pathogenic, it was postulated that its effect might be tissue-specific. RNA extracted from the brain stem and temporal lobe of a post-mortem FD brain sample was therefore examined. In contrast to FD lymphoblasts, RT-PCR of the FD brain tissue RNA using primers in exons 19 and 23 (expected to produce a normal product of 393 bp) revealed a 319 bp mutant product, indicating virtually complete absence of exon 20 from the IKBKAP mRNA (FIG. 5, lanes 10-11). As additional FD autopsy material could not be obtained, intensive analyses of additional lymphoblast and fibroblast cell lines were performed to determine whether exon-skipping could be detected. Fibroblast lines from homozygous FD patients yielded variable results. Some primary fibroblast lines displayed approximately equal expression of the mutant and wild-type mRNAs while others displayed primarily wild-type mRNA. In addition, extensive examination of additional patient lymphoblast lines indicated that the mutant message could sometimes be detected at low levels. An example of the variability seen in FD fibroblasts and the presence of the mutant message in some FD lymphoblasts is shown in FIG. 5. In fact, close re-examination of FIG. 4a shows a trace of the mutant band in 2 (lanes 1 and 2) of the 3 FD samples. The absence of exon 20 in the FD brain RNA and the preponderance of wild-type mRNA in fibroblasts and lymphoblasts indicate that the major FD mutation acts by altering splicing of IKBKAP in a tissue-specific manner.

Figure 2A:
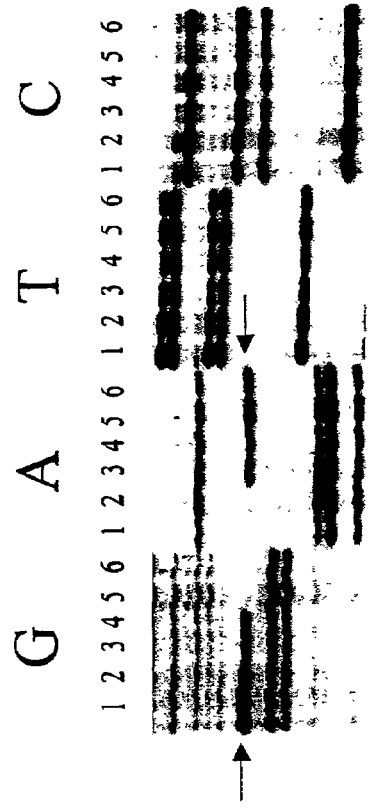
Figure 2B:
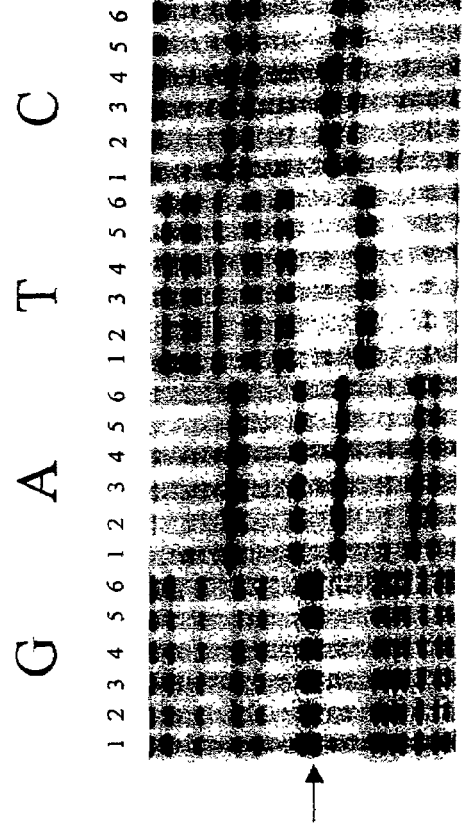

To identify the mutations associated with minor haplotypes 2 and 3, (Blumenfeld et al. 1999) we amplified each IKBKAP exon, including adjacent intron sequence, from genomic DNA. A single G-C change at bp 2397 (bp 73 of exon 19) that causes an arginine to proline missense mutation (R696P) was identified in all 4 patients with minor haplotype 2 (FIG. 2b). This was subsequently confirmed by RT-PCR in lymphoblast RNA as shown in FIG. 2c for a region that crosses the exon 19-20 border. The PCR product, generated from an FD patient who is a compound heterozygote with minor haplotype 2 and the major haplotype, clearly shows that RNA is being expressed equally from both alleles based on heterozygosity of the G-C point mutation in exon 19. However, the RNA from the major haplotype allele shows no evidence for skipping of exon 20 which would be expected to produce a mixture of exon 20 and 21 sequence beginning at the end of exon 19. This confirms our previous observation that lymphoblasts with the major FD mutation produce a predominance of normal IKBKAP transcript.

The R696P mutation is absent from 500 non-FD chromosomes, and it has been seen only once in 706 random AJ chromosomes in an individual who also carries the minor haplotype. This mutation is predicted to disrupt a potential threonine phosphorylation site at residue 699 identified by Netphos 2.0 (Blom et al. 1999), suggesting that it may affect regulation of IKAP. Interestingly, the presence of this minor mutation is associated with a relatively mild disease phenotype, suggesting that a partially functional IKAP protein may be expressed from this allele. No mutation has been identified for minor haplotype 3, which represents the only non-AJ putative FD chromosome.

Example 2

FD Diagnostic Assays

As discussed above, the allele-specific oligonucleotide (ASO) hybridization assay is highly effective for detecting single nucleotide changes in DNA and RNA, such as the T-C or G-C mutations or sequence variations, especially when used in conjunction with allele-specific PCR amplification. Thus, in accordance with the present invention, there is provided an assay kit to detect mutations in the FD gene through use of a PCR/ASO hybridization assay.

PCR Amplification

Genomic DNA samples are placed into a reaction vessel(s) with appropriate primers, nucleotides, buffers, and salts and subjected to PCR amplification.

Suitable genomic DNA-containing samples from patients can be readily obtained and the DNA extracted therefrom using conventional techniques. For example, DNA can be isolated and prepared in accordance with the method described in Dracopoli, N. et al. eds. Current Protocols in Human Genetics pp. 7.1.1-7.1.7 (J. Wiley & Sons, New York (1994)), the disclosure of which is hereby incorporated by reference in its entirety. Most typically, a blood sample, a buccal swab, a hair follicle preparation, or a nasal aspirate is used as a source of cells to provide the DNA.

Alternatively, RNA from an individual (i.e., freshly transcribed or messenger RNA) can be easily utilized in accordance with the present invention for the detection of the FD2 mutation. Total RNA from an individual can be isolated according to the procedure outlined in Sambrook, J. et al. Molecular Cloning—A Laboratory Manual pp. 7.3-7.76 (2nd Ed., Cold Spring Harbor Laboratory Press, New York (1989)) the disclosure of which is hereby incorporated by reference.

In a preferred embodiment, the DNA-containing sample is a blood sample from a patient being screened for FD.

In amplification, a solution containing the DNA sample (obtained either directly or through reverse transcription of RNA) is mixed with an aliquot of each of dATP, dCTP, dGTP and dTTP (i.e., Pharmacia LKB Biotechnology, N.J.), an aliquot of each of the DNA specific PCR primers, an aliquot of Taq polymerase (i.e., Promega, Wis.), and an aliquot of PCR buffer, including MgCl.sub.2 (i.e., Promega) to a final volume. Followed by pre-denaturation (i.e., at 95.degree. C. for 7 minutes), PCR is carried out in a DNA thermal cycler (i.e., Perkin-Elmer Cetus, Conn.) with repetitive cycles of annealing, extension, and denaturation. As will be appreciated, such steps can be modified to optimize the PCR amplification for any particular reaction, however, exemplary conditions utilized include denaturation at 95.degree. C. for 1 minute, annealing at 55.degree. C. for 1 minute, and extension at 72.degree. C. for 4 minutes, respectively, for 30 cycles. Further details of the PCR technique can be found in Erlich, "PCR Technology," Stockton Press (1989) and U.S. Pat. No. 4,683,202, the disclosure of which is incorporated herein by reference.

In a preferred embodiment, the amplification primers used for detecting the T-C mutation and the G-C mutation in the FD gene are 5'-GCCAGTGTTTTTGCCTGAG-3' (SEQ ID NO: 82)/5'-GACTGCTCTCATAGCATCGC-3' (SEQ ID NO: 84) and 5'-CGGATTGTCACTGTTGTGC-3' (SEQ ID NO: 83)/ 5'-GACTGCTCTCATAGCATCGC-3, (SEQ ID NO: 84) respectively.

Hybridization

Following PCR amplification, the PCR products are subjected to a hybridization assay using allele-specific oligonucleotides. In a preferred embodiment, the allele-specific oligonucleotides used to detect the mutatons in the FD gene are as follows:

5'-AAGTAAG(T/C)GCCATTG-3' (SEQ ID NO: 85) and
5'-GGTTCAC(G/C)GATTGTC (SEQ ID NO: 86).

Hybridization

In the ASO assay, when carried out in microtiter plates, for example, one well is used for the determination of the presence of the normal allele and a second well is used for the determination of the presence of the mutated allele. Thus, the results for an individual who is heterozygous for the T-C mutation (i.e. a carrier of FD) will show a signal in each of the wells, an individual who is homozygous for the T-C allele (i.e., affected with FD) will show a signal in only the C well, and an individual who does not have the FD mutation will show only one signal in the T well.

In another embodiment, a kit for detecting the FD mutation by ASO assay is provided. In the kit, amplification primers for DNA or RNA (or generally primers for amplifying a sequence of genomic DNA, reverse transcription products, complementary products) including the T-C mutated and normal alleles are provided. Allele-specific oligonucleotides are also preferably provided. The kit further includes separate reaction wells and reagents for detecting the presence of homozygosity or heterozygosity for the T-C mutation.

Within the same kit, or in separate kits, oligonucleotides for amplification and detection of other differences (such as the G-C mutation) can also be provided. If in the same kit as that used for detection of the T-C mutation, separate wells and reagents are provided, and homozygosity and heterozygosity can similarly be determined.

In another embodiment a kit combining other diseases (i.e., Canavan's).

Example 3

FD Diagnostic: Other Nucleotide Based Assays

As will be appreciated, a variety of other nucleotide based detection techniques are available for the detection of mutations in samples of RNA or DNA from patients. See, for example, the section, above, entitled "Nucleic Acid Based Screening." Any one or any combination of such techniques can be used in accordance with the invention for the design of a diagnostic device and method for the screening of samples of DNA or RNA for FD gene mutations in accordance with the invention, such as the mutations and sequence variants identified herein. Further, other techniques, currently available, or developed in the future, which allow for the specific detection of mutations and sequence variants in the FD gene are contemplated in accordance with the invention.

Through use of any such techniques, it will be appreciated that devices and methods can be readily developed by those of ordinary skill in art to rapidly and accurately screen for mutations and sequence variants in the FD gene in accordance with the invention.

Thus, in accordance with the invention, there is provided a nucleic acid based test for FD gene mutations and sequence variants which comprises providing a sample of a patient's DNA or RNA and assessing the DNA or RNA for the presence of one or more FD gene mutations or sequence variants.

Samples of patient DNA or RNA (or genomic, transcribed, reverse transcribed, and/or complementary sequences to the FD gene) can be readily obtained as described in Example 2. Through the identification and characterization of the FD gene as taught and disclosed in the present invention, one of ordinary skill in the art can readily identify the genomic, transcribed, reverse transcribed, and/or complementary sequences to the FD gene sequence in a sample and readily detect differences therein. Such differences in accordance with the present invention can be the T-C or G-C mutations or sequence variations identified and characterized in accordance herewith. Alternatively, other differences might similarly be detectable.

Kits for conducting and/or substantially automating the process of identification and detection of selected changes, as well as reagents utilized in connection therewith, are therefore envisioned in accordance with the invention of the present invention.

As discussed above, through knowledge of the gene-associated mutations responsible for FD disease, it is now possible to prepare transgenic animals as models of the FD disease. Such animals are useful in both understanding the mechanisms of FD disease as well as use in drug discovery efforts. The animals can be used in combination with cell-based or cell-free assays for drug screening programs.

Example 4

Creating Animal Models of FD

The first step in creating an animal model of FD is the identification and cloning of homologs of the IKBKAP gene in other species.

Isolation of Mouse cDNA Clones

The human IKBKAP sequence (GenBank Accession No. AF153419) was used to search the mouse expressed sequence tag database (dbEST) using the BLAST program (www.ncbi.nlm.nih.gov/BLAST). A single 5' EST from a mouse brain library (GenBank Association No. AU079160) was identified that showed marked similarity to the 5' end of IKBKAP. The corresponding cDNA clone, MNCB-3931, was obtained from the Japanese Collection of the Research Bioresource/National Institute of Infectious Disease. In addition, eight EST's that were similar to the 3' end of the ORF were found to belong to UniGene cluster Mn.46573 (www.ncbi.nlm.nih.gov/Unigene). Examination of this cluster yielded several poly (A+)-containing clones, and we obtained the clone UI-M-CG0p-bhb-g-07-0-U1 (GenBank Accession No. BE994893) from Research Genetics.

RT-PCR Analysis

RNA (1 ug/ml from BALB/c mouse brain was obtained commercially (Clontech). Oligo-dT 15 and random hexamer primers were annealed to the template at 6520 C. for 10 min in the presence of 1× first-strand buffer, 2 mM dNTP mix, and 4 mM DTT. The reaction mixture was incubated at 42° C. for 90 min after addition of Suuperscript TM II RT (200 U/ul) and Rnase inhibitor (80 U/ul) (GIBCO).

DNA Sequencing and Analysis

DNA sequencing was performed using the AmpliCycle sequencing kit (Applied Biosystems) for the 33 [P]-labeled dideoxynucleotide chain termination reaction, using the following conditions: 30 sec at 94° C., 30 sec at 60° C., and 30 sec at 72° C. for 30 cycles. The radioactively labeled sequence reaction product was denatured at 95° C. for 10 min and run on a denaturing 6% polyacrylamide gel for autoradiography. Basic sequencing manipulations and aligments were carried out using a program from Genetics Computer Group (GCC; Madison, Wis.). The cDNA sequence generated throughout the experiments were aligned and assembled into a 4799-bp cDNA named Ikbkap.

Isolation of Full-Length cDNA

To obtain the full-length cDNA sequence, PCR was performed on the mouse cDNA template using primers designed from the sequence of the 5'- and 3'-cDNA clones. The PCR conditions were as follows: 15 sec at 95° C., 30 sec at 54° C. to 60° C., and 3 min at 68° C. for 9 cycles; then 15 sec at 95° C., 30 sec at 54° C. to 60° C., and 3 min with increment of 5 sec for each succeeding cycle at 68 C. for 19 cycles, followed by 7 min at 72° C. The PCR products were electrophoresed on a 1% agarose gel stained with ethidium bromide and were cleaner using a Qiaquick PCR cleaning kit (Qiagen) in the preparation for cycle sequencing. Successive primers were designed in order to obtain the full-length Ikbkap sequence, which was deposited in GenBank under Accession No. AF367244.

Northern Blot Analysis

Expression of Ikbkap was examined using both mouse embryo and adult mouse multiple tissue Northern blots (Clontech). The blots were probed with a 1045-bp PCR fragment that contains exons 2 through 11, which was generated using primer 1 (5'-GGCGTCGTAGAAATTGC-3') (SEQ ID NO: 87) and primer 2 (5'-GTGGTGCTGAAGGGGCAGGC-3') (SEQ ID NO: 88). The probe was radiolabeled (Sambrook et al., 1989) and was hybridized according to the manufacturer's instructions.

Chromosome Mapping of the Mouse Ikbkap Gene

Several of the mouse Ikbkap ESTs belongned to the Unigene cluster Mn.46573, which has been mapped to chromosome 4 (UniSTS entry: 253051) between D4 Mit287 and D4 Mit197. To assess synteny between mouse chromosome 4 and human chromosome 9, we used several resources available at NCBI (www.nbei.nlm.nih.gov/Homology).

Determination of Genomic Structure of the Mouse Ikbkap

The 37 human IKBKAP exons were searched against the Celera database to obtain homologous mouse sequences. Approximately 130 mouse genomic fragments (500-700 bp) were obtained using the Celera Discovery System and Celera's associated database, and these fragements were assembled into seven contigs. In order to assemble the complete genomic sequence, we obtained six mouse bacterial artificial chromosomes (BACs) from Researcg Genetics after they screened an RPCI-23 mouse library using 4300 bp human probe that contained exon 2. To verify that these BAC clones contained the entire Tkbkap gene, we amplified fragments from the 5' and 3' ends of the gene, as well as a fragment from the 3' flanking gene Act17b (Slaugenhaupt et al., 2001). We designed primers at the ends of each of the seven contigs constructed from the Celera data and generated PCR products from the BACs. Subsequently, we sequenced and closed five of the gaps, with the resulting two contigs assembled and deposited to Celera (Accession No. CSN009).

Creating a Targeting Vector

After cloning and sequencing the mouse homolog of the human IKBKAP gene, a targeting vector can then be constructed from the mouse genomic DNA. The targeting vector would consist of two approximately 3 kb genomic fragments from the mouse FD gene as 5' and 3' homologous arms. These arms would be chosen to flank a region critical to the function of the FD gene product (for example, exon 20).

In place of exon 20, negative and positive selectable markers can be placed, for example, to abolish the activity of the FD gene. As a positive selectable marker a neo gene under control of phosphoglycerate kinase (pgk-1) promoter may be used and as a negative selectable marker the 5' arm of the vector can be flanked by a pgk-1 promoted herpes simplex thymidine kinase (HSV-TK) gene can be used.

The vector is then transfected into R1 ES cells and the transfectants are subjected to positive and negative selection (i.e., G418 and gancyclovir, respectively, where neo and HSV-TK are used). PCR is then used to screen for surviving colonies for the desired homologous recombination events. These are confirmed by Southern blot analysis.

Subsequently, several mutant clones are picked and injected into C57BL/6 blastocytes to produce high-percentage chimeric animals. The animals are then mated to C57BL/6 females. Heterozygous offspring are then mated to produce homozygous mutants. Such mutant offspring can then be tested for the FD gene mutation by Southern blot analysis. In addition, these animals are tested by RT-PCR to assess whether the targeted homologous recombination results in the ablation of the FD gene MRNA. These results are confirmed by Northern blot analysis and RNase protection assays.

Once established, the FD gene-/-mice can be studied for the development of FD-like disease and can also be utilized to examine which cells and tissue-types are involved in the FD disease process. The animals can also be used to introduce the mutant or normal FD gene or for the introduction of the homologous gene to that species (i.e., mouse) and containing the T-C or G-C mutations, or other disease causing mutations. Methods for the above-described transgenic procedures are well known to those versed in the art and are described in detail by Murphy and Carter supra (1993).

The techniques described above, can also be used to introduce the T-C or G-C mutations, or other homologous mutations in the animal, into the homologous animal gene. As will be appreciated, similar techniques to those described above, can be utilized for the creation of many transgenic animal lines.

To the extent that any reference (including books, articles, papers, patents, and patent applications) cited herein is not already incorporated by reference, they are hereby expressly incorporated by reference in their entirety.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A kit for assaying for the presence of a mutation associated with Familial Dysautonomia in an individual comprising primers 18F (SEQ ID NO:82) and 23R (SEQ ID NO:84) that are capable of amplifying a region of IKBKAP of sufficient size to detect a FD1 mutation at position 34,201 of SEQ ID NO:1 or a FD2 mutation at position 33,714 of SEQ ID NO:1, wherein said region amplified comprises a FD1 mutation at position 34,201 of SEQ ID NO:1 or a FD2 mutation at position 33,714 of SEQ ID NO:1.

2. The kit of claim 1, wherein the region amplified comprises position 2,397 of SEQ ID NO:2.

3. An isolated oligonucleotide probe consisting of at least 16 contiguous nucleotides of the portion of SEQ ID NO:1 from nucleotide 32,642 to nucleotide 36,846 which include position 34,201 of SEQ ID NO:1, or the complement thereof, said oligonucleotide probe being suitable for the detection of a FD1 mutation at position 34,201 of SEQ ID NO:1.

4. The oligonucleotide probe of claim 3 which is 16 nucleotides.

5. An isolated oligonucleotide probe consisting of at least 16 contiguous nucleotides of the portion of SEQ ID NO:1 from nucleotide 32,642 to nucleotide 36,846 which include position 34,201 of SEQ ID NO;1, or the complement thereof, except that the nucleotide which is at the same position as position 34,201 of SEQ ID NO:1 is a cytosine, or a guanine in said complement, said oligonucleotide probe being suitable for the detection of a FD1 mutation at position 34,201 of SEQ ID NO:1.

6. The oligonucleotide probe of claim 5 which is 16 nucleotides.

7. An isolated oligonucleotide probe consisting of at least 16 contiguous nucleotides of the portion of SEQ ID NO:1 from nucleotide 32,642 to nucleotide 36,846 which include position 33,714 of SEQ ID NO:1, or the complement thereof, except that the nucleotide which is at the same position as position 33,714 of SEQ ID NO:1 is a cytosine, or a guanine in said complement, said oligonucleotide probe being suitable for the detection of a FD2 mutation at position 33,714 of SEQ ID NO:1.

8. The oligonucleotide probe of claim 7 which is 16 nucleotides.

9. A kit for the detection of FD1 and FD2 mutations associated with Familial Dysautonomia in a sample from a human subject, said kit comprising two different isolated oligonucleotide probes as follows:

(1) an isolated oligonucleotide probe for the detection of the FD1 mutation selected from the group consisting of (a) through (d) below:

(a) an isolated oligonucleotide probe consisting of at least 16 contiguous nucleotides of the portion of SEQ ID NO:1 from nucleotide 32,642 to nucleotide 36,846 which include position 34,201 of SEQ ID NO:1 and being suitable for the detection of the FD1 mutation at position 34,201 of SEQ ID NO:1;

(b) the complement of an isolated oligonucleotide probe consisting of at least 16 contiguous nucleotides of the portion of SEQ ID NO:1 from nucleotide 32,642 to nucleotide 36,846 which include position 34,201 of SEQ ID NO:1 and being suitable for the detection of the FD1 mutation at position 34,201 of SEQ ID NO:1;

(c) an isolated oligonucleotide probe consisting of at least 16 contiguous nucleotides of the portion of SEQ ID NO:1 from nucleotide 32,642 to nucleotide 36,846 which include position 34,201 of SEQ ID NO:1 except that the nucleotide which is at the same position as position 34,201 of SEQ ID NO:1 is a cytosine and being suitable for the detection of the FD1 mutation at position 34,201 of SEQ ID NO:1; and (d) the complement of an isolated oligonucleotide probe consisting of at least 16 contiguous nucleotides of the portion of SEQ ID NO:1 from nucleotide 32,642 to nucleotide 36,846 which include position 34,201 of SEQ ID NO:1 except that the nucleotide which is at the same position as position 34,201 of SEQ ID NO:1 in the complement is a guanine and being suitable for the detection of the FD1 mutation the FD 1 mutation at position 34,201 of SEQ ID NO:1; and (2) an isolated oligonucleotide probe for the detection of the FD2 mutation selected from the group consisting of (e) through (h) below:
  (e) an isolated oligonucleotide probe consisting of at least 16 contiguous nucleotides of the portion of SEQ ID NO:1 from nucleotide 32,642 to nucleotide 36,846 which include position 33,714 of SEQ ID NO:1 and being suitable for the detection of the FD2 mutation at position 33,714 of SEQ ID NO:1;
  (f) the complement of an isolated oligonucleotide probe consisting of at least 16 contiguous nucleotides of the portion of SEQ ID NO:1 from nucleotide 32,642 to nucleotide 36,846 which include position 33,714 of SEQ ID NO:1 and being suitable for the detection of the FD2 mutation at position 33,714 of SEQ ID NO:1;
  (g) an isolated oligonucleotide probe consisting of at least 16 contiguous nucleotides of the portion of SEQ ID NO:1 from nucleotide 32,642 to nucleotide 36,846 which include position 33,714 of SEQ ID NO:1 except that the nucleotide which is at the same position as position 33,714 of SEQ ID NO:1 is a cytosine and being suitable for the detection of the FD2 mutation at position 33,714 of SEQ ID NO:1; and
  (h) the complement of an isolated oligonucleotide probe consisting of at least 16 contiguous nucleotides of the portion of SEQ ID NO:1 from nucleotide 32,642 to nucleotide 36,846 which include position 33,714 of SEQ ID NO:1 except that the nucleotide which is at the same position as position 33,714 of SEQ ID NO:1 in the complement is a guanine and being suitable for the detection of the FD2 mutation at position 33,714 of SEQ ID NO:1.

10. The kit of claim 9, wherein the isolated oligonucleotide probes are each 16 nucleotides.

* * * * *

SEQUENCE LISTING

<160> NUMBER OF SEQ ID NOS: 88

<210> SEQ ID NO 1
<211> LENGTH: 66479
<212> TYPE: DNA
<213> ORGANISM: Homo sapiens

<400> SEQUENCE: 1

| | | | | | |
|---|---|---|---|---|---|
| ccagtgctgc | ggctgcctag | ttgacgcacc | cattgagtcg | ctggcttctt | tgcagcgctt | 60 |
| cagcgttttc | ccctggaggg | cgcctccatc | cttggaggcc | tagtgccgtc | ggagagagag | 120 |
| cgggagccgc | ggacagagac | gcgtgcgcaa | ttcgagccg | actctgggtg | cggactgtgg | 180 |
| gagctgactc | tgggtagccg | gctgcgcgtg | gctgggagg | cgaggccgga | cgcacctctg | 240 |
| tttggggtc | ctcaggtaag | cgatccatcc | agggtagggg | cacgggagtg | gacctctccg | 300 |
| ccggcggtgt | ccgggtgaag | gagacccgga | gcctcctctg | cctgctgcgg | gccggggact | 360 |
| ggagtgcggg | ctgcaccacc | tctttcctag | agccttaaat | tcttttttgca | gccttgccac | 420 |
| ctgctccatc | gggggcgctg | ggaggcgcga | cagcccaggg | atgcctgctg | ccctccagc | 480 |
| cggacttaac | ccagcctctt | gattgcttgc | aggggttga | taataacgct | gaaagcgaga | 540 |
| gtattaattc | acgatggaag | gcggcggtta | atagaggctc | gggtgctgtg | gtgcgggtcc | 600 |
| tttctcgcgt | gtgagactt | tcgtggagg | tggtgtcctc | tgtgcttctc | catctaacgt | 660 |
| ggtgttttac | gtggctttct | ctcccgttaa | cgatgatctc | cgtggagaca | gtggctgagt | 720 |
| aatcttcaga | tcccagtact | tagcaagtgc | tcagtcggtg | ttggatgtag | gccacaaacc | 780 |
| ggatcgtaaa | gaattcaact | gtatattgac | agccacggaa | ctaatcaatg | aatagatccg | 840 |
| tatgaagagt | aagcaaaaag | gcagcaaaga | cagttttca | gcttgggac | atagagtaga | 900 |
| aatggtctgt | ccccaaatag | tgggaactgt | catttggggg | aagaatagca | agttctttgc | 960 |
| tttccaggtc | gcatttgatg | tgcatgtgag | acatgcttgt | gattctatca | ggaggttgaa | 1020 |
| aatgtgggtt | tagtggtaag | tttgggctaa | ttcagtcagg | gctaggcatt | taggcctaat | 1080 |
| cagcgtattg | gtgatctacc | tggtatatgt | aatcatgcat | gtgatgtcta | gccaagaggt | 1140 |
| ggatagtcga | aggagcaagg | gaagaaaatg | aagcagttat | caggaaatta | agagagaatc | 1200 |
| cacgattgac | ctttggtgtg | gagggatctt | tagcacattt | aagaactgcg | aagagtttga | 1260 |
| atcagtggag | gcaggaaggt | tggaggttgc | agatgtccaa | gaaagagtac | taataggcct | 1320 |
| aggtcctgtg | gcaatatgga | ggatattcct | ttcctagcct | ggaaagaagt | ggaggaagt | 1380 |
| cttcctccga | aagataagg | gaataaggct | gatgggtgtg | aaatttcaga | gaaactagtt | 1440 |
| ttgaggcgtt | tttatgatgt | ttaaagatga | aaaacgagca | ggcacggtgg | ctcaggcctg | 1500 |
| taatcccagc | actttgggag | gcagaggcgg | gtggatcact | tgaggttagg | agttcaagaa | 1560 |
| cagcctgggc | aacatggtga | aaccctgtct | ctactaaaaa | tacaaaaatt | aactgggcat | 1620 |
| ggtgccgggc | gcctgtaatc | ccagctactc | cggaggctga | ggcaggagaa | tcgcttgaac | 1680 |
| ccggaaggca | gatgttgcgg | tgagccgaga | tcgcgccatt | gcaccccagc | ctgggcaata | 1740 |
| agagcgaaac | tccgtctcaa | aaacaaaaa | aacctgcatg | atatgttaga | ggttcaagta | 1800 |
| atttctagca | gttcttgaat | ataattgtca | ccaaaactta | ctaaaatcat | tgtcttcctc | 1860 |
| acttccatca | tatataaact | tacctttctc | ttatcccaca | ttatatatta | tataattcct | 1920 |
| atgcacttg | acattatctt | ctgtgtacta | ttaggattga | ttcatctta | ttcttctat | 1980 |
| gtcatacata | tgtggggtgc | caagatgaga | gaagtctcct | tggattaaag | tgacaataag | 2040 |

-continued

```
accggtgtgg tccttgtaat tgctacccct aacataagtt agggacttac aatcataagc    2100
cttaaaggga tctgaatata ataaactagc acagtaacat tttttteccc tacttaggta    2160 atgttatgca tttaagcaag cctgattttg ccagaccaaa gtagatgtct tgtttagcac    2220
tcttttctca cgttttatat tgtcctggga aaagcctggc cagaagaaca aagttactgg    2280
aagtagttat gtcaggtcat cagggtcctt gaaatgttgg tcatcatttt gaagtaaatt    2340
gttgtcatgt cccagtattt tctcttcccc tttagaacag taaatgcttt tctatctttg    2400
atttcagttt ttttatgaat gtataaaacc agtttataaa tgaatagacc tggtgaatat    2460
taaagtcatt tcagattctc ttcaactgcc agtatataaa aatggatttt caaatagtgc    2520
taatcagtgg gatacccttt tgttttteet catgatttta taaagatgtc ctaatatgca    2580
aaaataaaat gtttccccat tcatttgttc tttcaacttt cccaaaggaa taactgatat    2640
tacatctttt ttgaagaaaa cattctaaag ttgagaatct tgcctctcct aaaaagaaca    2700
taaaataggt ttcagaattc ctaatttgta gaccataact gtatagagtg ggtcaggttg    2760
ctgctataat ccatacatgg gtgtgtactc agagaggtaa gtttttttett ttcttggtta    2820 ttctgattct gactaccact tcttcacccc ctgaatcatt tcatttaaat aaatatggtc    2880
atttatcact attaagctat ttattttttct cttagagatt aatgattcat caagggatag    2940
ttgtacttgt ctcgtgggaa tcacttcatc atgcgaaatc tgaaattatt tcggaccctg    3000
gagttcaggg atattcaagg tccagggaat cctcagtgct tctctctccg aactgaacag    3060
gggacggtgc tcattggttc agaacatggc ctgatagaag tagaccctgt tcaagagaa    3120 gtaagttact gatgtagaat gccagcatgt gggtatgacc cttgatttct cttcttccaa    3180
atttctttcc ccacatggtc tttcttttata tcttattgaa tttatatcct cccaaataaa    3240
catcttttgc ttcatatata tgccatgtta gacatagctt aaatcgtaat ccttctttaa    3300
ctctgctgct attttaacct aagtcagtag aactctgacc ttacttttttg agtgtgtgcc    3360 gtactttttta ccctctttgt catgcaaatt ctgtttataa gagtggtttt ttttttttttt    3420 tttttgagac ggagtctcgc tctgtcaccc aggctggagt gcagtggtgt gatcgtggct    3480
cactgcaagc tccgcctccc cgggttcaca ccattctcct gcctcagcct cccgagaagc    3540
tgggactaca ggcgcccgcc accgcgcccg gctaattttt tgtattttta gtagatgtgc    3600
ggtttcaccg tgttagccag gatggtcttg atctcctgac ctcgtgatcc gcctgcctca    3660
gcgcccggcc aagagtggtt tttaattggg aatgaacacg aaagttgccc atggagcttt    3720
ctaaaagttt gagcccacat ctcatgtcaa ctaaatcaga atctttagtg ttggctccta    3780
actatatgta ctttaaaaac ctctgtgggt tggttttgat atggtccctt gattatgttc    3840
ttctactaat acatttttagg cagttacatc ctttagtgcc ttttccccat actatagaaa    3900
tcttagaaaa gcatagctat tagcatcata ttttagtgga caattttaaa gagaccaggc    3960
ttattgtttt tgttttttgtg tttgtttggc aaaaaggtca cattacctat ttttcttgtt    4020
agagatgaca gagtagtgat atttctcaaa tgaaagtttg gattttcatc tagaaaaaat    4080
atttttgaaa gcttttatgt aataaaagaa gcattaaaaa gtatttctgg aaatgttatc    4140
aattattctt gaaagtagac tgggttaatt tgcttgtgtt tacttggtg aaaggtgaaa    4200 aatgaagttt ctttggtggc agaaggcttt ctcccagagg atggaagtgg ccgcattgtt    4260
ggtgttcagg acttgctgga tcaggagtct gtgtgtgtgg ccacagcctc tggagacgtc    4320
atactctgca gtctcagcac acaacaggta agtggaagac tccagtgagg ggggagtctc    4380
```

```
aagcatcctc aaataggtta cttgctattt gtggaagttt tcaaatcagt agccataata    4440
gttacacttt tgctaattaa ttttttgcatt atatatttct ttatttaaaa aattgttaac    4500
atggctttat ctatatgtta agattcttct aaaactgagt tttgtctgct gcatctatta    4560
atcagagtga tcagaatgtt ccaaatgaga atatatttttt ttaaaagtta aaactggcta    4620
ttcttatgtg gtgtagatca cctcttatca gaccctcatc ttgagttgca accttttgttt    4680 ctcaatttag gaagtctttg tttatctgac ttagattttc tgttatgaat gttgattggc    4740
taaatttaga gtccctgaag tctaggcact aaagtaaata cattgtcatt acctgcacat    4800
gtgatgactg ccagtagagc tagacttcaa gcaattgctt ctttctctac tttagtgtat    4860
agttgagttt ctgatttcta tcctcacctt cttaacagca agggtttcaa attacacttg    4920
gctgattctt taaatcttct tccattactt cattagttgt gatctcctta acattgatta    4980
tgtcacagaa gttagagtat tactaatagt aggataatga tagcagctta catttattaa    5040
ctatcatgtg cctggcactt tttaaagtgc ttttcatgca aatttattta atcttcacca    5100
tgaccttatg cagtaggttg ttgtttccta ttcttcagaa gaggcagtta aggcacagag    5160
tgcttaagta attagaccag ggtcacacag taatcaaatg gggtttgacc ctagcagtct    5220
aaatctggca cctctgctct taaccattcc atttagtaca atcataaacc tttacttgca    5280
gttcatggtg ggaaatatca aacttgtcat atacagcttg ttttttttttc gtatttgaaa    5340 gatagatgct tttactttcc aaacattttg tagcattgtt tcctggttac tgagctcttc    5400
cagtctattt atcttcattt aatggtgctg attctgccct ttagtggctt ctcaattgtc    5460
tgaaaggtag agcccactat tgtgccttat aagccccttt cactatctgt tccccacatt    5520 ccttttttagc ctcatccccc cattgttcct gtgtgtacgt aaaccttatg ttttagttgc    5580
agctgatttt taactgctct ttttttctggc tttgtgcctc tacactgtgt tttcttcctg    5640
gtctctcttt cctgtcctta ttaccactct ttgaaacacg tcagaaaaac ttttttctgga    5700 ctttgggcca cttgtcattc cctgtgctga gacgcatttt gctttccaga gatcttggtc    5760
attgctgtta tcctctgtag ggtcttcttt tatctcccctc gtgagacagc tctgggaaga    5820
aaaagatatt tatttctaat ccctgtgcct aataacaggt ctattctctt gatatccatt    5880
actgaagaaa tgtttgttga gtaagttctt gttttaattt ttaaatataa attttttaatt    5940 tttatgagta catagtaggt acatatattt atgggctaca tgagatgttc tgatacaggc    6000
atgcagtgca aaataaccac atcatggaga ataggatatc catcccatca agcgtttatc    6060
ctttgtgtta caaacaatcc aattacagtc ttttagttat tttaaaatgt gcaattactg    6120
ttgactgtag ttaccttgtt gtgctatcaa atagcaggtc ttatttattc tattttttttt    6180 tgtacctatt aaccatccca acttccctca gcccctcact acccttccca gcctctggta    6240
accatccttg tactctctgt gtccgtgagt tcaattgttt tgattttttag atcgcacaaa    6300 taagtgagaa catgtgatgt ttgtcttttt gtgtctggtt tatttcactt aatgtaatca    6360
tctccagttc catctatgtt gttgcagatg acaggatctt attctttttt tatggctgaa    6420
tagtactcca ttgtgtatag taccacaatt tctttatcca gtcatccatt gatggacact    6480
taggttgctt ccaaatctta gctattgtga acagagctgc aacaaacatg agagtgcaga    6540
tatctcttcc atatactgat gtcttttcgt tttgtttttt taattgtttt gattgaagtt    6600
gcagtcagtt tttactgaga tgctagtgtt tgaatctctc ttttcaattt tctctgtctc    6660
agctggagtg tgttgggagt gtagccagtg gtatctctgt tatgagttgg agtcctgacc    6720
aagagctggt gcttcttgcc acaggtaagc ttgttactgg tgcctcactg gcttttttaa    6780
```

```
aacattattc cagatgtctt acaggcttca tcagctttag gctgcttgaa tttcaaaaaa   6840
tttctttgaa ccagtataat accaattatg aaccagtata ataccaatta tgtatgtgtg   6900
tgtgtatata tatataaaac gtagagtgat ttttttttgg tgactgaagt tttgcctctt   6960
agtctatcat tataaaaagt tgtttcatgt aacttttaa gtctttggga gtaagaaaca    7020
aagtcataaa acttggggag gctgctaagt ccccagttag agttaaaaat gtcagcaata   7080
tgtattttaa cttattctaa gagttgctgt atggacacat tctaaaagcc cttcttgggt   7140
tctgttgctg ttttcccct taagtctca tcattccaga tgagtttagt aaaccagctc     7200
cactgatgac atttatattt agaggtatct tggggacaag gagtgttgaa gttagtggag   7260
gagggctttg tggacttta agttcaactg tacacacatt aatagctgag cataagcacc    7320
aggtgactta tctagggaaa gcttttggg gtttttgtc attgttgttt ttttaagtca     7380
aagcattttg gatgaattct gtctgctctg ttcagactaa ctccagctcc ttagcttaca   7440
gtgccatagg tacttaggaa tggcaaattt gttacatgaa aacaaaatca tttttgtttg   7500
tgtttctcta aggtcaacag accctgatta tgatgacaaa agattttgag ccaatcctgg   7560
agcagcagat ccatcaggat gattttggtg aaagtaagta tagctttgtg caatattttg   7620
tgacctacgt ttcttcccat ttttgaccat ttccttgtgc actaatagcc atgtcattag   7680
gccaaagaac tgtgaaagtt aaaccccag ctattaaatg tctattagcc cagttccttc    7740
agcccatccc aaatcttaaa aggcctactg atgcctctcc aggtctgagg gtttaaggtc   7800
acttagatag ttattaccca aaccctagga aagtcttagg ctgggctttc agtgaaaggg   7860
actgtacaag gtagtatttc tgggatacag ttttagggag aagaaaagaa gaaagatgga   7920
atagaaggct ggttttgtt actacgatta gatccaatct gcatttccat gggaacaatc    7980
agattatttt cttgctaaaa tctagccaag gtcatctggg cattaaggct gtgggggtat   8040
tgaagggcag tgcaggagaa gagagacgct tattaagcat aagctttggc catcttgaag   8100
tcacaaagta gctggcctga ttgaagaggg atggggaaga agatgttcca acttctgtta   8160
tggtctaact tcctgccttc ttgctccatc aactctgaga aatcatttag acaacttcta   8220
cccatttatt tacaaataat gtatttgttc agaaataatt ttggagggct gggcacagtg   8280
gctcatgcct gtaatcccag cacttttgga ggatgaggca ggaggattgc ttgagcccag   8340
gagtttgata ctagcctagg caacgtaggg agacccagca tctacaaaga atttaaaaat   8400
tagctgggct tggtggtatc agcacagtaa tgacatgatg tgcaggtact ggggtagcat   8460
aagggaagga aacgagtaac tagagaggga tgatttattt cccctaggag gccaacttga   8520
gctgagtctc agctgaattg gtgttgggta ggtgagggat aagggtgggg agtagtcagc   8580
tgaattggta ttgggcaggt gagggataag ggtttggagt agtcagctga attggtattg   8640
ggtaggtgag ggataagggt ggggaacagt ccaagcaagt gaatgtgtcc atttcaagtg   8700
tccatttcaa gggagggtta tttcatagaa acattgtggg ttactcaggg aactgtgagt   8760
aattcagcat tgctgaagtg gcagaatgtg agtgtagaat gaaataaatg gaacagattt   8820
gattgagttt gtagtaggga atatggacat tgagttatag ttgatcagcc attacaagtt   8880
ttgatgataa gaggtttaaa gagatttatt taatagaaag atggctcgtg atggcatatt   8940
tttgttgttt ttgtgtgtgg agagggaaga gatgagaggc agggtgatca ggtaggaggt   9000
tgctacagga atccagatga aagataagga aggtttgtgt ggggctagaa gcaggaatca   9060
ttcaggaaaa aacttgattc acaatgagga tgggagtaca ttttttagaa ttagctggga   9120
```

```
aactttttta gaatatatgt gcatgattcc ccttctgccc taggccagtt tgagaaatac    9180
caatttagaa agtgaaataa ataggctttg cgtatgtaag gtgaataaga aaaagttgag    9240
caggactcca gccagaacct caggtgttgg aataaagat gccagtaaca gggaagatgg     9300
agaagtgctg gtctgtaagg ggtgggtggt gagatctgtt ttggatttgt tgaaggacca    9360
tatgtgattg ccatgtggag tatgcaaata taaggctgaa gctcaggaga ggccagagct    9420
atggactgag agtagtgggt atgtaggaaa ttctgacagt tttgggaaca gatggactgt    9480
ctcagggagc agatgctgta caggaagagt ctagaatcca gggtggaact ctggggcatc    9540
cagctttgag gacagtcaga gagagagtaa cagcacacag tatactttgg gatgggaaag    9600
tgctctgggc ctggtgtttc ccactgactt tttcacacaa atcctaatgc agtaaatcaa    9660
aggaaatgta ggccaagtta agatcttagg tctcagaaat gtgtttctca gtacaaaaaa    9720
aaaaaaatca ttctatggag tgatgaatat ttttcctcta tcctggggtc agtagacttg    9780
ttctgaaaag ggctaggtca tgaatatgtt cagctttgca ggctgtatga tctgtgttgc    9840
agctgctcaa ttctaatgtt gaggtgtgaa agttatacat gatacataag cacatctatg    9900
ttccagtaaa cgtttgtttg taaaagcaga tgtaggctgt agttttgcaa atccctgctg    9960 taacccatc atttcttgtc ttccattgga aaagttctct ttcttcattc cttggtcctt     10020
aatctttctg tggaaacttg cagatagaag cctgggggtt tgcaccagga tagtcactac    10080
catttgtacg cagcagcaat tgaggtactg tagcacttgg atgtgagcag acaggaaatg    10140
gtcatatgga cccataattt ataggaattg caaacagccc tgcttcatca gaatcagaat    10200
caatggcagg aggaaagtat tgggtcctgg attaggtgat gttttcagga ccatctttat    10260
tgtgcttctt gcaaatggat cctacctcca ggaacagaag ggttgtgttg tttcagcaac    10320
tctgcctaat agtttatata agagaagtgt tacgatctag aaagaacccc agtcagcctg    10380
gaaggcagaa gacctgtgtt ctactttttg gctccaccat tagggagggt ctcaatctct    10440
aagtctatgt gaggagctgt tttgtgacct gcagcccctc tatcaccagt gagagcttgc    10500
aatcagaatt ttattcccag ttctcatctt ggggttttat gttccggaca tattttgtaa    10560
actctttatg tttcattctt cttacttata aggtgagggt gagatcgctg acttgtgtca    10620
tcaaagaaac ttggaatatg taagatggca gtaaaatgct ttccaaaata aggaagggca    10680
tttcaaattc ttcaaagtca ctgctgcata taatatgaaa tgggttttgt ttgtttgttt    10740
tgagatgggg gtctcgctgt gttacccagg ctagagagtg cagtagtaca atcagggctc    10800
actgcagcct tgaactcctg ggttcaagtg atcctcctac tttagtctct tgagtagctg    10860
ggaccacagg tgtgtgccat catgtccagc ttattttgta acttttttgt agagatgggt    10920
gtctccctat gttgcccagg ctggtctcga actcctggac tcaagtgatc ctcctgcctc    10980
agcctcccaa agtgttggga ctataggcat gagccaccat gcccagcctg aaacataggt    11040
ttctcaaata ttgactgctg gtcaatttat tgagaggcgt tagaggacct gagtaattgc    11100
caatgactaa cttcatgaag aatagcagtg aaactgtttt tgtttcattt catgtggctt    11160
attagttgtc ttgccaattg ttctgtaggc aagtttatca ctgttggatg gggtaggaag    11220
gagacacagt tccatggatc agaaggcaga caagcagctt tcagatgcaa aatggtaagt    11280
ttggtttgat ggataaaaag ccttgactgg aacaaatgta agtttgccac ccaccaggaa    11340
ctctttggtg tccacttaga tgccagtaat gaacagttct cttctgcttt agtaaaactg    11400
cctagaacct tcaggaaatg aatccctcta gaaagatcct ttttttcctt gttattgcca    11460
agttgctttg tgatttattt tcatagtagc aaataattat aaccaatatt catcacccag    11520
```

```
tttaaaaaat aaaacatcac agacaaagga aaccccctgt gtatcccgtc ccgatgtccc   11580
tccccttcct ctccagagag agctgccatc cttcattcac atgcatgttc tcatactttt   11640
cccatatatg tgtatattag atattttcct ttttctgttg gatgaaactc tttgttttcc   11700
ttacttctgg attggaaaat tctgaagacc atataatgat gtcttgatga ctcaaggcag   11760 gacttttaa tcttctaatg taggcggggc ggcccctgaa ggcagaggtg tgtggacaca    11820
agaagagtgc agactcttgg ggcacctggg gaagtagtgt ccgtgtcaca ttaaattcat   11880
ttaaactctt atattttatt ttaatttata caatatgaat atttttttaaa actatgaatt  11940 gaaaagtatt acccttgagt aaaattaatg ccccaagaag atgtgccata tttaccctct   12000
ggcacactac caagtacccc caggggcatt acagatctct gttagaaaag tacagattac   12060
attatcctca taacatttag aagctatgag accttggcag ggaagtttcc taatgtttct   12120
gagcctcagt attctctgta aagtggacaa cataatgtct ccttacaagg gttgagatgg   12180
gcaggtaata gcatatataa aacagctatc atagcatcag cacagtgtag gcactcaaat  12240
ggtagttgct gcttttgttt tagtagacaa ataattttttg aaacttttta aagcgtagtt  12300
tttatttcaa acaacttta ttgtgagtaa aatatgcata gtgggtctaa tttaacattc    12360
tgaaagctat tgacttatta gaacagtaaa ggattattag agggcagaaa catggagtaa   12420
gtactctgag acacaaccatt gcttctttgg gggtgatcca ctacaactgc ccagctttgg  12480
acaagtggtt ttcatgttcc cctgattttt aagtgatttt ttttttttt ggcaggactt   12540 aaaaggtatc cttgactaaa caggaacttg accaagtaaa tagttggtgc aatttgaata  12600
ttctttcttg ctataagcaa caagtaaatt atggtacagc tttctaagac catatctttt  12660
cgatttaaaa atagcacttt actcatacat gttatgacat gggtaaacct cataaagatt  12720
atgctaagtg aaagaagcca gtcataaaag atcacatata atatgatccc atttgtatga  12780
agtgcccaga aggggcaaat ccacagaggc agaaagtaga gtagtggttg ggtagggctg  12840
tggggtgggg tggggaaggg gtgactgcta atggatatgg ggtttctttt ggggatgatg  12900
aaaatgctca aaatttagat tatggtgatg gctattcaac tttgtaaata tactttaaaa  12960
acattgattc ttaccactga gtttaaacaa ccaaaaaaaa atcccaaggt gcattgaatt  13020
gtgtacttca aatgggtgaa ccttaataat atgtaaatta tatcccagta aaggtgttaa  13080
aaaatagtac tttaaaggaa tctatggtag ttttgaaaat aaggcagttt tccatacttt  13140
gttaaactct ggagaagatg acactttact actggtacct gctagagtaa gacttatcta  13200
gtattaacaa aattagggtt tattaatggt ataggatgat ccaggtaatg ggggaaaaaa  13260
accgagcatc ctgttatcta atgtactatc cagtaaacta ctctagctttt ttttcatgaa  13320 ctttttctaa aggctttcta gggcctcgtc ttggtttgaa agttcacagc taccccttcag 13380 aaaagaaaac aaaaatccat ggagtaggca gatacaagta ctcatgtgag cataatttac  13440
tttgattttt taagttgtgt tattctagcc ctcagcctgt tccctgcctg ggctctccta  13500
gtgcccagta acactgattc aagaggttgc atttagctgg gcacagtggc tgatgcctgc  13560
aatcccagca ctttgggagg ccaagttggg cagatcacct gaggtcagga gttcaagacc  13620
agcatgtcca acatggtgaa atcctatctc tactaaaaat acaaaaatta gccaggcatg  13680
gtggcagatg cctgtaatct cagctacttg agaagctaag gtagtagaat cacttgtacc  13740
tgggaggcag aggttgcggt gagccaagat tgtgccactg cactccagcc tgggccataa  13800
agcaagactc cgtctcaaaa aaaaaaaaaa aaaattggg tgagggggag gaattgagga   13860
```

```
ggataccaag ggttgggcct gaacaaatgg aagcataatt atatgtagaa atttctatga  13920
gctactcttc tagaatagat gactcaataa taccctgctt gccatctacg tttctgtcc   13980
ttaattattt ccagttctat ttcatataat gcctatttca ggccttaacc cttcagtaaa  14040
ggaggtttgg tttctatacc ctaggacagt ttcattgaga ataaattttg ttaggctacc  14100
tatgtattcc ctactgtgca gactacagta cagtactagc agaattctta ggctgttact  14160
agaatatgat gatgaatgcc cgggtggtca tctgtctccc acccggtaga gttggcttca  14220
ggattgagat acacgtggcc ctggaggaga cgtttcttcc cgtcatgctg cagaatgaga  14280
acatttccat gttttcgtca ttgtctgctg ctgcctttac cacctctgtg gctcctccct  14340
attcaccttg ttcacatctt aactcatctg tgccctgttg tgaagcttac acaatatgta  14400
aacaaaactc taccctgttg gacaaatgga acacttgttt ccttgttgta gttacctgat  14460
aggttcctta gctcattata ttcaggatct agatctgtag ctcttttcct cttttgctgt  14520
tctcagaggc cacttttttt tttttaatg ccgaaaggag gattttgttt gttttacatt   14580
tttttcttct ttttgatgat ttctgcgttc taagaaccaa cccttggatg gtttctgatt  14640
ctagaggcag gctttcaaag tagcttaaac ctcttaaaaa acatctgtat ctagtggtct  14700
gaggcttgtt tgattctggg atacttaagg tcccccagta atattggtgt ttgttcccct  14760
ttttagcatg agtctgcttt gccctgggat gaccatagac cacaagttac ctggcggggg  14820
gatggacagt ttttgctgt gagtgttgtt tgcccagaaa caggtatgga aatatattgc   14880
agttaaacaa caataaaaaa ttttatctt attaaaatta aggaaaattt tctttctttt    14940
gctttgagta gggtattaat tatacatatg aggcaaggat gtgctgcttt aaatgtgaaa  15000
tgaggttaga gttaagaatt agaagagtcc tttgaggcca tttggtccat cctcctacct  15060
ggtggacaca aatttgtaac aaaattaatc taattggcta tgtaaaacca tggcagtttt  15120
tatttgtaag gaaggtgttt gaatagttct gaattgacaa cttttatcat aatgtttaa   15180
gtgtgtatgt gtgtttgact ccactcccgc acagggctc ggaaggtcag agtgtggaac   15240
cgagagtttg ctttgcagtc aaccagtgag cctgtggcag gactgggacc agccctggct  15300
tggaagtgag tgggagaaga aaccttagag aaattcttgg aaccagagta gaggtggtgg  15360
tacacatgga tacagatgat acagatgttt gtgtaacaca aaaggatttt tacgtttctt  15420
catttggtta taaggctgta tctatctttg tttcttcttt tttttttttc ttattccctg  15480
aagtctgaat tcaactcgaa tagtagattt tacgcttctt cacagatttc attgttccaa  15540
ggccgcatat atttttgcatt cctaactctt aaaaggctgt ggttttaagg cagggtatat 15600
atgaagccat tgtacagagc agaaaatggt gtttagaagg gaaggcccag tttgcaaggc  15660
tctgtggggc aaatggtgct tttgtggaaa ttagggaaag agcctccttc cttggcacaa  15720
aattcctaca gcagaggatc tgcttgccaa ggagcatgca ggctggattc agaccctgct  15780
ctttccttcc attctcctcc ttgggcccagt acccttgtgc aggttacaat ttgcctgtca 15840
tatgtggctg cctgatttta gatagaagat gtatctcctc tgtttcggtg atatctgttg  15900
tatgtagacc tcttgtttcc caccagtatc tgaatggtat tatatgatag agcagaagag  15960
aaatgtatt gaattaaaac cctagagaca aatatgaata agatgaggca attaagatgt   16020
tttcaacatt tggtgaagtc ttaaaaaaga cctactggag catagaatat ttgctgaagt  16080
tgtataatgg aaggagaaat agattttgat ttttaggaca ttatacctgg aatggtttag  16140
ataacttatt atttttaaag tcatccaaat gcaatgtaaa tatgtaaggt tttgtgggca  16200
aatggagcct ctgtgtaaaa caggaaaagg cactctttcc tctgggcaag tacagtccca  16260
```

```
cagtgggatg aaccgctcgc cgagagacaa gggacacatg ggatttaaaa cttccttgga   16320
taaagatatt cattaattcg ttcattcatt cattcatgtt tgctggaaaa aaaactcttc   16380
tggattttat ctattcttta gttaggtgag ctttcgatat tgtaacactc tgagtttgct   16440
ttaagaccct caggcagttt gattgcatct acacaagata aacccaacca gcaggatatt   16500
gtgttttttg agaaaaatgg actccttcat ggacacttta cacttccctt ccttaaagat   16560
gaggttaagg taagtgcctg agttt gtttc accctcgaat gtagaggact ttccatagct   16620
atagagggaa tttttttttt tttttttga gatggagttt cattcttgtt gcccaggttg   16680
gagtgcgata gtgcaatctc ggttcactgc aacctccgcc tcctaggttc aagtgattct   16740
cctgcctcag cctcccgagt agctgggatt acaggcttgc ccaccacag ccagctaatt   16800 ttgtattttt agtagagacg ggtttctcc gtgttggtca ggctggtctc aaacccctga   16860
cctcaggtga tccacccgcc tctgcctccc aaagtgctgg gattacaggc gtgagccacc   16920
acgcctggcc tatagagggg atttatattt gatatggata tataaatagt agctttagag   16980
taaatagtaa taaaaatggt ggcttcctag aactgattt тaттттааata aatattgttt   17040

ttccagtgat ttt gcaaata atagcattt g tccccacct tagataaaac agaagtagga   17100 aatāaааaтg ctagttttta tt gtttattt tgacaaaagc ataatttttc cagtaatgaa   17160
gatgtttttc att tataaca tttaaatctt aagtggtttg taccatta agatt cttgc   17220

tgaagtgaga acacatcaaa tggtatctct gtgtaaaatt ttaaacatcc taagttgaga   17280 gacgaгттта atgaactccc atgtaactat tactcacttt cagtagatac caacatttt g   17340 caaaactatt ttcatcggtc cgcaactctt tggcctatac atatatatac ttacatatat   17400

ttttatttcc tggagtttta attctagaaa tcatattttc aatatttatt tataacagtt   17460 aaggacатттт tcttttacat aaccataatt ctatt attac atctt atctc tgtgttgtct   17520 aacacccagt ccatatt cca gtttctctga ttgtctaaaa atgtcacctt gtatttggtt   17580
aagtttctta agtctctttt aatctttaag cataatgtat tctttttttt taagtcctct   17640
acataataat gacatatttt acagatttgt ttaatgcctc tgtaggttag tgatttacag   17700
ctagggatga gctcaggtag tgggattatt tgatttgaga gaggaaatac agctattata   17760
aagatttgga agtaaatcca taactgaaag ccaatgacag atcttttttc ccttctaggt   17820
aaatgacttg ctctggaatg cagatt cctc tgtgctt gca gtctggctgg aagaccttca   17880
gagagaagaa agctccattc cgaaaacctg tggtaagaca gctgtagtac cccagccttc   17940
tgccccataa aacgtagttg aaagtagaca ggtatgggat ttccttcatc cctt ctactt   18000 agtcccttag tagaatcaaa gatgctgaag tgggtaggtg gaaatggggg tggttaggtt   18060

ttgattgatt gtggatttca gtcatgtatt ggtt ggggtt ctctagagaa acaaataata   18120
catatatata attcgtccct cagtatt ctc ggggatt ag ttct aggatt gcccatggac   18180 gccaaaatcc acacatggtc aagtcctgca gtcaaccctg cagaacactc agatatgaaa   18240
agtcagcctt tgtatacttt gggttttgca ttcctcaagt accatatttt tgatgtgcgt   18300

ttggttgcgg gtatagaatc cacaatatga agggccgact gtatt cat tg aaaaaaatac   18360 gaatataaat ggacct gt gt agttcaagcc tgtgttgttc aagggtcagc tgtacttaca   18420
tagagagacg gtgagagagg gaatagggtg gggcgggagg gagagagagt aatagagtgt   18480 ggatagatt т acttt aaaag att agctaat gtaggggatg gcaagtttga attt gt ggg   18540 ggcaggttgg caggct ggaa att caggtaa gaattgatgt tgctgtcttg agtatgaaat   18600
```

```
ctgtagggca ggctggaaac ttagggagga tttctgttac agccttaagg cagaattcct    18660
tcttttctgc gaagcctcag ttttgcttt taaggtcttc agctgaatga atgggacctt    18720
cccacattat ggggaataat ctgctttcct tatagtcagc cgattataaa tattaatcac    18780
atctacagaa taccttcaca gcaacatctg gagtttagca gatagctggg tgccatagcc    18840
tagccaactt gacacaataa aattaactgt tgtaagtcat cacgtgcttt ccctagtgca    18900
tggtattacc acagaaaaaa cactaaccaa aggaattctg tggacgtgaa agaagattta    18960
gattaagcgt aaaagtaaga atatttttat agcttttaaa atgtataagt gtgtggtttt    19020
aagtattaaa taatacttga aaatgttaga aaataagatg agaaaaaaat ctcatagttc    19080
taccacttcg taataatcac tattcaaatt ttcttgtctt ctaggttttt catgtatata    19140
tctcagtata gctatcatct tgtttttgtt aaaagtgtag taggtatggg ccaggtgcgg    19200
tggctcatgc actttggggg cccagcactt tgggaggccg aggcgggcgg atcacgaggt    19260
caggagatcg agaccgtcct ggctaacacg gtgtaacccc atctctacta aaaatacaaa    19320
aaattagctg ggcgtggtgg caggcgcctg tagtcccagc tactcaggag gctgaggcag    19380
gagaatggtg tgaacctgga ggaggcggag cttgcagtga atggagatcg tgccactgca    19440
ctccagcctt ggcgacagag tgagactgtc tcaaaacaaa acaaaaaaaa gtgtaggtgt    19500
gatacatctg catcatttta aattgctgta taatactcgt ttattctcgt tcattaaatc    19560
tcatgctgtt agacatttac agttttgtca tttctcatta ttgtaaacag caatgcatgg    19620
tacatttttg ttcataaatc ttttttacttg attattttct aagtagcttt caaactcttt    19680
aatcagtaga accccccccc ttttttttt tttttggaga cggagtctct ctctttcccc    19740
caggctggag tgcagtggcc cgatctcggt cactgcaagc tctgcctccc gggttcactc    19800
cattttcctg cctcagcttc ccgagtagct gggtctacag gcgcccgcca ccaagcctgg    19860 ctaattttt gtattttgg tagaggcagg gtttcaccgc gttagccagg atggtctcga    19920
tctccatctc gtgatctgcc cgtctcggcc tcccaaagtg ctgggattac aggcgtgagc    19980
caccgtgccc ggcctcagta gaacccttt aactgcaatg ttaagaaact cattattcat    20040
tcaacacaat agttcttaac cctggccaca cctttagaaa aaaatgata ttcaggcttc    20100 atctaagagt tcagttcagt gtgttggaat ggagattata cgtaagtatt taattaaaaa    20160
ccaaaagccc ccaagtgatt ttaaacagcc gcagttgaga accaccgatt aaccagtgtg    20220
tcaagggatg gcactgtgat atgctgagca taaaaatatt gcacaggatg aaaccctgtc    20280
tctactaaaa atgcaaaaat tagtccggcg tggtggtgcg cgcctgtagt cctagctact    20340
cgggaggctg agacaaggga atcgcttgaa ctgggaggca gaggttgccg tgagccgaga    20400
ttgagccact gcactccagc atgggtgaca gagtgagact ccatctcaaa aacatgtata    20460
tatatatata cacacacaca cacattgcac aagaacagcc acaacatctg tgctcacaga    20520
acatcagcat gtggtctaac ttcaaagtgt tgtaataatg cggttgaga ctaggttatg    20580 tttgctgtga tcactaagtt aagcattagt gagcaaggag attgagaaaa tccttaatat    20640
aaataatatt tcttaatata actataattc ctaatataac taaggtctta atttatatgt    20700
catctgttta gtaaaggttg gttttggcat gattaagtct tgcttgctta atagatgttg    20760
gaaggataat ttcatgctta tcttctttgg acagctgaat caggattaat acccagatag    20820
ccttgaacat aagtgcttgc aaagcacctg aaagaaaata agcatcttaa gcccaataca    20880
acacaatgat gctagtctag atcttggatt aagtgtttta atactttac tctaattgcc    20940 aagttatctt cttcctaaat cttcatgaga aaacccacta aagaatgct ttttcctggt    21000
```

```
agccttccat tgtgatcata aagtttggaa gtaaagttga aaataaacat gtgggccagg    21060
cacggtggct caggcctgta atctcagcac tttgggaggc cgaggcaggc ggatcacaag    21120
gtcaggagat caagaccatc ctggctaaca cggtgaaacc atgtttctac taaaaataca    21180
aaaaaaaaaa attagccggg tgtggtggtg ggcgcctgta gtcctagcta ctcgagaggc    21240
tgaggcagga gaatggcatg aacccgggag atggagcttg cagtgagccg agattgcgcc    21300
actgcactcc agcctggccg gcagagcgag actctgtgtc aataaaaaa aaaaaaaac     21360 gaaaataaac atatgaataa aagttaaaaa tagaaaaaaa acaagaaaat aaacatatat    21420
ttctgacctt attgattctt gatatttat ctgcatggaa agctatttt tggcagttat      21480 tattgttctt attttagaga cgaggctgag caggaagggt cctttgaaaa agaaaagatt    21540
gcccttgaac ccctctggca agtgggatga agtctgcttc ccagcctcta acggccttct    21600
tttcattttc ccttgcagtt cagctctgga ctgttggaaa ctatcactgg tatctcaagc    21660
aaagtttatc cttcagcacc tgtgggaaga gcaagattgt gtctctgatg tgggaccctg    21720
tgaccccata ccggctgcat gttctctgtc agggctggca ttacctcgcc tatgattggc    21780
actggacgac tgaccggagc gtgggagata attcaagtga cttgtccaat gtggctgtca    21840
ttgatggaag taagctcctg ggaagtgtgt ccatgagcct gcaagggtc ctgagcctag     21900 ggcctgcaga tgtggtggtt tgactggaac agtggggaat ctttatttgt tttggctgtt    21960
tgggttactt gttttttat tgaatgggat ataaggtggg gtatgttctc tcctgagaac     22020
cattgtcccc cctcccccac cagtttcctg ttatactgca tctgtggcct tcacacgttt    22080
acttgcctgg cctttgaaga cactgaaaac tttgactcta ggtagagagg atgacaacag    22140
tacagtcttg tgggattggg tgtgttagct ttatctgttt gccctgacac agatttataa    22200 ttgacccta taccacccca cttgtgttgc tttgtttcct gatacaaatg cttgctgata     22260
tatacctctc cagtatgttc agttcatgca taaacgtttg cctaatatga agattaggtt    22320
tatattttat aatgaggtag aaggttttt taggggggtgg ggtgggaagg gcaagactga    22380
agagtgaagt agtcacctta atgaatagtt tcattgctga tatgaaaggg agcactggct    22440
tctaagattg taatgtgagg tggatattaa ttcatattct gtgtaatatt ctacataata    22500
ctgattttat agtcatgtat tctatataga gaacttaatc agatctgcgt tattaccaaa    22560
tccacacata ggaaagtgct ttaaggattt tgaaagtatt aattcccttg gtttagtgtg    22620
gcttggttgc aggcccaggt ttaaagctag aggtctgacc tcttggcctt tttgccttag    22680
tccctggcac ctgaaactcc aggtactgag atggactccc ctaggcctag aggtgacaat    22740
agccaattat ggacagaacc catgacattt ccccatccca cactgttttt agacttgttc    22800
ctgagaaaaa cattgaaagt tattttttg tgaattgcca ttattgttta gatatactgt      22860
gatgttcaga tggcttatct tacaaattga atatccctag gtctaatcct cttctttctt    22920
tttcactgca gacagggtgt tggtgacagt cttccggcag actgtggttc cgcctcccat    22980
gtgcacctac caactgctgt tcccacaccc tgtgaatcaa gtcacattct tagcacaccc    23040
tcaaaagagt aatgaccttg ctgttctaga tgccagtaac cagatttctg tttataaatg    23100
tggtatgtta taaaactttt gccaagatgt tctgaatcaa gtcccttcta ctcctacata    23160
aaagcaaatt atagtttggt gttgccatag gtctagtgtt tctcaaaatt tttaagtctg    23220
cagttgatat cattatcatt atgatattta attgccttgg gttttgtttt ttttttttt     23280 taatcctata ctggtttgta cgagccattc cttttccctt actgacttga agagtcagtt    23340
```

```
atttaagaat aacattggac tctggaaata acatagtatg ttatacattg ttaacatgtt   23400
ttactctttt catagccttt acacatattt tcagttgatc tcatccctcc taggagctgt   23460
gtcagagatg gggttttcct cttttgtaga tgagggaaca cagtgtcaga ggttttgtaa   23520
tttgtttgaa caagaatgga caaggacctc aacacaggtg ttctagctcc taatccactt   23580
gtcctgccac agccccattg ctgtcagttc ttcattactt tcctgatgtg ctggagaatc   23640
tgaaatttgt ttttacttgt gagttctgtg gttatgtcat aaattctgct ggcatatggc   23700
agtgttagcc ttgttttcaa atatcttttg aattctcaga aaaagcctag atagttgcca   23760
agagagaata atcaaaatta attaatttaa atgggaagtc cttactttca tatcagcttt   23820
tctgttaagt cagcagccca ctgtgtacat ggatcctatc tggatgtatc accagtttct   23880
ctgattatag tttcagtgtg taaaatgctg ttacagtcct ccttaaactt ttcaaaatag   23940
cttttaaaaa aagtgcaaat atgttcattg tcaaggcaaa aagaatcaga tgtaagcttt   24000
tgtgggactt aactgtatga tgctaatgag tttatatgtc actttatgat gtatggtatg   24060
ttttgttctg cattcactta aaaaatagct ttatatcatt catctattta aagtgtacaa   24120
ttcaatggtt tatatgtgtg tgtatgaata tatatacata tgtatatgta tatatatgta   24180
tattcacaga gttgtacagc catcaccacg atcaattta ggacgttttt atctcctcag   24240
aatgaaaccc tgtaccaccc tgcattcatt ttacttgaga gaaaactccc tgtgatgaga   24300
taggacaggt tgagagctcc acttttgaaa gattgttcgg catcaatatg tggggttggc   24360
cataggtcag gggcacctgg aggcagagat tctagttagg agaagctgtt gtcaagtgtc   24420
caggcaggag ctagcaagag cttgagccag agcagtgttc atagaaatgg aaagaagaga   24480
aagatcataa caaatccatg aagtaaaaac cctgagaagt taaagaaccc actggggaga   24540
gtttggatat aagagaatct ggaaaaagag atcttggact ggaacaggtc agggctccgt   24600
gcccaagtgg aagggaaatt aagaacttgg agtcaagtgg tagacatttg agtggtgtgg   24660
agacaagttc gttgccaaag ttttcaaaga tggtgtttga tgcatcctga gtatcactcc   24720 ttttctccccc tcattgcttc ttgattgttt attatatgcc aggcttttt ctagtacttg   24780 gcttgttgta ctagaaaact agttgtactt tgtctacaac ttgttgttct aggtgtagac   24840
aaaagatatc aattaaatat gatctatcag atggcaagtg ctgtggagaa aaattaagca   24900
aaataagggg tagggagagc ttaaggataa gggtttacag ggggaaggtg tctttcctat   24960
ttagtgtgat cccaaaggcc tctctgtgaa ggtgacattg aagcagagac ctggtgagaa   25020
tcacagtggg agccacgcag acatctgggg taagagcgtc ccaagcattc tatgcttgaa   25080
ggcaaagaag aaaaaagaaa gagcgttcca agcagagtaa aaagcaacca ccgaagtgcc   25140
tgttgtgttt aggaaatagc caggaggcca gggtggctgc agcagagcaa aggaggggaa   25200
ggtggtgggt gagttcagag tggtgatggg aatctgctct tgtagggcct gcggcttttt   25260
actccgagtg agataggagc caccagaggg cttagaacag aggagtgcag tgttctggct   25320 gaattttta aaggcttgca ttggctgctg tgcagtgaat aaactggatg aagaatagaa   25380
agaaaatgtc tttaagcag gtgcttagga ctttggagaa tttgaggata ttgagaggtg   25440
gttgaagaca gtggaggaaa ttgtccacag cactgggctg agagggtagc cccttcacct   25500
ggtcttgctg agatgtggcc tttgtcaggg aagattatga ctgatgtgtt cttaaggaga   25560
aagcagagat tttaaggagg ttgagatgtg attattttct agattgctgt ttgccttcta   25620
gaactcatta attgcagaca ccatccccctt agtattaggt gaaatcttat aatttacgat   25680
gataatattt gcattttttgt tttccaggtg attgtccaag tgctgaccct acagtgaaac   25740
```

```
tgggagctgt gggtggaagt ggatttaaag tttgccttag aactcctcat ttggaaaaga   25800
gatacaagta ggttcttaat tatcttgggc ttctgggaac agaatcagcc agcatgcagt   25860
cctaaattca gccatctgat aacagttcta tgcctgttgc tgagtggaac aagaaataaa   25920
gacaacaccc aggccctgac tttcggatct gattggagaa gccagtcatg tagtttgtct   25980
gaatgccata taatttgata ggtagcagga gagcatgagt tgtaagccag cctaggacct   26040
actcccaata gcgcttggtt ctccaggaaa aatcatgtgg gaaagatgga gatgacaatg   26100
ataaggcgga gctgcattct cttacataaa tggggatgta tgggttgtta acatggatga   26160
cctaatgcag cctctgtctt tgctccatcc cagaatctag aacttctggg tgctgtgctt   26220
tgaggctcct gggatggaaa tcagaatgca ttcttccatt gaaacagtat tgtaaacaat   26280
tggatgttat tgaatacctc aggtacacta taggcatttg caaaatgacc tagaaaccaa   26340
attataatgc cacatctgtg agagaacttt tttaaaaagt accacttatt gagtacttac   26400
agattaaaaa aacaaagtgt agaggttagg taacttaccc aaggtcatgg acctggtaac   26460
tagagaattt agggtttgat tctattctgt ttgataagtc catgttcttc attactaaac   26520
tactctgcct ccagggaaca tttattgtta gattaataga ataattaac tgagtacaac   26580 aaatagcaga atttaataaa taatgttttct taaatatatg tgatatattt aataaataca   26640
gcagaagtgt tcaacctctg tatgattttg aggctgcctg tataatgctt agtagttttt   26700
aaagagcatt tacatgcatt atttcacttc atagacttga aaccactaga gtagagatag   26760
aggacaaatt agaaagtatg aggcagttta gaatatagtt tcatttaaaa aaaattgatg   26820
gggataatgc caattcgtct gagatttcac agaagacatg agtactcatc gtgatcttgg   26880
ggaagggata ggtttggggt tggcaaagaa ttgggaacat tgggtctggt ggggaagaaa   26940
gtgtcagtga aaaccagagg tgggactgat cctccatggg atactctatg tgaatgcaat   27000
ggagagcctg agtccgggga gagatgtttg aggaggaaga tcaggctagt gaccaacttc   27060
ttcagtggga gctgcggatt tgccacctga tctaaaaggc aggaagtagc cattgtcggt   27120
tcctacgtga ggtgacaaga acagtgcgct ggtcaggtgt ataaatgcta ccaaagaatg   27180
cattagagac atggagacca tctctcaagc tagtcagtca gtttaatgtg aggtgcttag   27240
gaaaggaccc attctactgc aagtgacata cctgccagag cctggtttga atgctggtaa   27300
gtcatggcag tggaaaagct ctggggttca ttagtgtagg gactagggct ggtaattttc   27360
ttgtgtagtc agtttcctca agtgttctct tcaaatttaa agatttcagg gtatgagaaa   27420
tttagggaaa atataaaaac gtattcttaa gccagacaaa gattaatttt agattttgta   27480
gtatttggta gtatctcagg ttttgtccct ccaaataatt aggagtggac tgtatacaag   27540
atgcttcagt cttccttcat ccaggaacgt ctcagtggtt tttaagtttt attcatgtct   27600
tggatattct tcaatattta caatagaatc cagtttgaga ataatgaaga tcaagatgta   27660
aacccgctga aactaggcct tctcacttgg attgaagaag acgtcttcct ggctgtaagc   27720
cacagtgagt tcagccccg gtctgtcatt caccatttga ctgcagcttc ttctgagatg   27780
gatgaagagc atggacagct caatgtcagg tattgcagtt tttccctgta ctccacatgt   27840
taagcaaatg gagttaggtt tttgtctttt atgagcatac aactttgac ttctattgat   27900 caaggttgag gagcagtagc tttcttgtta gacacactta acaagaaggt taagtctagt   27960
tatgagccat gtcaaaataa cagaccaaaa atatatcaaa aagtggtgaa aaataggata   28020
aatattagta gatgaagcaa cttttttaaag atatgttaaa tattttaatt tagcatctac   28080
```

```
ccacattttt ccagcgtgat tgttatatgt tataattgat tttaataact gtcaagcata    28140
attagagtgg ctaattctca tgggctaatg tgatgggaag aaattttgta taaatgcagt    28200
catgcgcata tatgtgtgtg tgtgtgtgtg tgtgtgtgtg tatacatacc ttttctatgt    28260
ttagatacac aaatacttga catggtatta caattgcctg tagtattctg taaagtaaca    28320
tgctgtccag gtttgtagcc tggtagcaat aggccatacc ccataggcta ggggtgtagt    28380
aggctacacc acctaggttt gtgtaagtac tctatgatgt ttgcacaatg atgaaatcac    28440
ctaacaacac atttctcaga cgtatcccca tcgttaaatg atgcataatt gcacatatat    28500
gctttgtttt gatgtggtga cttcaaaatg cttcttccag cctcctcttc tatatatcct    28560
attttgtacc tgactacatt taccattaga aagtctctat tcttctttgc tgaaatttca    28620
ctgttctctg ggcctgagtt ttgttttgat tcctgactat atcttcatta tgtaacaggt    28680
ttcagttaat gaatgctctt ctgtgtaatg taagccctgt tgtatagttg atagcatttt    28740
ctagccagtt cccagaactc cttgtttcca gtgtcaatac ttggcacctt tgtccactga    28800
cactaatccc cagattaatt tgtaattaaa gccctactgg tgagatttct gagaaacgtt    28860
gttgcaaaat taggaacctt tcctttatat atatacatta cataaattta tagacataaa    28920
acattttaat gcagtcattt gctgctactc tttgactcat agtctttcgt gatattttga    28980
aaaagccttt tgttaacatg tctaaatgca gaatatgttc tagaaatatg tagcacttaa    29040
agtaagccat tagattacct tttgaaaagc ggagcaattt actaagtttc tacttcttca    29100
gatttgaaat tcttcatcat tagcttgtag aggcaaaagc ttgatgcagt catctcattt    29160
gctgtaaagg aaatgagaag tcatttacag tatatttcta ctgcttttgac ttttatttct    29220 caaaaagact gttttgttca tataaaatat taatgctttt gaggactaca aagtccctcg    29280
atttagttta catttacttt agcttatact ttgtaaaaaa tactcttcta aatgctttgt    29340
ctgttttagc ttacttattt tcataaatac ctctgtaaag tatatgccat ttgcaccatc    29400
attttacaga tgagacaact aagacatgga gcagttaggt aacttgcctg agatcatgca    29460
ggtggagcca ggatcaaatc ccagcgagtc tagctccaga gtttgttctc ttcttgacag    29520
ataatttatc ctcacaaaat ttgaagcatt tgtagaggaa ttccctattg ttataatgtt    29580 tagtttttt gtagattggt taaaaacttt gaattaaatg ttagcattaa catcatttgc    29640
ttttatcact acttctttgt ctctttttc tttttttaat cactacctct tcctcctctt    29700
ttgagaaatt ctgcttccgt ggctatggtc caagctactt gagaaggtga ggtgggagga    29760
tcacttgagc ctaggaggtt gagattgcgg tgagctgtga ttgtgtcaac tgcatttcaa    29820
cctgggcaac agagcaagac actgtccaaa aaaaaaaaa aaaatagtga aattttactt    29880
cgctccattg actcagggaa aaaatgtaat ggtgataaca aattcccttc atctcattag    29940
tgaaaatcca caattttcca tcaatcgata tgatagtgat agagatattg agtgtgctca    30000
ttttcctaca gaccagctgc tttaactatt ttaagcagac agaaatgata ttggtaccat    30060
ccatgtctaa tgaaggcaat actttgtaat aagttgcagt aagttgtggc cagaagagga    30120
atgatgactt cacagtgtaa acaactacct tattgggttt gtggaaaatg gtgtcatgta    30180
gcagatgtgg ctttatctgg gctttggttt ggagtagttt tatctattca tctaaccgtc    30240
tgtctctaag tgtataagtg tgtgtgtgtg tgtgtgtata gtattgggtg tgtatatatg    30300
tattttgtct acattgtatt gaagtaggta gtgcagcatc aaaaggaaat tgttgatttt    30360
caaaatcagt gaaatgtcac tattttgag aaaaatggtc tgtttacact cccttctcct    30420
tttttttgtc agttcatctg cagcggtgga tgggtcata atcagtctat gttgcaattc    30480
```

-continued

```
caagaccaag tcagtagtat tacagctggc tgatggccag atatttaagt acctttgggg    30540
tgagtatcaa ggtgttagga aagcatgtta tgacttacat agatgcttag ttcttaagaa    30600
catgtacttg tatcttgtca gttcaatatt gattgtcagg tcttttaact accctggaaa    30660
accctaagct ttagagtgga attggcaagt gtattctact cctgtttcct cttttaatga    30720
actaacgtac tcttaaaaaa gtgattgatg actatcgcag ggacaaaaaa cgaaacaccg    30780
catgttctca ctcataggtg ggaactgaac agtgagaaca cttggacaca ggaaggagaa    30840
catcacacac ttgggcctgt cgtggggtgg gggagggtgg agggatagca ttaggagata    30900
tacctaatgt aaatgacaag ttaatgggtg cagcacacca acatggcaca tgtatacata    30960
tgtaacaaac ctgcacattg tgcacatgta ccctagaact aaagtataaa taaaaatata    31020
tatataaata aataatgcca gcattagaga aaaaaagtga ttgaaattgc atgttaagtg    31080
ttttagcaaa tgttgatgtt gatggttttt tgcaaagagc gcatcagcta tttgtgaact    31140
agatctgtga atcttgcaga gtcaccttct ctggctatta aaccatggaa gaactctggt    31200
ggatttcctg ttcggtttcc ttatccatgc acccagaccg aattggccat gattggagaa    31260
gaggtaggtg aacacggagc aggaaattta cttaaagtag ttacccaggg actgatggca    31320
ttaagtagaa agagcgtggg cttttggaggt ggacttgggt ctccactaaa tgcctagaca    31380
atagtgggaa atgatctcac tttcataagc cacaccttat tcatctataa aatgggaaaa    31440
tcagtatctg tctatcaggg ttcagaagac taaatgagat aatatatgtg attagcaacc    31500
ttttatcccct agttgtacaa atcattcaaa gttaatttta tttagtaggg gaaacagaaa    31560
tgtgatcttg agaatagttt tagtagattt ttattcaaca catactagaa tgcctataat    31620
tgtggtggat ggtagaatgc agtggctgga aaacaaaacc gcttgactaa ttcctgctct    31680
tctggaactt gtgatctatt aatttcaatg taatgattcc ctttgtttggg agtgtgatgg    31740
aaatggacag agtatactgg tagagaatac tgagatgttt gaggggtaat ttgaggatgg    31800
tggctatgag aatgggagtc ctgcatctgg tggtccagga aggcctctcg gaggcagtga    31860
tgtgtgtgct gagatgtgaa gaaaaagaag gctctgtctc caggcagaag gaacaacaaa    31920
ctccttgagc ttagcaagag ctcatcttat tcaagggact ggatggaagt attgtggctg    31980
gagctcagtg acagtcatag gagggaattt gggttcttta attgaacaaa gattagaaac    32040
ttcttgtgat tttttaataac agagtaatgt gttctgcttc atggtttgga cagtgattct    32100
ggctgcccag aagagacttg attggagagt gacgagactg gaatatggga tcaacaccgg    32160
ttgagtggag ttagtgaggg gaaaaaggag atgggtttga gatatgtgta ggagatggag    32220
atgtcagggc tcactgatgg attggatggc ttcacattcc gttttgcact ggaccagcca    32280
cgtcttaggt atctatcttt agtcctgatt acaggaactt aggtgtgaaa tcatagggtg    32340
gtagaactat gtgatagaaa aggtaggttt aactgatttg agatagaatt gcttgtgatt    32400
tcagttttat ttcttttgcag gaatgtgtcc ttggtctgac tgacaggtgt cgcttttttca    32460
tcaatgacat tgaggtatca aggcttggtt tggtgttgga tccttttcac agtgttagct    32520
ccgagtaatc tagctagctt tcacccatgc ctctctggcc ttctcttgca ggttgcgtca    32580
aatatcacgt catttgcagt atatgatgag ttttttattgt tgacaaccca ttcccatacc    32640
tgccagtgtt tttgcctgag ggatgcttca tttaaagta agttttcaat gtataaaaca    32700
gaaatggtcc cttctccaat gtcttttgga gtcttgatga cttttttgaat tcttcattta    32760
ttttggcttt ttatcaagga gtcctaggct ggagaaaatc tttagagtta ttttacttag    32820
```

-continued

```
accctaatct caacataata tctcagttaa atcattctgc actttagtaa agacatccaa    32880
ggaagggagt tccttcctta agcagcacat tctaaagtta aaacttttc aggaaatttt     32940 attatgtaac tgatctaata ttttatttgg aattactatg tagatcccca atgttttacc    33000
ttctgtgtag tcttttccca ctgtgcccac cctccactgt acatctgcgc tccatctagt    33060
ggtttgtagg atattggctg cattttgtct tctgttccat gccctatcta tctctgtgtg    33120
tgtggcgtgt atgtgtgtgt ggcgtgtatg tgtgtgtggc gtgtatgtgt gtgtggcgtg    33180
tatgtgtgtg tggcgtgtat gtgtgtgtgg cgtgtatgtg tgtgtggcgt gtatgtgtgt    33240
gtggcgtgta tgtgtgtgtg tgttcctatt tctaaaaagc aacttattt tctttgcttc     33300 caacttggaa atagggaatc tttctttcat tgatatgatt atagtacact gataatgcta    33360
agaaatagag aagttgcccc aattcttaac tgtgtttctc cacatcattt gagaagctgt    33420
gtatgtgaat gtgcatgagg gctctgtaag agagagggca agttccaggg atgagcgtgt    33480
tcatcagcag ggctgatagt cttgaggttc agtgggagag ctaaggcaca tggttgttat    33540
ttgttctctt ctatttcaca taatgtgtgc ggtttcaatt gcagttaatg gagagtggct    33600
tgttgtgata attaaggctt attagttaat ggtgtgttta gcattacagg ccggcctgag    33660
cagcaatcat gtgtcccatg gggaagttct gcggaaagtg gagaggggtt cacggattgt    33720
cactgttgtg ccccaggaca caaagcttgt attacaggta agctggtttt tcagacaaga    33780
tagatagtct gattgtcatt cagccaagta ccaagcataa ttcttgcagg ttgtatttta    33840
ggctttctta ttctttgtat cgtttattgt aaaccttttcc ttgatagttt tctgttagct    33900
ttattcaaag gagtgttgat acaggctgtg accataaggc tcaaagcgaa acttttcttg    33960
aaagtcaaga taaatataga gaacaacaag attctgctaa aagtgtgctg attttagaga    34020
gttgtggtaa ttctctgtga agagttaggt aaaatggtgt atcctggcta tttaaatgtt    34080
ttctacttaa ttaaaaatgt tactgcttta atttatttaa gatgccaagg ggaaacttag    34140
aagttgttca tcatcgagcc ctggttttag ctcagattcg gaagtggttg gacaagtaag    34200
tgccattgta ctgtttgcga ctagttagct tgtgatttat gtgtgaagac aataagtatt    34260
ttattacaat ttcgagaact taaaattatg aaaagccctc attacctata tcatcaatca    34320
gattcttaga ggctctttttt ttttttttta acttttttac tttaatgcag tattttgtag    34380
tggagattcc tagcagaaag aatcgtgaca ctcatcatat aaaggagggc ttctcttaac    34440
ctgagggaac acatgtgggt tttaggtggc ctgtgaaccc agggagattg tacacaccaa    34500
accttgtctt tgtgtattta ttcaagtaga aagcccacg ctttcaatag atttacagcg     34560
gggcctatga cccagaaaag cctgagctac tcttgtgaag gaaatgactg attttctgaa    34620
cctatttgga ggaaactttg tattggaaag atctatacta atgttttgtt taaaaagtag    34680
acctgaattc catgatgatt ttctttgttt ttttttgag acagagtctt gctctgtcac    34740
ccaggctgga gtacagtggc gcaatctcgg cttactgcaa cctctgcctt ctgggttcaa    34800
gcaatcctcc cacttcagcc tcccgcatag ctaggattac aggtgtgcac cacgcctggc    34860
taattttttt ttttgtattt tcagtagaga caggggtttca ccatgttggc caggctggtc    34920
tcaaactcct gacctcaagt gttctgccca cctcggcctc ccaaagtgct aggattacag    34980
gtgtgaacca ccgtgcccgg gcttctgtaa tgattttctg ttgtatgtat gtgaagatgt    35040
agttctcaga cagtcatgat gactaaatta cacctttaa gaaggtaaat gaatgtggta     35100
cctgattttt ttattctgta atttcagagt agaaatccag tgatagtagc ttggcattgg    35160
ggctgtaatc tgattataac tggtttgtat cataatgaaa atatgctggg cccatggagc    35220
```

```
tcagtttttg tgaatatctt ttctattctt tctctgtctt ctcacagact tatgtttaaa   35280
gaggcatttg aatgcatgag aaagctgaga atcaatctca atctgattta tgatcataac   35340
cctaaggtaa ctttctaagc tgtcatttac tctagcttac tttgtactta aactaatatg   35400
atctgaacga agatgttttg tcctttttt ggtaggtgtt tcttggaaat gtggaaacct   35460
tcattaaaca gatagattct gtgaatcata ttaacttgtt ttttacagaa ttgaagtaag   35520
tattttgaat aattcatgtg tatcttttcc atagttttct ctcttcttgt taaggaaatc   35580
aagcataaat agctagagaa gaaaaattcc ttactgttca tttttaaaaa ttgctataac   35640
tcttagatgc cagttggttt tttgctcttt tccgttcttt ttaaaacagc ctgtttaaaa   35700
ctatgtcctt aaaacatgtc attcagaatt attatttcac ttgatttta ggtatacata   35760 taaaactact tgttttcct aggagactga atcaaatgg catctttctc tctgatgatc   35820 tttccctca acttttaat gaaacacttt caaaatagag aaaagttgag agaattgtcc   35880
agtaagcaac ctatatatac cccacctgga ttcgccagtt tatatttc tgtatacaca   35940 ttctcattct ctataatctg tccatccatc attcatcttg tttgtagaca aattgctaag   36000
tgagttgtag acatcagtcc actctaccac ctgtacttct ccttgtatat cattaactag   36060
agggcattct ttgtgtatgg gttggttttg ttgtgttttt tcaggtcata tttatctaca   36120
gtgaaatgtc caaatcttaa gtgtgccact tagtgagttt tggcaaatgt acacttcatg   36180
taacctgaac ctctgtcaag ttagagggca tttactcctt ttcagaaagc tgcttcagat   36240
tcctttcaat cagtccctgt cccattcccc aggcaactac tcttctgaat ttttaccat   36300 aaatcagttt tgcctgttca agaacttcac ctaaatggaa gcatacagta ttactcttct   36360
gcataaagct gttttcattc agcatattgt cttgagattc atctgtgttt ttatatgtat   36420
cactagttca ttcttttttt attggtcagt agtatgccgt tgtgtaaata caccactatt   36480
tgcttattca ttccctgtt gctggacatg tggattgtac taccctgttt ggggctaatg   36540
tgactaaaac atctacaaac atttgtataa gtcttttgtg gacatgtttt atttctcaat   36600
atttttataa ttcaactctt ttccaaaagt cattttatt tatcatcatc agcatgccag   36660
gtgtatgtta gtaatttgat cgctgggcta catgttctgt tgatgaccat tccatacaca   36720
cctgttctta gagaagaaga tgtcacgaag accatgtacc ctgcaccagt taccagcagt   36780
gtctacctgt ccagggatcc tgacgggaat aaaatagacc ttgtctgcga tgctatgaga   36840
gcagtcatgg agagcataaa tcctcataag tatgtatgct gtcaccaggt ggcatccttt   36900
gaaaaaccga agtgtgtagt tgtccttgtc cagcctactt accttctca ttctggtgtt   36960 cttcacttat tacctcagat actgcctatc catacttaca tctcatgtaa agaagacaac   37020
cccagaactg gaaattgtac tgcaaaaagt acacgagctt caaggtagag atccgctcac   37080
agagaaagtg cttaaggtgg ccgtgactgc tactagtctg ctgcaggtga caatcaccat   37140
gtcattgcca caccacagat ttaacatgtg acttttagt tgccatttta agacccttgt   37200 cagtttttt cagtgctgcc ctctaaagca tatataaaag tatcagaagt atatattctt   37260
ctgatgtcca gttctattga gaaaaattta ttgtcttttt ggttatgttg ttaggtctgt   37320
ggattttttc cccaaatgat tgtgttctgt tttgttttct aaacactgtt aggaaatgct   37380
ccctctgatc ctgatgctgt gagtgctgaa gaggccttga atatttgct gcatctggta   37440 gatgttaatg aattatatga tcattctctt ggcacctatg actttgattt ggtcctcatg   37500
gtagctgaga agtcacagaa ggtatgtgga gttcttactt ttatgccatt tggttcttgt   37560
```

```
ttatataatg atagtgtgaa accctgcttc tggtagtgca gtagcttttc tgctatcact    37620
ctgtgagtgc agggctggag acagatctgt gagtttctag ggcccacatt cctaagcccc    37680
tgtgcttatg aaagtgtttt gattgtgagg ttgaagaagt gaagtaaaat tgcatggctt    37740
ttttttgttt ctttttttt gagacggagt ctcactcagt cgcccaggct ggagtgcagt    37800
ggtgcgatct cggcttactg caagttccac ctcccgtgtt cacgccattc tcctgcctca    37860
gcctctctag tagctgggac tacaggtgcc catcaccacg cccggctaat ttttgtatt    37920
tttagtagag acagggtttc actgtgttag ccaggatggt ctccatctcc tgacctcgtg    37980
atccgcctac ctcagtctcc caaagtgctg aattacaggt gtgggccac catgtgcggc     38040
ctaaaattac atggttattt ttaagatgat gggcatatgt gtgagctaat ttcttctctt    38100
ataaaggaaa tgtaacaagt ggttcatgtt ccactccggt tctttctcac atggctcttt    38160
tttctagtgg agggtgggca catggagcac agaaggctca tggcctcctt tcctatgttg    38220
gtacatttgc tatgatcaaa aactttgaac accactggta tgcatatttt ttatttattt    38280
ttttgcagcc tcagtctctt ccccatgacc tctccaaaaa tgaaaatcgg atccttcatc    38340
tctctgctta aaatacttca tgagctccca ttgttccgag gatataattc agaagccata    38400
atactgctta aaaaccttc cttgacctgg cctctgtgta tctttccatt ctcacttctt     38460
ggtattgtct ttttttcctc tgcccatgga ggaaagacaa tgcttttgtc ccccttccct    38520
tgcccctcac caccacatgc cttggtgggc agcattactt ctgccatcca tgggctttga    38580
ctgcttccac cctcaccatt cccctggcta attctcacta atctaggtta aaggatgcca    38640
aggtggcctc ttcccagtaa gccattcatg cttccctcca gggactgggt gaggtgaccc    38700
tcctatatgc ttctgttgca cacagtgcct acccctgcag actacagtgt gtctttatct    38760
agagtgcggt atttatttat ttattttga dacaaggtcg ggctctatca cccgggctgg    38820
agtgcagtgg caccatcttg gctcactgca acctacgcct cctaggctca agcaatctca    38880
cctcagctta caggcgtgca ccaccatgcc tggctaagtt ttgaattttt tttgttgaga    38940
cggggtttcg ccatgttgcc caggctggtc tcaaacttgt gagctgaagc aatccatctg    39000
cctcggcctc ccagagtgct gggaatgagc acttaattat ttgttgtctt gggttttctt    39060
cctatgttgt tcttacatgt atttatcctg tcagcccagg gaaattgcat taaaacagg     39120
aaacacctct ccattaggaa gaaaaacaat ttgcttacag ggcatggcat agagctggag    39180
atgatagtgc caataaatac taggttggca gggtctcaga gttttgtgtc caactcagta    39240
taattttatg tttgttttaa tgtgatcatt tcaggagagc atggaatgtc atgaaaacag    39300
caccaagagc aatgtcttag acttttagga gaaacttaga tgcatttgtt gaatatcttc    39360
tagactgaaa ccttatttcc cttattagcc tatgaaataa atgatactgt gagacttagt    39420
taaggaagtt actattattc caagtgtaac ttattaatat ccgtatgtga aagcatttt     39480
gccaaagctt gtttgatgtt cagctgaccc ttgcacaacg tgagtttcaa ctgtgcgagt    39540
ttgaactgtg tgggtttatc taaatgtgga tctctctcaa acacagttgg ccctttgtgt    39600
ccacggcttc tgcatccaca atcagtgtgg atcaaaagta caatatttgc aggatttgaa    39660
acttgcagat acagagggcc aacatttgt gtatccaggc tccatggggt caaatgtagg    39720
actggggtat gcttggattt tggtatcctt ggggtgtcct ggaaccaatt ccccatagat    39780
actggggac aactgtagtt tgattttata tattatataa tatgcagtta atatataata    39840
cacatttaaa aattatgtag ctttgggttt attgctatat gtaaatgcta gtttctattc    39900
ctatatatga atatcacaag taataaagtt ctcattaatc attttttag atcccaaag      39960
```

```
aatatcttcc atttcttaat acacttaaga aaatggaaac taattatcag cggtttacta   40020
tagacaaata cttgaaacga tatgaaaaag ccattggcca cctcagcaaa tgtggtaagt   40080
gtggggatta gtatgtttat ctctacttca gatcttcttt ggaactaggc aaggtataaa   40140
ttaaactgtt agtttagaca gtgactgatt tcacttccca ctcctgaaaa ctctaacaat   40200
tatgtatgct cacgttattt tgtcctgtgt tctgaaaagc tgaaggtaat cacttttaat   40260
gaactggagg agctccctag gtaagaacgt caagtagatc cttttttggt taagaatgag   40320
cacctgtgaa gttaacttca gtgtctcaga atcaaaattg gttgacagtt cttccttctc   40380
atgctgtttg cagacatgtc agggaaactc tgcttgtctg gagagagtga tgaggccacc   40440
tccccgtgcc ctgcaagacg cagttttaat tgacagtgat ggggtgccag ttgttcttcc   40500
catgctggaa cagttgtgat tctttactga ggactgatgg gggaaaggaa gaatcacctg   40560
gggtgcatgt taagccttca gctgctggca tccttggaga atctgattca ggtggtctgg   40620
gataggactg aggcgtgcat gtgtctaata agcttcccag gtgatgtctt ttcaaggagg   40680
ctgagaaaac actgggctgg aaagctggga ctcttaagta ggatgctgat cccaatcagt   40740
gctgctcttg cctcagaatc tgcagtggtg ctcattaaaa attcaaattc caggatccca   40800
ttcttcagat tctctgatta tttaggtctt aaaaagttcc tcatttattt tgtttggtga   40860
ccattggtat aaatgaagtc cattatgctt cccatgtctt aagcctgtct ttgtgtgaat   40920 cttttttcctg caggacctga gtacttccca gaatgcttaa acttgataaa agataaaaac   40980
ttgtataacg aagctctgaa gttatattca ccaagctcac aacagtacca ggtatgtggt   41040
atgtgaaaat gaggctctcc tggttttgct ttttgcttta gtaggaaagg agtgaggatc   41100
ctaagttcat aacaccatcc ttggcttcaa aatttatctt aaaactaatt agcctcaatt   41160
tgaacttctt atctgggaga atggtcctga cctgttctct gattcctcat ctggaatacc   41220
acagcacctt cctcgtgggg ttccctgctt ctttcccacc cctcctctag cccaaccttg   41280
ctgctgtaag tctgattatc ctaacaagta cagatctttc ccatatattt cagcataaag   41340
ggaaattttt gtttgcttga aaaagcatcc ctttagcttt ttttatatac cacacacttt   41400
gcttctaagt taaatgtgtt atatgatcct cttaacagcc tcataggtg ctgtacacaa   41460 tttgtagatg aggaagcaac ttgcctgagg atccagagct acaaagtgct ggacctggga   41520
tacagagccc aggctgcctg accaccctgc ccatgccatt aaccaccact ctaccatgcc   41580
accagcatca ccattttcag tttgtcctca gacaatatac acatctttct ttgatcaagc   41640
ccctgccagc ttctttagca ccagcttctg ccactgtcca cattcccagt tacttgtagg   41700
tagttctaca gatgtcacat cgtgtgattc ctctgtcatt tctctaccca ccagccttcc   41760
tttagcccca tttgtccatc agaacccttg ggttactcct gaatgccatt cctggaccag   41820
gcgccaaaca ctgagccccc agagcagcct gccctcgcct tggtgattgc atttgtcaaa   41880
ctgctgatta gctggtttgt cacctccacc aggctgtggg ctccttaagg gcagggactc   41940
catgttgtat tcctctctga atctctggct aacatccagc ctggagaatc gaggatttgg   42000
ccagtggata cctctttgcc cttgtttct gttctcttcc acactctctc tgctctagtc   42060
acactggccg tcctgttact cctcagacct gctatacaca ttcctgctgc atggccatgg   42120
tgccttctgt gccctctgcc tggtgccccc tatctcatca cgtggtttat tctcctgaca   42180
gccattagag ctcacactcc ctgagagctg caaggagact gtcctctgtc cctttactca   42240
cgtttgccat tatgctatag actatatttt gtccctaagt ccatcctctg ttactataag   42300
```

```
agcagcaact tggtggtggt tcttatatgg ttttcattt gtttggtttt atttttgcc    42360 ttgctgtagt atccatactg cccagaatgg tgcatatgta gttaagagta attatttgtt    42420
gagtgaataa atggcacatc ctcagtaagg ttttgaatga aaaaatgact gtactaactg    42480
atcaactgta agattttccc aggtaattct ttcaagggag ttccaagtat aggaactaag    42540
gcagctacac tggagcttta gagaaatgat tgtcatattt cctcctcagt cctaaatctc    42600
ctcttgtcac aggatatcag cattgcttat ggggagcacc tgatgcagga gcacatgtat    42660
gagccagcgg ggctcatgtt tgcccgttgc ggtgcccacg agaaagctct ctcagccttt    42720
ctgacatgtg gcaactggaa gcaagccctc tgtgtggcag cccagcttaa ctttaccaaa    42780
gaccagctgg tgggcctcgg cagaactctg gcaggtaagt acaatcattt atatgtttac    42840
atctacaaag gttttaaaaa atttatttct tttgtttggt aattttgcaa ataaatttag    42900
ggcagaatac tctgagacag tcttgttctc actgataaaa attaatttag aatgctttaa    42960
aggataagct actacagcaa gagtcccaga atgcagtggc ccaatatgga aagaagttta    43020
tttctctctc ccatagggat ttataggccc ttccgttgtg tggctctgca acctttaggg    43080
cagatggttg tagctgggtt atctccacag ctgtggggaa ggaaggagag tggggagaag    43140
ttagaatcat ggtaaaacat ttacctttaa gttggaaatg acctggatgg aagttaaact    43200
atcaccttct attccatctc ggccacgcca tgtagctgga tgggctgtgc cctgtaagaa    43260
ggtaaagatg aattttggga tgggtccatt ctgttataga cagtaggttg ttggaatagc    43320
caggaatgag gtggggaaaa taaaaggcca aatgtcgaag cattctgaaa gcaaaggcag    43380
tttagctgcg tcagggacaa gggttgcccg aaccagaggc gaggctggta ccaggggctc    43440
tagtaccaga gtggaggaaa gggtaaggac acctatgaaa agagatgagc agaagctctg    43500
gtcatctcag cagtgcttga agtaaagcaa tgactggtat attttttcc ctaacttgta    43560 aatattgttg agatctcaaa gaaaaaaata aaaagcagtc ctaaaaaaat tccaaactct    43620
atcctgttaa attttgttaa atttatgtac cagtccttct ttgtcatttg cagtattctt    43680
tttttcttgg gattataccc agtgtatggga ttatactttt tcttttctg gttattagcc    43740 tttcccaaat ccctccgttt ccatgctggc ctctttttac aaatgtcgag aattccttat    43800
ttcaggcctt ttagttattc gttcggtctc cattgttcct ttctgcttta gaaatttatg    43860
atattggttg tttataccttt ctatctctgt tcttggatct cttctattct ttacagctct    43920
tagcttgcta tttcccatgt cttatgaggg agtatttcta gttttttctca gatgtttagc    43980 aaaagtaggt ggggagggca gtggtcaaag atgtttgaga aatgttacac actggagtca    44040
ctctgtgtgt acatttaacg taggcagttt acacaagaga gcaaagaaa ggtaactatt    44100 taaatagtgg aggtgatttt acctactttt tttagtgata tatgcactgg agtgagcatg    44160
caatgagaga ccggaatcta ccagctcctt cgaaagcctt gggttctctg tgcctctcat    44220
tgtggtttat ctcaattggg ctgagagtga ttctaggatc taaagacact gcatgactca    44280
aacataagtc agctacctcc atctagtgct caaccaaaga aatagtggtc tcttactgtt    44340
aagggacgaa gtggtttagt gagagatacc aggtcatttt cccatataca tgctttggaa    44400
gcatctttca aggctaattt tggctgtata tgattttcaa ttcctgtgct aaatttagat    44460
tctagctgcc atttaagata ggactctgtg gtgtatatac ctattccctc acagaaattc    44520
agaaagtaca tagtttcata cataataaag acatattaaa gaagcacttg agctaaagta    44580
tctgtttaac tttgtagtca actgctgctt attgtctcta caggaaagct ggttgagcag    44640
aggaagcaca ttgatgcggc catggttttg gaagagtgtg cccaggtaaa ctcaattcct    44700
```

```
cccttctaaa ccccccagtc agcaagaaag gtcttctcaa ttgtatctta gtgatcatga   44760
aagttaaagg aactgtgcat aattgttaag tccagagata gtgtttgccc cagaggtctt   44820
atcttgctgg cttgacttgg aaatctaaat ttagtacatc tctaagtttg gtgaggtaga   44880
atatgaaggt gctctacttt aacataccac tggtttgacc ttggtagaaa gtacttaatt   44940
acatctcaag gtagctgtgc ttttaaaat tgagtttgcc aaagtagaaa caatgagaaa   45000
ggaccattat aaaacaggat cattgaaggc tacatactct tggcttttac tctcattctc   45060
cctattggaa atgtctcttt tacctcaggg acctggaggt acagcagatt ataaggataa   45120
gtacccatat gagcatttgg tagtattata ggatttatta tgaaaataat aaaactgcag   45180
taacactggc cacagactaa cagtacacag gtgcacagtt gacaccaggg attattgcct   45240
tgtagagttt tgacctttga tgagagagtg ttttttacag ttgttactga tagcacattt   45300
atgtaactta attgtgcttt aaaaatattt aattgtctct tgtgtaataa cagtaagtga   45360
aagacgataa ctaaaatttt atataattag atcctggaga gaatatttgt tgggtgattg   45420
aattgaaaat accagtgaat gaaacatacc taaaagggta gataggttgg gttggaaaga   45480
tataccacat cgagggttaa ttaaatggat aagatgtcat tatctttttt tctttgtaaa   45540
ggaagattaa tgcataaaat tatttgtgt aatttacata caataaaatt atgtgttgta   45600
cagttgtata atttacatat aataaagcta attcaccaat tttagatgaa gaattcagta   45660
catttggaca tatgtttgta gctgtgtaac caccattgca ctcatgatct agaacatttc   45720
taacaccccc aaaagttccc tacttcccct tttgcagtca gccttctccc tccactgcca   45780
gcctttggca aactgatcag tcagtaaagt ttcacattat ctagaatttc atataaacag   45840
aaccatatgg tatgtagtct ttttaatctg gctcctttca ctcacatagt gcattggaga   45900
tgcatccatg ttgtagttta ttccttgta ttgctgaata gtatcccatt atatgtatat   45960
gtcagaattt gttgatttac cagttgatgt acatttggat tgtttcagt ttggggttat    46020 tatgaataac gcagccatga acattctagt gcaggtcttt atggggacag gagtaggaat   46080
gccacatccc gtggtaagtg gatgtttaac tttttaggaa gctgcagaac taatctgcag   46140
tggccgtatc attttgcatt cccctcagtg atatgtgaga gtgcttcagt gactcctata   46200
ctcaccaaca ctgggtgtat tactgtgaca ctagatgtat tatctattgc tacgtaacaa   46260
cttaccttaa aagctggcag cttaaaacaa cagaccctat tatcccactt tttcaatggg   46320
ccaagaatct tggctgggct tagctggggc ctctggctca gggtcctta caaggctgca   46380 attaaggtat tggccagggc tagagtcatc tcaaggcttg actagttttt aatttcattt   46440
tctaatgttt tattactagt atatagaaat atagctgaag tgttttgcag ggaggctgta   46500
taattgacct tgtatcctgc aaccttgcta aactcattta ttagttctag aagctcttgg   46560
gtgtattctc taggattttc tacatcaaca aacatggttt ctataaatat agttttatgt   46620
ctttcttaca atcaatactt ttttctatct gtattgcatt ttctagggct tccagtgtgg   46680
tgttgaatag aagtgttaag agtgaacatc cttgcctttt tcctgatatt ggagaaaatt   46740
cacttgtctt ttagcattaa gtgtcatgtt tgctttttta aaattttatt ctatattatt   46800 ttattttga gacagagtct tgctctgtca cccaggctgg agtgcagtgg tgtgatctca   46860
gctcactaca accttgacct cctaggctca agcgatcctc ccacctcagc ctcctgagta   46920
gctgggactg caggaacatg ccaccatgcc tggctaattt ttgtattttt tgtagggatg   46980
gggttttgcc atgttgccca ggctggtctt gaactgttgg attcaagcaa ttcgcctgtc   47040
```

```
tcagcctccc aaagtgctgg gattacaggc atgagcctcc gtgcctggcc tgatatttgc    47100
tttttttttt ttttttaatg ctctctattg cagagttggc aaactacaac ctgtgacaaa    47160
tccagcatgc cacctgtttt tgtaaataaa gctttattgg agcatagcca tgctcattag    47220
tttacatctt gtgtatggct gctttaacac tacagcagca gagttagagt tgtgacacag    47280
atagtttggc ccataaggcc tatatttact gtctaatctt ttacaggaaa aatttgccaa    47340
ttcctgccct cttggtttga ggaaattccc ttctgttcct tgttctgaga gtttgtatca    47400
tgaatgggtg ttaaatttg tcaaatgcat tttcaactat gaagggtttt gttttagac     47460 gagtgatatg ggggactagg tgattgattt tctactgtta aaccaacctt gcatctctgg    47520
gttcaacccc acttggtatt atagatttat taccctttt ctcttgtggc agattagatc     47580
tactaaaatt ttcttgagga ttttgtgtt tgtgttcatg agggatattg tagtttttc      47640 gtgtctttgc catgttttgg gtatcaggat aatgctgctg tcattgaggg gtgacaaaaa    47700
tgaggggtgg tgtcctttac acttctgttt tctggaggat ttcatgtaga attggtatga    47760
gagtctagct tatggttaaa aacctatgtg tgatgtttca gacctgacca taaacaatta    47820
cagactttac ctaggaggcc acatggggaa aagctgccct ccctacacca gacttggcgt    47880
actgccaatg cattacagtt tctaaaggga gttgcagtca aggactcagg gcccctgtt     47940 agtcatgctc ttgtaacagt atttgcattg agagtcctgg cactttcatt cttaggtctc    48000
tctatctgag gacatgggcc aaggtcttct tcaggcacct ctgccaaggc ctgtttatgc    48060
aagaaggagt ggaaaaacct tgacattttt ttccactgtg actcactacc cagtactttt    48120
ccacccttag ccccccttcct ttgcacccat accccccaaga tccatcaaac tgctaaagcc   48180 ttttttttcca agctccttca acagtgaacc aaccctcatg tctgtgtgga tccagctgac    48240
tcttgactag tgagttgttc cttgggaaaa aatggaacag agagagttgg tgctttccct    48300
ggttttagcc tcttgcttat accaatgcaa tgcctgaagg cttaattcat ttttgacttg    48360
ttgctttgat cagctactcc aacacctgac agctcagctc tttctcccag ctcttgggag    48420 atatttttt ctttaaatgt ttagtagaat ataccagtaa ggccatctcg gccaggagtt     48480
ttctttaatg aaagtttttc actattagtt cagttacttt agtagacatt aacctattca    48540
agtttatctg tgtcttctgg aatgagcatt ggtagtttat gtctttcaag taatttgttc    48600
atttcatcta aattgtcaga tttattggta tgaagtgttt atagtattct cttattttac    48660
tgtccgtagg gtctatggtg atgtcctgtc tttcattgta gatattgatg tgtcttcttt    48720
tttctgatta ttctggccag aggtttatca attttattga tcttattaaa gaatgaactg    48780
tttcattgtt tttctctatg attttctgt attctatatc attctttttt tattatttta     48840
ttattttatt tgctctttat ttttctagtt tcttaaggtg atggcttact tttatttttt    48900
tcttattttt ttcttttgtt gttgttgttt ttttaaagaa acagggtccc actcttgctc    48960
aggctggagt gcagtggcac gatcatggtt cactgcagtc tcaaactcct acattcaagc    49020
tgtcctcccc cctcagcctc cagagtagtt gggattacag gtgcatgcca ccatgcctgg    49080
ctaattttta attttttttg tagagatggg gtgttactag ttgcccacgc tggtctgaaa    49140
ctcctggcct caagtgatcc ctccacctct gcctcccaaa gtgctgggat tccatgtgta    49200
agccactgtg cctggccaag gtgatggctt aaagctattg atttgagatg attccttact    49260
ttatagttta agcatataat gccataattt tcctcaagca ccgttttagt tacgttatac    49320
aaattttgaa atgtttgtt ttcatttcct aatttccctt tgatttcttt tattgaacct     49380
tggcttattt agaagtatgt ttaacttgca gatattggag atttgccagc catcttttg     49440
```

```
ttattaattt ctactttaat tttgttgtga ttagagaaca tacattttat taatttaaat   49500
ttataattta ttttaattta taatatggtc tgttttacag aatgttgtgt gtgtatttga   49560
aaataatatg aaagctacta ttattggatg gagtgttcta taaatgtcag ttagattagg   49620
ttgatcatgc tgttctagct ttttatatcc ttattgattt cctcactact tgctctatca   49680
atgactggga aagtgttgaa gtctcccagt atttgtctat ttctcctttg attctaccag   49740
tgtttgctta atgtattttg aagctctgtt ataggtgcat acatgtttat gagtatgtta   49800
tagatgtatt cattttgata tccttctttc tctgttacta ttcctaattc tgaatttgac   49860
tttaatgtta ttaatataat tcttccagcc ttctcttggt tagtcttttc attgcatatc   49920
tttttctatc cttttacttt taatctagct gaatgtagtc tttattttga aagtgcgttc   49980
cttgttgata gcattattgg ttctttttttt tttttaaatc taatttgaca atctctgtct   50040
tttaattgga gggtttagac atttgcattg aatgtgatta ccaatatagt tagatttaaa   50100
cctacagtct tgctgtttgc ttttttgtttg tttcattgat cctttgtttc ttgttttttt   50160 cttttttttgc tttcctttgg atttagtatt tttcataatt ccattttacc tccactgttg   50220
gcttattagc tatacttctt catttcagta ttttagtggt tgctgtagga tttataataa   50280
atatcattaa ctgaccatat cttcagataa tcgtatacta cttcatatat agtgtaaaaa   50340
ccttacaaga gtattcactc cataatactt tgttattgct tttgctttaa gtgatcaatg   50400
attgtttaag gaaattttttt aatgaccttt catgtttatt cttttttttt tttttccaaa   50460
agattcagta ttttccgagt tttcaaaaac tgctggccac tcaaagtgga tcaacaaaaa   50520
tttaagagct aaaactgtaa aactcttgaa ggctgggcac agaggttcat gcctgtgatt   50580
ccagcacttt gagaagctga ggtgggacaa tcacttgagc caggggttt gagaccagcc   50640 tgggtaacat agaaagacct tgtttctaca aaaataaaa acacaattag ccaggcatgg   50700
cggtgtgcac ctgtagtccc aacttcttgg gaggccaagg tggcaggatt tcctgagcct   50760
gtaagtttga gactgcagtg agctgagttc acgccactgc acttcagcct ggacaacaga   50820
acaagaccct gtctcaaaac cagaacgaaa ctataaaact cttagaagaa acagggcta   50880 aatcttcatg actttggatt tggcaatgga tggttagaat taataccaaa acacaatca   50940 ataaattgat aaattggatt taataaaaat taagaacttt tgtgtatcaa ggacattgtc   51000
aagaatgtga aaagacagca tatagaatgg aagaagatat ttgcaaatcc tatatctgat   51060
aaaggtttaa tatccagaat atgtaaggaa ctcctgcagc tcaacaacag aaagccagtt   51120
aaatcaattt tgaaatgagc aaacgcctgt aaacccagct gcttggcaga ttgagacagg   51180
aggattgctt gaggctagga gttcaagacc aacctggaca acatagtgag accctgtcta   51240
aaaacatttt tttaattagc tgggtgtggt ggcatattcc tgtagtccca gctacatggg   51300
agaccgaggc aggaggatca cttggggcca ggcagtcaag gctgccgtga gctgtgatta   51360
tgccactgca tcccagcctg ggcgacagag tgagaccctg tctgagaaaa aaaaaaaaa   51420 aagaacaaaa aaaaatttag aagattgcta ttcagtctca ctattttttc aaagggtggt   51480
cttgttaaca attctggagc ccacctaaac ctgctaaatc aaacttggta gtaaagctgg   51540
ggagatgggc atgtctaaca gacgtttctg gtggttttga tgtccaggcg tgcagagaga   51600
tgatgcttac cttgtgtttt gtcattattt tcaggattta cacccctttcc ttgtcttttg   51660 tatcaatatt tatggagtca tgaactctag gataggcatg atgttgagaa ctaggagttc   51720 tccctggcc agggagatag aggcaggtct gtggttagtt ttgtagttgg ctgtgatgac   51780
```

```
atctgacatg ctctcttcac ttgttgtctt cttcctgttc ccttgtcagg attatgaaga    51840
agctgtgctc ttgctgttag aaggagctgc ctgggaagaa gctttgaggc tggtaagaat    51900
cttgtaaatc ctctggatgt tgggtgctaa gcagagagag caagcaaggg attccaggtc    51960
agttggaatc tcttgtcttc tgaggttcat gaaataagta gaaataggtc aggttcctgg    52020
cttaaggaaa agcggtgtta ctaaaatcat ttttatcatt cttgataata atttgaaata    52080
ttactgtctt ttactgaaat gaattgaatt tccttggctg ccttgtagga ggcctgtttt    52140
tcaggaaaat attctgatta cctctgaaag taatccatgt cttttctaagt atcttaactc    52200 tccagtgact agaagttttc cttcctaaaa tatcgtgttt ttccttctag gtatgcaaat    52260
ataacagact ggatattata gaaaccaacg taaagccttc cattttagaa ggtgagggtt    52320
ccattttaga tagaattcct catttggaag aaggtgagga gagagagatg agagagtctc    52380
ctcctattta ctgtgttttc ttaataatat gtcatgtaga ctcaatcaaa attaccacct    52440
ggatataata tttaattctc actagaattt ttaaatatgc tgaactatta aatggtaaca    52500
aaatatttaa atgttagaaa cctgtgatca aatatgatta agaatctttg tatttggaaa    52560
tagtaaactt gaatatgaac tatattagat aataatataa cactgataaa tttctggcat    52620
ttaataatca tgttgtggtt ataaagata atatcctatt attctcaaga gataaatgct    52680
gaaatattta ggaatgaagg atcatatctc tgccttactc ttaaaaggtt ccacaaaagt    52740
attaatgaat gtgtgtatgc atgcagagaa acaggaagca aaaaaatgtc aaaatgttag    52800
taattggtaa atcaaagtga agggtatatg tgtgttcatt gaactcttac aacttttatg    52860
taggtttcaa cgtttcaaag tatttttttaa aagttaccttt ttcaaatgaa gtttgtggtt    52920
cttagagaac atatgaatat taccagttct agaatactca gatggtcact gtgacctctt    52980
aaaagcaaag tggagaagga catcagtttg acttatagaa accttaggga gtggttgatt    53040
ttaagttctg cattttttatg cacatctacc ctgtaagtaa cgtctggcct ttctgacatt    53100
tacatgtatg cacattctta ccttgtctgc acccccttcc tccatcctaa ttaaaacgtt    53160 gctgggggtac tttttatgtc attcacttta ggtacctcta actgggtact gaaaacatca    53220
ttcctcatct ataataatct aaccagctct tacttagatt ttcaccacta atgagaacct    53280
ttcttagata aatgccgata attcatctac ataggcccaa aacctattaa taaaatgcat    53340
ccttggatag tagtattttg cttttttaaa atgtattcta ctagtgttat ttttctcttg    53400 tgtattttc cattggacaa tatttattag atacattttt tccacatcca tgggcatttt    53460
gatggatgtt tagccagaaa catttaggta atttctcttt tatttttgtt aactgagctc    53520 ccctcccctaa cccccccttt ttttgtttgt ttgttttgtt tgtttgtttg ttttgccaat    53580
cctcccttgc tttaggtatc aagtcttcgt tcaggtgatt tttacaagttc agtggtagcg    53640 catattctgg gataatgttg atgaactcta agatctggaa tctcagtctc taatttgtta    53700
atgcttatta aggaaaaaga gctcgcttgg aaaacctagt aacctctttc tttttgctga    53760
attttaaccc tccttcactg ctccccgcct ttagtttttt ctctttgctt aaacctcatg    53820
ctcaaactat tttccattct gcatctccag cccagaaaaa ttatatggca tttctggact    53880
ctcagacagc cacattcagt cgccacaaga aacgttatt ggtagttcga gagctcaagg    53940
agcaagccca gcaggcaggt ctgggtgagt atctgcgtga aggccatcga cgtgcggggg    54000 cagtgggggtt gggtaacgcc acacattgtc tagattgctt ggtgatccgc ctgcaatctg    54060
attactgtgc catgggcaag tgtgaggctt ctgtggagcc ccttcaggggc cctctgtgtc    54120 tgtgtttgtg tgttggtgaa gggcaggacc aagcatgaat ggggagagct ctgccagaca    54180
```

```
ttcccaccta cccccattca cccagagcag ctgaccactt ccgtgtctaa caaaatgagt    54240
ttcctcattt ccagaaaaaa gttcaggaaa ctactgattt acattagtaa ttactgtatt    54300
taatattatc tcattcattt tgagatcaac tttgcaatca ttttcatcca tcctttgata    54360
tgcaccagtt gactctagtt agttcattta ccgccctgaa agtaaaccca cacattagca    54420
ggcagtgttt tcatcggctt ctggttcttc ttttctagat gatgaggtac cccacgggca    54480
agagtcagac ctcttctctg aaactagcag tgtcgtgagt ggcagtgaga tgagtggcaa    54540
atactcccat agtaactcca ggatatcagc gtacgtatca cattgattca gcacattgac    54600
tatatcctgg gcatataggg aaagtggaag caaatagatt ggttttctac tgggacggtg    54660
tagtgggagt ggggagaata ttcttcagcg ctgtgtggaa gttgttcaga cactttccca    54720
gcatatctga gacattaaac ttggcattgg aaggttttct tcctcagctt tgtggcttgt    54780
gtgttttccc attccccacg aggcagttcc tcccctgaat gctcagttta tattaacatc    54840
tgattttatt ttttgaacaa atgttgtgac taaattatag gcactgaaaa aatgaaaaga    54900
taagcttctt caattcaaaa tcaggattgg aagagaccat aaatgtaaaa taagtcataa    54960
cacttttacc aaatatagta atttgtcaga aatatttatt cagcactcat atggtaggtg    55020
cagtagatgt taccaaaaac ttataaggag atatgagtta taagagttta tagtcttgct    55080
tgggatgtgt aaagcaatgc aagattatat attcaaactg aattttgctt taggaattta    55140
aaatggagat ctgtgaagtt gtgtggggtc atcagcaact gcaagaaagt agccaggcaa    55200
ggtagcacat gcctgtagtc ctagctactc aggaggctta aaaatatctg tgtaatttct    55260
aacaggagat catccaagaa tcgccgaaaa gcggagcgga agaagcacag cctcaaagaa    55320
ggcagtccgc tggaggacct ggccctcctg gaggcactga gtgaagtggt gcagaacact    55380
gaaaacctga aggtatatt ctcagtcctg atgatgattc ctgaccacaa acaatagtga    55440
ataggcagta cagacaggca gagttcagta ggtgattaag ctaccatttt cccaatttga    55500
ggaaagatga gaacttttag caggaagggt catgtctgca cacattcctg aagcagccct    55560
tcttagctgg taactgagaa gccttcctcc atttggcatc cccctaactg aactgggaga    55620
gatgcttaag ccaggataaa gaattgtggg acactgcttt ctgcgtaggc cccccagcgt    55680
gcttgatttt cttttttgtag tacatgtgtt taattattcc agcatttggg aagaaaaaag    55740
ataatgtggg agaaaggacc tgcagtggga tcatagaaat ttttggcttt ggatagaagc    55800
tatgtatgat tctgtcaatg gagctgggaa tataacttac cactcttttca aatttcttct    55860 ctctagatga agtataccat attttaaagg tactcttttct ctttgagttt gatgaacaag    55920
gaagggaatt acagaaggcc tttgaagata cgctgcagtt gatggaaagg tcacttccag    55980
aaatttggac tcttacttac cagcagaatt cagctacccc ggtaagtttt ctcagagacg    56040
gtgtgcattt ttttcatcat tttcatgggt tattgtattc acacaatctc caagtcaaaa    56100
agttttcctg ttcttaaaac ataagatgcc atagttaaat tatcttagca tttatgtgta    56160
agctgtcagt aagatttgat atttgcctgt agagtgacta gtataccttg gcataggtta    56220
aatggactgt cattttcctt tctggatgaa gtagctgtca tggagaaaat gggaaagtca    56280
catgattgct cctggccttc aatgaggttg gagtggggag agatggggga agatgggggtc    56340 agagacggcc tctcactttc ctttcagaac tcagggatgg gatcaggctt taagggggacc    56400 ccaggcaatt gcttttcctt ttgtttttatg aaaaatttga cttgtcactt ctatgttgtt    56460
atgatggact ttgcgggttg tgtttaaggc tgaatcagct ttgtatcgca gaattctagt    56520
```

```
atattgtcat ctgttttatta tttatacctc tgttcactct cttatacttc aagtctattg    56580
ttaagagttt ttatttggat tcaaaaaggc tggtgtatca gtcaagatct agaaaggaaa    56640
acaaaagcct atctattatt ttatcacaga atttaatata tggatttgtt aaataagtat    56700
tagaggacta aacaaggcaa aagggaaata cagaggaagg acattgagat agtaactgta    56760
ggaagcagct ttaccctcta gctgagggaa caggaggagt tgttgggaat tattagaatt    56820
tagaagcctg gaagtggggc cctgtagagc tggctcttga acctctgaga ggagggtgcc    56880
agccagctaa tcctggcatt tctgagggag ctggttccaa gcgtacagaa gtaaatggaa    56940
actggaagga acagctgctg ctgggggaaa agccagccgg tcgggccagg tgtggtggtg    57000
gctcacgcct gtaatcccag cactttggga ggccaaggca ggcggatcac ctgaagtcag    57060
gagttcgtga ctaatgtggc caacatggag aagccccgtc tctactaaaa atacaaaatt    57120
acccgggcat ggtggcgcat gcctgtaatc ccagctactc aggaggctga ggcaagagaa    57180
tcgcttgaac ctgggagaca gaggttgtga tgagccaaga tcgtgccatt gtactccaac    57240
ctgggcagca agagcgaatc tccgtttaaa aaaaaaaaa aaaagccag ccaatcacgg    57300 aagaaatcta gaaatctttt gttcatcctc cagctttgta ctcccctct ggtgttcact    57360 gtaggcagga catgatggga agccagcagc aaggaagaat atctttcagg tgcccagccc    57420
cagcaccaca agcagtggat agaagggtgg gttggagctg agagattaca aatcagctca    57480
gtgtttagaa acacatacgc ttatcatgtc ttgatttcct catttagaaa tgggcataag    57540
acttctctgt gtgcttcaat agaatgcttt gaaggttaaa taagagggtg tgtgtaaaag    57600
cactttacaa accgttgaaa taaaagcaac taggaatcag ggccccagaa cttcttgaat    57660
ttattataat aggtatttct tagaagaaat gtgatcatca tcttcaaaac tgtagtactt    57720
ttgaagataa ttgttttttgt tttttgagac agggtctcac tctgttgctc aggctggagt    57780
gcagtgatca ccgctcactg cagcatccac cgccccgggc tcaggtgatc ctcccacctc    57840
agcctcttga gtagctggga ctacaggcgc atgccacaac acctggttaa ttttcaaatt    57900
ttctgtagag acagggtgtc accaagttgt ccccgctggt cttgaacaac tcctgggctc    57960
aagtggtctg cccacctcac ctctccaaag tgctgggact ataggcatca gccaccatgc    58020
ccggcttgaa gataataatt tataatacca ctcccatgag tgatcttctc ttctgatcac    58080
atattcacat taaggtctat tttattttat ttttttcttg ctctgtcacc caggctagag    58140
tgcagtgaca gtatgatcaa tcatggcttg gtgcagcctc gaatgcctgg gctaaagcag    58200
tcctcccacc gcagtctcct gagtaattgg gaccacaggt gcacaccacc atgcccagct    58260
aattttaaaa ttttttccta gacatgggga gagggagtct tgctgtgttg cccaagctgg    58320
tcttgaactc ctggcctcaa gtgatcctcc tgccttggcc tcccaaagtg ctgagattac    58380
aggtgtaagc caccatgcct cccacattaa gttctaagac atcaatttta tgattgtggt    58440
tttgattggt gaagtatggt tgtggtatgt gcaggatacc gtgagtgact tctcatggca    58500
ttgctcttga gagtgtgcca ccaagggtct gcactaacca ggggtgtgcc cagaggctcg    58560
ctgcaggctt gaaattcctg cggagtcttg tgttttacct ggagcacatg tgcacagttt    58620
ccattctgct ccatagtatg cacatgtttg tatttatttc aacctaaaaa tgtttgtttc    58680
ccataactct ttgcgtataa ttgatactct acgtatttgt agcctctttt actcttttcc    58740
ctttcctcag ggagtggttt gctcatttag aaaaggccaa gatatatcac tgtagagttt    58800
cgtttctttt cttttcctcc accccccatc tttaccttgt tctgggagaa aggagaatta    58860
gaagtctgag ttgcagctgg agaaactggc aaattaaaat cacattggga aagagaatta    58920
```

```
ctgtgtttca caccatacca gtagaaatga caggctgttt tctgctggta gggatttggc    58980 cttttggtatt ggcagtcttg agaagtatta gataatcttt gctgatacag tctattttct   59040
cctcaggttc taggtcccaa ttctactgca aatagtatca tggcatctta tcagcaacag    59100
aagacttcgg ttcctgttct tggttagtat ttttttctcat ttaatattac aatactaagc   59160
agaaggacta tctttctgta agtattgaga agatcagcag tataaggaga gattggatac    59220 aattttttcac tacaaaaaat tgactacaat tcttcctcaa ttctaagacc gcatctttag   59280
tatgatcagt ttcatgcttc tagcggtggg ggacctggtg caggaaaatc cagcatgacc    59340
attgtatgtg taatttttaa aaatatttat gtggcatatg cttgttcata aaggcacacc    59400
acagttccag tttcagtcta aactgtctac atttacatat acatcaaaag attcttctga    59460
agcatcatta ctggctattg gcagttatgc tttgcatctt gggggcattt tcataaacct    59520
tgcttatgag tgggacccttt ttattatgtt taggattgac aatataattt gaaggcaaat   59580
ccaaagaata ttagcatttt atacatattt cctgtttagt tatgcatgaa gtgttttatt    59640
tgttgagggg agatgattct caattagatt acttatttcc ctaaaaatta aaaaccctaa    59700
gcgcttcttt ttgaaagttg gttagaaaca tttgatgagt cagcttggga cttcagtat    59760 ttgcccttac ttatagttgg atcaatgaag catcttagct ttgaaaagtg aatgatagtt    59820
tctaaaataa ttggcagttt taactgctat tatttgcatt tctagcatgt gacaagcaac    59880
tttctgaaat tttttttcac cgaagtgcta cactgtaata gcattttgat gacatttgaa    59940
gtagcctgtg gggattcaaa ttaagtttga ctttaacagc ttatgttgct accaggaaga    60000
acagctacct tccatcccag ctaaactcat acatccagac tgtaactact gtattcctag    60060
ctcctcttct gtctagagaa tggcaaggtt cttttggtat gcagtttcga catatccact    60120
tattcctttt tttttcttaa gttttttcat ttagaaaaaa aaacagatgg ggtcttaata    60180
tgttgcccag ctggtctca gcctcctggt ctcaagtgat cctcctgcct cggcctccca    60240
aagtgctggg attacaggcg tctgcccctg tgcccagccc acttatttcc cagatgctag    60300
gaacttacat tagacctgag gccatttggt cattgtttat tttgtgctgt agtccaatcc    60360
agttgtgatt tctgcctcct gtgttcctcg ttgctggcct gatgctgacc ttcaggttag    60420
gtcagtccca tcattcccca gggtattcta atggctttc ccacttcaaa gagcactttc    60480
ttgttttcca gctgagcctt aaagacactc tgtaatattt gagagcccct cattatctga    60540
gtgtttatta tcattaccct tgtggtttca aggatgtata ggaaaaggta agttcctata    60600
attcaaaaat tgccactgat gaactaatca caaaattagt gccactcaaa tattactcag    60660 ctgccccctcc ccagctaaca atagttaagt atattggcac atccccacaa gtgaaatcaa    60720
tgacttgatg ggtcatttct gattgtttcc tgctttgatg caatacaata tcatgcagat    60780
caattgcaag tcttgcaaaa atttagtatt acataaaata gattaaaatg atattggaaa    60840
agtacttgaa tcacagctgg gttggacttg ttgcaattga tgacaaaata agtgcttcaa    60900
atgattttga ctatcaaagg attgagagag gtccttagaa aaattgaaaa gccctcaagt    60960 tattttttata aaaatggcct ttttttgtgtg ctgtgaaatc cacatatgga aatgtgaaat   61020
atgtcatgtc ctgctgtcat ataatttgtc agaataatta ctttcttgcc caaaagtctg    61080
tactttgtgt ttatttcaag ttaagtctag aatcaaatat agttgtagtt atgcctaatt    61140
ttaaaaaatg agatagagca cattattttt gtaactagtt tttttttttt ttttcagac    61200 agagtcttgc tctgtggccc aggcgggagt gcagtggcgc aatctcggct cactgcaagc    61260
```

```
tccgcctccc gggttcacgc cattctcctg cctcaccctc ctgagtagct gggactacag    61320
gcgcccgcca tcacgcccgg ctaattttt tgtattttta gtagagacgg ggtttcaccg    61380
tgttagccag gatggtctcg atctcctgac ctcgtgatcc acccgcctcg gcctcccaaa    61440
gtgctgggat tacaagcgtg agccaccgcg cccggcctgt aaatagtttt tttaagataa    61500
agtcttattc caactttaat tggaatttat gaaataacct gttgatagtg aatttattta    61560
agtagccttt tttcagtatt gatattctta tatctttatg gcaccattta gtggagagaa    61620
atgtaaacaa acataaagat gtagtattaa atcataactg cataaaatta actgtagtat    61680
gtactgcact actgtaataa tttttgtagct acctcctgtt gctattgtgg tgagtgagct    61740
caagtgttac caatatctgc ttaaaatgcc atgtgccgct aaccatctcc acatgagcag    61800
cacatgagag tctccattaa ttgcatatgg cagcgaaaag tgatctcttg cattgtcgtg    61860 tatttttat cacgtttaat gtaatatcgt aaaccttaaa taacaccatg agacctatag    61920
gaagtaccac aagtgttgct cccaggaagc agagaaaagt cataacatta caagaaaaag    61980
ttgacttgct cgatatgtac tatagattga ggtctgcagc tgtagttgcc caccacttca    62040
agataaatga acccagtgca aggactatta taaagaaaa ggaaatttat gaagctgtca    62100
ctgcagttat gccagcaggc atgaaaacct tgtactttt gcaaaatacc tttttatgtt    62160
gtattgaaga tgcagctttt atgtgggtgc aggattgcta tgagaaaggc atacctatac    62220 aactatatg atttgagaaa agcacagtc attgtatgag aacttaaagc aaaagatga    62280 aggatcaaag ctggagaatt taatgccagc aaaggatggt ttgataattt tagaaagagg    62340
tttggctttg taaatgtctg gataatagga aaagcagctc ctgccatcca ggaggcagca    62400
gcaaaggcag tcaggtttat gatcaggact gcccttatct gtaaagctgc taaccccga    62460 gcctggaagg gaaaagatta acaccagctg ccaggcttt ggttgtacca tacaacaaga    62520
aggcttggac aaggagaaca ctttttctgg attggttcca ttgtcgattt gtccctgaag    62580
ttaagtagta tcttgccagt aagggggactg cctttaaag ttcttttgat actggagaat    62640
gcccgaggcc acccaaact ccatgagttc aacaccgaag acattgaagt gatctacttg    62700
cccccaaaca cacatctcta attcagcctc tagatcaggg tgtcataagg acctttaagg    62760
ctcgttacaa acagtactct atagaaagga ttgtcaaatg tatggaaaag aaccttgaca    62820
gaacatgaaa gtctgaaaga attacaccat caatgatgcc atcattgtta tagaaaaagc    62880
tgtgaaagcc atcaagccca ggacaataaa ttcctgctag agaaaactgt gtccagatgt    62940
gcatgacttc acaggcttta cgacagccaa tcaggaaat catgaaaaag attgtggatc    63000
tggcacaaaa aaaaaaaaa aaaaaaaaaa tggtgcatga aggatttcaa gataggaatc    63060
ttggagaaat tcaagaggtg atagacatca caccggagga attaacagaa gatgacttga    63120
tggagatgag tacttccaaa ccagcgccag acaatgagga agattacata aagaagcag    63180 tgccagaaaa taaattgaca tttgttccaa aggttccaat tattcaagac tgcctttggc    63240 ttctttaca acatggatga ttctatgtta tgggcactga aactaaaaga aactgtggaa    63300
ggattggtac cttagagaaa tgaaaaagca aaaacatcag aaattatggt gtatttctgt    63360
aaagttagtg acactgagtg tgcccacctc tcttgcctcc tctttaacct ccctacctg    63420 tttcatctct accaccctg agacagcaag accaacccct ccacttcctc ctctacttca    63480
gcctactcaa cgtggagatg acaaagatga agacctttat gatgatccac ttccatttaa    63540
tgaatagtaa atattgtttt ctttatgatt ttccttaatat tttcttttct ctagcttact    63600
ttattgtagg aatgtagtat ataatacata taacatacaa aacatttgtt aactgacttt    63660
```

```
ttatgctgcc aatacactgc cgaacaacag taagctattg gtacttgagt tttggagatt    63720
cagaagttaa acatggggcc aggtgtggtg gctcacacct gtaatcccag cactttggga    63780
ggctgaggtg ggtggaacga gaccaggagt tttgagagta gcctgggcag catggtgaaa    63840
ccttgtctct acagaaatta gccaggtatg gtggtgtaca cttgtagtcc cagctacttg    63900
ggaggctgag gcaggagaat cgcttgaacc caggggggtcg aggctgcagt gagtcatgat    63960
cgtgccactg cactccaacc tgggcaacaa aatgagaccc tgtctcaaaa aaagaaaaaa    64020
aaaaggtata tgcagatttt tgactgtgca ggggggtccg cacccataac cctacattca    64080
aggatcaact gtaattttc atgcctgcat ggctcatatg tacagattta ctgctggaag    64140
tttatcataa ataatgctga aaagaaaat cctatatat acatattttc tcctatctct    64200
gcttgcagta tatgattcct ggttagaaaa gaaacttaac aaatctaagt gaaagagtgc    64260
ctgggagttt taggttacaa tgacagaatc ttttcctaac cctctctctc cattcacttt    64320
ttttaaagca ggggcatctt tattgatcaa catgtttgtc gaagtttcat cataaagtag    64380
ttcctgtcca ttaacttcac ttactgaata tgtgctatca cattttgcta ttccttaaaa    64440
attgagctag actttacata tagtgaaatg cagagatttc aggtgtacaa tttgatgagt    64500
tttaataaat gtatacagcc atgtgactgc tgccaccacc cctcccacca gtttgaaata    64560
cagaacattc ttccactttg aatcactggg tgagcatgcc tgaggttgaa atgcagtccc    64620
tcctctcagg gcgggggcctc caggttgtgt ttgctctgac ctggaggttg caggggtagc    64680
agacacatga actctggctc tgatggtctt attgctgcaa actccacctg cctagtttgt    64740
ttagtttaga gttactgcct cagcgccctc caacaagagt atgtctgtca caatttccct    64800
tcctttcttg cttttagatg ctgagctttt tataccacca aagatcaaca gaagaaccca    64860
gtggaagctg agcctgctag actgagtgac tgcagttagg agggatccga cagagaagac    64920
catttccact cattcctgtt gtcctaccac cccttgctct ttgagggctg ctattgaga    64980
actggaaaga gtaaaatgat aacttacctt agcattgcca agaacttcag cagacaacaa    65040
gcaattctat ttattttatg ttgtgtatac atcttgatca ttagcaagac attaagcttt    65100
aaccattatg gcaccatttt gtgagaatga ttgttctttc acttgggctg tttgagagca    65160
taattatggt aatcatgaga ttaatgtttc atgatttcta cctccaaagt gtgaagacaa    65220
gtaaaacaat gtttctaaat tgtcttattt tgttggcgga gaagattaca atggctatta    65280
gtgctacatt tggtcaaatg taatcactta aatagcttct tgtcaccta aactaaagca    65340
gaataaaaag tatcctttga aattataagc cctcctttgc tgacagctat tattttgtaa    65400
catcttacca ggtcatgtgc tttcagttat aactgggctg agcctcctat aattacaatg    65460
tctataggga ctgttttact gcctgtgtat tttctgctag agagttagca atgttagagc    65520
tagaacagat tagaatttct aaacagtatc atgcacagtt ggtgtgagtg atcagtgtgc    65580
attgtatggc atgcatggtt gtgaattatt ctctgttctc caaatactgt ttctttaact    65640
cagatatttt tgttagtgtc taggccactt catttatttt tcgtcatggt actttactga    65700
cttctcttta ttcaattctc cacgccctca ccaaaaaaaa ctgtctcaaa atgagaatat    65760
tttatttca tggtgagtct agaaaacgcc cacttcattc tgattaaaaa ttcttccatg    65820
ttttaaatat cagaaccaga cctttcttac tgtgtatctt agcccatttg tgtctctata    65880
acaacaacca gctttcaaag gaactaatag agtgaaaact cactcattac cacgaggatg    65940
gcacaagcga ttcacgtagg atctgcccct gtgaccaaaa cacctcccat tgggcccac     66000
```

-continued

| | |
|---|---|
| ttccaacact ggtgatcaca tttcaacatg aggtttaggg aaacaaatgc ctaaactaca | 66060 |
| gcactgtaca taaactaaca ggaaatgctg cttttgatcc tcaaagaagt gatatagcca | 66120 |
| aaattgtaat ttaagaagcc tttcccagta tagcaagatg ttaactatag aatcaatcta | 66180 |
| ggagtattca ctgtaaaatt caacttttct gtatgtttga acattttcac aatctcatag | 66240 |
| gagtttttaa aaagaagaga aagaagatat actttgcttt ggagaaatct acttttttgac | 66300 |
| ttacatgggt ttgctgtaat taagtgccca atattgaaag gctgcaagta ctttgtaatc | 66360 |
| actctttggc atgggtaaat aagcatggta acttatattg aaatatagtg ctcttgcttt | 66420 |
| ggataactgt aaagggaccc atgctgatag actggaaata aagtaaatg tgtttattg | 66479 |

<210> SEQ ID NO 2
<211> LENGTH: 5924
<212> TYPE: DNA
<213> ORGANISM: Homo sapiens

<400> SEQUENCE: 2

| | |
|---|---|
| ccagtgctgg ggctgcctag ttgacgcacc cattgagtcg ctggcttctt tgcagcgctt | 60 |
| cagcgttttc ccctggaggg cgcctccatc cttggaggcc tagtgccgtc ggagagagag | 120 |
| cgggagccgc ggacagagac gcgtgcgcaa ttcggagccg actctgggtg cggactgtgg | 180 |
| gagctgactc tgggtagccg gctgcgcgtg gctgggagg cgaggccgga cgcacctctg | 240 |
| tttgggggtc ctcagagatt aatgattcat caagggatag ttgtactgtt ctcgtgggaa | 300 |
| tcacttcatc atgcgaaatc tgaaattatt tcggaccctg gagttcaggg atattcaagg | 360 |
| tccagggaat cctcagtgct tctctctccg aactgaacag gggacggtgc tcattggttc | 420 |
| agaacatggc ctgatagaag tagaccctgt ctcaagagaa gtgaaaaatg aagtttctttt | 480 |
| ggtggcagaa ggctttctcc cagaggatgg aagtggccgc attgttggtg ttcaggactt | 540 |
| gctggatcag gagtctgtgt gtgtggccac agcctctgga gacgtcatac tctgcagtct | 600 |
| cagcacacaa cagctggagt gtgttgggag tgtagccagt ggtatctctg ttatgagttg | 660 |
| gagtcctgac caagagctgg tgcttcttgc cacaggtcaa cagaccctga ttatgatgac | 720 |
| aaaagatttt gagccaatcc tggagcagca gatccatcag gatgattttg gtgaaagcaa | 780 |
| gtttatcact gttggatggg gtaggaagga gacacagttc catggatcag aaggcagaca | 840 |
| agcagctttt cagatgcaaa tgcatgagtc tgctttgccc tgggatgacc atagaccaca | 900 |
| agttacctgg cgggggatg acagttttt tgctgtgagt gttgtttgcc cagaaacagg | 960 |
| ggctcggaag gtcagagtgt ggaaccgaga gtttgctttg cagtcaacca gtgagcctgt | 1020 |
| ggcaggactg ggaccagccc tggcttggaa accctcaggc agtttgattg catctacaca | 1080 |
| agataaaccc aaccagcagg atattgtgtt ttttgagaaa aatggactcc ttcatggaca | 1140 |
| ctttacactt cccttcctta agatgaggt taaggtaaat gacttgctct ggaatgcaga | 1200 |
| ttcctctgtg cttgcagtct ggctggaaga ccttcagaga aagaaagct ccattccgaa | 1260 |
| aacctgtgtt cagctctgga ctgttggaaa ctatcactgg tatctcaagc aaagtttatc | 1320 |
| cttcagcacc tgtgggaaga gcaagattgt gtctctgatg tgggaccctg tgaccccata | 1380 |
| ccggctgcat gttctctgtc agggctggca ttacctcgcc tatgattggc actggacgac | 1440 |
| tgaccggagc gtgggagata attcaagtga cttgtccaat gtggctgtca ttgatgaaa | 1500 |
| cagggtgttg gtgacagtct tccggcagac tgtggttccg cctcccatgt gcacctacca | 1560 |
| actgctgttc ccacaccctg tgaatcaagt cacattctta gcacaccctc aaaagagtaa | 1620 |
| tgaccttgct gttctagatg ccagtaacca gatttctgtt tataaatgtg gtgattgtcc | 1680 |

-continued

```
aagtgctgac cctacagtga aactgggagc tgtgggtgga agtggattta aagtttgcct    1740
tagaactcct catttggaaa agagatacaa aatccagttt gagaataatg aagatcaaga    1800
tgtaaacccg ctgaaactag gccttctcac ttggattgaa gaagacgtct tcctggctgt    1860
aagccacagt gagttcagcc cccggtctgt cattcaccat ttgactgcag cttcttctga    1920
gatggatgaa gagcatggac agctcaatgt cagttcatct gcagcggtgg atggggtcat    1980
aatcagtcta tgttgcaatt ccaagaccaa gtcagtagta ttacagctgg ctgatggcca    2040
gatatttaag tacctttggg agtcaccttc tctggctatt aaaccatgga agaactctgg    2100
tggatttcct gttcggtttc cttatccatg cacccagacc gaattggcca tgattggaga    2160
agaggaatgt gtccttggtc tgactgacag gtgtcgcttt ttcatcaatg acattgaggt    2220
tgcgtcaaat atcacgtcat tgcagtatat tgatgagttt ttattgttga cacccattc    2280
ccatacctgc cagtgttttt gcctgaggga tgcttcattt aaaacattac aggccggcct    2340
gagcagcaat catgtgtccc atggggaagt tctgcggaaa gtggagaggg gttcacggat    2400
tgtcactgtt gtgccccagg acacaaagct tgtattacag atgccaaggg gaaacttaga    2460
agttgttcat catcgagccc tggttttagc tcagattcgg aagtggttgg acaaactttat   2520
gtttaaagag gcatttgaat gcatgagaaa gctgagaatc aatctcaatc tgatttatga    2580
tcataaccct aaggtgtttc ttggaaatgt ggaaaccttc attaaacaga tagattctgt    2640
gaatcatatt aacttgtttt ttacagaatt gaaagaagaa gatgtcacga agaccatgta    2700
ccctgcacca gttaccagca gtgtctacct gtccagggat cctgacggga ataaaataga    2760
ccttgtctgc gatgctatga gagcagtcat ggagagcata aatcctcata aatactgcct    2820
atccatactt acatctcatg taaagaagac aaccccagaa ctggaaattg tactgcaaaa    2880
agtacacgag cttcaaggaa atgctccctc tgatcctgat gctgtgagtg ctgaagaggc    2940
cttgaaatat ttgctgcatc tggtagatgt taatgaatta tatgatcatt ctcttggcac    3000
ctatgacttt gatttggtcc tcatggtagc tgagaagtca cagaaggatc ccaaagaata    3060
tcttccattt cttaatacac ttaagaaaat ggaaactaat tatcagcggt ttactataga    3120
caaatacttg aaacgatatg aaaaagccat tggccacctc agcaaatgtg gacctgagta    3180
cttcccagaa tgcttaaact tgataaaaga taaaaacttg tataacgaag ctctgaagtt    3240
atattcacca agctcacaac agtaccagga tatcagcatt gcttatgggg agcacctgat    3300
gcaggagcac atgtatgagc cagcggggct catgtttgcc cgttgcggtg cccacgagaa    3360
agctctctca gcctttctca catgtggcaa ctggaagcaa gccctctgtg tggcagccca    3420
gcttaacttt accaaagacc agctggtggg cctcggcaga actctggcag gaaagctggt    3480
tgagcagagg aagcacattg atgcggccat ggttttggaa gagagtgccc aggattatga    3540
agaagctgtg ctcttgctgt tagaaggagc tgcctgggaa gaagctttga ggctggtata    3600
caaatataac agactggata ttatagaaac caacgtaaag ccttccattt tagaagccca    3660
gaaaaattat atggcatttc tggactctca gacagccaca ttcagtcgcc acaagaaacg    3720
tttattggta gttcgagagc tcaaggagca agcccagcag gcaggtctgg atgatgaggt    3780
accccacggg caagagtcag acctcttctc tgaaactagc agtgtcgtga gtggcagtga    3840
gatgagtggc aaatactccc atagtaactc caggatatca gcgagatcat ccaagaatcg    3900
ccgaaaagcg gagcggaaga agcacagcct caaagaaggc agtccgctgg aggacctggc    3960
cctcctggag gcactgagtg aagtggtgca gaacactgaa aacctgaaag atgaagtata    4020
```

```
ccatatttta aaggtactct ttctctttga gtttgatgaa caaggaaggg aattacagaa    4080
ggcctttgaa gatacgctgc agttgatgga aaggtcactt ccagaaattt ggactcttac    4140
ttaccagcag aattcagcta ccccggttct aggtcccaat tctactgcaa atagtatcat    4200
ggcatcttat cagcaacaga agacttcggt tcctgttctt gatgctgagc ttttatacc     4260 accaaagatc aacagaagaa cccagtggaa gctgagcctg ctagactgag tgactgcagt    4320
taggagggat ccgacagaga agaccatttc cactcattcc tgttgtccta ccaccccttg    4380
ctctttgagg gctggctatt gagaactgga aagagtaaaa tgataactta ccttagcatt    4440
gccaagaact tcagcagaca caagcaatt ctatttattt tatgttgtgt atacatcttg     4500
atcattagca agacattaag ctttaaccat tatggcacca ttttgtgaga atgattgttc    4560
tttcacttgg gctgtttgag agcataatta tggtaatcat gagattaatg tttcatgatt    4620
tctacctcca aagtgtgaag acaagtaaaa caatgtttct aaattgtctt attttgttgg    4680
cggagaagat tacaatggct attagtgcta catttggtca aatgtaatca cttaaatagc    4740
ttcttgtcac cttaaactaa agcagaataa aaagtatcct ttgaaattat aagccctcct    4800
ttgctgacag ctatttttt gtaacatctt accaggtcat gtgctttcag ttataactgg     4860
gctgagcctc ctataattac aatgtctata gggactgttt tactgcctgt gtattttctg    4920
ctagagagtt agcaatgtta gagctagaac agattagaat ttctaaacag tatcatgcac    4980
agttggtgtg agtgatcagt gtgcattgta tggcatgcat ggttgtgaat tattctctgt    5040
tctccaaata ctgtttcttt aactcagata ttttgttag tgtctaggcc acttcattta     5100
tttttcgtca tggtacttta ctgacttctc tttattcaat tctccacgcc ctcaccaaaa    5160
aaaactgtct caaatgaga atattttat tcttcatggt gagtctagaa acgcccac       5220 ttcattctga ttaaaaaatt cttccatgtt tttaaatatc agaaccagac ctttcttact    5280
gtgtatctta gcccatttgt gtctctataa caacaaccag ctttcaaagg aactaataga    5340
gtgaaaactc actcattacc acgaggatgg cacaagcgat tcacgtagga tctgcccctg    5400
tgaccaaaac acctcccatt gggccccact tccaacactg gtgatcacat ttcaacatga    5460
ggtttaggga aacaaatgcc taaactacag cactgtacat aaactaacag gaaatgctgc    5520
ttttgatcct caagaagtg atatagccaa aattgtaatt taagaagcct tgtcagtat     5580 agcaagatgt taactataga atcaatctag gagtattcac tgtaaaattc aacttttctg    5640
tatgtttgaa cattttcaca atctcatagg agttttaaa aagaagagaa agaagatata    5700
ctttgctttg gagaaatcta cttttgact tacatggtt tgctgtaatt aagtgcccaa      5760
tattgaaagg ctgcaagtac tttgtaatca ctctttggca tgggtaaata agcatggtaa    5820
cttatattga aatatagtgc tcttgctttg gataactgta aagggaccca tgctgataga    5880
ctggaaatag aagtaaatgt gtttattgaa aaaaaaaaa aaaa                      5924
```

<210> SEQ ID NO 3
<211> LENGTH: 1332
<212> TYPE: PRT
<213> ORGANISM: Homo sapiens

<400> SEQUENCE: 3

Met Arg Asn Leu Lys Leu Phe Arg Thr Leu Glu Phe Arg Asp Ile Gln
 1               5                  10                  15

Gly Pro Gly Asn Pro Gln Cys Phe Ser Leu Arg Thr Glu Gln Gly Thr
            20                  25                  30

Val Leu Ile Gly Ser Glu His Gly Leu Ile Glu Val Asp Pro Val Ser

-continued

```
                35                  40                  45
Arg Glu Val Lys Asn Glu Val Ser Leu Val Ala Glu Gly Phe Leu Pro
 50                  55                  60
Glu Asp Gly Ser Gly Arg Ile Val Gly Val Gln Asp Leu Leu Asp Gln
 65                  70                  75                  80
Glu Ser Val Cys Val Ala Thr Ala Ser Gly Asp Val Ile Leu Cys Ser
                 85                  90                  95
Leu Ser Thr Gln Gln Leu Glu Cys Val Gly Ser Val Ala Ser Gly Ile
                100                 105                 110
Ser Val Met Ser Trp Ser Pro Asp Gln Glu Leu Val Leu Leu Ala Thr
                115                 120                 125
Gly Gln Gln Thr Leu Ile Met Met Thr Lys Asp Phe Glu Pro Ile Leu
130                 135                 140
Glu Gln Gln Ile His Gln Asp Asp Phe Gly Glu Ser Lys Phe Ile Thr
145                 150                 155                 160
Val Gly Trp Gly Arg Lys Glu Thr Gln Phe His Gly Ser Glu Gly Arg
                165                 170                 175
Gln Ala Ala Phe Gln Met Gln Met His Glu Ser Ala Leu Pro Trp Asp
                180                 185                 190
Asp His Arg Pro Gln Val Thr Trp Arg Gly Asp Gly Gln Phe Phe Ala
                195                 200                 205
Val Ser Val Val Cys Pro Glu Thr Gly Ala Arg Lys Val Arg Val Trp
210                 215                 220
Asn Arg Glu Phe Ala Leu Gln Ser Thr Ser Glu Pro Val Ala Gly Leu
225                 230                 235                 240
Gly Pro Ala Leu Ala Trp Lys Pro Ser Gly Ser Leu Ile Ala Ser Thr
                245                 250                 255
Gln Asp Lys Pro Asn Gln Gln Asp Ile Val Phe Phe Glu Lys Asn Gly
                260                 265                 270
Leu Leu His Gly His Phe Thr Leu Pro Phe Leu Lys Asp Glu Val Lys
                275                 280                 285
Val Asn Asp Leu Leu Trp Asn Ala Asp Ser Ser Val Leu Ala Val Arg
290                 295                 300
Leu Glu Asp Leu Gln Arg Glu Lys Ser Ser Ile Pro Lys Thr Cys Val
305                 310                 315                 320
Gln Leu Trp Thr Val Gly Asn Tyr His Trp Tyr Leu Lys Gln Ser Leu
                325                 330                 335
Ser Phe Ser Thr Cys Gly Lys Ser Lys Ile Val Ser Leu Met Trp Asp
                340                 345                 350
Pro Val Thr Pro Tyr Arg Leu His Val Leu Cys Gln Gly Trp His Tyr
                355                 360                 365
Leu Ala Tyr Asp Trp His Trp Thr Thr Asp Arg Ser Val Gly Asp Asn
                370                 375                 380
Ser Ser Asp Leu Ser Asn Val Ala Val Ile Asp Gly Asn Arg Val Leu
385                 390                 395                 400
Val Thr Val Phe Arg Gln Thr Val Pro Pro Met Cys Thr Tyr
                405                 410                 415
Gln Leu Leu Phe Pro His Pro Val Asn Gln Val Thr Phe Leu Ala His
                420                 425                 430
Pro Gln Lys Ser Asn Asp Leu Ala Val Leu Asp Ala Ser Asn Gln Ile
                435                 440                 445
Ser Val Tyr Lys Cys Gly Asp Cys Pro Ser Ala Asp Pro Thr Val Lys
450                 455                 460
```

```
Leu Gly Ala Val Gly Gly Ser Gly Phe Lys Val Cys Leu Arg Thr Pro
465                 470                 475                 480

His Leu Glu Lys Arg Tyr Lys Ile Gln Phe Glu Asn Asn Glu Asp Gln
                485                 490                 495

Asp Val Asn Pro Leu Lys Leu Gly Leu Leu Thr Trp Ile Glu Glu Asp
                500                 505                 510

Val Phe Leu Ala Val Ser His Ser Glu Phe Ser Pro Arg Ser Val Ile
                515                 520                 525

His His Leu Thr Ala Ala Ser Ser Glu Met Asp Glu Glu His Gly Gln
530                 535                 540

Leu Asn Val Ser Ser Ser Ala Ala Val Asp Gly Val Ile Ile Ser Leu
545                 550                 555                 560

Cys Cys Asn Ser Lys Thr Lys Ser Val Val Leu Gln Leu Ala Asp Gly
                565                 570                 575

Gln Ile Phe Lys Tyr Leu Trp Glu Ser Pro Ser Leu Ala Ile Lys Pro
                580                 585                 590

Trp Lys Asn Ser Gly Gly Phe Pro Val Arg Phe Pro Tyr Pro Cys Thr
                595                 600                 605

Gln Thr Glu Leu Ala Met Ile Gly Glu Glu Glu Cys Val Leu Gly Leu
610                 615                 620

Thr Asp Arg Cys Arg Phe Phe Ile Asn Asp Ile Glu Val Ala Ser Asn
625                 630                 635                 640

Ile Thr Ser Phe Ala Val Tyr Asp Glu Phe Leu Leu Leu Thr Thr His
                645                 650                 655

Ser His Thr Cys Gln Cys Phe Cys Leu Arg Asp Ala Ser Phe Lys Thr
                660                 665                 670

Leu Gln Ala Gly Leu Ser Ser Asn His Val Ser His Gly Glu Val Leu
                675                 680                 685

Arg Lys Val Glu Arg Gly Ser Arg Ile Val Thr Val Pro Gln Asp
                690                 695                 700

Thr Lys Leu Val Leu Gln Met Pro Arg Gly Asn Leu Glu Val Val His
705                 710                 715                 720

His Arg Ala Leu Val Leu Ala Gln Ile Arg Lys Trp Leu Asp Lys Leu
                725                 730                 735

Met Phe Lys Glu Ala Phe Glu Cys Met Arg Lys Leu Arg Ile Asn Leu
                740                 745                 750

Asn Pro Ile Tyr Asp His Asn Pro Lys Val Phe Leu Gly Asn Val Glu
                755                 760                 765

Thr Phe Ile Lys Gln Ile Asp Ser Val Asn His Ile Asn Leu Phe Phe
770                 775                 780

Thr Glu Leu Lys Glu Glu Asp Val Thr Lys Thr Met Tyr Pro Ala Pro
785                 790                 795                 800

Val Thr Ser Ser Val Tyr Leu Ser Arg Asp Pro Asp Gly Asn Lys Ile
                805                 810                 815

Asp Leu Val Cys Asp Ala Met Arg Ala Val Met Glu Ser Ile Asn Pro
                820                 825                 830

His Lys Tyr Cys Leu Ser Ile Leu Thr Ser His Val Lys Lys Thr Thr
                835                 840                 845

Pro Glu Leu Glu Ile Val Leu Gln Lys Val His Glu Leu Gln Gly Asn
                850                 855                 860

Ala Pro Ser Asp Pro Asp Ala Val Ser Ala Glu Glu Ala Leu Lys Tyr
865                 870                 875                 880
```

```
Leu Leu His Leu Val Asp Val Asn Glu Leu Tyr Asp His Ser Leu Gly
            885                 890                 895

Thr Tyr Asp Phe Asp Leu Val Leu Met Val Ala Glu Lys Ser Gln Lys
            900                 905                 910

Asp Pro Lys Glu Tyr Leu Pro Phe Leu Asn Thr Leu Lys Lys Met Glu
            915                 920                 925

Thr Asn Tyr Gln Arg Phe Thr Ile Asp Lys Tyr Leu Lys Arg Tyr Glu
            930                 935                 940

Lys Ala Ile Gly His Leu Ser Lys Cys Gly Pro Glu Tyr Phe Pro Glu
945                 950                 955                 960

Cys Leu Asn Leu Ile Lys Asp Lys Asn Leu Tyr Asn Glu Ala Leu Lys
                965                 970                 975

Leu Tyr Ser Pro Ser Ser Gln Gln Tyr Gln Asp Ile Ser Ile Ala Tyr
            980                 985                 990

Gly Glu His Leu Met Gln Glu His Met Tyr Glu Pro Ala Gly Leu Met
            995                 1000                1005

Phe Ala Arg Cys Gly Ala His Glu Lys Ala Leu Ser Ala Phe Leu Thr
            1010                1015                1020

Cys Gly Asn Trp Lys Gln Ala Leu Cys Val Ala Ala Gln Leu Asn Phe
1025                1030                1035                1040

Thr Lys Asp Gln Leu Val Gly Leu Gly Arg Thr Leu Ala Gly Lys Leu
            1045                1050                1055

Val Glu Gln Arg Lys His Ile Asp Ala Ala Met Val Leu Glu Glu Ser
            1060                1065                1070

Ala Gln Asp Tyr Glu Glu Ala Val Leu Leu Leu Glu Gly Ala Ala
            1075                1080                1085

Trp Glu Glu Ala Leu Arg Leu Val Tyr Lys Tyr Asn Arg Leu Asp Ile
            1090                1095                1100

Ile Glu Thr Asn Val Lys Pro Ser Ile Leu Glu Ala Gln Lys Asn Tyr
1105                1110                1115                1120

Met Ala Phe Leu Asp Ser Gln Thr Ala Thr Phe Ser Arg His Lys Lys
            1125                1130                1135

Arg Leu Leu Val Val Arg Glu Leu Lys Glu Gln Ala Gln Gln Ala Gly
            1140                1145                1150

Leu Asp Asp Glu Val Pro His Gly Gln Glu Ser Asp Leu Phe Ser Glu
            1155                1160                1165

Thr Ser Ser Val Val Ser Gly Ser Glu Met Ser Gly Lys Tyr Ser His
            1170                1175                1180

Ser Asn Ser Arg Ile Ser Ala Arg Ser Ser Lys Asn Arg Arg Lys Ala
1185                1190                1195                1200

Glu Arg Lys Lys His Ser Leu Lys Glu Gly Ser Pro Leu Glu Asp Leu
            1205                1210                1215

Ala Leu Leu Glu Ala Leu Ser Glu Val Val Gln Asn Thr Glu Asn Leu
            1220                1225                1230

Lys Asp Glu Val Tyr His Ile Leu Lys Val Leu Phe Leu Phe Glu Phe
            1235                1240                1245

Asp Glu Gln Gly Arg Glu Leu Gln Lys Ala Phe Glu Asp Thr Leu Gln
            1250                1255                1260

Leu Met Glu Arg Ser Leu Pro Glu Ile Trp Thr Leu Thr Tyr Gln Gln
1265                1270                1275                1280

Asn Ser Ala Thr Pro Val Leu Gly Pro Asn Ser Thr Ala Asn Ser Ile
            1285                1290                1295

Met Ala Ser Tyr Gln Gln Gln Lys Thr Ser Val Pro Val Leu Asp Ala
```

-continued

```
                1300                1305                1310
Glu Leu Phe Ile Pro Pro Lys Ile Asn Arg Arg Thr Gln Trp Lys Leu
        1315                1320                1325

Ser Leu Leu Asp
    1330

<210> SEQ ID NO 4
<211> LENGTH: 1332
<212> TYPE: PRT
<213> ORGANISM: Mus musculus

<400> SEQUENCE: 4

Met Arg Asn Leu Lys Leu His Arg Thr Leu Glu Phe Arg Asp Ile Gln
  1               5                   10                  15

Ala Pro Gly Lys Pro Gln Cys Phe Cys Leu Arg Ala Glu Gln Gly Thr
            20                  25                  30

Val Leu Ile Gly Ser Glu Arg Gly Leu Thr Glu Val Asp Pro Val Arg
        35                  40                  45

Arg Glu Val Lys Thr Glu Ile Ser Leu Val Ala Glu Gly Phe Leu Pro
 50                  55                  60

Glu Asp Gly Ser Gly Cys Ile Val Gly Ile Gln Asp Leu Leu Asp Gln
 65                  70                  75                  80

Glu Ser Val Cys Val Ala Thr Ala Ser Gly Asp Val Ile Val Cys Asn
                85                  90                  95

Leu Ser Thr Gln Gln Leu Glu Cys Val Gly Ser Val Ala Ser Gly Ile
            100                 105                 110

Ser Val Met Ser Trp Ser Pro Asp Gln Glu Leu Leu Leu Leu Ala Thr
        115                 120                 125

Ala Gln Gln Thr Leu Ile Met Met Thr Lys Asp Phe Glu Val Ile Ala
130                 135                 140

Glu Glu Gln Ile His Gln Asp Asp Phe Gly Glu Gly Lys Phe Val Thr
145                 150                 155                 160

Val Gly Trp Gly Ser Lys Gln Thr Gln Phe His Gly Ser Glu Gly Arg
                165                 170                 175

Pro Thr Ala Phe Pro Val Gln Leu Pro Glu Asn Ala Leu Pro Trp Asp
            180                 185                 190

Asp Arg Arg Pro His Ile Thr Trp Arg Gly Asp Gly Gln Tyr Phe Ala
        195                 200                 205

Val Ser Val Val Cys Arg Gln Thr Glu Ala Arg Lys Ile Arg Val Trp
210                 215                 220

Asn Arg Glu Phe Ala Leu Gln Ser Thr Ser Glu Ser Val Pro Gly Leu
225                 230                 235                 240

Gly Pro Ala Leu Ala Trp Lys Pro Ser Gly Ser Leu Ile Ala Ser Thr
                245                 250                 255

Gln Asp Lys Pro Asn Gln Gln Asp Val Val Phe Phe Glu Lys Asn Gly
            260                 265                 270

Leu Leu His Gly His Phe Thr Leu Pro Phe Leu Lys Asp Glu Val Lys
        275                 280                 285

Val Asn Asp Leu Leu Trp Asn Ala Asp Ser Ser Val Leu Ala Ile Trp
290                 295                 300

Leu Glu Asp Leu Pro Lys Glu Asp Ser Ser Thr Leu Lys Ser Tyr Val
305                 310                 315                 320

Gln Leu Trp Thr Val Gly Asn Tyr His Trp Tyr Leu Lys Gln Ser Leu
                325                 330                 335
```

-continued

```
Pro Phe Ser Thr Thr Gly Lys Asn Gln Ile Val Ser Leu Leu Trp Asp
            340                 345                 350

Pro Val Thr Pro Cys Arg Leu His Val Leu Cys Thr Gly Trp Arg Tyr
            355                 360                 365

Leu Cys Cys Asp Trp His Trp Thr Thr Asp Arg Ser Ser Gly Asn Ser
        370                 375                 380

Ala Asn Asp Leu Ala Asn Val Ala Val Ile Asp Gly Asn Arg Val Leu
385                 390                 395                 400

Val Thr Val Phe Arg Gln Thr Val Pro Pro Met Cys Thr Tyr
                405                 410                 415

Arg Leu Leu Ile Pro His Pro Val Asn Gln Val Ile Phe Ser Ala His
                420                 425                 430

Leu Gly Asn Asp Leu Ala Val Leu Asp Ala Ser Asn Gln Ile Ser Val
            435                 440                 445

Tyr Lys Cys Gly Asp Lys Pro Asn Met Asp Ser Thr Val Lys Leu Gly
            450                 455                 460

Ala Val Gly Gly Asn Gly Phe Lys Val Pro Leu Thr Thr Pro His Leu
465                 470                 475                 480

Glu Lys Arg Tyr Ser Ile Gln Phe Gly Asn Asn Glu Glu Glu Glu
                485                 490                 495

Glu Asp Phe Ala Leu Gln Leu Ser Phe Leu Thr Trp Val Glu Asp Asp
            500                 505                 510

Thr Phe Leu Ala Ile Ser Tyr Ser His Ser Ser Gln Ser Ile Ile
            515                 520                 525

His His Leu Thr Val Thr His Ser Glu Val Asp Glu Glu Gln Gly Gln
            530                 535                 540

Leu Asp Val Ser Ser Val Thr Val Asp Gly Val Val Ile Gly Leu
545                 550                 555                 560

Cys Cys Cys Ser Lys Thr Lys Ser Leu Ala Val Gln Leu Ala Asp Gly
                565                 570                 575

Gln Val Leu Lys Ile Leu Trp Glu Ser Pro Ser Leu Ala Val Glu Pro
            580                 585                 590

Trp Lys Asn Ser Glu Gly Ile Pro Val Arg Phe Val His Pro Cys Thr
            595                 600                 605

Gln Met Glu Val Ala Thr Ile Gly Gly Glu Glu Cys Val Leu Gly Leu
            610                 615                 620

Thr Asp Arg Cys Arg Phe Phe Ile Leu Val Thr Glu Val Ala Ser Asn
625                 630                 635                 640

Ile Thr Ser Phe Ala Val Cys Asp Asp Phe Leu Val Thr Thr His
                645                 650                 655

Ser His Thr Cys Gln Gly Phe Ser Leu Ser Gly Ala Ser Leu Lys Met
            660                 665                 670

Leu Gln Ala Ala Leu Ser Gly Ser His Glu Ala Ser Gly Glu Ile Leu
            675                 680                 685

Arg Lys Val Val Trp Gly Ser Arg Ile Val Thr Val Pro Gln Asp
690                 695                 700

Thr Lys Leu Ile Leu Gln Met Pro Arg Gly Asn Leu Glu Val Val His
705                 710                 715                 720

His Arg Ala Leu Val Leu Ala Gln Ile Arg Lys Trp Leu Asp Lys Leu
                725                 730                 735

Met Phe Lys Glu Ala Phe Glu Cys Met Arg Lys Leu Arg Ile Asn Leu
            740                 745                 750

Asn Leu Ile His Asp His Asn Pro Lys Val Phe Leu Glu Asn Val Glu
```

-continued

```
                755                 760                 765
Thr Phe Val Phe Gln Ile Asp Ser Val Asn His Ile Asn Leu Phe Phe
    770                 775                 780

Thr Glu Leu Arg Glu Glu Asp Val Thr Lys Thr Met Tyr Pro Pro Pro
785                 790                 795                 800

Ile Thr Lys Ser Val Gln Val Ser Thr His Pro Asp Gly Lys Lys Leu
                805                 810                 815

Asp Leu Ile Cys Asp Ala Met Arg Ala Ala Met Glu Ala Ile Asn Pro
            820                 825                 830

Arg Lys Phe Cys Leu Ser Ile Leu Thr Ser His Val Lys Lys Thr Thr
        835                 840                 845

Pro Glu Leu Glu Ile Val Leu Gln Lys Val Gln Glu Leu Gln Gly Asn
    850                 855                 860

Leu Pro Phe Asp Pro Glu Ser Val Ser Val Glu Glu Ala Leu Lys Tyr
865                 870                 875                 880

Leu Leu Leu Leu Val Asp Val Asn Glu Leu Phe Asn His Ser Leu Gly
                885                 890                 895

Thr Tyr Asp Phe Asn Leu Val Leu Met Val Ala Glu Lys Ser Gln Lys
            900                 905                 910

Asp Pro Lys Glu Tyr Leu Pro Phe Leu Asn Thr Leu Lys Lys Met Glu
        915                 920                 925

Thr Asn Tyr Gln Arg Phe Thr Ile Asp Lys Tyr Leu Lys Arg Tyr Glu
    930                 935                 940

Lys Ala Leu Gly His Leu Ser Lys Cys Gly Pro Glu Tyr Phe Thr Glu
945                 950                 955                 960

Cys Leu Asn Leu Ile Lys Asp Lys Asn Leu Tyr Lys Glu Ala Leu Lys
                965                 970                 975

Leu Tyr Arg Pro Asp Ser Pro Gln Tyr Gln Ala Val Ser Met Ala Tyr
            980                 985                 990

Gly Glu His Leu Met Gln Glu His Leu Tyr Glu Pro Ala Gly Leu Val
        995                 1000                1005

Phe Ala Arg Cys Gly Ala Gln Glu Lys Ala Leu Glu Ala Phe Leu Ala
    1010                1015                1020

Cys Gly Ser Trp Gln Gln Ala Leu Cys Val Ala Ala Gln Leu Gln Met
1025                1030                1035                1040

Ser Lys Asp Lys Val Ala Gly Leu Ala Arg Thr Leu Ala Gly Lys Leu
                1045                1050                1055

Val Glu Gln Arg Lys His Ser Glu Ala Ala Thr Val Leu Glu Gln Tyr
            1060                1065                1070

Ala Gln Asp Tyr Glu Glu Ala Val Leu Leu Leu Leu Glu Gly Ser Ala
        1075                1080                1085

Trp Glu Glu Ala Leu Arg Leu Val Tyr Lys Tyr Asp Arg Val Asp Ile
    1090                1095                1100

Ile Glu Thr Ser Ile Lys Pro Ser Ile Leu Glu Ala Gln Lys Asn Tyr
1105                1110                1115                1120

Met Asp Phe Leu Asp Ser Glu Thr Ala Thr Phe Ile Arg His Lys Asn
                1125                1130                1135

Arg Leu Gln Val Val Arg Ala Leu Arg Arg Gln Ala Pro Gln Val His
            1140                1145                1150

Val Asp His Glu Val Ala His Gly Pro Glu Ser Asp Leu Phe Ser Glu
        1155                1160                1165

Thr Ser Ser Ile Met Ser Gly Ser Glu Met Ser Gly Arg Tyr Ser His
    1170                1175                1180
```

```
Ser Asn Ser Arg Ile Ser Ala Arg Ser Ser Lys Asn Arg Arg Lys Ala
1185                1190                1195                1200

Glu Arg Lys Lys His Ser Leu Lys Glu Gly Ser Pro Leu Glu Gly Leu
                1205                1210                1215

Ala Leu Leu Glu Ala Leu Ser Glu Val Val Gln Ser Val Glu Lys Leu
            1220                1225                1230

Lys Asp Glu Val Arg Ala Ile Leu Lys Val Leu Phe Leu Phe Glu Phe
        1235                1240                1245

Glu Glu Gln Ala Lys Glu Leu Gln Arg Ala Phe Glu Ser Thr Leu Gln
    1250                1255                1260

Leu Met Glu Arg Ala Val Pro Glu Ile Trp Thr Pro Ala Gly Gln Gln
1265                1270                1275                1280

Ser Ser Thr Thr Pro Val Leu Gly Pro Ser Ser Thr Ala Asn Ser Ile
                1285                1290                1295

Thr Ala Ser Tyr Gln Gln Gln Lys Thr Cys Val Pro Ala Leu Asp Ala
            1300                1305                1310

Gly Val Tyr Met Pro Pro Lys Met Asp Pro Arg Ser Gln Trp Lys Leu
        1315                1320                1325

Ser Leu Leu Glu
    1330

<210> SEQ ID NO 5
<211> LENGTH: 1332
<212> TYPE: PRT
<213> ORGANISM: Homo sapiens

<400> SEQUENCE: 5

Met Arg Asn Leu Lys Leu Phe Arg Thr Leu Glu Phe Arg Asp Ile Gln
1               5                   10                  15

Gly Pro Gly Asn Pro Gln Cys Phe Ser Leu Arg Thr Glu Gln Gly Thr
                20                  25                  30

Val Leu Ile Gly Ser Glu His Gly Leu Ile Glu Val Asp Pro Val Ser
            35                  40                  45

Arg Glu Val Lys Asn Glu Val Ser Leu Val Ala Glu Gly Phe Leu Pro
        50                  55                  60

Glu Asp Gly Ser Gly Arg Ile Val Gly Val Gln Asp Leu Leu Asp Gln
65                  70                  75                  80

Glu Ser Val Cys Val Ala Thr Ala Ser Gly Asp Val Ile Leu Cys Ser
                85                  90                  95

Leu Ser Thr Gln Gln Leu Glu Cys Val Gly Ser Val Ala Ser Gly Ile
            100                 105                 110

Ser Val Met Ser Trp Ser Pro Asp Gln Glu Leu Val Leu Leu Ala Thr
        115                 120                 125

Gly Gln Gln Thr Leu Ile Met Met Thr Lys Asp Phe Glu Pro Ile Leu
130                 135                 140

Glu Gln Gln Ile His Gln Asp Asp Phe Gly Glu Ser Lys Phe Ile Thr
145                 150                 155                 160

Val Gly Trp Gly Arg Lys Glu Thr Gln Phe His Gly Ser Glu Gly Arg
                165                 170                 175

Gln Ala Ala Phe Gln Met Gln Met His Glu Ser Ala Leu Pro Trp Asp
            180                 185                 190

Asp His Arg Pro Gln Val Thr Trp Arg Gly Asp Gly Gln Phe Phe Ala
        195                 200                 205

Val Ser Val Val Cys Pro Glu Thr Gly Ala Arg Lys Val Arg Val Trp
```

-continued

```
            210                 215                 220
Asn Arg Glu Phe Ala Leu Gln Ser Thr Ser Glu Pro Val Ala Gly Leu
225                 230                 235                 240

Gly Pro Ala Leu Ala Trp Lys Pro Ser Gly Ser Leu Ile Ala Ser Thr
                245                 250                 255

Gln Asp Lys Pro Asn Gln Gln Asp Ile Val Phe Phe Glu Lys Asn Gly
            260                 265                 270

Leu Leu His Gly His Phe Thr Leu Pro Phe Leu Lys Asp Glu Val Lys
                275                 280                 285

Val Asn Asp Leu Leu Trp Asn Ala Asp Ser Ser Val Leu Ala Val Trp
290                 295                 300

Leu Glu Asp Leu Gln Arg Glu Glu Ser Ser Ile Pro Lys Thr Cys Val
305                 310                 315                 320

Gln Leu Trp Thr Val Gly Asn Tyr His Trp Tyr Leu Lys Gln Ser Leu
                325                 330                 335

Ser Phe Ser Thr Cys Gly Lys Ser Lys Ile Val Ser Leu Met Trp Asp
                340                 345                 350

Pro Val Thr Pro Tyr Arg Leu His Val Leu Cys Gln Gly Trp His Tyr
                355                 360                 365

Leu Ala Tyr Asp Trp His Trp Thr Thr Asp Arg Ser Val Gly Asp Asn
370                 375                 380

Ser Ser Asp Leu Ser Asn Val Ala Val Ile Asp Gly Asn Arg Val Leu
385                 390                 395                 400

Val Thr Val Phe Arg Gln Thr Val Val Pro Pro Met Cys Thr Tyr
                405                 410                 415

Gln Leu Leu Phe Pro His Pro Val Asn Gln Val Thr Phe Leu Ala His
                420                 425                 430

Pro Gln Lys Ser Asn Asp Leu Ala Val Leu Asp Ala Ser Asn Gln Ile
                435                 440                 445

Ser Val Tyr Lys Cys Gly Asp Cys Pro Ser Ala Asp Pro Thr Val Lys
                450                 455                 460

Leu Gly Ala Val Gly Gly Ser Gly Phe Lys Val Cys Leu Arg Thr Pro
465                 470                 475                 480

His Leu Glu Lys Arg Tyr Lys Ile Gln Phe Glu Asn Asn Glu Asp Gln
                485                 490                 495

Asp Val Asn Pro Leu Lys Leu Gly Leu Leu Thr Trp Ile Glu Glu Asp
                500                 505                 510

Val Phe Leu Ala Val Ser His Ser Glu Phe Ser Pro Arg Ser Val Ile
                515                 520                 525

His His Leu Thr Ala Ala Ser Ser Glu Met Asp Glu Glu His Gly Gln
                530                 535                 540

Leu Asn Val Ser Ser Ser Ala Ala Val Asp Gly Val Ile Ile Ser Leu
545                 550                 555                 560

Cys Cys Asn Ser Lys Thr Lys Ser Val Leu Gln Leu Ala Asp Gly
                565                 570                 575

Gln Ile Phe Lys Tyr Leu Trp Glu Ser Pro Ser Leu Ala Ile Lys Pro
                580                 585                 590

Trp Lys Asn Ser Gly Gly Phe Pro Val Arg Phe Pro Tyr Pro Cys Thr
                595                 600                 605

Gln Thr Glu Leu Ala Met Ile Gly Glu Glu Glu Cys Val Leu Gly Leu
                610                 615                 620

Thr Asp Arg Cys Arg Phe Phe Ile Asn Asp Ile Glu Val Ala Ser Asn
625                 630                 635                 640
```

```
Ile Thr Ser Phe Ala Val Tyr Asp Glu Phe Leu Leu Thr Thr His
                645             650                 655

Ser His Thr Cys Gln Cys Phe Cys Leu Arg Asp Ala Ser Phe Lys Thr
            660             665             670

Leu Gln Ala Gly Leu Ser Ser Asn His Val Ser His Gly Glu Val Leu
            675             680             685

Arg Lys Val Glu Arg Gly Ser Arg Ile Val Thr Val Pro Gln Asp
        690             695             700

Thr Lys Leu Val Leu Gln Met Pro Arg Gly Asn Leu Glu Val Val His
705             710             715                 720

His Arg Ala Leu Val Leu Ala Gln Ile Arg Lys Trp Leu Asp Lys Leu
                725             730             735

Met Phe Lys Glu Ala Phe Glu Cys Met Arg Lys Leu Arg Ile Asn Leu
            740             745             750

Asn Leu Ile Tyr Asp His Asn Pro Lys Val Phe Leu Gly Asn Val Glu
            755             760             765

Thr Phe Ile Lys Gln Ile Asp Ser Val Asn His Ile Asn Leu Phe Phe
    770             775             780

Thr Glu Leu Lys Glu Glu Asp Val Thr Lys Thr Met Tyr Pro Ala Pro
785             790             795                 800

Val Thr Ser Ser Val Tyr Leu Ser Arg Asp Pro Asp Gly Asn Lys Ile
                805             810             815

Asp Leu Val Cys Asp Ala Met Arg Ala Val Met Glu Ser Ile Asn Pro
            820             825             830

His Lys Tyr Cys Leu Ser Ile Leu Thr Ser His Val Lys Lys Thr Thr
            835             840             845

Pro Glu Leu Glu Ile Val Leu Gln Lys Val His Glu Leu Gln Gly Asn
    850             855             860

Ala Pro Ser Asp Pro Asp Ala Val Ser Ala Glu Glu Ala Leu Lys Tyr
865             870             875                 880

Leu Leu His Leu Val Asp Val Asn Glu Leu Tyr Asp His Ser Leu Gly
            885             890             895

Thr Tyr Asp Phe Asp Leu Val Leu Met Val Ala Glu Lys Ser Gln Lys
            900             905             910

Asp Pro Lys Glu Tyr Leu Pro Phe Leu Asn Thr Leu Lys Lys Met Glu
            915             920             925

Thr Asn Tyr Gln Arg Phe Thr Ile Asp Lys Tyr Leu Lys Arg Tyr Glu
    930             935             940

Lys Ala Ile Gly His Leu Ser Lys Cys Gly Pro Glu Tyr Phe Pro Glu
945             950             955                 960

Cys Leu Asn Leu Ile Lys Asp Lys Asn Leu Tyr Asn Glu Ala Leu Lys
            965             970             975

Leu Tyr Ser Pro Ser Ser Gln Gln Tyr Gln Asp Ile Ser Ile Ala Tyr
            980             985             990

Gly Glu His Leu Met Gln Glu His Met Tyr Glu Pro Ala Gly Leu Met
            995             1000            1005

Phe Ala Arg Cys Gly Ala His Glu Lys Ala Leu Ser Ala Phe Leu Thr
    1010            1015            1020

Cys Gly Asn Trp Lys Gln Ala Leu Cys Val Ala Ala Gln Leu Asn Phe
1025            1030            1035            1040

Thr Lys Asp Gln Leu Val Gly Leu Gly Arg Thr Leu Ala Gly Lys Leu
            1045            1050            1055
```

```
Val Glu Gln Arg Lys His Ile Asp Ala Ala Met Val Leu Glu Glu Ser
        1060                1065                1070

Ala Gln Asp Tyr Glu Ala Val Leu Leu Leu Glu Gly Ala Ala
        1075                1080                1085

Trp Glu Ala Leu Arg Leu Val Tyr Lys Tyr Asn Arg Leu Asp Ile
        1090                1095                1100

Ile Glu Thr Asn Val Lys Pro Ser Ile Leu Glu Ala Gln Lys Asn Tyr
1105                1110                1115                1120

Met Ala Phe Leu Asp Ser Gln Thr Ala Thr Phe Ser Arg His Lys Lys
                1125                1130                1135

Arg Leu Leu Val Val Arg Glu Leu Lys Glu Gln Ala Gln Gln Ala Gly
            1140                1145                1150

Leu Asp Asp Glu Val Pro His Gly Gln Glu Ser Asp Leu Phe Ser Glu
        1155                1160                1165

Thr Ser Ser Val Val Ser Gly Ser Glu Met Ser Gly Lys Tyr Ser His
    1170                1175                1180

Ser Asn Ser Arg Ile Ser Ala Arg Ser Ser Lys Asn Arg Arg Lys Ala
1185                1190                1195                1200

Glu Arg Lys Lys His Ser Leu Lys Glu Gly Ser Pro Leu Glu Asp Leu
                1205                1210                1215

Ala Leu Leu Glu Ala Leu Ser Glu Val Val Gln Asn Thr Glu Asn Leu
            1220                1225                1230

Lys Asp Glu Val Tyr His Ile Leu Lys Val Leu Phe Leu Phe Glu Phe
        1235                1240                1245

Asp Glu Gln Gly Arg Glu Leu Gln Lys Ala Phe Glu Asp Thr Leu Gln
        1250                1255                1260

Leu Met Glu Arg Ser Leu Pro Glu Ile Trp Thr Leu Thr Tyr Gln Gln
1265                1270                1275                1280

Asn Ser Ala Thr Pro Val Leu Gly Pro Asn Ser Thr Ala Asn Ser Ile
                1285                1290                1295

Met Ala Ser Tyr Gln Gln Gln Lys Thr Ser Val Pro Val Leu Asp Ala
            1300                1305                1310

Glu Leu Phe Ile Pro Pro Lys Ile Asn Arg Arg Thr Gln Trp Lys Leu
        1315                1320                1325

Ser Leu Leu Asp
    1330

<210> SEQ ID NO 6
<211> LENGTH: 1213
<212> TYPE: PRT
<213> ORGANISM: Drosophila melanogaster

<400> SEQUENCE: 6

Met Arg Asn Leu Lys Leu Arg Tyr Cys Lys Glu Leu Asn Ala Val Ala
1               5                   10                  15

His Pro Gln His Leu Leu Gln Pro Glu Leu Asn Gly Gly Ala Ser
            20                  25                  30

Asp Ile Tyr Phe Val Val Ala Asp Asn Lys Thr Tyr Ala Val Gln Glu
        35                  40                  45

Ser Gly Asp Val Arg Leu Lys Val Ile Ala Asp Leu Pro Asp Ile Val
    50                  55                  60

Gly Val Glu Phe Leu Gln Leu Asp Asn Ala Ile Cys Val Ala Ser Gly
65                  70                  75                  80

Ala Gly Glu Val Ile Leu Val Asp Pro Gln Thr Gly Ala Thr Ser Glu
                85                  90                  95
```

```
Gly Thr Phe Cys Asp Val Gly Ile Glu Ser Met Ala Trp Ser Pro Asn
            100                 105                 110

Gln Glu Val Val Ala Phe Val Thr Arg Thr His Asn Val Val Leu Met
        115                 120                 125

Thr Ser Thr Phe Asp Val Ile Ala Glu Gln Pro Leu Asp Ala Glu Leu
    130                 135                 140

Asp Pro Asp Gln Gln Phe Val Asn Val Gly Trp Gly Lys Lys Glu Thr
145                 150                 155                 160

Gln Phe His Gly Ser Glu Gly Lys Gln Ala Ala Lys Gln Lys Glu Ser
                165                 170                 175

Asp Ser Thr Phe Thr Arg Asp Glu Gln Glu Leu Asn Gln Asp Val Ser
            180                 185                 190

Ile Ser Trp Arg Gly Asp Gly Glu Phe Phe Val Val Ser Tyr Val Ala
        195                 200                 205

Ala Gln Leu Gly Arg Thr Phe Lys Val Tyr Asp Ser Glu Gly Lys Leu
    210                 215                 220

Asn His Thr Ala Glu Lys Ser Ala Asn Leu Lys Asp Ser Val Val Trp
225                 230                 235                 240

Arg Pro Thr Gly Asn Trp Ile Ala Val Pro Gln Gln Phe Pro Asn Lys
                245                 250                 255

Ser Thr Ile Ala Leu Phe Glu Lys Asn Gly Leu Arg His Arg Glu Leu
            260                 265                 270

Val Leu Pro Phe Asp Leu Gln Glu Glu Pro Val Val Gln Leu Arg Trp
        275                 280                 285

Ser Glu Asp Ser Asp Ile Leu Ala Ile Arg Thr Cys Ala Lys Glu Glu
    290                 295                 300

Gln Arg Val Tyr Leu Tyr Thr Ile Gly Asn Tyr His Trp Tyr Leu Lys
305                 310                 315                 320

Gln Val Leu Ile Phe Glu Gln Ala Asp Pro Leu Ala Leu Leu His Trp
                325                 330                 335

Asp Thr Arg Cys Gly Ala Glu His Thr Leu His Val Leu Lys Glu Ser
            340                 345                 350

Gly Lys His Leu Val Tyr Arg Trp Ala Phe Ala Val Asp Arg Asn Asn
        355                 360                 365

Ser Ile Val Gly Val Ile Asp Gly Lys Arg Leu Leu Leu Thr Asp Phe
    370                 375                 380

Asp Glu Ala Ile Val Pro Pro Met Ser Lys Glu Leu Gln Lys Pro
385                 390                 395                 400

Ile Met Leu Met Pro Asp Ala Glu Leu Ser Gly Leu His Leu Ala Asn
                405                 410                 415

Leu Thr His Phe Ser Pro His Tyr Leu Leu Ala Thr His Ser Ser Ala
            420                 425                 430

Gly Ser Thr Arg Leu Leu Leu Ser Tyr Lys Asp Asn Asp Asn Lys
        435                 440                 445

Pro Gly Glu Trp Phe Tyr Arg Val His Ser Ser Val Arg Ile Asn Gly
    450                 455                 460

Leu Val Asn Ala Val Ala Val Ala Pro Tyr Ala Met Asn Glu Phe Tyr
465                 470                 475                 480

Val Gln Thr Val Asn Asn Gly His Thr Tyr Glu Val Ser Leu Lys Ala
                485                 490                 495

Asp Lys Thr Leu Lys Val Glu Arg Ser Tyr Val Gln Leu His Glu Pro
            500                 505                 510
```

```
Ala Asp Gln Ile Asp Trp Val Ile Val Lys Gly Cys Ile Trp Asp Gly
        515                 520                 525
Tyr Thr Gly Ala Leu Val Thr Leu Arg Asn Gln His Leu Leu His Ile
        530                 535                 540
Asp Gly Tyr Arg Ile Gly Glu Asp Val Thr Ser Phe Cys Val Val Thr
545                 550                 555                 560
Asn Tyr Leu Val Tyr Thr Gln Leu Asn Ala Met His Phe Val Gln Leu
                565                 570                 575
Asp Asp Arg Arg Gln Val Ala Ser Arg Asn Ile Glu Arg Gly Ala Lys
            580                 585                 590
Ile Val Thr Ala Val Ala Arg Lys Ala Arg Val Val Leu Gln Leu Pro
        595                 600                 605
Arg Gly Asn Leu Glu Ala Ile Cys Pro Arg Val Leu Val Leu Glu Leu
        610                 615                 620
Val Gly Asp Leu Leu Glu Arg Gly Lys Tyr Gln Lys Ala Ile Glu Met
625                 630                 635                 640
Ser Arg Lys Gln Arg Ile Asn Leu Asn Ile Ile Phe Asp His Asp Val
                645                 650                 655
Lys Arg Phe Val Ser Ser Val Gly Ala Phe Leu Asn Asp Ile Asn Glu
                660                 665                 670
Pro Gln Trp Leu Cys Leu Phe Leu Ser Glu Leu Gln Asn Glu Asp Phe
            675                 680                 685
Thr Lys Gly Met Tyr Ser Ser Asn Tyr Asp Ala Ser Lys Gln Thr Tyr
        690                 695                 700
Pro Ser Asp Tyr Arg Val Asp Gln Lys Val Phe Tyr Val Cys Arg Leu
705                 710                 715                 720
Leu Glu Gln Gln Met Asn Arg Phe Val Ser Arg Phe Arg Leu Pro Leu
                725                 730                 735
Ile Thr Ala Tyr Val Lys Leu Gly Cys Leu Glu Met Ala Leu Gln Val
                740                 745                 750
Ile Trp Lys Glu Gln Gln Glu Asp Ala Ser Leu Ala Asp Gln Leu Leu
        755                 760                 765
Gln His Leu Leu Tyr Leu Val Asp Val Asn Asp Leu Tyr Asn Val Ala
        770                 775                 780
Leu Gly Thr Tyr Asp Phe Gly Leu Val Leu Phe Val Ala Gln Lys Ser
785                 790                 795                 800
Gln Lys Asp Pro Lys Glu Phe Leu Pro Tyr Leu Asn Asp Leu Lys Ala
                805                 810                 815
Leu Pro Ile Asp Tyr Arg Lys Phe Arg Ile Asp His Leu Lys Arg
            820                 825                 830
Tyr Thr Ser Ala Leu Ser His Leu Ala Ala Cys Gly Glu Gln His Tyr
        835                 840                 845
Glu Glu Ala Leu Glu Tyr Ile Arg Lys His Gly Leu Tyr Thr Asp Gly
        850                 855                 860
Leu Ala Phe Tyr Arg Glu His Ile Glu Phe Gln Lys Asn Ile Tyr Val
865                 870                 875                 880
Ala Tyr Ala Asp His Leu Arg Ala Ile Ala Lys Leu Asp Asn Ala Ser
                885                 890                 895
Leu Met Tyr Glu Arg Gly Gly Gln Leu Gln Gln Ala Leu Leu Ser Ala
            900                 905                 910
Lys His Thr Leu Asp Trp Gln Arg Val Leu Val Leu Ala Lys Lys Leu
        915                 920                 925
Ser Glu Pro Leu Asp Gln Val Ala Gln Ser Leu Val Gly Pro Leu Gln
```

```
                930                935                940
Gln Gln Gly Arg His Met Glu Ala Tyr Glu Leu Val Lys Glu His Cys
945                950                955                960

Gln Asp Arg Lys Arg Gln Phe Asp Val Leu Leu Glu Gly His Leu Tyr
                965                970                975

Ser Arg Ala Ile Tyr Glu Ala Gly Leu Glu Asp Asp Val Ser Glu
                980                985                990

Lys Ile Ala Pro Ala Leu Leu Ala Tyr Gly Val Gln Leu Glu Ser Ser
                995                1000               1005

Leu Gln Ala Asp Leu Gln Leu Phe Leu Asp Tyr Lys Gln Arg Leu Leu
    1010               1015               1020

Asp Ile Arg Arg Asn Gln Ala Lys Ser Gly Glu Gly Tyr Ile Asp Thr
    1025               1030               1035               1040

Asp Val Asn Leu Lys Glu Val Asp Leu Leu Ser Asp Thr Thr Ser Leu
                1045               1050               1055

His Ser Ser Gln Tyr Ser Gly Thr Ser Arg Arg Thr Gly Lys Thr Phe
            1060               1065               1070

Arg Ser Ser Lys Asn Arg Arg Lys His Glu Arg Lys Leu Phe Ser Leu
        1075               1080               1085

Lys Pro Gly Asn Pro Phe Glu Asp Ile Ala Leu Ile Asp Ala Leu His
    1090               1095               1100

Asn His Val Thr Lys Ile Ala Gln Gln Gln Pro Val Arg Asp Thr
1105               1110               1115               1120

Cys Lys Ala Leu Leu Gln Leu Ala Asn Ala Ala Asp Ala Asp Pro Leu
                1125               1130               1135

Ala Ala Ala Leu Gln Arg Glu Phe Lys Thr Leu Leu Gln Ala Val Asp
                1140               1145               1150

Ala Ala Leu Asp Glu Ile Trp Thr Pro Glu Leu Arg Gly Asn Gly Leu
            1155               1160               1165

Met Ala Asp His Leu Thr Gly Pro Asn Val Asp Tyr Leu Ala Leu Gln
        1170               1175               1180

Lys Glu Gln Arg Tyr Ala Leu Leu Ser Pro Leu Lys Arg Phe Lys Pro
1185               1190               1195               1200

Gln Leu Ile Met Met Asp Trp Gln His Glu Ile Leu Gln
            1205               1210

<210> SEQ ID NO 7
<211> LENGTH: 1349
<212> TYPE: PRT
<213> ORGANISM: Saccharomyces cerevisiae

<400> SEQUENCE: 7

Met Val Glu His Asp Lys Ser Gly Ser Lys Arg Gln Glu Leu Arg Ser
  1               5                  10                 15

Asn Met Arg Asn Leu Ile Thr Leu Asn Lys Gly Lys Phe Lys Pro Thr
                20                  25                 30

Ala Ser Thr Ala Glu Gly Asp Glu Asp Leu Ser Phe Thr Leu Leu
            35                  40                  45

Asp Ser Val Phe Asp Thr Leu Ser Asp Ser Ile Thr Cys Val Leu Gly
    50                  55                  60

Ser Thr Asp Ile Gly Ala Ile Glu Val Gln Gln Phe Met Lys Asp Gly
65                  70                  75                  80

Ser Arg Asn Val Leu Ala Ser Phe Asn Ile Gln Thr Phe Asp Asp Lys
                85                  90                  95
```

-continued

```
Leu Leu Ser Phe Val His Phe Ala Asp Ile Asn Gln Leu Val Phe Val
            100                 105                 110

Phe Glu Gln Gly Asp Ile Ile Thr Ala Thr Tyr Asp Pro Val Ser Leu
            115                 120                 125

Asp Pro Ala Glu Thr Leu Ile Glu Ile Met Gly Thr Ile Asp Asn Gly
            130                 135                 140

Ile Ala Ala Ala Gln Trp Ser Tyr Asp Glu Glu Thr Leu Ala Met Val
145                 150                 155                 160

Thr Lys Asp Arg Asn Val Val Leu Ser Lys Leu Phe Glu Pro Ile
            165                 170                 175

Ser Glu Tyr His Leu Glu Val Asp Asp Leu Lys Ile Ser Lys His Val
            180                 185                 190

Thr Val Gly Trp Gly Lys Lys Glu Thr Gln Phe Arg Gly Lys Gly Ala
            195                 200                 205

Arg Ala Met Glu Arg Glu Ala Leu Ala Ser Leu Lys Ala Ser Gly Leu
            210                 215                 220

Val Gly Asn Gln Leu Arg Asp Pro Thr Met Pro Tyr Met Val Asp Thr
225                 230                 235                 240

Gly Asp Val Thr Ala Leu Asp Ser His Glu Ile Thr Ile Ser Trp Arg
            245                 250                 255

Gly Asp Cys Asp Tyr Phe Ala Val Ser Ser Val Glu Glu Val Pro Asp
            260                 265                 270

Glu Asp Asp Glu Thr Lys Ser Ile Lys Arg Arg Ala Phe Arg Val Phe
            275                 280                 285

Ser Arg Glu Gly Gln Leu Asp Ser Ala Ser Glu Pro Val Thr Gly Met
            290                 295                 300

Glu His Gln Leu Ser Trp Lys Pro Gln Gly Ser Leu Ile Ala Ser Ile
305                 310                 315                 320

Gln Arg Lys Thr Asp Leu Gly Glu Glu Asp Ser Val Asp Val Ile Phe
            325                 330                 335

Phe Glu Arg Asn Gly Leu Arg His Gly Glu Phe Asp Thr Arg Leu Pro
            340                 345                 350

Leu Asp Glu Lys Val Glu Ser Val Cys Trp Asn Ser Asn Ser Glu Ala
            355                 360                 365

Leu Ala Val Val Leu Ala Asn Arg Ile Gln Leu Trp Thr Ser Lys Asn
            370                 375                 380

Tyr His Trp Tyr Leu Lys Gln Glu Leu Tyr Ala Ser Asp Ile Ser Tyr
385                 390                 395                 400

Val Lys Trp His Pro Glu Lys Asp Phe Thr Leu Met Phe Ser Asp Ala
            405                 410                 415

Gly Phe Ile Asn Ile Val Asp Phe Ala Tyr Lys Met Ala Gln Gly Pro
            420                 425                 430

Thr Leu Glu Pro Phe Asp Asn Gly Thr Ser Leu Val Val Asp Gly Arg
            435                 440                 445

Thr Val Asn Ile Thr Pro Leu Ala Leu Ala Asn Val Pro Pro Met
            450                 455                 460

Tyr Tyr Arg Asp Phe Glu Thr Pro Gly Asn Val Leu Asp Val Ala Cys
465                 470                 475                 480

Ser Phe Ser Asn Glu Ile Tyr Ala Ala Ile Asn Lys Asp Val Leu Ile
            485                 490                 495

Phe Ala Ala Val Pro Ser Ile Glu Glu Met Lys Lys Gly Lys His Pro
            500                 505                 510

Ser Ile Val Cys Glu Phe Pro Lys Ser Glu Phe Thr Ser Glu Val Asp
```

```
                515                 520                 525
Ser Leu Arg Gln Val Ala Phe Ile Asn Asp Ser Ile Val Gly Val Leu
    530                 535                 540

Leu Asp Thr Asp Asn Leu Ser Arg Ile Ala Leu Leu Asp Ile Gln Asp
545                 550                 555                 560

Ile Thr Gln Pro Thr Leu Ile Thr Ile Val Glu Val Tyr Asp Lys Ile
                565                 570                 575

Val Leu Leu Ser Ser Asp Phe Asp Tyr Asn His Leu Val Tyr Glu Thr
                580                 585                 590

Arg Asp Gly Thr Val Cys Gln Leu Asp Ala Glu Gly Gln Leu Met Glu
                595                 600                 605

Ile Thr Lys Phe Pro Gln Leu Val Arg Asp Phe Arg Val Lys Arg Val
            610                 615                 620

His Asn Thr Ser Ala Glu Asp Asp Asn Trp Ser Ala Glu Ser Ser
625                 630                 635                 640

Glu Leu Val Ala Phe Gly Ile Thr Asn Asn Gly Lys Leu Phe Ala Asn
                645                 650                 655

Gln Val Leu Leu Ala Ser Ala Val Thr Ser Leu Glu Ile Thr Asp Ser
            660                 665                 670

Phe Leu Leu Phe Thr Thr Ala Gln His Asn Leu Gln Phe Val His Leu
        675                 680                 685

Asn Ser Thr Asp Phe Lys Pro Leu Pro Leu Val Glu Glu Gly Val Glu
    690                 695                 700

Asp Glu Arg Val Arg Ala Ile Glu Arg Gly Ser Ile Leu Val Ser Val
705                 710                 715                 720

Ile Pro Ser Lys Arg Ser Val Val Leu Gln Ala Thr Arg Gly Asn Leu
                725                 730                 735

Glu Thr Ile Tyr Pro Arg Ile Met Val Leu Ala Glu Val Arg Lys Asn
            740                 745                 750

Ile Met Ala Lys Arg Tyr Lys Glu Ala Phe Ile Val Cys Arg Thr His
        755                 760                 765

Arg Ile Asn Leu Asp Ile Leu His Asp Tyr Ala Pro Glu Leu Phe Ile
    770                 775                 780

Glu Asn Leu Glu Val Phe Ile Asn Gln Ile Gly Arg Val Asp Tyr Leu
785                 790                 795                 800

Asn Leu Phe Ile Ser Cys Leu Ser Glu Asp Val Thr Lys Thr Lys
                805                 810                 815

Tyr Lys Glu Thr Leu Tyr Ser Gly Ile Ser Lys Ser Phe Gly Met Glu
                820                 825                 830

Pro Ala Pro Leu Thr Glu Met Gln Ile Tyr Met Lys Lys Lys Met Phe
            835                 840                 845

Asp Pro Lys Thr Ser Lys Val Asn Lys Ile Cys Asp Ala Val Leu Asn
850                 855                 860

Val Leu Leu Ser Asn Pro Glu Tyr Lys Lys Tyr Leu Gln Thr Ile
865                 870                 875                 880

Ile Thr Ala Tyr Ala Ser Gln Asn Pro Gln Asn Leu Ser Ala Ala Leu
                885                 890                 895

Lys Leu Ile Ser Glu Leu Glu Asn Ser Glu Lys Asp Ser Cys Val
            900                 905                 910

Thr Tyr Leu Cys Phe Leu Gln Asp Val Asn Val Val Tyr Lys Ser Ala
        915                 920                 925

Leu Ser Leu Tyr Asp Val Ser Leu Ala Leu Leu Val Ala Gln Lys Ser
    930                 935                 940
```

```
Gln Met Asp Pro Arg Glu Tyr Leu Pro Phe Leu Gln Glu Leu Gln Asp
945                 950                 955                 960

Asn Glu Pro Leu Arg Arg Lys Phe Leu Ile Asp Asp Tyr Leu Gly Asn
                965                 970                 975

Tyr Glu Lys Ala Leu Glu His Leu Ser Glu Ile Asp Lys Asp Gly Asn
            980                 985                 990

Val Ser Glu Glu Val Ile Asp Tyr Val Glu Ser His Asp Leu Tyr Lys
        995                 1000                1005

His Gly Leu Ala Leu Tyr Arg Tyr Asp Ser Glu Lys Gln Asn Val Ile
    1010                1015                1020

Tyr Asn Ile Tyr Ala Lys His Leu Ser Ser Asn Gln Met Tyr Thr Asp
1025                1030                1035                1040

Ala Ala Val Ala Tyr Glu Met Leu Gly Lys Leu Lys Glu Ala Met Gly
                1045                1050                1055

Ala Tyr Gln Ser Ala Lys Arg Trp Arg Glu Ala Met Ser Ile Ala Val
            1060                1065                1070

Gln Lys Phe Pro Glu Glu Val Glu Ser Val Ala Glu Glu Leu Ile Ser
        1075                1080                1085

Ser Leu Thr Phe Glu His Arg Tyr Val Asp Ala Ala Asp Ile Gln Leu
    1090                1095                1100

Glu Tyr Leu Asp Asn Val Lys Glu Ala Val Ala Leu Tyr Cys Lys Ala
1105                1110                1115                1120

Tyr Arg Tyr Asp Ile Ala Ser Leu Val Ala Ile Lys Ala Lys Lys Asp
                1125                1130                1135

Glu Leu Leu Glu Glu Val Val Asp Pro Gly Leu Gly Glu Gly Phe Gly
            1140                1145                1150

Ile Ile Ala Glu Leu Leu Ala Asp Cys Lys Gly Gln Ile Asn Ser Gln
        1155                1160                1165

Leu Arg Arg Leu Arg Glu Leu Arg Ala Lys Lys Glu Glu Asn Pro Tyr
    1170                1175                1180

Ala Phe Tyr Gly Gln Glu Thr Glu Gln Ala Asp Asp Val Ser Val Ala
1185                1190                1195                1200

Pro Ser Glu Thr Ser Thr Gln Glu Ser Phe Phe Thr Arg Tyr Thr Gly
                1205                1210                1215

Lys Thr Gly Gly Thr Ala Lys Thr Gly Ala Ser Arg Arg Thr Ala Lys
            1220                1225                1230

Asn Lys Arg Arg Glu Glu Arg Lys Arg Ala Arg Gly Lys Lys Gly Thr
        1235                1240                1245

Ile Tyr Glu Glu Glu Tyr Leu Val Gln Ser Val Gly Arg Leu Ile Glu
    1250                1255                1260

Arg Leu Asn Gln Thr Lys Pro Asp Ala Val Arg Val Val Glu Gly Leu
1265                1270                1275                1280

Cys Arg Arg Asn Met Arg Glu Gln Ala His Gln Ile Gln Lys Asn Phe
                1285                1290                1295

Val Glu Val Leu Asp Leu Leu Lys Ala Asn Val Lys Glu Ile Tyr Ser
            1300                1305                1310

Ile Ser Glu Lys Asp Arg Glu Arg Val Asn Glu Asn Gly Glu Val Tyr
        1315                1320                1325

Tyr Ile Pro Glu Ile Pro Val Pro Glu Ile His Asp Phe Pro Lys Ser
    1330                1335                1340

His Ile Val Asp Phe
1345
```

```
<210> SEQ ID NO 8
<211> LENGTH: 1319
<212> TYPE: PRT
<213> ORGANISM: Arabidopsis thaliana

<400> SEQUENCE: 8

Met Lys Asn Leu Lys Leu Phe Ser Glu Val Pro Gln Asn Ile Gln Leu
  1               5                  10                  15

His Ser Thr Glu Glu Val Val Gln Phe Ala Ala Thr Asp Ile Asp Gln
             20                  25                  30

Ser Arg Leu Phe Phe Ala Ser Ala Asn Phe Val Tyr Ala Leu Gln
         35                  40                  45

Leu Ser Ser Phe Gln Asn Glu Ser Ala Gly Ala Lys Ser Ala Met Pro
     50                  55                  60

Val Glu Val Cys Ser Ile Asp Ile Glu Pro Gly Asp Phe Ile Thr Ala
 65                  70                  75                  80

Phe Asp Tyr Leu Ala Glu Lys Glu Ser Leu Ile Gly Thr Ser His
                 85                  90                  95

Gly Leu Leu Val His Asn Val Glu Ser Asp Val Thr Glu Leu Val
                100                 105                 110

Gly Asn Ile Glu Gly Gly Val Lys Cys Ile Ser Pro Asn Pro Thr Gly
            115                 120                 125

Asp Leu Leu Gly Leu Ile Thr Gly Leu Gly Gln Leu Ile Val Met Thr
    130                 135                 140

Tyr Asp Trp Ala Leu Met Tyr Glu Lys Ala Leu Gly Glu Val Pro Glu
145                 150                 155                 160

Gly Gly Tyr Val Arg Glu Thr Asn Asp Leu Ser Val Asn Cys Gly Gly
                165                 170                 175

Ile Ser Ile Ser Trp Arg Gly Asp Gly Lys Tyr Phe Ala Thr Met Gly
            180                 185                 190

Glu Val Tyr Glu Ser Gly Cys Met Ser Lys Lys Ile Lys Ile Trp Glu
        195                 200                 205

Ser Asp Ser Gly Ala Leu Gln Ser Ser Ser Glu Thr Lys Glu Phe Thr
    210                 215                 220

Gln Gly Ile Leu Glu Trp Met Pro Ser Gly Ala Lys Ile Ala Ala Val
225                 230                 235                 240

Tyr Lys Arg Lys Ser Asp Asp Ser Ser Pro Ser Ile Ala Phe Phe Glu
                245                 250                 255

Arg Asn Gly Leu Glu Arg Ser Ser Phe Arg Ile Gly Glu Pro Glu Asp
            260                 265                 270

Ala Thr Glu Ser Cys Glu Asn Leu Lys Trp Asn Ser Ala Ser Asp Leu
        275                 280                 285

Leu Ala Gly Val Val Ser Cys Lys Thr Tyr Asp Ala Ile Arg Val Trp
    290                 295                 300

Phe Phe Ser Asn Asn His Trp Tyr Leu Lys Gln Glu Ile Arg Tyr Pro
305                 310                 315                 320

Arg Glu Ala Gly Val Thr Val Met Trp Asp Pro Thr Lys Pro Leu Gln
                325                 330                 335

Leu Ile Cys Trp Thr Leu Ser Gly Gln Val Ser Val Arg His Phe Met
            340                 345                 350

Trp Val Thr Ala Val Met Glu Asp Ser Thr Ala Phe Val Ile Asp Asn
        355                 360                 365

Ser Lys Ile Leu Val Thr Pro Leu Ser Leu Ser Leu Met Pro Pro Pro
    370                 375                 380
```

```
Met Tyr Leu Phe Ser Leu Ser Phe Ser Ser Ala Val Arg Asp Ile Ala
385                 390                 395                 400

Tyr Tyr Ser Arg Asn Ser Lys Asn Cys Leu Ala Val Phe Leu Ser Asp
            405                 410                 415

Gly Asn Leu Ser Phe Val Glu Phe Pro Ala Pro Asn Thr Trp Glu Asp
                420                 425                 430

Leu Glu Gly Lys Asp Phe Ser Val Glu Ile Ser Asp Cys Lys Thr Ala
            435                 440                 445

Leu Gly Ser Phe Val His Leu Leu Trp Leu Asp Val His Ser Leu Leu
            450                 455                 460

Cys Val Ser Ala Tyr Gly Ser His Asn Lys Cys Leu Ser Ser Gly
465             470                 475                 480

Gly Tyr Asp Thr Glu Leu His Gly Ser Tyr Leu Gln Glu Val Glu Val
                485                 490                 495

Val Cys His Glu Asp His Val Pro Asp Gln Val Thr Cys Ser Gly Phe
            500                 505                 510

Lys Ala Ser Ile Thr Phe Gln Thr Leu Leu Glu Ser Pro Val Leu Ala
            515                 520                 525

Leu Ala Trp Asn Pro Ser Lys Arg Asp Ser Ala Phe Val Glu Phe Glu
530                 535                 540

Gly Gly Lys Val Leu Gly Tyr Ala Ser Arg Ser Glu Ile Met Glu Thr
545                 550                 555                 560

Arg Ser Ser Asp Asp Ser Val Cys Phe Pro Ser Thr Cys Pro Trp Val
                565                 570                 575

Arg Val Ala Gln Val Asp Ala Ser Gly Val His Lys Pro Leu Ile Cys
                580                 585                 590

Gly Leu Asp Asp Met Gly Arg Leu Ser Ile Asn Gly Lys Asn Leu Cys
                595                 600                 605

Asn Asn Cys Ser Ser Phe Ser Phe Tyr Ser Glu Leu Ala Asn Glu Val
            610                 615                 620

Val Thr His Leu Ile Ile Leu Thr Lys Gln Asp Phe Leu Phe Ile Val
625                 630                 635                 640

Asp Thr Lys Asp Val Leu Asn Gly Asp Val Ala Leu Gly Asn Val Phe
                645                 650                 655

Phe Val Ile Asp Gly Arg Arg Asp Glu Glu Asn Met Ser Tyr Val
                660                 665                 670

Asn Ile Trp Glu Arg Gly Ala Lys Val Ile Gly Val Leu Asn Gly Asp
                675                 680                 685

Glu Ala Ala Val Ile Leu Gln Thr Met Arg Gly Asn Leu Glu Cys Ile
690                 695                 700

Tyr Pro Arg Lys Leu Val Leu Ser Ser Ile Thr Asn Ala Leu Ala Gln
705                 710                 715                 720

Gln Arg Phe Lys Asp Ala Phe Asn Leu Val Arg Arg His Arg Ile Asp
                725                 730                 735

Phe Asn Val Ile Val Asp Leu Tyr Gly Trp Gln Ala Phe Leu Gln Ser
                740                 745                 750

Ala Val Ala Phe Val Glu Gln Val Asn Asn Leu Asn His Val Thr Glu
            755                 760                 765

Phe Val Cys Ala Met Lys Asn Glu Asp Val Thr Glu Thr Leu Tyr Lys
            770                 775                 780

Lys Phe Ser Phe Ser Lys Lys Gly Asp Glu Val Phe Arg Val Lys Asp
785                 790                 795                 800
```

-continued

```
Ser Cys Ser Asn Lys Val Ser Val Leu Gln Ala Ile Arg Lys Ala
            805                 810                 815

Leu Glu Glu His Ile Pro Glu Ser Pro Ser Arg Glu Leu Cys Ile Leu
            820                 825                 830

Thr Thr Leu Ala Arg Ser Asp Pro Pro Ala Ile Glu Glu Ser Leu Leu
            835                 840                 845

Arg Ile Lys Ser Val Arg Glu Met Glu Leu Leu Asn Ser Ser Asp Asp
        850                 855                 860

Ile Arg Lys Lys Ser Cys Pro Ser Ala Glu Glu Ala Leu Lys His Leu
865                 870                 875                 880

Leu Trp Leu Leu Asp Ser Glu Ala Val Phe Glu Ala Ala Leu Gly Leu
                885                 890                 895

Tyr Asp Leu Asn Leu Ala Ala Ile Val Ala Leu Asn Ser Gln Arg Asp
            900                 905                 910

Pro Lys Glu Phe Leu Pro Tyr Leu Gln Glu Leu Glu Lys Met Pro Glu
            915                 920                 925

Ser Leu Met His Phe Lys Ile Asp Ile Lys Leu Gln Arg Phe Asp Ser
        930                 935                 940

Ala Leu Arg Asn Ile Val Ser Ala Gly Val Gly Tyr Phe Pro Asp Cys
945                 950                 955                 960

Met Asn Leu Ile Lys Lys Asn Pro Gln Leu Phe Pro Leu Gly Leu Leu
                965                 970                 975

Leu Ile Thr Asp Pro Glu Lys Lys Leu Val Val Leu Glu Ala Trp Ala
            980                 985                 990

Asp His Leu Ile Asp Glu Lys Arg Phe Glu Asp Ala Ala Thr Thr Tyr
        995                 1000                1005

Leu Cys Cys Cys Lys Leu Glu Lys Ala Ser Lys Ala Tyr Arg Glu Cys
    1010                1015                1020

Gly Asp Trp Ser Gly Val Leu Arg Val Gly Ala Leu Met Lys Leu Gly
1025                1030                1035                1040

Lys Asp Glu Ile Leu Lys Leu Ala Tyr Glu Leu Cys Glu Glu Val Asn
                1045                1050                1055

Ala Leu Gly Lys Pro Ala Glu Ala Ala Lys Ile Ala Leu Glu Tyr Cys
            1060                1065                1070

Ser Asp Ile Ser Gly Gly Ile Ser Leu Leu Ile Asn Ala Arg Glu Trp
        1075                1080                1085

Glu Glu Ala Leu Arg Val Ala Phe Leu His Thr Ala Asp Asp Arg Ile
    1090                1095                1100

Ser Val Val Lys Ser Ser Ala Leu Glu Cys Ala Ser Gly Leu Val Ser
1105                1110                1115                1120

Glu Phe Lys Glu Ser Ile Glu Lys Val Gly Lys Tyr Leu Thr Arg Tyr
                1125                1130                1135

Leu Ala Val Arg Gln Arg Arg Leu Leu Leu Ala Ala Lys Leu Lys Ser
            1140                1145                1150

Glu Glu Arg Ser Val Val Asp Leu Asp Asp Asp Thr Ala Ser Glu Ala
        1155                1160                1165

Ser Ser Asn Leu Ser Gly Met Ser Ala Tyr Thr Leu Gly Thr Arg Arg
    1170                1175                1180

Gly Ser Ala Ala Ser Val Ser Ser Ser Asn Ala Thr Ser Arg Ala Arg
1185                1190                1195                1200

Asp Leu Arg Arg Gln Arg Lys Ser Gly Lys Ile Arg Ala Gly Ser Ala
            1205                1210                1215

Gly Glu Glu Met Ala Leu Val Asp His Leu Lys Gly Met Arg Met Thr
```

```
                    1220                1225               1230
Asp Gly Gly Lys Arg Glu Leu Lys Ser Leu Leu Ile Cys Leu Val Thr
            1235                1240                1245

Leu Gly Glu Met Glu Ser Ala Gln Lys Leu Gln Gln Thr Ala Glu Asn
    1250                1255                1260

Phe Gln Val Ser Gln Val Ala Ala Val Glu Leu Ala His Asp Thr Val
1265                1270                1275                1280

Ser Ser Glu Ser Val Asp Glu Val Tyr Cys Phe Glu Arg Tyr Ala
                1285                1290                1295

Gln Lys Thr Arg Ser Thr Ala Arg Asp Ser Asp Ala Phe Ser Trp Met
            1300                1305                1310

Leu Lys Val Phe Ile Ser Pro
        1315

<210> SEQ ID NO 9
<211> LENGTH: 1178
<212> TYPE: PRT
<213> ORGANISM: Caenorhabditis elegans

<400> SEQUENCE: 9

Met Lys Asn Leu Gln Ile Gly Ser Val Lys Thr Phe Glu Asn Pro Glu
  1               5                  10                  15

Ile Ala Gly Ala Asp Asp Phe Ala Val His Pro Ile Leu Gln Thr Ile
                20                  25                  30

Ala Val Ser Thr Lys Asn Glu Leu Leu Leu Leu Glu Asn Asn Leu Ile
            35                  40                  45

Ser Ser Thr Ile Lys Trp Ala Glu Gln Arg Arg Glu Leu Glu Val Ile
        50                  55                  60

Ser Leu Ser Phe Arg Thr Asp Gly Asn Gln Ile Val Val Ile Leu Ala
 65                  70                  75                  80

Asp Gly Arg Ala Leu Ile Val Glu Asp Gly Glu Val Met Asp Leu Glu
                85                  90                  95

Ile Ala Glu Leu Thr Asp Thr Thr Val Ser Ala Ala Glu Trp Thr Ala
            100                 105                 110

Asp Glu Gln Thr Leu Ala Leu Ala Asp Asn Gln Thr Leu Tyr Leu Ala
        115                 120                 125

Asp Ser Ser Leu Val Pro Phe Ala Glu Arg Pro Leu Ile Phe Ser Glu
    130                 135                 140

Asn Glu Arg Lys Ser Ala Pro Val Asn Val Gly Trp Gly Ser Glu Ser
145                 150                 155                 160

Thr Gln Phe Arg Gly Ser Ala Gly Lys Leu Lys Pro Gly Glu Lys Ile
                165                 170                 175

Glu Lys Glu Lys Glu Gln Ile Glu Gln His Ser Arg Lys Thr Ser Val
            180                 185                 190

His Trp Arg Trp Asp Gly Glu Ile Val Ala Val Ser Phe Tyr Ser Ser
        195                 200                 205

Gln Asn Asp Thr Arg Asn Leu Thr Val Phe Asp Arg Asn Gly Glu Ile
    210                 215                 220

Leu Asn Asn Met Asn Ile Arg Asn Ile Tyr Leu Ser His Cys Phe Ala
225                 230                 235                 240

His Lys Pro Asn Ala Asn Leu Leu Cys Ser Ala Ile Gln Glu Asn Gly
                245                 250                 255

Ser Asp Asp Arg Ile Val Ile Tyr Glu Arg Asn Gly Glu Thr Arg Asn
            260                 265                 270
```

```
Ser Tyr Val Val Lys Trp Pro Ala Asn Gln Ile Glu Asp Arg Arg Ile
        275                 280                 285

Ile Glu Lys Ile Glu Trp Asn Ser Thr Gly Thr Ile Leu Ser Met Gln
            290                 295                 300

Thr Ser Leu Gly Lys Lys His Gln Leu Glu Phe Trp His Leu Ser Asn
305                 310                 315                 320

Tyr Glu Phe Thr Arg Lys Cys Tyr Trp Lys Phe Ser Glu Ser Ile Ile
                325                 330                 335

Trp Lys Trp Ser Thr Val Glu Cys Gln Asn Ile Glu Val Leu Leu Glu
            340                 345                 350

Ser Gly Gln Phe Phe Ser Val His Ile Thr Pro Thr Ala Ser Phe Ser
        355                 360                 365

Asp Val Ile Ser Gln Asn Val Val Ala Thr Asp Glu Leu Arg Met
370                 375                 380

Tyr Ser Leu Cys Arg Arg Val Val Pro Pro Met Cys Asp Tyr Ser
385                 390                 395                 400

Ile Gln Cys Leu Ser Asp Ile Val Ala Tyr Thr Thr Ser Thr His His
                405                 410                 415

Val His Val Ile Thr Ser Asp Trp Lys Ile Ile Ser Cys Met Leu Phe
            420                 425                 430

Phe Lys Lys Lys Lys Arg Asn Tyr Ser Asn Pro Phe Phe Arg Lys Lys
        435                 440                 445

Tyr Ile Leu Glu Ile Leu Lys Val Pro Ser His Lys Thr Tyr Phe Ala
    450                 455                 460

Cys Phe Ala Val Ser Gln Asp Thr Asp Gly Tyr Lys Phe Asn Ser Asp
465                 470                 475                 480

Arg Ala Ser Ile Asp Glu Val Leu His Thr Glu Val Thr Glu Gly Ile
                485                 490                 495

Ile Cys Gly Phe Val Tyr Asp Glu Pro Ser Glu Ser Tyr Ile Ile Trp
            500                 505                 510

Asn Val Ser His Gly Lys His Gln Ile Ser Arg Val Gly Ala Asn Pro
        515                 520                 525

Glu Lys Ile Phe Glu Gly Glu Asn Ile Gly Trp Ile Gly Val Asn Pro
    530                 535                 540

Ser Asn Lys His Val Glu Ile Ala Ser Asn Asp Gly Lys Phe Ile Asp
545                 550                 555                 560

Leu Asn Thr Lys Glu Glu Leu Phe Lys Ile Asp Lys Phe Glu Ser Thr
                565                 570                 575

Glu Val His Phe Ile Gln Val Cys His Gly Ile Leu Asn His His Val
            580                 585                 590

Ile Gln Val Asp Asn Ser Met Leu Phe Leu Asp Ser Glu Arg Val Ser
        595                 600                 605

Gln Asp Ala Ile Ser Ile Leu Thr Arg Gly Ser Asp Ile Leu Leu Ile
    610                 615                 620

Asp Phe Asp Asn Lys Leu Arg Phe Ile Asp Ala Glu Ser Gly Lys Thr
625                 630                 635                 640

Leu Glu Asp Val Arg Asn Val Glu Ala Gly Cys Glu Leu Val Ala Cys
                645                 650                 655

Asp Ser Gln Ser Ala Asn Val Ile Leu Gln Ala Arg Gly Asn Leu
            660                 665                 670

Glu Thr Ile Gln Pro Arg Arg Tyr Val Met Ala His Thr Arg Asp Leu
        675                 680                 685

Leu Asp Arg Lys Glu Tyr Ile Ala Ser Phe Lys Trp Met Lys Lys His
```

-continued

```
            690                 695                 700
Arg Val Asp Met Ser Phe Ala Met Lys Tyr Lys Gly Asp Asp Leu Glu
705                 710                 715                 720
Asp Asp Ile Pro Ile Trp Leu Lys Thr Ser Asn Asp Ser Gln Phe Leu
                725                 730                 735
Glu Gln Leu Leu Ile Ser Cys Thr Glu Val Phe Glu Asp Ala Gly Ser
            740                 745                 750
Ser Leu Cys Met Thr Val Ala Arg Tyr Val Arg Asp Leu Ser Asp Ala
            755                 760                 765
Glu Lys Thr Lys Met Phe Pro Leu Leu Leu Thr Ala Leu Leu Ser Ala
770                 775                 780
Arg Ser Lys Pro Ser Lys Val Asn Asp Cys Leu Lys Glu Val Gln Glu
785                 790                 795                 800
His Val Glu Lys Ile Ala Asp Arg Lys Asp Val Phe Thr Arg Asn Ser
                805                 810                 815
Leu His His Ile Ser Phe Val Pro Ala Lys Glu Leu Phe Asn Cys
                820                 825                 830
Ala Leu Ser Thr Tyr Asp Leu Lys Leu Ala Gln Gln Val Ala Glu Ala
            835                 840                 845
Ser Asn Tyr Asp Pro Lys Glu Tyr Leu Pro Val Leu Asn Lys Leu Asn
850                 855                 860
Arg Val Met Cys Thr Leu Glu Arg Gln Tyr Arg Ile Asn Val Val Arg
865                 870                 875                 880
Glu Ala Trp Ile Asp Ala Val Ser Ser Leu Phe Leu Leu Asp Ser Ser
                885                 890                 895
Lys Glu Arg Gly Ser Glu Glu Thr Trp Trp Asn Asp Ile Glu Asp Ile
                900                 905                 910
Ile Ile Gln Arg Glu Lys Leu Tyr Gln Asp Ala Leu Thr Leu Val Lys
            915                 920                 925
Pro Gly Asp Arg Arg Tyr Lys Gln Cys Cys Glu Leu Tyr Ala Glu Leu
            930                 935                 940
Glu Arg Lys Val His Trp Arg Glu Ala Ala Leu Phe Tyr Glu Leu Ser
945                 950                 955                 960
Gly Asn Ser Glu Lys Thr Leu Lys Cys Trp Glu Met Ser Arg Asp Val
                965                 970                 975
Asp Gly Leu Ala Ala Ser Ala Arg Arg Leu Ala Val Asp Ala Gly Lys
            980                 985                 990
Leu Lys Ile His Ala Ile Lys Met Ser Thr Thr Leu Arg Glu Ala Arg
            995                 1000                1005
Gln Pro Lys Glu Leu Ala Lys Ala Leu Lys Leu Ala Gly Ser Ser Ser
        1010                1015                1020
Thr Gln Ile Val His Val Leu Cys Asp Ala Phe Glu Trp Leu Asp Ala
1025                1030                1035                1040
Ser Arg Glu Val Glu Val Gly Lys Glu Glu Ala Leu Lys Lys Ala Ala
                1045                1050                1055
Leu Ser Arg Asn Asp Gln Val Leu Met Asp Leu Glu Arg Arg Lys Thr
            1060                1065                1070
Glu Phe Glu Asn Tyr Lys Lys Arg Leu Ala Val Val Arg Glu Asn Lys
        1075                1080                1085
Leu Lys Arg Val Glu Gln Phe Ala Ala Gly Glu Val Asp Asp Leu Arg
        1090                1095                1100
Asp Asp Ile Ser Val Ile Ser Ser Ile Ser Ser Arg Ser Gly Ser Ser
1105                1110                1115                1120
```

-continued

```
Lys Val Ser Met Ala Ser Thr Val Arg Arg Lys Gln Ile Glu Lys Lys
             1125                1130                1135

Lys Ser Ser Leu Lys Glu Gly Gly Glu Tyr Glu Asp Ser Ala Leu Leu
         1140                1145                1150

Asn Val Leu Ser Glu Asn Tyr Arg Trp Leu Glu Asn Ile Gly Ser Glu
     1155                1160                1165

Phe Cys Phe Pro Trp Asn Phe Asn Ile Leu
     1170                1175

<210> SEQ ID NO 10
<211> LENGTH: 17
<212> TYPE: DNA
<213> ORGANISM: Mus sp.

<400> SEQUENCE: 10
ttttttttcc ctcagaa                                              17

<210> SEQ ID NO 11
<211> LENGTH: 17
<212> TYPE: DNA
<213> ORGANISM: Mus sp.

<400> SEQUENCE: 11
tatgctttgt gaaaggt                                              17

<210> SEQ ID NO 12
<211> LENGTH: 17
<212> TYPE: DNA
<213> ORGANISM: Mus sp.

<400> SEQUENCE: 12
ttttctctga tgcagct                                              17

<210> SEQ ID NO 13
<211> LENGTH: 17
<212> TYPE: DNA
<213> ORGANISM: Mus sp.

<400> SEQUENCE: 13
acatgaactc ctaagct                                              17

<210> SEQ ID NO 14
<211> LENGTH: 17
<212> TYPE: DNA
<213> ORGANISM: Mus sp.

<400> SEQUENCE: 14
cttgaaaaac tgtaggc                                              17

<210> SEQ ID NO 15
<211> LENGTH: 17
<212> TYPE: DNA
<213> ORGANISM: Mus sp.

<400> SEQUENCE: 15
ggtgtctctc ttcagcc                                              17

<210> SEQ ID NO 16
<211> LENGTH: 17
<212> TYPE: DNA
<213> ORGANISM: Mus sp.
```

```
<400> SEQUENCE: 16
ctacctcctt tgcag ag                                               17

<210> SEQ ID NO 17
<211> LENGTH: 17
<212> TYPE: DNA
<213> ORGANISM: Mus sp.

<400> SEQUENCE: 17
aggttctgct ttcagac                                                17

<210> SEQ ID NO 18
<211> LENGTH: 17
<212> TYPE: DNA
<213> ORGANISM: Mus sp.

<400> SEQUENCE: 18
ttttgtccct accaggt                                                17

<210> SEQ ID NO 19
<211> LENGTH: 17
<212> TYPE: DNA
<213> ORGANISM: Mus sp.

<400> SEQUENCE: 19
tccctccaca cacagtc                                                17

<210> SEQ ID NO 20
<211> LENGTH: 17
<212> TYPE: DNA
<213> ORGANISM: Mus sp.

<400> SEQUENCE: 20
cttttcattg tgtagac                                                17

<210> SEQ ID NO 21
<211> LENGTH: 17
<212> TYPE: DNA
<213> ORGANISM: Mus sp.

<400> SEQUENCE: 21 tttttttgttt tctaggt                                               17

<210> SEQ ID NO 22
<211> LENGTH: 17
<212> TYPE: DNA
<213> ORGANISM: Mus sp.

<400> SEQUENCE: 22
ctaatatttg aacagga                                                17

<210> SEQ ID NO 23
<211> LENGTH: 17
<212> TYPE: DNA
<213> ORGANISM: Mus sp.

<400> SEQUENCE: 23 tttttttgc tttagtt                                                 17

<210> SEQ ID NO 24
<211> LENGTH: 17
<212> TYPE: DNA
```

```
<400> SEQUENCE: 24
ttaatcttac aacagag                                                  17

<210> SEQ ID NO 25
<211> LENGTH: 17
<212> TYPE: DNA
<213> ORGANISM: Mus sp.

<400> SEQUENCE: 25
ttcatttctt tgcagga                                                  17

<210> SEQ ID NO 26
<211> LENGTH: 17
<212> TYPE: DNA
<213> ORGANISM: Mus sp.

<400> SEQUENCE: 26
tcttgcctgt tgcaggt                                                  17

<210> SEQ ID NO 27
<211> LENGTH: 17
<212> TYPE: DNA
<213> ORGANISM: Mus sp.

<400> SEQUENCE: 27
cactggtatt tttagtg                                                  17

<210> SEQ ID NO 28
<211> LENGTH: 17
<212> TYPE: DNA
<213> ORGANISM: Mus sp.

<400> SEQUENCE: 28
gggttttatt ttgagat                                                  17

<210> SEQ ID NO 29
<211> LENGTH: 17
<212> TYPE: DNA
<213> ORGANISM: Mus sp.

<400> SEQUENCE: 29
ttcctgtcct cacagac                                                  17

<210> SEQ ID NO 30
<211> LENGTH: 17
<212> TYPE: DNA
<213> ORGANISM: Mus sp.

<400> SEQUENCE: 30
tactttcttt gataggt                                                  17

<210> SEQ ID NO 31
<211> LENGTH: 17
<212> TYPE: DNA
<213> ORGANISM: Mus sp.

<400> SEQUENCE: 31
tactgtggtt cttaggg                                                  17

<210> SEQ ID NO 32
<211> LENGTH: 17
<212> TYPE: DNA
```

-continued

```
<213> ORGANISM: Mus sp.

<400> SEQUENCE: 32
cacttactac ctcaggt                                                    17

<210> SEQ ID NO 33
<211> LENGTH: 17
<212> TYPE: DNA
<213> ORGANISM: Mus sp.

<400> SEQUENCE: 33
cttaaactcc aacagga                                                    17

<210> SEQ ID NO 34
<211> LENGTH: 17
<212> TYPE: DNA
<213> ORGANISM: Mus sp.

<400> SEQUENCE: 34 aactttttc ctaggga                                                     17

<210> SEQ ID NO 35
<211> LENGTH: 17
<212> TYPE: DNA
<213> ORGANISM: Mus sp.

<400> SEQUENCE: 35
tttttttttt ttcagga                                                    17

<210> SEQ ID NO 36
<211> LENGTH: 17
<212> TYPE: DNA
<213> ORGANISM: Mus sp.

<400> SEQUENCE: 36
cgtctcttgt cacaggc                                                    17

<210> SEQ ID NO 37
<211> LENGTH: 17
<212> TYPE: DNA
<213> ORGANISM: Mus sp.

<400> SEQUENCE: 37
ttgctgtctt ttcagga                                                    17

<210> SEQ ID NO 38
<211> LENGTH: 17
<212> TYPE: DNA
<213> ORGANISM: Mus sp.

<400> SEQUENCE: 38 ctcttcccctt gtcagga                                                   17

<210> SEQ ID NO 39
<211> LENGTH: 17
<212> TYPE: DNA
<213> ORGANISM: Mus sp.

<400> SEQUENCE: 39
tttcttccct cttaggt                                                    17

<210> SEQ ID NO 40
<211> LENGTH: 17
```

```
<212> TYPE: DNA
<213> ORGANISM: Mus sp.

<400> SEQUENCE: 40
attatgcatc ctcagcc                                                  17

<210> SEQ ID NO 41
<211> LENGTH: 17
<212> TYPE: DNA
<213> ORGANISM: Mus sp.

<400> SEQUENCE: 41
gttcatcttc tctagat                                                  17

<210> SEQ ID NO 42
<211> LENGTH: 17
<212> TYPE: DNA
<213> ORGANISM: Mus sp.

<400> SEQUENCE: 42
tgtaatttct gacagga                                                  17

<210> SEQ ID NO 43
<211> LENGTH: 17
<212> TYPE: DNA
<213> ORGANISM: Mus sp.

<400> SEQUENCE: 43
ccatttcttc tctagat                                                  17

<210> SEQ ID NO 44
<211> LENGTH: 17
<212> TYPE: DNA
<213> ORGANISM: Mus sp.

<400> SEQUENCE: 44
ctgttttctg cttaggt                                                  17

<210> SEQ ID NO 45
<211> LENGTH: 17
<212> TYPE: DNA
<213> ORGANISM: Mus sp.

<400> SEQUENCE: 45
cattcttgct tccagat                                                  17

<210> SEQ ID NO 46
<211> LENGTH: 17
<212> TYPE: DNA
<213> ORGANISM: Mus sp.

<400> SEQUENCE: 46
aggtgagcat tcgcccg                                                  17

<210> SEQ ID NO 47
<211> LENGTH: 17
<212> TYPE: DNA
<213> ORGANISM: Mus sp.

<400> SEQUENCE: 47
aagtaggtca ctgatgc                                                  17

<210> SEQ ID NO 48
```

```
<211> LENGTH: 17
<212> TYPE: DNA
<213> ORGANISM: Mus sp.

<400> SEQUENCE: 48
aggtaggtgt aaggcct                                                  17

<210> SEQ ID NO 49
<211> LENGTH: 17
<212> TYPE: DNA
<213> ORGANISM: Mus sp.

<400> SEQUENCE: 49
aggtaagctt tgcactg                                                  17

<210> SEQ ID NO 50
<211> LENGTH: 17
<212> TYPE: DNA
<213> ORGANISM: Mus sp.

<400> SEQUENCE: 50
aggtaagcgt ttcttgg                                                  17

<210> SEQ ID NO 51
<211> LENGTH: 17
<212> TYPE: DNA
<213> ORGANISM: Mus sp.

<400> SEQUENCE: 51
tggtaaggcg ggatgat                                                  17

<210> SEQ ID NO 52
<211> LENGTH: 17
<212> TYPE: DNA
<213> ORGANISM: Mus sp.

<400> SEQUENCE: 52
tggtgtctct cttcagc                                                  17

<210> SEQ ID NO 53
<211> LENGTH: 17
<212> TYPE: DNA
<213> ORGANISM: Mus sp.

<400> SEQUENCE: 53
aagtgagtga gcataaa                                                  17

<210> SEQ ID NO 54
<211> LENGTH: 17
<212> TYPE: DNA
<213> ORGANISM: Mus sp.

<400> SEQUENCE: 54
aggtaggggt cagagtt                                                  17

<210> SEQ ID NO 55
<211> LENGTH: 17
<212> TYPE: DNA
<213> ORGANISM: Mus sp.

<400> SEQUENCE: 55
tggtatgaca gcttgtg                                                  17
```

```
<210> SEQ ID NO 56
<211> LENGTH: 17
<212> TYPE: DNA
<213> ORGANISM: Mus sp.

<400> SEQUENCE: 56
aagtaagttg ctgcgaa                                                  17

<210> SEQ ID NO 57
<211> LENGTH: 17
<212> TYPE: DNA
<213> ORGANISM: Mus sp.

<400> SEQUENCE: 57
tggtaagtgg aagcagg                                                  17

<210> SEQ ID NO 58
<211> LENGTH: 17
<212> TYPE: DNA
<213> ORGANISM: Mus sp.

<400> SEQUENCE: 58
tcgtaagttc ctaaata                                                  17

<210> SEQ ID NO 59
<211> LENGTH: 17
<212> TYPE: DNA
<213> ORGANISM: Mus sp.

<400> SEQUENCE: 59
aggtatcatg gttcatc                                                  17

<210> SEQ ID NO 60
<211> LENGTH: 17
<212> TYPE: DNA
<213> ORGANISM: Mus sp.

<400> SEQUENCE: 60
gggtgaggat cagagtt                                                  17

<210> SEQ ID NO 61
<211> LENGTH: 17
<212> TYPE: DNA
<213> ORGANISM: Mus sp.

<400> SEQUENCE: 61
aggtgaatag acacggc                                                  17

<210> SEQ ID NO 62
<211> LENGTH: 17
<212> TYPE: DNA
<213> ORGANISM: Mus sp.

<400> SEQUENCE: 62
aggtatgtag gcttggt                                                  17

<210> SEQ ID NO 63
<211> LENGTH: 17
<212> TYPE: DNA
<213> ORGANISM: Mus sp.

<400> SEQUENCE: 63
aagtaagctc tcctata                                                  17
```

```
<210> SEQ ID NO 64
<211> LENGTH: 17
<212> TYPE: DNA
<213> ORGANISM: Mus sp.

<400> SEQUENCE: 64
aggtaagctg actcttc                                                    17

<210> SEQ ID NO 65
<211> LENGTH: 17
<212> TYPE: DNA
<213> ORGANISM: Mus sp.

<400> SEQUENCE: 65
aagtaagtat ttattct                                                    17

<210> SEQ ID NO 66
<211> LENGTH: 17
<212> TYPE: DNA
<213> ORGANISM: Mus sp.

<400> SEQUENCE: 66
aggtacactt tgcgtct                                                    17

<210> SEQ ID NO 67
<211> LENGTH: 17
<212> TYPE: DNA
<213> ORGANISM: Mus sp.

<400> SEQUENCE: 67
aggtaagtat tttgata                                                    17

<210> SEQ ID NO 68
<211> LENGTH: 17
<212> TYPE: DNA
<213> ORGANISM: Mus sp.

<400> SEQUENCE: 68
aagtgggtgc tgtgtgt                                                    17

<210> SEQ ID NO 69
<211> LENGTH: 17
<212> TYPE: DNA
<213> ORGANISM: Mus sp.

<400> SEQUENCE: 69
aggtagagac ctgcgcg                                                    17

<210> SEQ ID NO 70
<211> LENGTH: 17
<212> TYPE: DNA
<213> ORGANISM: Mus sp.

<400> SEQUENCE: 70
aggtatgtgg agttgag                                                    17

<210> SEQ ID NO 71
<211> LENGTH: 17
<212> TYPE: DNA

<400> SEQUENCE: 71
tggtaagggt tttttt                                                     17
```

<210> SEQ ID NO 72
<211> LENGTH: 17
<212> TYPE: DNA
<213> ORGANISM: Mus sp.

<400> SEQUENCE: 72
aggtatgtgg tgggtta                                               17

<210> SEQ ID NO 73
<211> LENGTH: 17
<212> TYPE: DNA
<213> ORGANISM: Mus sp.

<400> SEQUENCE: 73
aggtaagcag ggccatt                                               17

<210> SEQ ID NO 74
<211> LENGTH: 17
<212> TYPE: DNA
<213> ORGANISM: Mus sp.

<400> SEQUENCE: 74
aggtgagctc ctccccg                                               17

<210> SEQ ID NO 75
<211> LENGTH: 17
<212> TYPE: DNA
<213> ORGANISM: Mus sp.

<400> SEQUENCE: 75
tggtaaggaa gctctga                                               17

<210> SEQ ID NO 76
<211> LENGTH: 17
<212> TYPE: DNA
<213> ORGANISM: Mus sp.

<400> SEQUENCE: 76
aggtgaggat tacattt                                               17

<210> SEQ ID NO 77
<211> LENGTH: 17
<212> TYPE: DNA
<213> ORGANISM: Mus sp.

<400> SEQUENCE: 77
gggtgagtgc ctccaaa                                               17

<210> SEQ ID NO 78
<211> LENGTH: 17
<212> TYPE: DNA
<213> ORGANISM: Mus sp.

<400> SEQUENCE: 78
gcgtacgtac gagacct                                               17

<210> SEQ ID NO 79
<211> LENGTH: 17
<212> TYPE: DNA
<213> ORGANISM: Mus sp.

<400> SEQUENCE: 79

```
aggtatggct tcagtgc                                                  17

<210> SEQ ID NO 80
<211> LENGTH: 17
<212> TYPE: DNA
<213> ORGANISM: Mus sp.

<400> SEQUENCE: 80
cggtaagctt cctcaga                                                  17

<210> SEQ ID NO 81
<211> LENGTH: 17
<212> TYPE: DNA
<213> ORGANISM: Mus sp.

<400> SEQUENCE: 81
cggtgtactg ctcgttc                                                  17

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 82
gccagtgttt ttgcctgag                                                19

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 83
cggattgtca ctgttgtgc                                                19

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 84
gactgctctc atagcatcgc                                               20

<210> SEQ ID NO 85
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 85
aagtaagygc cattg                                                    15

<210> SEQ ID NO 86
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 86
```

```
ggttcacsga ttgtc                                                          15

<210> SEQ ID NO 87
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 87
ggcgtcgtag aaattgc                                                        17

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 88
gtggtgctga aggggcaggc                                                     20
```